United States Patent
Bengtsson et al.

(10) Patent No.: US 7,868,188 B2
(45) Date of Patent: Jan. 11, 2011

(54) 5-HETEROARYL THIAZOLES AND THEIR USE AS PI3K INHIBITORS

(75) Inventors: Malena Bengtsson, Lund (SE); Joakim Larsson, Lund (SE); Grigorios Nikitidis, Lund (SE); Peter Storm, Mölndal (SE); John Peter Bailey, Macclesfield (GB); Edward Jolyon Griffen, Macclesfield (GB); Jean-Claude Arnould, Reims (FR); Thomas Geoffrey Colerick Bird, Reims (FR)

(73) Assignee: AstraZeneca AB, Sodertalje (SE)

( * ) Notice: Subject to any disclaimer, the term of this patent is extended or adjusted under 35 U.S.C. 154(b) by 875 days.

(21) Appl. No.: 11/667,064

(22) PCT Filed: Nov. 7, 2005

(86) PCT No.: PCT/GB2005/004268
§ 371 (c)(1),
(2), (4) Date: May 4, 2007

(87) PCT Pub. No.: WO2006/051270
PCT Pub. Date: May 18, 2006

(65) Prior Publication Data
US 2008/0132502 A1 Jun. 5, 2008

(30) Foreign Application Priority Data
Nov. 9, 2004 (SE) .................................... 0402735

(51) Int. Cl.
*C07D 207/00* (2006.01)
(52) U.S. Cl. ...................................................... 548/544
(58) Field of Classification Search .................. 546/544
See application file for complete search history.

(56) References Cited

U.S. PATENT DOCUMENTS 4,649,146 A * 3/1987 Takaya et al. ................ 514/307
4,735,957 A * 4/1988 Takaya et al. ................ 514/342

FOREIGN PATENT DOCUMENTS

| EP | 0 117 082 | 8/1984 |
| WO | WO 0049015 | 8/2000 |
| WO | WO 03/072557 | 9/2003 |
| WO | WO 2004/078754 | 9/2004 |
| WO | WO 2004/096797 | 11/2004 |

* cited by examiner

*Primary Examiner*—Janet L. Andres
*Assistant Examiner*—Raymond Covington

(57) ABSTRACT

The invention provides thiazole derivatives of formula (I), or pharmaceutically acceptable salts thereof in which Ring A, $R^1$, $R^2$ and $R^3$ are as defined in the specification; a processes for their preparation; pharmaceutical compositions containing them; and their use in therapy, for example in the treatment of disease mediated by a PI3K enzyme and/or a mTOR kinase.

16 Claims, No Drawings

5-HETEROARYL THIAZOLES AND THEIR USE AS PI3K INHIBITORS

The present invention relates to thiazole derivatives, processes for their preparation, pharmaceutical compositions containing them and their use in therapy, for example in the treatment of disease mediated by a PI3K enzyme and/or a mTOR kinase.

Phosphatidylinositol (PI) 3-kinases (PI3Ks) are ubiquitous lipid kinases that function both as signal transducers downstream of cell-surface receptors and in constitutive intracellular membrane and protein trafficking pathways. All PI3Ks are dual-specificity enzymes with a lipid kinase activity that phosphorylates phosphoinositides at the 3-hydroxy position, and a less well characterised protein kinase activity. The lipid products of PI3K-catalysed reactions comprising phosphatidylinositol 3,4,5-trisphosphate [PI(3,4,5)P$_3$], phosphatidylinositol 3,4-bisphosphate [PI(3,4)P$_2$] and phosphatidylinositol 3-monophosphate [PI(3)P] constitute second messengers in a variety of signal transduction pathways, including those essential to cell proliferation, adhesion, survival, cytoskeletal rearrangement and vesicle trafficking. PI(3)P is constitutively present in all cells and its levels do not change dramatically following agonist stimulation. Conversely, PI(3,4)P$_2$ and PI(3,4,5)P$_3$ are nominally absent in most cells but they rapidly accumulate on agonist stimulation.

The downstream effects of PI3K-produced 3-phosphoinositide second messengers are mediated by target molecules containing 3-phosphoinositide binding domains such as the pleckstrin homology (PH) domain and the recently identified FYVE and phox domains. Well-characterised protein targets for PI3K include PDK1 and protein kinase B (PKB). In addition, tyrosine kinases like Btk and Itk are dependent on PI3K activity.

The PI3K family of lipid kinases can be classified into three groups according to their physiological substrate specificity (Vanhaesebroeck et al., *Trends in Biol. Sci.*, 1997, 22, 267). Class III PI3K enzymes phosphorylate PI alone. In contrast, Class II PI3K enzymes phosphorylate both PI and PI 4-phosphate [PI(4)P]. Class I PI3K enzymes phosphorylate PI, PI(4)P and PI 4,5-bisphosphate [PI(4,5)P$_2$], although only PI(4,5)P$_2$ is believed to be the physiological cellular substrate. Phosphorylation of PI(4,5)P$_2$ produces the lipid second messenger PI(3,4,5)P$_3$. More distantly related members of the lipid kinase superfamily are Class IV kinases such as mTOR and DNA-dependent kinase that phosphorylate serine/threonine residues within protein substrates. The most studied and understood of these lipid kinases are the Class I PI3K enzymes.

Class I PI3Ks are heterodimers consisting of a p110 catalytic subunit and a regulatory subunit. The family is further divided into Class Ia and Class Ib enzymes on the basis of regulatory partners and the mechanism of regulation. Class Ia enzymes consist of three distinct catalytic subunits (p110α, p110β and p110δ) that dimerise with five distinct regulatory subunits (p85α, p55α, p50α, p85β and p55γ), with all catalytic subunits being able to interact with all regulatory subunits to form a variety of heterodimers. Class Ia PI3Ks are generally activated in response to growth factor-stimulation of receptor tyrosine kinases via interaction of their regulatory subunit SH2 domains with specific phospho-tyrosine residues of activated receptor or adaptor proteins such as IRS-1. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor systems (GPCRs) and its expression appears to be limited to leukocytes and cardiomyocytes.

There is now considerable evidence indicating that Class Ia PI3K enzymes contribute to tumourigenesis in a wide variety of human cancers, either directly or indirectly (Vivanco and Sawyers, *Nature Reviews Cancer*, 2002, 2, 489-501). For example, the p110α subunit is amplified in some tumours such as those of the ovary (Shayesteh et al., *Nature Genetics*, 1999, 21, 99-102) and cervix (Ma et al., *Oncogene*, 2000, 19, 2739-2744). More recently, activating mutations within the catalytic site of the p110α catalytic subunit have been associated with various other tumours such as those of the colorectal region and of the breast and lung (Samuels et al, *Science*, 2004, 304, 554). Tumour-related mutations in the p85α regulatory subunit have also been identified in cancers such as those of the ovary and colon (Philp et al., *Cancer Research*, 2001, 61, 7426-7429). In addition to direct effects, it is believed that activation of Class Ia PI3Ks contributes to tumourigenic events that occur upstream in signalling pathways, for example by way of ligand-dependent or ligand-independent activation of receptor tyrosine kinases, GPCR systems or integrins (Vara et al, *Cancer Treatment Reviews*, 2004, 30, 193-204). Examples of such upstream signalling pathways include over-expression of the receptor tyrosine kinase erbB2 in a variety of tumours leading to activation of PI3K-mediated pathways (Harari et al., *Oncogene*, 2000, 19, 6102-6114) and over-expression of the ras oncogene (Kauffman-Zeh et al., *Nature*, 1997, 385, 544-548). In addition, Class Ia PI3Ks may contribute indirectly to tumourigenesis caused by various downstream signalling events. For example, loss of the effect of the PTEN tumour-suppressor phosphatase that catalyses conversion of PI(3,4,5)P3 back to PI(4,5)P2 is associated with a very broad range of tumours via deregulation of PI3K-mediated production of PI(3,4,5)P3 (Simpson and Parsons, *Exp. Cell Res.*, 2001, 264, 29-41). Furthermore, augmentation of the effects of other PI3K-mediated signalling events is believed to contribute to a variety of cancers, for example by activation of Akt (Nicholson and Anderson, *Cellular Signalling*, 2002, 14, 381-395).

In addition to a role in mediating proliferative and survival signalling in tumour cells, there is evidence that Class Ia PI3K enzymes contribute to tumourigenesis in tumour-associated stromal cells. For example, PI3K signalling is known to play an important role in mediating angiogenic events in endothelial cells in response to pro-angiogenic factors such as VEGF (Abid et al, *Arterioscler. Thromb. Vasc. Biol.*, 2004, 24, 294-300). As Class I PI3K enzymes are also involved in motility and migration (Sawyer, *Expert Opinion Investig. Drugs*, 2004, 13, 1-19), PI3K enzyme inhibitors should provide therapeutic benefit via inhibition of tumour cell invasion and metastasis. In addition, Class I PI3K enzymes play an important role in the regulation of immune cells contributing to pro-tumourigenic effects of inflammatory cells (Coussens and Werb, *Nature*, 2002, 420, 860-867).

These findings suggest that pharmacological inhibitors of Class I PI3K enzymes will be of therapeutic value for the treatment of various diseases including different forms of the disease of cancer comprising solid tumours such as carcinomas and sarcomas and the leukaemias and lymphoid malignancies. In particular, inhibitors of Class I PI3K enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

PI3Kγ, the Class Ib PI3K, is activated by GPCRs, as was finally demonstrated in mice lacking the enzyme. Thus, neutrophils and macrophages derived from PI3Kγ-deficient animals failed to produce PI(3,4,5)P$_3$ in response to stimulation with various chemotactic substances (such as IL-8, C5a, fMLP and MIP-1a, whereas signalling through protein tyrosine kinase-coupled receptors to Class Ia PI3Ks was intact (Hirsch et al., *Science,* 2000, 287(5455), 1049-1053; Li et al., *Science,* 2002, 287(5455), 1046-1049; Sasaki et al., *Science* 2002, 287(5455), 1040-1046). Furthermore, PI(3,4,5)P$_3$-mediated phosphorylation of PKB was not initiated by these GPCR ligands in PI3Kγ-null cells. Taken together, the results demonstrated that, at least in resting haematopoietic cells, PI3Kγ is the sole PI3K isoform that is activated by GPCRs in vivo. When murine bone marrow-derived neutrophils and peritoneal macrophages from wild-type and PI3Kγ$^{-/-}$ mice were tested in vitro, a reduced, but not completely abrogated, performance in chemotaxis and adherence assays was observed. However, this translated into a drastic impairment of IL-8 driven neutrophil infiltration into tissues (Hirsch et al., Science, 2000, 287(5455), 1049-1053). Recent data suggest that PI3Kγ is involved in the path finding process rather than in the generation of mechanical force for motility, as random migration was not impaired in cells that lacked PI3Kγ (Hannigan et al., *Proc. Nat. Acad. of Sciences of U.S.A.,* 2002, 99(6), 3603-8). Data linking PI3Kγ to respiratory disease pathology came with the demonstration that PI3Kγ has a central role in regulating endotoxin-induced lung infiltration and activation of neutrophils leading to acute lung injury (Yum et al., *J. Immunology,* 2001, 167(11), 6601-8). The fact that although PI3Kγ is highly expressed in leucocytes, its loss seems not to interfere with haematopoiesis, and the fact that PI3Kγ-null mice are viable and fertile further implicates this PI3K isoform as a potential drug target. Work with knockout mice also established that PI3Kγ is an essential amplifier of mast cell activation (Laffargue et al., *Immunity,* 2002, 16(3), 441-451).

Thus, in addition to tumourigenesis, there is evidence that Class I PI3K enzymes play a role in other diseases (Wymann et al., *Trends in Pharmacological Science,* 2003, 24, 366-376). Both Class Ia PI3K enzymes and the single Class Ib enzyme have important roles in cells of the immune system (Koyasu, *Nature Immunology,* 2003, 4, 313-319) and thus they are therapeutic targets for inflammatory and allergic indications. Recent reports demonstrate that mice deficient in PI3Kγ and PI3Kδ are viable, but have attenuated inflammatory and allergic responses (Ali et al., *Nature,* 2004, 431 (7011), 1007-11). Inhibition of PI3K is also useful to treat cardiovascular disease via anti-inflammatory effects or directly by affecting cardiac myocytes (Prasad et al., *Trends in Cardiovascular Medicine,* 2003, 13, 206-212). Thus, inhibitors of Class I PI3K enzymes are expected to be of value in the prevention and treatment of a wide variety of diseases in addition to cancer.

Several compounds that inhibit PI3Ks have been identified, including wortmannin and the quercetin derivative LY294002. These compounds are reasonably specific inhibitors of PI3Ks over other kinases but they lack potency and display little selectivity within the PI3K families.

Accordingly, it would be desirable to provide further effective PI3K inhibitors for use in the treatment of cancer, inflammatory or obstructive airways diseases, immune or cardiovascular diseases.

International Patent Applications WO 03/072557 and WO 2004/078754 describe 5-phenylthiazole derivatives as PI3K inhibitors. Copending International Patent Application WO 2005/021519 also describes 5-phenylthiazole derivatives as PI3K inhibitors.

Copending International Patent Application WO 2004/096797 describes certain 5-heteroaryl substituted thiazole derivatives as PI3K inhibitors. The heteroaryl group at the 5-position on the thiazole ring is a pyridin-4-yl group or a pyrimidin-4-yl group.

Copending International Patent Application WO 2005/068444 describes certain 2-acylamino-5-thiazol-4-ylthiazole derivatives as PI3K inhibitors.

European Patent Application No. 0117082 describes certain thiazole derivatives, including certain 2-aminothiazole derivatives, that are stated to possess cardiotonic activity. The disclosed compounds include certain 5-heteroaryl substituted thiazole derivatives where the heteroaryl group is a pyridin-2-yl group, a pyridin-3-yl group or a pyridin-4-yl group such as:—
2-amino-4-methyl-5-pyridin-2-ylthiazole,
2-methylamino-4-methyl-5-pyridin-2-ylthiazole,
2-amino-4-methyl-5-(4-methylpyridin-2-yl)thiazole,
2-amino-4-methyl-5-(6-methylpyridin-2-yl)thiazole,
2-amino-4-methyl-5-pyridin-3-ylthiazole,
2-methylamino-4-methyl-5-pyridin-3-ylthiazole,
2-anilino-4-methyl-5-pyridin-3-ylthiazole,
2-amino-4-methyl-5-pyridin-4-ylthiazole,
2-methylamino-4-methyl-5-pyridin-4-ylthiazole and
2-anilino-4-methyl-5-pyridin-4-ylthiazole, International Patent Application WO 00/49015 describes certain 2-pyridyl compounds as inhibitors of nitric oxide production. The disclosed compounds include a series of 2-guanidino-4-methyl-5-pyridin-2-ylthiazole derivatives. There is also the disclosure of the compounds:—
2-amino-4-methyl-5-(4-methylpyridin-2-yl)thiazole and
2-pyridin-2-ylamino-4-methyl-5-(4-methylpyridin-2-yl) thiazole.

International Patent Application WO 99/65884 describes certain 2-aminothiazole derivatives as tyrosine kinase inhibitors. There is no specific disclosure of any 4-alkyl-2-aminothiazole compounds.

International Patent Application WO 01/17995 describes certain 2-aminopyridine compounds as inhibitors of tyrosine kinases, in particular of VEGF receptor tyrosine kinase. The disclosed compounds include a series of 5-aryl-2-(2-pyridylamino)thiazole derivatives. There is no specific disclosure of any 4-alkyl-5-aryl-2-(2-pyridylamino)thiazole compounds.

International Patent Applications WO 01/72745, WO 03/029248 and WO 2004/043953 describe 2-aminopyrimidinyl derivatives substituted at the 4-position with, for example, a 5-thiazolyl group. The compounds are stated to be inhibitors of cyclin-dependent kinases that are useful in the treatment of proliferative disorders such as cancer.

European Patent Application No. 1 256 578 and U.S. Pat. No. 6,720,427 describe certain 2-aminothiazole derivatives as inhibitors of the serine/threonine kinase cdk5. There is no specific disclosure of any 4-alkyl-2-aminothiazole compounds.

International Patent Application WO 2004/001059 describes certain 2-anilino- and 2-heteroarylamino-substituted thiazole derivatives as tyrosine kinase inhibitors. There is no specific disclosure of any 4-alkyl-2-anilino- or 4-alkyl-2-heteroarylamino-substituted thiazole compounds.

Copending International Patent Application WO 2005/047273 describes certain 5-aryl- and 5-heteroaryl-substituted 2-anilinothiazole derivatives as FLT-3 tyrosine kinase inhibitors. There is no specific disclosure of any 4-alkyl-5-heteroaryl-2-anilinothiazole compounds.

Copending International Patent Application WO 2005/068458 describes certain 4-aryl- and 4-heteroaryl-substituted 2-alkylaminothiazole derivatives and 2-acylaminothiazole derivatives as Src tyrosine kinase inhibitors. There is no specific disclosure of any 4-alkyl-5-heteroarylthiazole compounds.

It has now been found that another series of thiazole derivatives has inhibitory activity against the PI3K enzymes and against the Class IV kinase mTOR.

It is now well understood that deregulation of oncogenes and tumour-suppressor genes contributes to the formation of malignant tumours, for example by way of increased cell proliferation or increased cell survival. It is also now known that signalling pathways mediated by the PI3K/mTOR families have a central role in a number of cell processes including proliferation and survival, and deregulation of these pathways is a causative factor in a wide spectrum of human cancers and other diseases.

The mammalian target of the macrolide antibiotic Rapamycin (sirolimus) is the enzyme mTOR that belongs to the phosphatidylinositol (PI) kinase-related kinase (PIKK) family of protein kinases, which includes ATM, ATR, DNA-PK and hSMG-1. mTOR, like other PIKK family members, does not possess detectable lipid kinase activity, but instead functions as a Ser/Thr kinase. Much of the knowledge of mTOR signalling is based upon the use of Rapamycin. Rapamycin first binds to the 12 kDa immunophilin FK506-binding protein (FKBP12) and this complex inhibits mTOR signalling (Tee and Blenis, *Seminars in Cell and Developmental Biolog,* 2005, 16, 29-37). mTOR protein consists of a catalytic kinase domain, an FKBP12-Rapamycin binding (FRB) domain, a putative repressor domain near the C-terminus and up to 20 tandemly-repeated HEAT motifs at the N-terminus, as well as FRAP-ATM-TRRAP (FAT) and FAT C-terminus domain (Huang and Houghton, *Current Opinion in Pharmacology,* 2003, 3, 371-377).

mTOR kinase is a key regulator of cell growth and has been shown to regulate a wide range of cellular functions including translation, transcription, mRNA turnover, protein stability, actin cytoskeleton reorganisation and autophagy (Jacinto and Hall, *Nature Reviews Molecular and Cell Biology,* 2005, 4, 117-126). mTOR kinase, integrates signals from growth factors (such as insulin or insulin-like growth factor) and nutrients (such as amino acids and glucose) to regulate cell growth. mTOR kinase is activated by growth factors through the PI3K-Akt pathway. The most well characterised function of mTOR kinase in mammalian cells is regulation of translation through two pathways, namely activation of ribosomal S6K1 to enhance translation of mRNAs that bear a 5'-terminal oligopyrimidine tract (TOP) and suppression of 4E-BP1 to allow CAP-dependent mRNA translation.

Generally, investigators have explored the physiological and pathological roles of mTOR using inhibition with Rapamycin and related Rapamycin analogues based on their specificity for mTOR as an intracellular target. However, recent data suggests that Rapamycin displays variable inhibitory actions on mTOR signalling functions and suggest that direct inhibition of the mTOR kinase domain may display substantially broader anti-cancer activities than that achieved by Rapamycin (Edinger et al., *Cancer Research,* 2003, 63, 8451-8460). For this reason, potent and selective inhibitors of mTOR kinase activity would be useful to allow a more complete understanding of mTOR kinase function and to provide useful therapeutic agents.

There is now considerable evidence indicating that the pathways upstream of mTOR are frequently activated in cancer (Vivanco and Sawyers, *Nature Reviews Cancer,* 2002, 2, 489-501; Bjornsti and Houghton, *Nature Reviews Cancer,* 2004, 4, 335-348; Inoki et al., *Nature Genetics,* 2005, 37, 19-24). For example, components of the PI3K pathway that are mutated in different human tumours include activating mutations of growth factor receptors and the amplification and/or overexpression of PI3K and Akt.

In addition there is evidence that endothelial cell proliferation may also be dependent upon mTOR signalling. Endothelial cell proliferation is stimulated by vascular endothelial cell growth factor (VEGF) activation of the PI3K-Akt-mTOR signalling pathway (Dancey, *Expert Opinion on Investigational Drugs,* 2005, 14, 313-328). Moreover, mTOR kinase signalling is believed to partially control VEGF synthesis through effects on the expression of hypoxia-inducible factor-1α (HIF-1α) (Hudson et al, *Molecular and Cellular Biology,* 2002, 22, 7004-7014). Therefore, tumour angiogenesis may depend on mTOR kinase signalling in two ways, through hypoxia-induced synthesis of VEGF by tumour and stromal cells, and through VEGF stimulation of endothelial proliferation and survival through PI3K-Akt-mTOR signalling.

These findings suggest that pharmacological inhibitors of mTOR kinase should be of therapeutic value for treatment of the various forms of the disease of cancer comprising solid tumours such as carcinomas and sarcomas and the leukaemias and lymphoid malignancies.

In addition to tumourigenesis, there is evidence that mTOR kinase plays a role in an array of hamartoma syndromes. Recent studies have shown that the tumour suppressor proteins such as TSC1, TSC2, PTEN and LKB1 tightly control mTOR kinase signalling. Loss of these tumour suppressor proteins leads to a range of hamartoma conditions as a result of elevated mTOR kinase signalling (Tee and Blenis, *Seminars in Cell and Developmental Biology,* 2005, 16, 29-37). Syndromes with an established molecular link to dysregulation of mTOR kinase include Peutz-Jeghers syndrome (PJS), Cowden disease, Bannayan-Riley-Ruvalcaba syndrome (BRRS), Proteus syndrome, Lhermitte-Duclos disease and TSC (Inoki et al., *Nature Genetics,* 2005, 37, 19-24). Patients with these syndromes characteristically develop benign hamartomatous tumours in multiple organs.

Recent studies have revealed a role for mTOR kinase in other diseases (Easton & Houghton, *Expert Opinion on Therapeutic Targets,* 2004, 8, 551-564). Rapamycin has been demonstrated to be a potent immunosuppressant by inhibiting antigen-induced proliferation of T cells, B cells and antibody production (Sehgal, *Transplantation Proceedings,* 2003, 35, 7S-14S) and thus mTOR kinase inhibitors may also be useful immunosuppressives. Inhibition of the kinase activity of mTOR may also be useful in the prevention of restenosis, that is the control of undesired proliferation of normal cells in the vasculature in response to the introduction of stents in the treatment of vasculature disease (Morice et al., *New England Journal of Medicine,* 2002, 346, 1773-1780). Furthermore, the Rapamycin analogue, everolimus, can reduce the severity and incidence of cardiac allograft vasculopathy (Eisen et al., *New England Journal of Medicine,* 2003, 349, 847-858). Elevated mTOR kinase activity has been associated with cardiac hypertrophy, which is of clinical importance as a major risk factor for heart failure and is a consequence of increased cellular size of cardiomyocytes (Tee & Blenis, *Seminars in Cell and Developmental Biology,* 2005, 16, 29-37). Thus mTOR kinase inhibitors are expected to be of value in the prevention and treatment of a wide variety of diseases in addition to cancer.

It has been found that thiazole derivatives of the present invention have inhibitory activity against the mTOR PI kinase-related kinase family of enzymes as well as against PI3K enzymes.

In accordance with the present invention, there is provided a thiazole derivative of formula (I), or a pharmaceutically acceptable salt thereof,

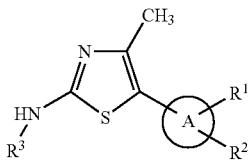

(I)

wherein,

Ring A is a 6-membered heteroaromatic ring containing at least one nitrogen atom with the proviso that Ring A is not pyridin-4-yl and is not pyrimidin-4-yl;

$R^1$ is hydrogen, halo, $C_1$-$C_6$ alkyl or $C_1$-$C_6$ alkoxy;

$R^2$ is hydrogen, halo, $C_1$-$C_6$ alkyl, $C_1$-$C_6$ alkoxy, $NR^4R^5$, or —$R^6$-$R^7$;

with the proviso that at least one of $R^1$ and $R^2$ is not hydrogen;

$R^4$ is H, $C_1$-$C_6$ alkyl, $C_3$-$C_7$ cycloalkyl or $C_2$-$C_6$ alkyl substituted with one or more groups selected from hydroxy or benzyloxy, or $R^4$ is —$CH_2$—$R^8$;

$R^5$ is H, or $C_1$-$C_6$ alkyl;

$R^6$ is —N($R^9$)—$SO_2$—, —$SO_2$—N($R^{10}$)—, —N($R^{12}$)—C(=O)—N($R^{13}$)—, —N($R^9$)—$SO_2$—N($R^{10}$)— or —$SO_2$—;

$R^7$ is $R^{14}$ or —$C_1$-$C_6$ alkyl or $C_2$-$C_8$ alkoxyalkyl;

or $R^7$ is $C_1$-$C_6$ alkyl substituted with one or more groups selected from halogen, or hydroxy, or $R^7$ is $C_1$-$C_6$ alkyl substituted with $R^{14}$, or $R^7$ is $C_1$-$C_6$ alkyl substituted with $NR^{15}R^{16}$, or $R^7$ is —$R^{17}$—X—$R^{18}$;

$R^8$ is $C_3$-$C_7$ cycloalkyl, phenyl or a 5 or 6-membered heteroaromatic ring containing 1 to 3 heteroatoms independently selected from O, S or N, each of which may be optionally substituted with one or more groups selected from halo, cyano, $C_1$-$C_6$ alkyl, $C_1$-$C_6$ alkoxy, hydroxy, $C_1$-$C_6$ alkylsulfonyl, $C_2$-$C_6$ alkanoylamino, $C_1$-$C_6$ alkoxycarbonyl, phenyl, pyridyl or $C_2$-$C_6$ alkoxy substituted with one or more groups selected from hydroxy, amino, $C_1$-$C_6$ alkylamino or di($C_1$-$C_6$ alkyl)amino;

$R^{14}$ is $C_3$-$C_7$ cycloalkyl, phenyl, benzyl, phenoxy, a 5 or 6-membered heteroaromatic ring containing 1 to 3 heteroatoms independently selected from O, S or N, a 9 or 10-membered bicyclic heteroaromatic ring containing 1 to 4 heteroatoms independently selected from O, S or N, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —C(=O)—$NH_2$, —$NO_2$, halogen, —$OCF_3$, —C(=O)—$CF_3$, $C_1$-$C_6$ alkylcarbonyl, $C_2$-$C_6$ alkanoylamino, —O—$CH_2$—$CH_2$—CN, $C_1$-$C_6$ alkylsulfonyl, or —$NR^{19}R^{20}$;

$R^{15}$ is independently H, $C_3$-$C_6$ cycloalkyl or $C_1$-$C_6$ alkyl optionally substituted with $C_3$-$C_6$ cycloalkyl;

or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;

$R^{16}$ is independently H, or $C_1$-$C_6$ alkyl; or $R^{15}$ and $R^{16}$ together with the nitrogen to which they are attached form a 5 or 6-membered saturated ring optionally containing a further heteroatom selected from O or N, and optionally being substituted with $C_1$-$C_6$ alkyl or $C_1$-$C_6$ alkylcarbonyl;

$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, cyano, $C_1$-$C_6$ alkyl, $C_1$-$C_6$ alkoxy or $C_1$-$C_6$ alkylthio;

X is a bond, —$CH_2$—NH—C(=O)—, or O;

$R^{19}$ and $R^{20}$ are independently H or $C_1$-$C_6$ alkyl, or $R^{19}$ and $R^{20}$ together with the nitrogen to which they are attached form a 5 or 6-membered saturated ring optionally containing a further heteroatom independently selected from O or N, and optionally being substituted with $C_1$-$C_6$ alkyl or $C_1$-$C_6$ alkylcarbonyl;

and $R^3$ is phenyl or benzyl, each being optionally substituted with one or more groups selected from halo, $C_1$-$C_6$ alkyl, or $C_1$-$C_6$ alkoxy;

or $R^3$ is a 5 or 6-membered heteroaromatic ring containing nitrogen and optionally one or more further heteroatoms independently selected from O, S or N, said ring being optionally substituted with one or more of the following groups: (i) halogen or $C_1$-$C_6$ alkyl optionally substituted by carboxy, $C_1$-$C_6$ alkoxycarbonyl, —$NR^{21}R^{22}$ or a 5 or 6-membered heterocyclic ring containing at least one heteroatom independently selected from O, S or N, (ii) $C_1$-$C_6$ alkoxy, —$NR^{21}R^{22}$, $C_3$-$C_8$ cycloalkyl optionally substituted with carboxy, or (iii) a 5 or 6-membered heterocyclic ring containing at least one heteroatom independently selected from O, S or N optionally substituted with $C_1$-$C_6$ alkyl;

or $R^3$ is —(C=O)—(NH)$_p$—$R^{23}$, —(C=O)—(NH)$_q$—$CH_2$—$R^{24}$, —(C=O)—(NH)$_q$—$CH_2$—$CH_2$—$R^{24}$ or —(C=O)—$NH_2$;

p and q are each independently 0 or 1;

or $R^3$ is hydrogen or $C_1$-$C_6$ alkyl;

$R^{21}$ is hydrogen or $C_1$-$C_6$ alkyl;

$R^{22}$ is $C_1$-$C_6$ alkyl optionally substituted with hydroxy, $C_1$-$C_6$ alkoxy, di($C_1$-$C_6$ alkyl)amino or a 5 or 6-membered heterocyclic ring containing at least one heteroatom selected from O, S or N and optionally substituted with $C_1$-$C_6$ alkyl;

$R^{23}$ is $C_1$-$C_6$ alkyl or $C_3$-$C_7$ cycloalkyl each being optionally substituted with one or more groups selected from halogen, hydroxy, amino, $C_1$-$C_6$ alkylamino, di($C_1$-$C_6$ alkyl)amino, $C_1$-$C_6$ alkoxycarbonyl, nitrile, carboxy, $C_1$-$C_6$ alkoxy optionally substituted with hydroxy, $C_3$-$C_8$ cycloalkyl optionally substituted with hydroxy, or phenyl optionally substituted with hydroxy or $C_1$-$C_6$ alkyl, or $R^{23}$ is phenyl, benzyl, or a 5 or 6-membered heteroaromatic ring containing at least one heteroatom independently selected from O, S or N, each being optionally substituted with one or more groups selected from halogen, hydroxy, $C_1$-$C_6$ alkyl, $C_1$-$C_6$ alkoxy, or by a 5 or 6-membered saturated heterocyclic ring containing at least one heteroatom independently selected from O, S or N, or $R^{23}$ is a 5 or 6-membered heteroaromatic ring containing at least one heteroatom independently selected from O, S or N, which ring is substituted with phenyl and is optionally substituted with one or more groups selected from halogen, hydroxy, $C_1$-$C_6$ alkyl or $C_1$-$C_6$ alkoxy;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$, $R^{10}$, $R^{11}$, $R^{12}$, and $R^{13}$ are H, $C_1$-$C_6$ alkyl, or $C_1$-$C_6$ alkylcarbonyl;

with the proviso that the compounds:—
2-amino-4-methyl-5-pyridin-2-ylthiazole,
2-methylamino-4-methyl-5-pyridin-2-ylthiazole,
2-amino-4-methyl-5-(4-methylpyridin-2-yl)thiazole,
2-amino-4-methyl-5-(6-methylpyridin-2-yl)thiazole,
2-amino-4-methyl-5-pyridin-3-ylthiazole,
2-methylamino-4-methyl-5-pyridin-3-ylthiazole,
2-anilino-4-methyl-5-pyridin-3-ylthiazole and
2-pyridin-2-ylamino-4-methyl-5-(4-methylpyridin-2-yl) thiazole are excluded.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention. Solvates and mixtures thereof also form an aspect of the present invention. For example, a suitable solvate of a compound of the formula (I) is, for example, a hydrate such as a hemi-hydrate, a mono-hydrate, a di-hydrate or a tri-hydrate or an alternative quantity thereof.

In the context of the present specification, unless otherwise indicated, an alkyl group or an alkyl moiety in a substituent group may be saturated or unsaturated and may be linear, branched or cyclic. Examples of alkyl groups/moieties containing up to 6 carbon atoms include methyl, ethyl, vinyl, ethynyl, n-propyl, isopropyl, allyl, 2-propynyl, cyclopropyl, n-butyl, isobutyl, tert-butyl, cyclobutyl, n-pentyl, cyclopentyl, cyclopentenyl, n-hexyl, cyclohexyl and cyclohexenyl. An analogous convention applies to other generic terms, for example $C_1$-$C_6$ alkoxy includes methoxy, ethoxy, propoxy, isopropoxy, allyloxy, 2-propynyloxy, cyclopropyloxy and cyclobutyloxy.

A haloalkyl substituent may contain one or more, e.g. one, two, three, four or five halogen atoms. A hydroxyalkyl substituent may contain one or more hydroxy groups, e.g. one, two or three hydroxy groups, but preferably contains one hydroxy group.

Ring A is a 6-membered heteroaromatic ring containing at least one nitrogen atom (preferably containing 1 to 3 nitrogen atoms, more preferably containing 1 or 2 nitrogen atoms). In an embodiment of the invention, Ring A is pyridyl or pyrimidinyl (with the proviso that Ring A is not pyridin-4-yl or pyrimidin-4-yl). Conveniently, Ring A is pyridin-2-yl, pyridin-3-yl, pyrimidin-5-yl, pyrazin-2-yl, pyridazin-3-yl or pyridazin-4-yl. More conveniently, Ring A is pyridin-3-yl or pyridazin-4-yl.

$R^1$ is hydrogen, halo (e.g. fluorine, bromine, or chlorine), $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), or $C_1$-$C_6$, preferably $C_1$-$C_4$, alkoxy (e.g. methoxy, ethoxy, n-propoxy, n-butoxy, n-pentyloxy or n-hexyloxy). In an embodiment of the invention, $R^1$ is halogen (preferably chlorine) or $C_1$-$C_6$ alkoxy. Conveniently, $R^1$ is halogen (preferably chlorine).

$R^2$ is hydrogen, halo (e.g. fluorine, bromine, or chlorine), $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy, n-butoxy, n-pentyloxy or n-hexyloxy), or —$R^6$-$R^7$. In an embodiment of the invention, $R^2$ is halogen (preferably chlorine), or —$R^6$-$R^7$. Conveniently, $R^2$ is —$R^6$-$R^7$.

At least one of $R^1$ and $R^2$ is not hydrogen i.e. $R^1$ and $R^2$ are not simultaneously hydrogen. In a further embodiment, $R^1$ is halo, $C_1$-$C_6$ alkyl or $C_1$-$C_6$ alkoxy and $R^2$ is halo, $C_1$-$C_6$ alkoxy, $NR^4R^5$, or —$R^6$-$R^7$. Preferably $R^1$ is substituted on a carbon atom of Ring A. Preferably $R^2$ is substituted on a carbon atom of Ring A.

Conveniently, $R^2$ is $NR^4R^5$. $R^4$ is H, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_3$-$C_7$, preferably $C_5$-$C_6$, cycloalkyl or —$CH_2$—$R^8$. $R^5$ is H, or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl). In an embodiment of the invention, $R^4$ is H or $CH_2$—$R^8$, and $R^5$ is H.

When $R^2$ is —$R^6$-$R^7$, $R^6$ is —N($R^9$)—$SO_2$—, —$SO_2$—N($R^{11}$)—, —N($R^{11}$)—C(=O)—, —N($R^{12}$)—C(=O)—N($R^{13}$)— or —$SO_2$—. In an embodiment of the invention $R^6$ is —N($R^9$)—$SO_2$—.

When $R^2$ is —$R^6$-$R^7$, $R^7$ is $R^{14}$ or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_2$-$C_8$ alkoxyalkyl (where $C_2$-$C_8$ refers to the total number of carbons in the alkoxyalkyl group, e.g. methoxy-methyl or methoxy-ethyl), $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) substituted with one or more (e.g. one, two, three or four, preferably one or two) groups selected from halogen (e.g. fluorine, chlorine or bromine) or hydroxy, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) substituted with $R^{14}$, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) substituted with $NR^{15}R^{16}$, or —$R^{17}$—X—$R^{18}$.

In an embodiment of the invention, when $R^2$ is —$R^6$-$R^7$, $R^7$ is $R^{14}$, —$CH_2$—$R^{14}$, —$CH_2$—$CH_2$—$R^{14}$, $C_1$-$C_6$ haloalkyl (preferably $C_1$-$C_6$ chloroalkyl), $C_1$-$C_6$ hydroxyalkyl, $C_1$-$C_6$ alkyl, —$R^{17}$—X—$R^{18}$, or $C_1$-$C_6$ alkyl substituted with $NR^{15}R^{16}$.

When $R^2$ is NH—$CH_2$—$R^8$, $R^8$ is a group selected from phenyl or a 5 or 6-membered heteroaromatic ring containing 1 to 3 heteroatoms (e.g. 1, 2 or 3 heteroatoms) independently selected from O, S or N, each group of which may be optionally substituted with one or more (e.g. one, two or three) groups independently selected from halogen (e.g. fluorine, chlorine, bromine or iodine), $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) $C_1$-$C_6$, preferably $C_1$-$C_4$, alkoxy (e.g. methoxy, ethoxy, n-propoxy, n-butoxy, n-pentyloxy or n-hexyloxy) or hydroxy.

Examples of preferred 5 or 6-membered heteroaromatic rings for $R^8$ include thienyl, furanyl, pyrrolyl, imidazolyl, pyridyl, pyrazinyl, pyrimidinyl, pyridazinyl, triazinyl, oxazolyl, thiazolyl, isoxazolyl, pyrazolyl, oxadiazolyl, thiadiazolyl, and triazolyl, which rings may be optionally substituted as described hereinabove.

When $R^2$ is —$R^6$-$R^7$ and $R^7$ is $R^{14}$ or $C_1$-$C_6$ alkyl substituted with $R^4$, $R^{14}$ is a group selected from phenyl, phenoxy, benzyl, a 5 or 6-membered heteroaromatic ring containing 1 to 3 (e.g. 1, 2 or 3) heteroatoms independently selected from O, S or N, a 9 or 10-membered bicyclic heteroaromatic ring containing 1 to 4 (e.g. 1, 2, 3 or 4) heteroatoms independently selected from O, S or N, or a phenyl-fused 5 or 6-membered cycloheteroalkyl ring containing 1 or 2 heteroatoms independently selected from O, S or N, each group of which may be optionally substituted with one or more (e.g. one or two) groups independently selected from $C_1$-$C_6$, preferably $C_1$-$C_4$, allyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy, n-butoxy, n-pentyloxy or n-hexyloxy), cyano, —$NO_2$, halogen (e.g. fluorine, chlorine, bromine or iodine), —O—$CH_2$—$CH_2$—CN, $C_1$-$C_6$ alkylsulfonyl (e.g. methyl, ethyl, n-propyl, n-butyl, n-pentyl or n-hexyl-sulfonyl), or —$NR^{19}R^{20}$.

Examples of preferred 5 or 6-membered heteroaromatic rings for $R^{14}$ include thienyl, furanyl, pyrrolyl, imidazolyl, pyridyl, pyrazinyl, pyrimidinyl, pyridazinyl, triazinyl, oxazolyl, thiazolyl, isoxazolyl, isothiazolyl, pyrazolyl, oxadiazolyl, thiadiazolyl and triazolyl, which rings may be optionally substituted as described hereinabove.

Examples of preferred 9 or 10-membered bicyclic heteroaromatic rings for $R^{14}$ include benzoxadiazolyl, benzothiadiazolyl, or indolyl, which rings may be optionally substituted as described hereinabove.

Examples of preferred phenyl-fused-5 or 6-membered cycloheteroalkyl rings for $R^{14}$ include 1,3-benzodioxolyl, 1,3-benzodioxanyl, tetrahydroquinolinyl or tetrahydroisoquinolinyl which ring may be optionally substituted as described hereinabove and which ring may be optionally substituted with one or two oxo or thioxo groups.

In an embodiment of the invention, $R^{14}$ is a group selected from phenyl, benzyl, a 5 or 6-membered heteroaromatic ring containing 1 or 2 heteroatoms independently selected from O, S or N, one or both of said heteroatoms being nitrogen, or a 9-membered bicyclic heteroaromatic ring containing 1 to 4 heteroatoms independently selected from O, S or N, each of said groups being optionally and independently substituted with one or more groups independently selected from $C_1$-$C_6$ alkyl, $C_1$-$C_6$ alkoxy, cyano, —$NO_2$, halogen, —O—$CH_2$—$CH_2$—CN, $C_1$-$C_6$ alkylsulfonyl, or —$NR^{19}R^{20}$.

When $R^2$ is —$R^6$-$R^7$ and $R^7$ is $C_1$-$C_6$ alkyl substituted with $NR^5R^6$, $R^{15}$ is independently H, $C_3$-$C_6$, preferably $C_5$-$C_6$, cycloalkyl (e.g. cyclopentyl or cyclohexyl), or $C_1$-$C_6$, preferably $C_1$-$C_4$, alkyl (e.g. methyl, ethyl, n-propyl, n-butyl, n-pentyl or n-hexyl) optionally substituted with $C_3$-$C_6$, preferably $C_5$-$C_6$, cycloalkyl. $R^{15}$ may also be a group selected from phenyl, a 5 or 6-membered heteroaromatic ring containing 1 to 4 (e.g. one, two, three or four) heteroatoms independently selected from O, S and N, or benzyl, each group of which may be optionally substituted with one or more groups selected from halo (e.g. fluorine, chlorine, bromine or iodine), $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy, n-butoxy, n-pentyloxy or n-hexyloxy) or hydroxy.

$R^{16}$ is independently H, or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl).

$R^{15}$ and $R^{16}$ may together with the nitrogen to which they are attached form a 6-membered saturated ring optionally containing a further heteroatom selected from O or N, and optionally being substituted with $C_1$-$C_6$ alkyl, preferably $C_1$-$C_4$, alkyl (e.g. methyl, ethyl, n-propyl, isopropyl, n-butyl, isobutyl, tert-butyl, n-pentyl or n-hexyl). In an embodiment of the invention, both $R^{15}$ and $R^{16}$ are $C_1$-$C_6$ alkyl, or $R^{15}$ and $R^{16}$ together with the nitrogen to which they are attached form a 6-membered saturated ring containing a further heteroatom selected from O or N (e.g. morpholine).

When $R^2$ is —$R^6$-$R^7$ and $R^7$ is —$R^{17}$—X—$R^{18}$, $R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen (e.g. fluorine, chlorine, bromine or iodine), $C_1$-$C_6$ alkyl, preferably $C_1$-$C_4$, alkyl (e.g. methyl, ethyl, n-propyl, isopropyl, n-butyl, isobutyl, tert-butyl, n-pentyl or n-hexyl) or $C_1$-$C_6$, preferably $C_1$-$C_4$, alkoxy (e.g. methoxy, ethoxy, n-propoxy, n-butoxy, n-pentyloxy or n-hexyloxy). Where $R^{17}$ and/or $R^{18}$ is a 5 or 6-membered heteroaromatic ring, examples are pyridyl, thienyl, furanyl, pyrrolyl, imidazolyl, pyridyl, pyrazinyl, pyrimidinyl, pyridazinyl, triazinyl, oxazolyl, thiazolyl, isoxazolyl, pyrazolyl, oxadiazolyl, thiadiazolyl, and triazolyl, which rings may be optionally substituted as described hereinabove.

It should be noted that when referring to the example rings for $R^{17}$ and/or $R^{18}$ above, a reference to e.g. pyridyl in the context of $R^{17}$ clearly refers to the corresponding di-radical (pyridylene). This principle applies to all other examples of $R^{17}$ and/or $R^{18}$.

In an embodiment of the invention, at least one of $R^{17}$ and $R^{18}$ is phenyl, pyridyl or thienyl, which rings may be optionally substituted as described hereinabove. In a further embodiment, at least one of $R^{17}$ and $R^{18}$ is phenyl or pyridyl, which rings may be optionally substituted as described hereinabove. In a further embodiment $R^{17}$ and $R^{18}$ are selected from the group consisting of phenyl, pyridyl or thienyl, which rings may be optionally substituted as described hereinabove. In a further embodiment $R^{17}$ and $R^{18}$ are selected from the group consisting of phenyl, or pyridyl, which rings may be optionally substituted as described hereinabove.

When $R^2$ is —$R^6$-$R^7$ and $R^7$ is —$R^{17}$—X—$R^{18}$, X is a bond, —$CH_2$—NH—C(=O)—, or O. In an embodiment of the invention, X is a bond, or —$CH_2$—NH—C(=O)—.

When $R^2$ is —$R^6$-$R^7$ and $R^7$ is $R^{14}$ or $C_1$-$C_6$ alkyl substituted with $R^{14}$ and $R^{14}$ is substituted with one or more —$NR^{19}R^{20}$ groups, $R^{19}$ and $R^{20}$ are independently H or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), or $R^{19}$ and $R^{20}$ together with the nitrogen to which they are attached form a 6-membered saturated ring optionally containing a further heteroatom selected from O or N, and optionally being substituted with $C_1$-$C_6$ alkyl (e.g. methyl, ethyl, n-propyl, isopropyl, n-butyl, isobutyl, tert-butyl, n-pentyl or n-hexyl). When $R^{19}$ and $R^{20}$ together with the nitrogen to which they are attached form a 6-membered saturated ring optionally containing a further heteroatom selected from O or N, an example of such a ring is morpholine.

$R^3$ is phenyl or benzyl, each being optionally substituted with one or more groups selected from halo (e.g. fluorine, chlorine, bromine or iodine), $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), or $C_1$-$C_6$ alkoxy, preferably $C_1$-$C_4$, alkoxy (e.g. methoxy, ethoxy, n-propoxy, n-butoxy, n-pentyloxy or n-hexyloxy), or $R^3$ is a 5 or 6-membered heteroaromatic ring containing nitrogen and optionally one or more (e.g. one, two or three) further heteroatoms selected from the group consisting of O, S or N, said ring being optionally substituted with one or more of the following groups: (i) halogen (e.g. fluorine, chlorine, bromine or iodine) or $C_1$-$C_6$, preferably $C_1$-$C_4$, alkyl optionally substituted with carboxy, $C_1$-$C_6$ alkoxycarbonyl (e.g. methoxy-, ethoxy-, propoxy-, butoxy-, pentyloxy-, or hexyloxy-carbonyl, —$NR^{21}R^{22}$ or a 5 or 6-membered heterocyclic ring containing at least one (e.g. one, two, three or four) heteroatom selected from the group consisting of O, S or N, (ii) $C_1$-$C_6$ alkoxy, preferably $C_1$-$C_4$ alkoxy (e.g. methoxy, ethoxy, n-propoxy, n-butoxy, n-pentyloxy or n-hexyloxy), —$NR^{21}R^{22}$, $C_3$-$C_8$ cycloalkyl optionally substituted with carboxy, or (iii) a 5 or 6-membered heterocyclic ring containing at least one (e.g. one, two, three or four) heteroatom independently selected from O, S or N and optionally substituted with $C_1$-$C_6$ alkyl, preferably $C_1$-$C_4$ alkyl (e.g. methyl, ethyl, n-propyl, isopropyl, n-butyl, isobutyl, tert-butyl, n-pentyl or n-hexyl).

$R^3$ may also be —(C=O)—(NH)$_p$—$R^{23}$ or —(C=O)—(NH)$_q$—$CH_2$—$R^{24}$, or —(C=O)—$NH_2$ where p and q are independently 0 or 1.

When $R^3$ is —(C=O)—(NH)$_p$—$R^{23}$, $R^{21}$ is $C_1$-$C_6$ alkyl optionally substituted with one or more groups selected from halogen (e.g. fluorine, chlorine, bromine or iodine), hydroxy, amino, $C_1$-$C_6$ alkylamino (e.g. methylamino, ethylamino, propylamino, butylamino, pentylamino, hexylamino), di($C_1$-$C_6$ alkyl)amino, $C_1$-$C_6$ alkoxycarbonyl (e.g. methoxycarbonyl, ethoxycarbonyl, propoxycarbonyl), nitrile, carboxy, $C_1$-$C_6$ alkoxy (e.g. methoxy, ethoxy, n-propoxy, n-butoxy, n-pentyloxy or n-hexyloxy) optionally substituted with hydroxy, $C_3$-$C_8$ cycloalkyl optionally substituted with hydroxy, or phenyl optionally substituted with hydroxy or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl).

Alternatively, $R^{23}$ is phenyl, benzyl, or a 5 or 6-membered heteroaromatic ring containing at least one (e.g. one, two, three or four) heteroatom selected from the group consisting of O, S or N, each being optionally substituted with one or more (e.g. one or two) groups selected from halogen (e.g. fluorine, chlorine, bromine or iodine), hydroxy, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy, n-butoxy, n-pentyloxy or n-hexyloxy), or by a 5 or 6-membered saturated heterocyclic ring containing at least one heteroatom selected from the group consisting of O, S or N. Alternatively, $R^{23}$ is a 5 or 6-membered heteroaromatic ring containing at least one heteroatom (e.g. one, two, three or four heteroatoms) selected from the group consisting of O, S or N, which ring is substituted with optionally substituted phenyl.

When $R^{23}$ is a 5 or 6-membered heteroaromatic ring containing at least one heteroatom selected from the group consisting of O, S or N, examples of such rings include furanyl, pyridyl or triazole.

In an embodiment of the invention, $R^3$ is —(C=O)—(NH)$_p$—$R^{23}$, where p is equal to zero and $R^{23}$ is $C_1$-$C_6$ alkyl (e.g. methyl), $C_2$-$C_6$ alkoxy-alkyl (where $C_2$-$C_6$ refers to the total number of carbon atoms in the alkoxy-alkyl), or $R^{23}$ is a group selected from phenyl, benzyl, or a 5 or 6-membered heteroaromatic ring containing at least one heteroatom independently selected from O, S or N, each group being optionally substituted with one or more groups selected from halogen, hydroxy, $C_1$-$C_6$ alkyl, $C_1$-$C_6$ alkoxy, or with a 5 or 6-membered saturated heterocyclic ring containing at least one heteroatom selected from the group consisting of O, S or N, or $R^{23}$ is a 5 or 6-membered heteroaromatic ring containing at least one heteroatom selected from the group consisting of O, S or N, which ring is substituted with optionally substituted phenyl.

When $R^3$ is —(C=O)—(NH)$_q$—$CH_2$—$R^{24}$, $R^{24}$ is benzyloxy or a 5 to 7-membered (preferably 5 or 6-membered) heteroaromatic ring containing 1 to 3 heteroatoms (e.g. one, two or three heteroatoms) independently selected from O, S and N, either of which being optionally substituted with one or more groups selected from halogen (e.g. fluorine, chlorine, bromine or iodine), $C_1$-$C_6$ alkyl, preferably $C_1$-$C_4$ alkyl (e.g. methyl, ethyl, n-propyl, isopropyl, n-butyl, isobutyl, tert-butyl, n-pentyl or n-hexyl) or $C_1$-$C_6$ alkoxy (e.g. methoxy, ethoxy, n-propoxy, n-butoxy, n-pentyloxy or n-hexyloxy). When $R^{24}$ is a 5 to 7-membered heteroaromatic ring containing at least one heteroatom selected from the group consisting of O, S or N, examples of such rings include furanyl, and pyridyl.

When $R^3$ is a 5 or 6-membered heteroaromatic ring substituted with one or more —$NR^{21}R^{22}$ groups, $R^{21}$ is hydrogen or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl). $R^{22}$ is $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) optionally substituted with hydroxy, $C_1$-$C_6$ alkoxy, di($C_1$-$C_6$ alkyl)amino or a 5 or 6-membered heterocyclic ring containing at least one heteroatom (e.g. one, two, three or four heteroatoms) selected from the group consisting of O, S or N and optionally substituted with $C_1$-$C_6$ alkyl, preferably $C_1$-$C_4$ alkyl.

When $R^6$ is —N($R^9$)—$SO_2$—, —$SO_2$—N($R^{10}$)—, —N($R^{11}$)—C(=O)—, —N($R^{12}$)—C(=O)N($R^{13}$)— or —N($R^9$)—$SO_2$—N($R^{10}$)—, $R^9$, $R^{10}$, $R^{11}$, $R^{12}$ and $R^{13}$ are H, $C_1$-$C_6$ allyl, preferably $C_1$-$C_4$ alkyl (e.g. methyl, ethyl, n-propyl, isopropyl, n-butyl, isobutyl, tert-butyl, n-pentyl or n-hexyl) or $C_1$-$C_6$, preferably $C_1$-$C_4$, alkyl carbonyl (e.g. acetyl, ethylcarbonyl, propylcarbonyl, butylcarbonyl, pentylcarbonyl or hexylcarbonyl). In one embodiment, $R^9$, $R^{10}$, $R^{11}$, $R^{12}$ and $R^{13}$ are each H. In a further embodiment, $R^9$, $R^{10}$, $R^{11}$, $R^{12}$ and $R^{13}$ are acetyl. In a further embodiment, $R^9$ is $C_1$-$C_6$ alkyl, preferably methyl.

A suitable pharmaceutically acceptable salt of a compound of formula (I) is, for example, where the compound is sufficiently acidic, a base salt such as an alkali metal salt, for example sodium or potassium, an alkaline earth metal salt, for example calcium or magnesium, an organic amine salt, for example a salt with triethylamine, morpholine, N-methylpiperidine, N-ethylpiperidine, procaine, dibenzylamine, N,N-dibenzylethylamine or an amino acid, for example lysine. Where the compound is sufficiently basic, a suitable salt is, for example, an acid addition salt such as a hydrochloride, hydrobromide, phosphate, acetate, fumarate, maleate, tartrate, citrate, oxalate, methanesulfonate or p-toluenesulfonate salt. There may be more than one cation or anion depending on the number of charged functions and the valency of the cations or anions. Other pharmaceutically acceptable salts, as well as pro-drugs such as pharmaceutically acceptable esters and pharmaceutically acceptable amides may be prepared using conventional methods.

For example, the compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of formula (I) and in vivo cleavable amide derivatives that may be formed at a carboxy group or an amino group in a compound of formula (I).

Accordingly, the present invention includes those compounds of formula (I) as defined hereinbefore when made available by organic synthesis and when made available within the human or animal body by way of cleavage of a pro-drug thereof. Accordingly, the present invention includes those compounds of formula (I) that are produced by organic synthetic means and also such compounds that are produced in the human or animal body by way of metabolism of a precursor compound, that is a compound of formula (I) may be a synthetically-produced compound or a metabolically-produced compound.

A suitable pharmaceutically acceptable pro-drug of a compound of formula (I) is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of formula (I) that possesses a carboxy group is, for example, an in vivo cleavable ester thereof. An in vivo cleavable ester of a compound of formula (I) containing a carboxy group is, for example, a pharmaceutically acceptable ester which is cleaved in the human or animal body to produce the parent acid. Suitable pharmaceutically acceptable esters for carboxy include $C_{1-6}$ alkyl esters such as methyl, ethyl and tert-butyl, (1-6C)alkoxymethyl esters such as methoxymethyl esters, $C_{1-6}$ alkanoyloxymethyl esters such as pivaloyloxymethyl esters, 3-phthalidyl esters, $C_{3-8}$ cycloalkylcarbonyloxy-$C_{1-6}$ alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$ alkoxycarbonyloxy-$C_{1-6}$ alkyl esters such as methoxycarbonyloxymethyl and 1-methoxycarbonyloxyethyl esters.

A suitable pharmaceutically acceptable pro-drug of a compound of formula (I) that possesses a hydroxy group is, for example, an in vivo cleavable ester or ether thereof. An in vivo cleavable ester or ether of a compound of formula (I) containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{2-10}$ alkanoyl groups such as acetyl, benzoyl, phenylacetyl and substituted benzoyl and phenylacetyl groups, $C_{1-10}$ alkoxycarbonyl groups such as ethoxycarbonyl, N,N-[di($C_{1-4}$)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-6}$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of formula (I) that possesses a carboxy group is, for example, an in vivo cleavable amide thereof, for example an amide formed with an amine such as ammonia, a $C_{1-4}$ alkylamine such as methylamine, a di($C_{1-4}$)alkylamine such as dimethylamine, N-ethyl-N-methylamine or diethylamine, a $C_{1-4}$ alkoxy-$C_{2-4}$ alkylamine such as 2-methoxyethylamine, a phenyl-$C_{1-4}$ alkylamine such as benzylamine and amino acids such as glycine or an ester thereof.

A suitable pharmaceutically acceptable pro-drug of a compound of formula (I) that possesses an amino group is, for example, an in vivo cleavable amide derivative thereof. Suitable pharmaceutically acceptable amides from an amino group include, for example an amide formed with $C_{2-10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$ alkyl)piperazin-1-ylmethyl.

The in vivo effects of a compound of formula (I) may be exerted in part by one or more metabolites that are formed within the human or animal body after administration of a compound of formula (I). As stated hereinbefore, the in vivo effects of a compound of formula (I) may also be exerted by way of metabolism of a precursor compound (a pro-drug).

According to a further embodiment of the invention, there is provided a compound of formula (I), or a pharmaceutically acceptable salt thereof,

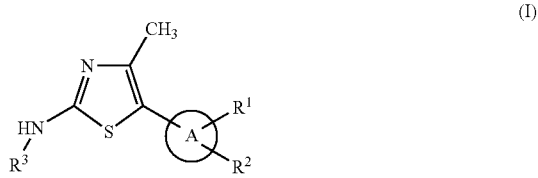

(I)

wherein,

Ring A is a 6-membered heteroaromatic ring containing at least one nitrogen atom with the proviso that Ring A is not pyridin-4-yl and is not pyrimidin-4-yl;

$R^1$ is hydrogen, halo, $C_1$-$C_6$ alkyl or $C_1$-$C_6$ alkoxy;

$R^2$ is hydrogen, halo, $C_1$-$C_6$ alkyl, $C_1$-$C_6$ alkoxy, $NR^4R^5$, or —$R^6$-$R^7$;

with the proviso that at least one of $R^1$ and $R^2$ is not hydrogen;

$R^4$ is H, $C_1$-$C_6$ alkyl, $C_3$-$C_7$ cycloalkyl or —$CH_2$—$R^8$, and $R^5$ is H, or $C_1$-$C_6$ alkyl;

$R^6$ is —N($R^9$)—$SO_2$—, —$SO_2$—N($R^{10}$)—, —N($R^{11}$)—C(=O)—, —N($R^{12}$)—C(=O)—N($R^{13}$)—, or —$SO_2$;

$R^7$ is $R^{14}$ or $C_1$-$C_6$ alkyl or $C_2$-$C_8$ alkoxyalkyl;

or $R^7$ is $C_1$-$C_6$ alkyl substituted with one or more groups selected from halogen, or hydroxy, or $R^7$ is $C_1$-$C_6$ alkyl substituted with $R^{14}$ or phenoxy, or $R^7$ is $C_1$-$C_6$ alkyl substituted with $NR^{15}R^{16}$, or $R^7$ is —$R^{17}$—X—$R^{18}$;

$R^8$ is phenyl or a 5 or 6-membered heteroaromatic ring containing 1 to 3 heteroatoms independently selected from O, S or N, each of which may be optionally substituted with one or more groups selected from halo, $C_1$-$C_6$ alkyl, $C_1$-$C_6$ alkoxy, or hydroxy;

$R^{14}$ is phenyl, benzyl, a 5 or 6-membered heteroaromatic ring containing 1 to 3 heteroatoms independently selected from O, S or N, a 9 or 10-membered bicyclic heteroaromatic ring containing 1 to 4 heteroatoms independently selected from O, S or N, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —$NO_2$, halogen, —O—$CH_2$—$CH_2$—CN, $C_1$-$C_6$ alkylsulfonyl, or —$NR^{19}R^{20}$;

$R^{15}$ is independently H, $C_3$-$C_6$ cycloalkyl or $C_1$-$C_6$ alkyl optionally substituted with $C_3$-$C_6$ cycloalkyl;

or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;

$R^{16}$ is independently H, or $C_1$-$C_6$ alkyl; or $R^{15}$ and $R^{16}$ together with the nitrogen to which they are attached form a 6-membered saturated ring optionally containing a further heteroatom selected from O or N, and optionally being substituted with $C_1$-$C_6$ alkyl;

$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, $C_1$-$C_6$ alkyl, or $C_1$-$C_6$ alkoxy;

X is a bond, —$CH_2$—NH—C(=O)—, or O;

$R^{19}$ and $R^{20}$ are independently H or $C_1$-$C_6$ alkyl, or $R^{19}$ and $R^{20}$ together with the nitrogen to which they are attached form a 6-membered saturated ring optionally containing a further heteroatom independently selected from O or N, and optionally being substituted with $C_1$-$C_6$ alkyl;

and $R^3$ is phenyl or benzyl, each being optionally substituted with one or more groups selected from halo, $C_1$-$C_6$ alkyl, or $C_1$-$C_6$ alkoxy;

or $R^3$ is a 5 or 6-membered heteroaromatic ring containing nitrogen and optionally one or more further heteroatoms independently selected from O, S or N, said ring being optionally substituted with one or more of the following groups: (i) halogen or $C_1$-$C_6$ alkyl optionally substituted by carboxy, $C_1$-$C_6$ alkoxycarbonyl, —$NR^{21}R^{22}$ or a 5 or 6-membered heterocyclic ring containing at least one heteroatom independently selected from O, S or N, (ii) $C_1$-$C_6$ alkoxy, —$NR^{21}R^{22}$, $C_3$-$C_8$ cycloalkyl optionally substituted with carboxy, or (iii) a 5 or 6-membered heterocyclic ring containing at least one heteroatom independently selected from O, S or N optionally substituted with $C_1$-$C_6$ alkyl;

or $R^3$ is —(C=O)—(NH)$_p$—$R^{23}$, —(C=O)—(NH)$_q$—$CH_2$—$R^{24}$ or —(C=O)—$NH_2$;

p and q are each independently 0 or 1;

$R^{21}$ is hydrogen or $C_1$-$C_6$ alkyl;

$R^{22}$ is $C_1$-$C_6$ alkyl optionally substituted with hydroxy, $C_1$-$C_6$ alkoxy, di($C_1$-$C_6$ allyl)amino or a 5 or 6-membered heterocyclic ring containing at least one heteroatom selected from O, S or N and optionally substituted with $C_1$-$C_6$ alkyl;

$R^{23}$ is $C_1$-$C_6$ alkyl optionally substituted with one or more groups selected from halogen, hydroxy, amino, $C_1$-$C_6$ alkylamino, di($C_1$-$C_6$ alkyl)amino, $C_1$-$C_6$ alkoxycarbonyl, nitrile, carboxy, $C_1$-$C_6$ alkoxy optionally substituted with hydroxy, $C_3$-$C_8$ cycloalkyl optionally substituted with hydroxy, or phenyl optionally substituted with hydroxy or $C_1$-$C_6$ alkyl, or $R^{23}$ is phenyl, benzyl, or a 5 or 6-membered heteroaromatic ring containing at least one heteroatom independently selected from O, S or N, each being optionally substituted with one or more groups selected from halogen, hydroxy, $C_1$-$C_6$ alkyl, $C_1$-$C_6$ alkoxy, or by a 5 or 6-membered saturated heterocyclic ring containing at least one heteroatom independently selected from O, S or N, or $R^{23}$ is a 5 or 6-membered heteroaromatic ring containing at least one heteroatom independently selected from O, S or N, which ring is substituted with phenyl;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$, $R^{10}$, $R^{11}$, $R^{12}$, and $R^{13}$ are H, $C_1$-$C_6$ alkyl, or $C_1$-$C_6$ alkylcarbonyl.

According to a further embodiment of the invention, there is provided a thiazole derivative of formula (I), or a pharmaceutically acceptable salt thereof,

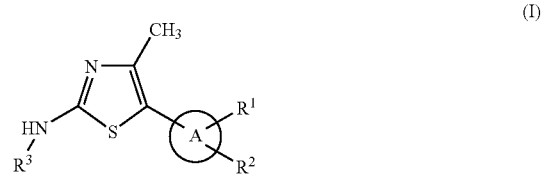

(I)

wherein,

Ring A is a 6-membered heteroaromatic ring containing at least one nitrogen atom;

$R^1$ is hydrogen, halo, $C_1$-$C_6$ alkyl or $C_1$-$C_6$ alkoxy;

$R^2$ is —$R^6$-$R^7$;

$R^6$ is —N($R^9$)—$SO_2$—;

$R^7$ is $R^{14}$ or $C_1$-$C_6$ alkyl or $C_2$-$C_8$ alkoxyalkyl;

or $R^7$ is $C_1$-$C_6$ alkyl substituted with one or more groups selected from halogen, or hydroxy, or $R^7$ is $C_1$-$C_6$ alkyl substituted with $R^{14}$ or phenoxy, or $R^7$ is $C_1$-$C_6$ alkyl substituted with $NR^{15}R^{16}$, or $R^7$ is —$R^{17}$—X—$R^{18}$;

$R^{14}$ is phenyl, benzyl, a 5 or 6-membered heteroaromatic ring containing 1 to 3 heteroatoms independently selected from O, S or N, a 9 or 10-membered bicyclic heteroaromatic ring containing 1 to 4 heteroatoms independently selected from O, S or N, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —$NO_2$, halogen, —O—$CH_2$—$CH_2$—CN, $C_1$-$C_6$ alkylsulfonyl, or —$NR^{19}R^{20}$;

$R^{15}$ is independently H, $C_3$-$C_6$ cycloalkyl or $C_1$-$C_6$ alkyl optionally substituted with $C_3$-$C_6$ cycloalkyl;

or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;

$R^{16}$ is independently H, or $C_1$-$C_6$ alkyl; or $R^{15}$ and $R^{16}$ together with the nitrogen to which they are attached form a 6-membered saturated ring optionally containing a further heteroatom selected from O or N, and optionally being substituted with $C_1$-$C_6$ alkyl;

$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, $C_1$-$C_6$ alkyl, or $C_1$-$C_6$ alkoxy;

X is a bond, —$CH_2$—NH—C(=O)—, or O;

$R^{19}$ and $R^{20}$ are independently H or $C_1$-$C_6$ alkyl, or $R^{19}$ and $R^{20}$ together with the nitrogen to which they are attached form a 6-membered saturated ring optionally containing a further heteroatom independently selected from O or N, and optionally being substituted with $C_1$-$C_6$ alkyl;

and $R^3$ is phenyl or benzyl, each being optionally substituted with one or more groups selected from halo, $C_1$-$C_6$ alkyl, or $C_1$-$C_6$ alkoxy;

or $R^3$ is a 5 or 6-membered heteroaromatic ring containing nitrogen and optionally one or more further heteroatoms independently selected from O, S or N, said ring being optionally substituted with one or more of the following groups: (i) halogen or $C_1$-$C_6$ alkyl optionally substituted by carboxy, $C_1$-$C_6$ alkoxycarbonyl, —$NR^{21}R^{22}$ or a 5 or 6-membered heterocyclic ring containing at least one heteroatom independently selected from O, S or N, (ii) $C_1$-$C_6$ alkoxy, —$NR^{21}R^{22}$, $C_3$-$C_8$ cycloalkyl optionally substituted with carboxy, or (iii) a 5 or 6-membered heterocyclic ring containing at least one heteroatom independently selected from O, S or N optionally substituted with $C_1$-$C_6$ alkyl;

or $R^3$ is —(C=O)—(NH)$_p$—$R^{23}$, —(C=O)—(NH)$_q$—$CH_2$—$R^{24}$ or —(C=O)—$NH_2$;

p and q are each independently 0 or 1;

$R^{21}$ is hydrogen or $C_1$-$C_6$ alkyl;

$R^{22}$ is $C_1$-$C_6$ alkyl optionally substituted with hydroxy, $C_1$-$C_6$ alkoxy, di($C_1$-$C_6$ alkyl)amino or a 5 or 6-membered heterocyclic ring containing at least one heteroatom selected from O, S or N and optionally substituted with $C_1$-$C_6$ alkyl;

$R^{23}$ is $C_1$-$C_6$ alkyl optionally substituted with one or more groups selected from halogen, hydroxy, amino, $C_1$-$C_6$ alkylamino, di($C_1$-$C_6$ alkyl)amino, $C_1$-$C_6$ alkoxycarbonyl, nitrile, carboxy, $C_1$-$C_6$ alkoxy optionally substituted with hydroxy, $C_3$-$C_8$ cycloalkyl optionally substituted with hydroxy, or phenyl optionally substituted with hydroxy or $C_1$-$C_6$ alkyl, or $R^{23}$ is phenyl, benzyl, or a 5 or 6-membered heteroaromatic ring containing at least one heteroatom independently selected from O, S or N, each being optionally substituted with one or more groups selected from halogen, hydroxy, $C_1$-$C_6$ alkyl, $C_1$-$C_6$ alkoxy, or by a 5 or 6-membered saturated heterocyclic ring containing at least one heteroatom independently selected from O, S or N, or $R^3$ is a 5 or 6-membered heteroaromatic ring containing at least one heteroatom independently selected from O, S or N, which ring is substituted with phenyl;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$ is H, $C_1$-$C_6$ alkyl, or $C_1$-$C_6$ alkylcarbonyl.

According to a further embodiment of the invention, there is provided a compound of formula (I) wherein:—

Ring A is a 6-membered heteroaromatic ring containing at least one nitrogen atom;

$R^1$ is hydrogen, halo, $C_1$-$C_6$ alkyl or $C_1$-$C_6$ alkoxy;

—$R^2$ is —$R^6$-$R^7$;

$R^6$ is —N($R^9$)—$SO_2$—, —$SO_2$—N($R^{10}$)—, —N($R^{11}$)—C(=O)—, —N($R^{12}$)—C(=O)—N($R^{13}$)—, or —$SO_2$—;

$R^7$ is $R^{14}$ or $C_1$-$C_6$ alkyl or $C_2$-$C_8$ alkoxyalkyl;

or $R^7$ is $C_1$-$C_6$ alkyl substituted with one or more groups selected from halogen, or hydroxy, or $R^7$ is $C_1$-$C_6$ alkyl substituted with either $R^{14}$ or phenoxy, or $R^7$ is $C_1$-$C_6$ alkyl substituted with $NR^{15}R^{16}$, or $R^7$ is —$R^{17}$—X—$R^{18}$;

$R^{14}$ is phenyl, benzyl, a 5 or 6-membered heteroaromatic ring containing 1 to 3 heteroatoms independently selected from O, S or N, a 9 or 10-membered bicyclic heteroaromatic ring containing 1 to 4 heteroatoms independently selected from O, S or N, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —$NO_2$, halogen, —O—$CH_2$—$CH_2$—CN, $C_1$-$C_6$ alkylsulfonyl, or —$NR^{19}R^{20}$;

$R^{15}$ is independently H, $C_3$-$C_6$ cycloalkyl or $C_1$-$C_6$ alkyl optionally substituted with $C_3$-$C_6$ cycloalkyl;

or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;

$R^{16}$ is independently H, or $C_1$-$C_6$ alkyl; or $R^{15}$ and $R^{16}$ together with the nitrogen to which they are attached form a 6-membered saturated ring optionally containing a further heteroatom selected from O or N, and optionally being substituted with $C_1$-$C_6$ alkyl;

$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, $C_1$-$C_6$ alkyl, or $C_1$-$C_6$ alkoxy;

X is a bond, —$CH_2$—NH—C(=O)—, or O;

$R^{19}$ and $R^{20}$ are independently H or $C_1$-$C_6$ alkyl, or $R^{19}$ and $R^{20}$ together with the nitrogen to which they are attached form a 6-membered saturated ring optionally containing a further heteroatom selected from O or N, and optionally being substituted with $C_1$-$C_6$ alkyl;

$R^3$ is phenyl or benzyl, each being optionally substituted with one or more groups selected from halo, $C_1$-$C_6$ alkyl, or $C_1$-$C_6$ alkoxy;

or $R^3$ is a 5 or 6-membered heteroaromatic ring containing nitrogen and optionally one or more further heteroatoms selected from the group consisting of O, S or N, said ring being optionally substituted with one or more of the following groups: (i) halogen or $C_1$-$C_6$ alkyl optionally substituted with carboxy, $C_1$-$C_6$ alkoxycarbonyl, —$NR^{21}R^{22}$ or a 5 or 6-membered heterocyclic ring containing at least one heteroatom selected from the group consisting of O, S or N, (ii) $C_1$-$C_6$ alkoxy, —$NR^{21}R^{22}$, $C_3$-$C_8$ cycloalkyl optionally substituted with carboxy, or (iii) a 5 or 6-membered heterocyclic ring containing at least one heteroatom selected from the group consisting of O, S or N optionally substituted with $C_1$-$C_6$ alkyl;

or $R^3$ is —(C=O)—$(NH)_p$—$R^{23}$, —(C=O)—$(NH)_q$—$CH_2$—$R^{24}$ or —(C=O)—$NH_2$;

p and q are independently 0 or 1;

$R^{21}$ is hydrogen or $C_1$-$C_6$ alkyl;

$R^{22}$ is $C_1$-$C_6$ alkyl optionally substituted with hydroxy, $C_1$-$C_6$ alkoxy, di($C_1$-$C_6$ alkyl)amino or a 5 or 6-membered heterocyclic ring containing at least one heteroatom selected from the group consisting of O, S or N and optionally substituted with $C_1$-$C_6$ alkyl;

$R^{23}$ is $C_1$-$C_6$ alkyl optionally substituted with one or more groups selected from halogen, hydroxy, amino, $C_1$-$C_6$ alkylamino, di($C_1$-$C_6$-alkyl)amino, $C_1$-$C_6$ alkoxycarbonyl, nitrile, carboxy, $C_1$-$C_6$ alkoxy optionally substituted with hydroxy, $C_3$-$C_8$ cycloalkyl optionally substituted with hydroxy, or phenyl optionally substituted with hydroxy or $C_1$-$C_6$ alkyl, or $R^{23}$ is phenyl, benzyl, or a 5 or 6-membered heteroaromatic ring containing at least one heteroatom selected from the group consisting of O, S or N, each being optionally substituted with one or more groups selected from halogen, hydroxy, $C_1$-$C_6$ alkyl, $C_1$-$C_6$ alkoxy, or with a 5 or 6-membered saturated heterocyclic ring containing at least one heteroatom selected from the group consisting of O, S or N;

or $R^{23}$ is a 5 or 6-membered heteroaromatic ring containing at least one heteroatom selected from the group consisting of O, S or N, which ring is substituted with phenyl;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$, $R^{10}$, $R^{11}$, $R^{12}$, and $R^{13}$ are H, $C_1$-$C_6$ alkyl, or $C_1$-$C_6$ alkylcarbonyl.

According to a further embodiment of the invention, there is provided a compound of formula (I) wherein:—

Ring A is a 6-membered heteroaromatic ring containing at least one nitrogen atom;

$R^1$ is halo;

$R^2$ is —$R^6$-$R^7$;

$R^6$ is —$N(R^9)$—$SO_2$—, —$SO_2$—$N(R^{10})$—, —$N(R^{11})$—C(=O)—, —$N(R^{12})$—C(=O)—$N(R^{13})$—, or —$SO_2$—;

$R^7$ is $R^{14}$ or $C_1$-$C_6$ alkyl or $C_2$-$C_8$ alkoxyalkyl;

or $R^7$ is $C_1$-$C_6$ alkyl substituted with one or more groups selected from halogen, or hydroxy, or $R^7$ is $C_1$-$C_4$ alkyl substituted with either $R^{14}$ or phenoxy, or $R^7$ is $C_1$-$C_6$ alkyl substituted with $NR^{15}R^{16}$, or $R^7$ is —$R^{17}$—X—$R^{18}$;

$R^{14}$ is phenyl, benzyl, a 5 or 6-membered heteroaromatic ring containing 1 to 3 heteroatoms independently selected from O, S or N, a 9 or 10-membered bicyclic heteroaromatic ring containing 1 to 4 heteroatoms independently selected from O, S or N, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —$NO_2$, halogen, —O—$CH_2$—$CH_2$—CN, $C_1$-$C_6$ alkylsulfonyl, or —$NR^{19}R^{20}$;

$R^{15}$ is independently H, $C_3$-$C_6$ cycloalkyl or $C_1$-$C_6$ alkyl optionally substituted with $C_3$-$C_6$ cycloalkyl;

or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;

$R^{16}$ is independently H, or $C_1$-$C_6$ alkyl; or $R^{15}$ and $R^{16}$ together with the nitrogen to which they are attached form a 6-membered saturated ring optionally containing a further heteroatom selected from O or N, and optionally being substituted with $C_1$-$C_6$ alkyl;

$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, $C_1$-$C_6$ alkyl, or $C_1$-$C_6$ alkoxy;

X is a bond, —$CH_2$—NH—C(=O)—, or O;

$R^{19}$ and $R^{20}$ are independently H or $C_1$-$C_6$ alkyl, or $R^{19}$ and $R^{20}$ together with the nitrogen to which they are attached form a 6-membered saturated ring optionally containing a further heteroatom selected from O or N, and optionally being substituted with $C_1$-$C_6$ alkyl;

$R^3$ is —(C=O)—$NH_2$, —(C=O)—$R^{23}$, —(C=O)—$(NH)_q$—$CH_2$—$R^{24}$;

q is 0 or 1;

$R^{23}$ is $C_1$-$C_6$ alkyl or $C_2$-$C_6$ alkoxy-alkyl, or $R^{23}$ is phenyl, benzyl, or a 5 or 6-membered heteroaromatic ring containing at least one heteroatom selected from the group consisting of O, S or N, each being optionally substituted with one or more groups selected from halogen, hydroxy, $C_1$-$C_6$ alkyl, $C_1$-$C_6$ alkoxy, or with a 5 or 6-membered saturated heterocyclic ring containing at least one heteroatom selected from the group consisting of O, S or N;

or $R^{23}$ is a 5 or 6-membered heteroaromatic ring containing at least one heteroatom selected from the group consisting of O, S or N, which ring is substituted with phenyl;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$, $R^{10}$, $R^{11}$, $R^{12}$, and $R^{13}$ are H, $C_1$-$C_6$ alkyl, or $C_1$-$C_6$ alkylcarbonyl.

When Ring A is pyridine, the pyridyl nitrogen is preferably disposed in a meta position relative to the bond connecting Ring A to the thiazole ring shown in formula (I). A particularly preferable orientation of the pyridyl group is shown in formula (Ia) as follows

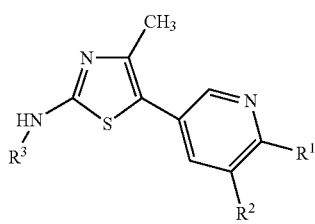

(Ia)

wherein $R^1$, $R^2$, and $R^3$ are as hereinbefore defined.

According to a further embodiment of the invention, there is provided a thiazole derivative of formula (Ia), or a pharmaceutically acceptable salt thereof,

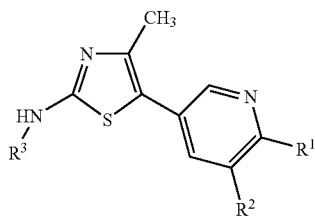

(Ia)

wherein, $R^1$ is hydrogen, halo, $C_1$-$C_6$ alkyl or $C_1$-$C_6$ alkoxy;

$R^2$ is hydrogen, halo, $C_1$-$C_6$ alkyl, $C_1$-$C_6$ alkoxy, $NR^4R^5$, or —$R^6$-$R^7$;

with the proviso that at least one of $R^1$ and $R^2$ is not hydrogen;

$R^4$ is H, $C_1$-$C_6$ alkyl, $C_3$-$C_7$ cycloalkyl or —$CH_2$—$R^8$, and $R^5$ is H, or $C_1$-$C_6$alkyl;

$R^6$ is —N($R^9$)—$SO_2$—, —$SO_2$—N($R^{10}$)—, —N($R^{11}$)—C(=O)—, —N($R^{12}$)—C($R^{13}$)—N($R^{13}$)—, or —$SO_2$—;

$R^7$ is $R^{14}$ or $C_1$-$C_6$ alkyl or $C_2$-$C_8$ alkoxyalkyl;

or $R^7$ is $C_1$-$C_6$ alkyl substituted with one or more groups selected from halogen, or hydroxy, or $R^7$ is $C_1$-$C_6$ alkyl substituted with $R^{14}$ or phenoxy, or $R^7$ is $C_1$-$C_6$ alkyl substituted with $NR^{15}R^{16}$, or $R^7$ is —$R^{17}$—X—$R^{18}$;

$R^8$ is phenyl or a 5 or 6-membered heteroaromatic ring containing 1 to 3 heteroatoms independently selected from O, S or N, each of which may be optionally substituted with one or more groups selected from halo, $C_1$-$C_6$ alkyl, $C_1$-$C_6$ alkoxy, or hydroxy;

$R^{14}$ is phenyl, benzyl, a 5 or 6-membered heteroaromatic ring containing 1 to 3 heteroatoms independently selected from O, S or N, a 9 or 10-membered bicyclic heteroaromatic ring containing 1 to 4 heteroatoms independently selected from O, S or N, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —$NO_2$, halogen, —O—$CH_2$—$CH_2$—CN, $C_1$-$C_6$ alkylsulfonyl, or —$NR^{19}R^{20}$;

$R^{15}$ is independently H, $C_3$-$C_6$ cycloalkyl or $C_1$-$C_6$ alkyl optionally substituted with $C_3$-$C_6$ cycloalkyl;

or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ allyl, $C_1$-$C_6$ alkoxy or hydroxy;

$R^{16}$ is independently H, or $C_1$-$C_6$ alkyl; or $R^{15}$ and $R^{16}$ together with the nitrogen to which they are attached form a 6-membered saturated ring optionally containing a further heteroatom selected from O or N, and optionally being substituted with $C_1$-$C_6$ alkyl;

$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, $C_1$-$C_6$ alkyl, or $C_1$-$C_6$ alkoxy;

X is a bond, —$CH_2$—NH—C(=O)—, or O;

$R^{19}$ and $R^{20}$ are independently H or $C_1$-$C_6$ alkyl, or $R^{19}$ and $R^{20}$ together with the nitrogen to which they are attached form a 6-membered saturated ring optionally containing a further heteroatom independently selected from O or N, and optionally being substituted with $C_1$-$C_6$ alkyl;

and $R^3$ is phenyl or benzyl, each being optionally substituted with one or more groups selected from halo, $C_1$-$C_6$ alkyl, or $C_1$-$C_6$ alkoxy;

or $R^3$ is a 5 or 6-membered heteroaromatic ring containing nitrogen and optionally one or more further heteroatoms independently selected from O, S or N, said ring being optionally substituted with one or more of the following groups: (i) halogen or $C_1$-$C_6$ alkyl optionally substituted by carboxy, $C_1$-$C_6$ alkoxycarbonyl, —$NR^{21}R^{22}$ or a 5 or 6-membered heterocyclic ring containing at least one heteroatom independently selected from O, S or N, (ii) $C_1$-$C_6$ alkoxy, —$NR^{21}R^{22}$, $C_3$-$C_8$ cycloalkyl optionally substituted with carboxy, or (iii) a 5 or 6-membered heterocyclic ring containing at least one heteroatom independently selected from O, S or N optionally substituted with $C_1$-$C_6$ alkyl;

or $R^3$ is —(C=O)—(NH)$_p$—$R^{23}$, —(C=O)—(NH)$_q$—$CH_2$—$R^{24}$ or —(C=O)—$NH_2$;

p and q are each independently 0 or 1;

$R^{21}$ is hydrogen or $C_1$-$C_6$ alkyl;

$R^{22}$ is $C_1$-$C_6$ alkyl optionally substituted with hydroxy, $C_1$-$C_6$ alkoxy, di($C_1$-$C_6$ alkyl)amino or a 5 or 6-membered heterocyclic ring containing at least one heteroatom selected from O, S or N and optionally substituted with $C_1$-$C_6$ alkyl;

$R^{23}$ is $C_1$-$C_6$ alkyl optionally substituted with one or more groups selected from halogen, hydroxy, amino, $C_1$-$C_6$ alkylamino, di($C_1$-$C_6$ alkyl)amino, $C_1$-$C_6$ alkoxycarbonyl, nitrile, carboxy, $C_1$-$C_6$ alkoxy optionally substituted with hydroxy, $C_3$-$C_8$ cycloalkyl optionally substituted with hydroxy, or phenyl optionally substituted with hydroxy or $C_1$-$C_6$ alkyl, or $R^{23}$ is phenyl, benzyl, or a 5 or 6-membered heteroaromatic ring containing at least one heteroatom independently selected from O, S or N, each being optionally substituted with one or more groups selected from halogen, hydroxy, $C_1$-$C_6$ alkyl, $C_1$-$C_6$ alkoxy, or by a 5 or 6-membered saturated heterocyclic ring containing at least one heteroatom independently selected from O, S or N, or $R^{23}$ is a 5 or 6-membered heteroaromatic ring containing at least one heteroatom independently selected from O, S or N, which ring is substituted with phenyl;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$, $R^{10}$, $R^{11}$, $R^{12}$, and $R^{13}$ are H, $C_1$-$C_6$ alkyl, or $C_1$-$C_6$ alkylcarbonyl.

According to a further embodiment of the invention, there is provided a compound of formula (Ia):—

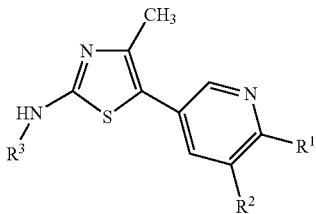

(Ia)

wherein $R^1$ is hydrogen or halo;

$R^2$ is —$R^6$-$R^7$;

$R^6$ is —N($R^9$)—$SO_2$—, —$SO_2$N($R^{10}$)—, —N($R^{11}$)—C(=O)—, —N($R^{12}$)—C(=O)—N($R^{13}$)—, or —$SO_2$—;

$R^7$ is $R^{14}$ or $C_1$-$C_6$ alkyl or $C_2$-$C_8$ alkoxyalkyl;

or $R^7$ is $C_1$-$C_6$ alkyl substituted with one or more groups selected from halogen, or hydroxy, or $R^7$ is $C_1$-$C_4$ alkyl substituted with either $R^{14}$ or phenoxy, or $R^7$ is $C_1$-$C_6$ alkyl substituted with $NR^{15}R^{16}$, or $R^7$ is —$R^{17}$—X—$R^{11}$;

$R^{14}$ is phenyl, benzyl, a 5 or 6-membered heteroaromatic ring containing 1 to 3 heteroatoms independently selected from O, S or N, a 9 or 10-membered bicyclic heteroaromatic ring containing 1 to 4 heteroatoms independently selected from O, S or N, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —$NO_2$, halogen, —O—$CH_2$—$CH_2$—CN, $C_1$-$C_6$ alkylsulfonyl, or —$NR^{19}R^{20}$;

$R^{15}$ is independently H, $C_3$-$C_6$ cycloalkyl or $C_1$-$C_6$ alkyl optionally substituted with $C_3$-$C_6$ cycloalkyl;

or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;

$R^{16}$ is independently H, or $C_1$-$C_6$ alkyl; or $R^{15}$ and $R^{16}$ together with the nitrogen to which they are attached form a 6-membered saturated ring optionally containing a further heteroatom selected from O or N, and optionally being substituted with $C_1$-$C_6$ alkyl;

$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, $C_1$-$C_6$ alkyl, or $C_1$-$C_6$ alkoxy;

X is a bond, —$CH_2$—NH—C(=O)—, or O;

$R^{19}$ and $R^{20}$ are independently H or $C_1$-$C_6$ alkyl, or $R^{19}$ and $R^{20}$ together with the nitrogen to which they are attached form a 6-membered saturated ring optionally containing a further heteroatom selected from O or N, and optionally being substituted with $C_1$-$C_6$ alkyl;

$R^3$ is —(C=O)—$NH_2$, —(C=O)—$R^{23}$ or —(C=O)—(NH)$_q$—$CH_2$—$R^{24}$;

q is 0 or 1;

$R^{23}$ is $C_1$-$C_6$ alkyl or $C_2$-$C_6$ alkoxy-alkyl, or $R^{23}$ is phenyl, benzyl, or a 5 or 6-membered heteroaromatic ring containing at least one heteroatom selected from the group consisting of O, S or N, each being optionally substituted with one or more groups selected from halogen, hydroxy, $C_1$-$C_6$ alkyl, $C_1$-$C_6$ alkoxy, or with a 5 or 6-membered saturated heterocyclic ring containing at least one heteroatom selected from the group consisting of O, S or N;

or $R^{23}$ is a 5 or 6-membered heteroaromatic ring containing at least one heteroatom selected from the group consisting of O, S or N, which ring is substituted with phenyl;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$, $R^{10}$, $R^{11}$, $R^{12}$, and $R^{13}$ are H, $C_1$-$C_6$ alkyl, or $C_1$-$C_6$ alkylcarbonyl.

According to a further embodiment of the invention, there is provided a thiazole derivative of formula (Ia):—

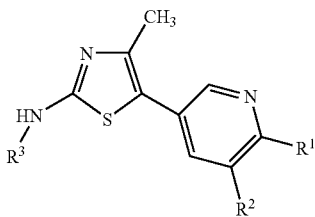

(Ia)

wherein $R^1$ is hydrogen or halo;

$R^2$ is —$R^6$-$R^7$;

$R^6$ is —N($R^9$)—SO$_2$—;

$R^7$ is $R^{14}$ or $C_1$-$C_6$ alkyl or $C_2$-$C_8$ alkoxyalkyl;

or $R^7$ is $C_1$-$C_6$ alkyl substituted with one or more groups selected from halogen, or hydroxy, or $R^7$ is $C_1$-$C_4$ alkyl substituted with either $R^{14}$ or phenoxy, or $R^7$ is $C_1$-$C_6$ alkyl substituted with $NR^{15}R^{16}$, or $R^7$ is —$R^{17}$—X—$R^{18}$;

$R^{14}$ is phenyl, benzyl, a 5 or 6-membered heteroaromatic ring containing 1 to 3 heteroatoms independently selected from O, S or N, a 9 or 10-membered bicyclic heteroaromatic ring containing 1 to 4 heteroatoms independently selected from O, S or N, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —NO$_2$, halogen, —O—CH$_2$—CH$_2$—CN, $C_1$-$C_6$ alkylsulfonyl, or —NR$^{19}$R$^{20}$;

$R^{15}$ is independently H, $C_3$-$C_6$ cycloalkyl or $C_1$-$C_6$ alkyl optionally substituted with $C_3$-$C_6$ cycloalkyl;

or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;

$R^{16}$ is independently H, or $C_1$-$C_6$ alkyl; or $R^{15}$ and $R^{16}$ together with the nitrogen to which they are attached form a 6-membered saturated ring optionally containing a further heteroatom selected from O or N, and optionally being substituted with $C_1$-$C_6$ alkyl;

$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, $C_1$-$C_6$ alkyl, or $C_1$-$C_6$ alkoxy;

X is a bond, —CH$_2$—NH—C(=O)—, or O;

$R^{19}$ and $R^{20}$ are independently H or $C_1$-$C_6$ alkyl, or $R^{19}$ and $R^{20}$ together with the nitrogen to which they are attached form a 6-membered saturated ring optionally containing a further heteroatom selected from O or N, and optionally being substituted with $C_1$-$C_6$ alkyl;

$R^3$ is —(C=O)—NH$_2$, —(C=O)—$R^{23}$ or —(C=O)—(NH)$_q$—CH$_2$—$R^{24}$;

q is 0 or 1;

$R^{23}$ is $C_1$-$C_6$ alkyl or $C_2$-$C_6$ alkoxy-alkyl, or $R^{23}$ is phenyl, benzyl, or a 5 or 6-membered heteroaromatic ring containing at least one heteroatom selected from the group consisting of O, S or N, each being optionally substituted with one or more groups selected from halogen, hydroxy, $C_1$-$C_6$ alkyl, $C_1$-$C_6$ alkoxy, or with a 5 or 6-membered saturated heterocyclic ring containing at least one heteroatom selected from the group consisting of O, S or N;

or $R^{23}$ is a 5 or 6-membered heteroaromatic ring containing at least one heteroatom selected from the group consisting of O, S or N, which ring is substituted with phenyl;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$ is H, $C_1$-$C_6$ alkyl, or $C_1$-$C_6$ alkylcarbonyl.

According to a further embodiment of the invention, there is provided a compound of formula (Ia):—

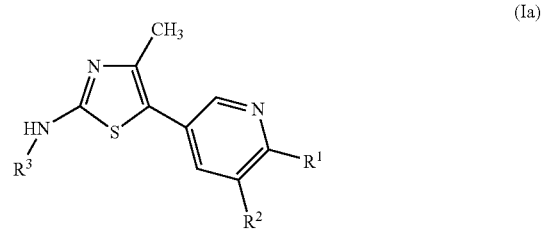

(Ia)

wherein $R^1$ is hydrogen, fluoro, chloro or bromo;

$R^2$ is —$R^6$-$R^7$;

$R^6$ is —N($R^9$)—SO$_2$—;

$R^7$ is $R^{14}$ or methyl, ethyl, propyl, methoxymethyl or 2-methoxyethyl;

or $R^7$ is 2-fluoroethyl, 2,2-difluoroethyl, 2,2,2-trifluoroethyl, 2-chloroethyl, 3-chloropropyl, hydroxymethyl, 2-hydroxyethyl or 3-hydroxypropyl, or $R^7$ is methyl, ethyl or propyl substituted with either $R^{14}$ or phenoxy, or $R^7$ is methyl, ethyl or propyl substituted with $NR^{15}R^{16}$, or $R^7$ is —$R^{17}$—X—$R^{18}$;

$R^{14}$ is phenyl, benzyl, thienyl, furanyl, pyrrolyl, imidazolyl, pyridyl, pyrazinyl, pyrimidinyl, pyridazinyl, triazinyl, oxazolyl, thiazolyl, isoxazolyl, pyrazolyl, oxadiazolyl, thiadiazolyl, triazolyl, benzothiadiazolyl, indolyl or 1,3-benzodioxolyl, each being optionally substituted with one, two or three groups independently selected from methyl, ethyl, propyl, isopropyl, methoxy, ethoxy, cyano, nitro, fluoro, chloro, acetyl, propionyl, 2-cyanoethoxy, methylsulfonyl, methylamino, ethylamino, dimethylamino, diethylamino or morpholino;

$R^{15}$ is independently H, cyclopentyl, cyclohexyl, methyl, ethyl, propyl, isopropyl, butyl, isobutyl, pentyl, neopentyl, 3-methylbutyl, cyclopentylmethyl or cyclohexylmethyl, or R$^{15}$ is phenyl, tetrazolyl, or benzyl, each being optionally substituted with one or two groups selected from fluoro, chloro, methyl, methoxy or hydroxy, R$^{16}$ is independently H, or methyl; or R$^{15}$ and R$^{16}$ together with the nitrogen to which they are attached form a morpholino, piperazin-1-yl or 4-methylpiperazin-1-yl ring;

R$^{17}$ and R$^{18}$ are independently phenyl, 2-thienyl, 2-pyridyl or 3-pyridyl, wherein one or both of R$^{17}$ and R$^{18}$ may be optionally and independently substituted with one or two groups selected from fluoro, chloro, methyl or methoxy;

X is a bond or O;

R$^3$ is —(C═O)—NH$_2$, —(C═O)—R$^{23}$ or —(C═O)—(NH)$_q$—CH$_2$—R$^{24}$;

q is 0 or 1;

R$^{23}$ is methyl, ethyl, propyl or methoxymethyl, or R$^{23}$ is phenyl, benzyl, 2-furanyl or 3-pyridyl, each being optionally substituted with one or two groups selected from fluoro, chloro, methyl or methoxy, or R$^{23}$ is 1,2,3-triazolyl which is substituted with phenyl;

R$^{24}$ is benzyloxy or 2-furanyl, either of which being optionally substituted with one or two groups selected from fluoro, chloro, methyl or methoxy; and R$^9$ is H, methyl, ethyl or acetyl.

According to a further embodiment of the invention, there is provided a thiazole derivative of formula (Ia):—

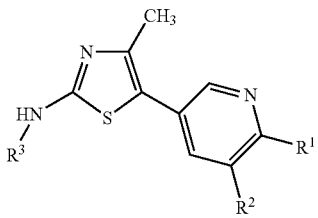

(Ia)

wherein R$^1$ is H, halo, C$_1$-C$_6$ alkyl or C$_1$-C$_6$ alkoxy;

R$^2$ is —R$^6$-R$^7$;

R$^6$ is —N(R$^9$)—SO$_2$— and R$^9$ is H, C$_1$-C$_6$ alkyl or C$_1$-C$_6$ alkylcarbonyl;

R$^7$ is R$^{14}$ or C$_1$-C$_6$ alkyl, or R$^7$ is C$_1$-C$_6$ alkyl substituted with one or more groups selected from halogen or hydroxy, or R$^7$ is C$_1$-C$_4$ alkyl substituted with R$^{14}$, or R$^7$ is C$_1$-C$_6$ alkyl substituted with NR$^{15}$R$^{16}$, or R$^7$ is —R$^{17}$—X—R$^{18}$;

R$^{14}$ is phenyl, benzyl, phenoxy, a 5 or 6-membered heteroaromatic ring containing 1 to 3 heteroatoms independently selected from O, S or N, a 9 or 10-membered bicyclic heteroaromatic ring containing 1 to 4 heteroatoms independently selected from O, S or N, or a phenyl-fused 5 or 6-membered cycloheteroalkyl ring containing 1 or 2 heteroatoms independently selected from O, S or N, each being optionally substituted with one or more groups independently selected from C$_1$-C$_6$ alkyl, C$_1$-C$_6$ alkoxy, cyano, —C(═O)—NH$_2$, —NO$_2$, halogen, —OCF$_3$, —C(═O)—CF$_3$, C$_1$-C$_6$ alkylcarbonyl, C$_2$-C$_6$ alkanoylamino, —O—CH$_2$—CH$_2$—CN, C$_1$-C$_6$ alkylsulfonyl, or —NR$^{19}$R$^{20}$ R$^{15}$ is independently H, C$_3$-C$_6$ cycloalkyl or C$_1$-C$_6$ alkyl optionally substituted with C$_3$-C$_6$ cycloalkyl, or R$^{15}$ is phenyl, a 5 or 6-membered heteroaromatic ring containing 1 to 4 heteroatoms independently selected from O, S and N, or benzyl, each being optionally substituted with one or more groups selected from halo, C$_1$-C$_6$ alkyl, C$_1$-C$_6$ alkoxy or hydroxy;

R$^{16}$ is independently H, or C$_1$-C$_6$ alkyl, or R$^{15}$ and R$^{16}$ together with the nitrogen to which they are attached form a 5 or 6-membered saturated ring optionally containing a further heteroatom selected from O or N, and optionally being substituted with C$_1$-C$_6$ alkyl or C$_1$-C$_6$ alkylcarbonyl;

R$^{17}$ is phenyl or a 5 or 6-membered heteroaromatic ring containing 1 or 2 heteroatoms independently selected from O, S or N, X is a bond, —CH$_2$—NH—C(═O)— or O, and R$^{18}$ is phenyl or a 5 or 6-membered heteroaromatic ring containing 1 or 2 heteroatoms independently selected from O, S or N, each R$^{18}$ ring being optionally substituted with one or more groups selected from halogen, cyano, C$_1$-C$_6$ alkyl, C$_1$-C$_6$ alkoxy or C$_1$-C$_6$ alkylthio;

R$^{19}$ and R$^{20}$ are independently H or C$_1$-C$_6$ alkyl, or R$^{19}$ and R$^{20}$ together with the nitrogen to which they are attached form a 5 or 6-membered saturated ring optionally containing a further heteroatom selected from O or N, and optionally being substituted with C$_1$-C$_6$ alkyl or C$_1$-C$_6$ alkylcarbonyl; and R$^3$ is (C═O)—NH$_2$, —(C═O)—(NH)$_p$—R$^{23}$, (C═O)—(NH)—CH$_2$—R$^{24}$ or —(C═O)—(NH)—CH$_2$—CH$_2$—R$^{24}$, p is 0 or 1, R$^{23}$ is C$_1$-C$_6$ alkyl, C$_3$-C$_7$ cycloalkyl or C$_2$-C$_6$ hydroxy-alkyl, or R$^{23}$ is phenyl, benzyl, or a 5 or 6-membered heteroaromatic ring containing at least one heteroatom selected from the group consisting of O, S or N, each being optionally substituted with one or more groups selected from halogen, hydroxy, C$_1$-C$_6$ alkyl, C$_1$-C$_6$ alkoxy, or R$^{23}$ is a 5 or 6-membered heteroaromatic ring containing at least one heteroatom selected from the group consisting of O, S or N, which ring is substituted with phenyl and is optionally substituted with one or two groups selected from halogen, hydroxy, C$_1$-C$_6$ alkyl or C$_1$-C$_6$ alkoxy, and R$^{24}$ is benzyloxy or a 5 to 7-membered heteroaromatic ring containing 1 to 3 heteroatoms independently selected from O, S and N, each being optionally substituted with one or more groups selected from halogen, C$_1$-C$_6$ alkyl or C$_1$-C$_6$ alkoxy;

or a pharmaceutically acceptable salt thereof.

According to a further embodiment of the invention, there is provided a thiazole derivative of formula (Ia):—

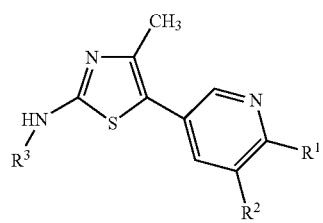

(Ia)

wherein R¹ is H, fluoro, chloro, bromo, methyl, ethyl, methoxy or ethoxy;

R² is —R⁶-R⁷;

R⁶ is —N(R⁹)—SO₂— and R⁹ is H, methyl, ethyl or acetyl;

R⁷ is R¹⁴ or methyl, ethyl or propyl, or R⁷ is 2,2-difluoroethyl, 2,2,2-trifluoroethyl, 2-chloroethyl, 3-chloropropyl, 2-hydroxyethyl or 3-hydroxypropyl, or R⁷ is methyl substituted with R¹⁴, or R⁷ is methyl, ethyl or propyl substituted with NR¹⁵R¹⁶, or R⁷ is —R¹⁷—X—R¹⁸;

R¹⁴ is phenyl, benzyl, phenoxy, thienyl, imidazolyl, pyridyl, pyrazinyl, pyrimidinyl, pyridazinyl, oxazolyl, thiazolyl, isoxazolyl, isothiazolyl, pyrazolyl, oxadiazolyl, thiadiazolyl, triazolyl, benzo-2,1,3-oxadiazolyl, 2,1,3-benzothiadiazolyl, 2-oxo-1,2,3,4-tetrahydroquinolinyl or 1,2,3,4-tetrahydroisoquinolinyl, each being optionally substituted with one, two or three groups independently selected from methyl, ethyl, propyl, isopropyl, methoxy, ethoxy, cyano, nitro, fluoro, chloro, trifluoromethoxy, 2,2,2-trifluoroacetyl, acetyl, propionyl, acetamido, propionamido, 2-cyanoethoxy, methylsulfonyl, methylamino, ethylamino, dimethylamino, diethylamino, pyrrolidin-1-yl, piperidino, morpholino, piperazin-1-yl, 4-methylpiperazin-1-yl or 4-acetylpiperazin-1-yl;

R¹⁵ is independently H, cyclopropyl, cyclobutyl, cyclopentyl, cyclohexyl, methyl, ethyl, propyl, isopropyl, butyl, isobutyl, pentyl, neopentyl, 3-methylbutyl, cyclopropylmethyl, cyclobutylmethyl, cyclopentylmethyl or cyclohexylmethyl, or R¹⁵ is phenyl or benzyl, each being optionally substituted with one or two groups selected from fluoro, chloro, methyl, methoxy or hydroxy, and R¹⁶ is independently H or methyl, or R¹⁵ and R¹⁶ together with the nitrogen to which they are attached form pyrrolidin-1-yl, piperidino, morpholino, piperazin-1-yl, 4-methylpiperazin-1-yl or 4-acetylpiperazin-1-yl;

R¹⁷ is phenyl, 2-thienyl, 2-pyridyl or 3-pyridyl, X is a bond or O, and R¹⁸ is phenyl, 2-pyridyl, 3-pyridyl or 4-pyrimidinyl, each R¹⁸ ring being optionally substituted with one or two groups selected from fluoro, chloro, cyano, methyl, methoxy or methylthio; and R³ is —(C=O)—NH₂, —(C=O)—(NH)ₚ—R²³, or —(C=O)—(NH)—CH₂—R²⁴, p is 0 or 1, R²³ is methyl, ethyl, propyl, isopropyl, 1-methylpropyl, 2-hydroxyethyl or 1-hydroxymethylpropyl, or R²³ is phenyl, benzyl, 2-furanyl or 3-pyridyl, each being optionally substituted with one or two groups selected from fluoro, chloro, methyl or methoxy, and R²⁴ is 2-furanyl, 2-thienyl or 4-isoxazolyl each being optionally substituted with one or two groups selected from fluoro, chloro, methyl or methoxy;

or a pharmaceutically acceptable salt thereof.

According to a further embodiment of the invention, there is provided a thiazole derivative of formula (Ib):—

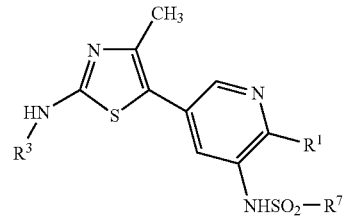

(Ib)

wherein R¹ is H, fluoro, chloro, methyl, ethyl or methoxy;

R⁷ is R¹⁴ or methyl, ethyl or propyl, or R⁷ is methyl substituted with R¹⁴, or R⁷ is propyl substituted with NR¹⁵R¹⁶, or R⁷ is —R¹⁷—X—R¹⁸;

R¹⁴ is phenyl, benzyl, 2-thienyl, 3-thienyl, 4-imidazolyl, 3-pyridyl, 5-oxazolyl, 5-thiazolyl, 4-isoxazolyl, 4-isothiazolyl, 4-pyrazolyl, benzo-2,1,3-oxadiazol-4-yl or 2,1,3-benzothiadiazol-4-yl, each being optionally substituted with one, two or three groups independently selected from methyl, ethyl, methoxy, ethoxy, cyano, nitro, fluoro, chloro, trifluoromethoxy, acetyl, acetamido, 2-cyanoethoxy, methylsulfonyl, methylamino, dimethylamino, piperidino, morpholino, piperazin-1-yl or 4-methylpiperazin-1-yl;

R¹⁵ is independently H, cyclopentyl, methyl, ethyl, neopentyl, 3-methylbutyl, cyclopentylmethyl or cyclohexylmethyl, or R¹⁵ is phenyl or benzyl, each being optionally substituted with one or two groups selected from fluoro, chloro, methyl, methoxy or hydroxy, and R¹⁶ is independently H or methyl, or R¹⁵ and R¹⁶ together with the nitrogen to which they are attached form piperidino, morpholino, piperazin-1-yl or 4-methylpiperazin-1-yl;

R¹⁷ is phenyl, 2-thienyl or 3-pyridyl, X is a bond or O, and R¹⁸ is phenyl, 2-pyridyl or 4-pyrimidinyl, each being optionally substituted with one or two groups selected from chloro, cyano, methyl, methoxy or methylthio; and R³ is —(C=O)—NH₂ or —(C=O)—(NH)ₚ—R²³, p is 0 or 1 and R²³ is methyl or ethyl;

or a pharmaceutically acceptable salt thereof.

According to a further embodiment of the invention, there is provided a thiazole derivative of formula (Ib):—

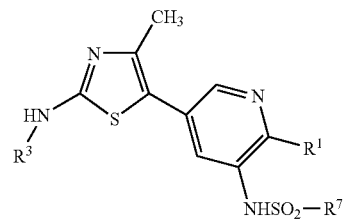

(Ib)

wherein R¹ is fluoro, chloro, methyl or methoxy;

R⁷ is methyl, ethyl, propyl or R¹⁴,

R¹⁴ is phenyl, 2-thienyl, 3-thienyl, 4-imidazolyl, 3-pyridyl, 5-thiazolyl, 4-isoxazolyl, 4-pyrazolyl, each being optionally substituted with one, two or three groups independently selected from methyl, methoxy, cyano, fluoro, chloro, acetamido or morpholino; and $R^3$ is —(C=O)—$NH_2$ or —(C=O)—$R^{23}$, and $R^{23}$ is methyl;

or a pharmaceutically acceptable salt thereof.

According to a further embodiment of the invention, there is provided a thiazole derivative of formula (Ib):—

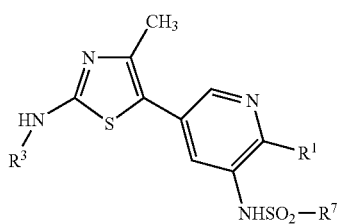

(Ib)

wherein $R^1$ is fluoro, chloro, methyl or methoxy;

$R^7$ is phenyl, 3-tolyl, 4-tolyl, 3-methoxyphenyl, 4-methoxyphenyl, 2,4-dimethoxyphenyl, 3,4-dimethoxyphenyl, 2,5-dimethoxyphenyl, 2-methoxy-4-methylphenyl, 2-methoxy-5-methylphenyl, 2-thienyl, 3-thienyl, 1-methyl-1H-imidazol-4-yl, 1,2-dimethylimidazol-4-yl, 1,2-dimethylimidazol-5-yl, 2,4-dimethyl-1,3-thiazol-5-yl, 2-acetamido-4-methyl-1,3-thiazol-5-yl, 3,5-dimethylisoxazol-4-yl, 5-chloro-1,3-dimethyl-1H-pyrazol-4-yl or 3-pyridyl; and $R^3$ is acetyl;

or a pharmaceutically acceptable salt thereof.

According to a further embodiment of the invention, there is provided a thiazole derivative of formula (Ia):—

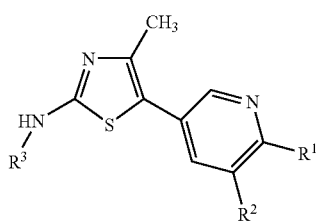

(Ia)

wherein $R^1$ is H, fluoro, chloro, bromo, methyl, ethyl, methoxy or ethoxy;

$R^2$ is —$R^6R^7$;

$R^6$ is —$SO_2$—$N(R^{10})$— and $R^{10}$ is H, methyl, ethyl or acetyl;

$R^7$ is $R^{14}$ or methyl, ethyl or propyl, or $R^7$ is 2,2-difluoroethyl, 2,2,2-trifluoroethyl, 2-chloroethyl, 3-chloropropyl, 2-hydroxyethyl or 3-hydroxypropyl, or $R^7$ is methyl substituted with $R^{14}$, or $R^7$ is methyl, ethyl or propyl substituted with $NR^{15}R^{16}$, or $R^7$ is —$R^{17}$—X—$R^{18}$;

$R^{14}$ is phenyl, benzyl, phenoxy, cyclopropyl, thienyl, imidazolyl, pyridyl, pyrazinyl, pyrimidinyl, pyridazinyl, oxazolyl, thiazolyl, isoxazolyl, isothiazolyl, pyrazolyl, oxadiazolyl, thiadiazolyl or triazolyl, each being optionally substituted with one, two or three groups independently selected from methyl, ethyl, propyl, isopropyl, methoxy, ethoxy, cyano, nitro, fluoro, chloro, trifluoromethoxy, acetyl, propionyl, acetamido, propionamido, 2-cyanoethoxy, methylsulfonyl, methylamino, ethylamino, dimethylamino, diethylamino, pyrrolidin-1-yl, piperidino, morpholino, piperazin-1-yl, 4-methylpiperazin-1-yl or 4-acetylpiperazin-1-yl;

$R^{15}$ is independently H, cyclopropyl, cyclobutyl, cyclopentyl, cyclohexyl, methyl, ethyl, propyl, isopropyl, butyl, isobutyl, pentyl, neopentyl, 3-methylbutyl, cyclopropylmethyl, cyclobutylmethyl, cyclopentylmethyl or cyclohexylmethyl, or $R^{15}$ is phenyl or benzyl, each being optionally substituted with one or two groups selected from fluoro, chloro, methyl, methoxy or hydroxy, and $R^{16}$ is independently H or methyl, or $R^{15}$ and $R^{16}$ together with the nitrogen to which they are attached form pyrrolidin-1-yl, piperidino, morpholino, piperazin-1-yl, 4-methylpiperazin-1-yl or 4-acetylpiperazin-1-yl;

$R^{17}$ is phenyl, 2-thienyl, 2-pyridyl or 3-pyridyl, X is a bond or O, and $R^{18}$ is phenyl, 2-pyridyl, 3-pyridyl or 4-pyrimidinyl, each $R^{18}$ ring being optionally substituted with one or two groups selected from fluoro, chloro, cyano, methyl, methoxy or methylthio; and $R^3$ is —(C=O)—$NH_2$, —(C=O)—$(NH)_p$—$R^{23}$, or —(C=O)—(NH)—$CH_2$—$R^{24}$, p is 0 or 1, $R^{23}$ is methyl, ethyl, propyl, isopropyl, 1-methylpropyl, 2-hydroxyethyl or 1-hydroxymethylpropyl, or $R^{23}$ is phenyl, benzyl, 2-furanyl or 3-pyridyl, each being optionally substituted with one or two groups selected from fluoro, chloro, methyl or methoxy, and $R^{24}$ is 2-furanyl, 2-thienyl or 4-isoxazolyl each being optionally substituted with one or two groups selected from fluoro, chloro, methyl or methoxy;

or a pharmaceutically acceptable salt thereof.

According to a further embodiment of the invention, there is provided a thiazole derivative of formula (Ic):—

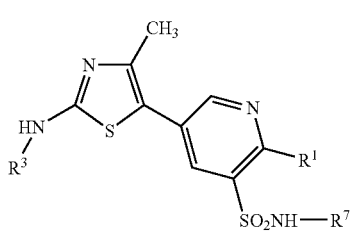

(Ic)

wherein $R^1$ is H or chloro;

$R^7$ is methyl, ethyl, propyl, cyclopropyl, cyclopropylmethyl or $R^{14}$, $R^{14}$ is phenyl, 4-imidazolyl, 3-pyridyl, 5-thiazolyl, 4-isoxazolyl or 4-pyrazolyl, each being optionally substituted with one, two or three groups independently selected from methyl, methoxy, cyano, fluoro, chloro or acetamido; and $R^3$ is —(C=O)—$NH_2$ or —(C=O)—$R^{23}$, and $R^{23}$ is methyl;

or a pharmaceutically acceptable salt thereof.

According to a further embodiment of the invention, there is provided a thiazole derivative of formula (I):—

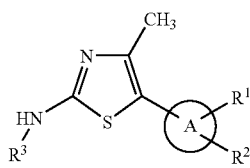

(I)

wherein Ring A is pyrazin-2-yl or pyridazin-4-yl;

$R^1$ is hydrogen, fluoro, chloro, bromo, methyl, ethyl, methoxy or ethoxy;

$R^2$ is —$R^6$-$R^7$;

$R^6$ is —N($R^9$)—$SO_2$— and $R^9$ is H, methyl, ethyl or acetyl;

$R^7$ is $R^{14}$ or methyl, ethyl or propyl, or $R^7$ is 2,2-difluoroethyl, 2,2,2-trifluoroethyl, 2-chloroethyl, 3-chloropropyl, 2-hydroxyethyl or 3-hydroxypropyl, or $R^7$ is methyl substituted with $R^{14}$, or $R^7$ is methyl, ethyl or propyl substituted with $NR^{15}R^{16}$, or $R^7$ is —$R^{17}$—X—$R^{18}$;

$R^{14}$ is phenyl, benzyl, phenoxy, cyclopropyl, thienyl, imidazolyl, pyridyl, pyrazinyl, pyrimidinyl, pyridazinyl, oxazolyl, thiazolyl, isoxazolyl, isothiazolyl, pyrazolyl, oxadiazolyl, thiadiazolyl or triazolyl, each being optionally substituted with one, two or three groups independently selected from methyl, ethyl, propyl, isopropyl, methoxy, ethoxy, cyano, nitro, fluoro, chloro, trifluoromethoxy, acetyl, propionyl, acetamido, propionamido, 2-cyanoethoxy, methylsulfonyl, methylamino, ethylamino, dimethylamino, diethylamino, pyrrolidin-1-yl, piperidino, morpholino, piperazin-1-yl, 4-methylpiperazin-1-yl or 4-acetylpiperazin-1-yl;

$R^{15}$ is independently H, cyclopropyl, cyclobutyl, cyclopentyl, cyclohexyl, methyl, ethyl, propyl, isopropyl, butyl, isobutyl, pentyl, neopentyl, 3-methylbutyl, cyclopropylmethyl, cyclobutylmethyl, cyclopentylmethyl or cyclohexylmethyl, or $R^{15}$ is phenyl or benzyl, each being optionally substituted with one or two groups selected from fluoro, chloro, methyl, methoxy or hydroxy, and $R^{16}$ is independently H or methyl, or $R^{15}$ and $R^{16}$ together with the nitrogen to which they are attached form pyrrolidin-1-yl, piperidino, morpholino, piperazin-1-yl, 4-methylpiperazin-1-yl or 4-acetylpiperazin-1-yl;

$R^{17}$ is phenyl, 2-thienyl, 2-pyridyl or 3-pyridyl, X is a bond or O, and $R^{18}$ is phenyl, 2-pyridyl, 3-pyridyl or 4-pyrimidinyl, each $R^{18}$ ring being optionally substituted with one or two groups selected from fluoro, chloro, cyano, methyl, methoxy or methylthio; and $R^3$ is —(C=O)—$NH_2$, —(C=O)—(NH)$_p$—$R^{23}$, or —(C=O)—(NH)—$CH_2$—$R^{24}$, p is 0 or 1, $R^{23}$ is methyl, ethyl, propyl, isopropyl, 1-methylpropyl, 2-hydroxyethyl or 1-hydroxymethylpropyl, or $R^{23}$ is phenyl, benzyl, 2-furanyl or 3-pyridyl, each being optionally substituted with one or two groups selected from fluoro, chloro, methyl or methoxy, and $R^{24}$ is 2-furanyl, 2-thienyl or 4-isoxazolyl each being optionally substituted with one or two groups selected from fluoro, chloro, methyl or methoxy;

or a pharmaceutically acceptable salt thereof.

According to a further embodiment of the invention, there is provided a thiazole derivative of formula (I):—

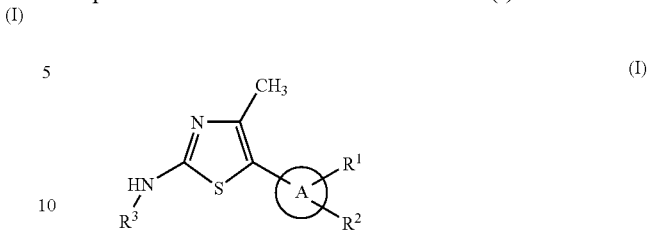

(I)

wherein Ring A is pyrazin-2-yl or pyridazin-4-yl;

$R^1$ is H or chloro;

$R^2$ is —$R^6$-$R^7$;

$R^6$ is —N($R^9$)—$SO_2$— and $R^9$ is H;

$R^7$ is methyl, ethyl, propyl, cyclopropyl, cyclopropylmethyl or $R^{14}$, $R^{14}$ is phenyl, 4-imidazolyl, 3-pyridyl, 5-thiazolyl, 4-isoxazolyl or 4-pyrazolyl, each being optionally substituted with one, two or three groups independently selected from methyl, methoxy, cyano, fluoro, chloro or acetamido; and $R^3$ is —(C=O)—$NH_2$ or —(C=O)—$R^{23}$, and $R^{23}$ is methyl;

or a pharmaceutically acceptable salt thereof.

According to a further embodiment of the invention, there is provided a thiazole derivative of formula (Ia):—

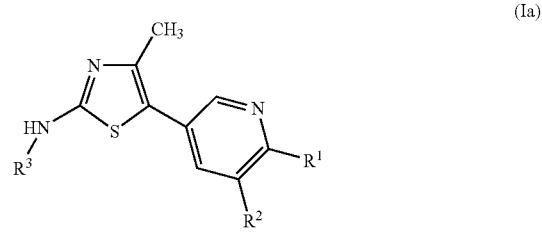

(Ia)

wherein $R^1$ is H, fluoro, chloro, bromo, methyl, ethyl, methoxy or ethoxy;

$R^2$ is —$R^4R^5$;

$R^4$ is —$CH_2$—$R^8$;

$R^5$ is H, methyl or ethyl;

$R^8$ is cyclopropyl, phenyl, thienyl, pyrrolyl, imidazolyl, pyridyl, pyrazinyl, pyrimidinyl, pyridazinyl, oxazolyl, thiazolyl, isoxazolyl, isothiazolyl, pyrazolyl, oxadiazolyl, thiadiazolyl or triazolyl, each being optionally substituted with one, two or three groups independently selected from fluoro, chloro, cyano, methyl, ethyl, propyl, isopropyl, methoxy, ethoxy, hydroxy, methylsulfonyl, acetamido, propionamido, methoxycarbonyl, ethoxycarbonyl, phenyl, 3-pyridyl, 2-hydroxyethoxy, 3-hydroxypropoxy, 2-methylaminoethoxy, 3-methylaminopropoxy, 2-dimethylaminoethoxy, 3-dimethylaminopropoxy, 2-diethylaminoethoxy or 3-diethylaminopropoxy; and $R^3$ is —(C=O)—$NH_2$, —(C=O)—(NH)$_p$—$R^{23}$, or —(C=O)—(NH)—$CH_2$—$R^{24}$, p is 0 or 1, $R^{23}$ is methyl, ethyl, propyl, isopropyl, 1-methylpropyl, 2-hydroxyethyl or 1-hydroxymethylpropyl, or $R^{23}$ is phenyl, benzyl, 2-furanyl or 3-pyridyl, each being optionally substituted with one or two groups selected from fluoro, chloro, methyl or methoxy, and R²⁴ is 2-furanyl, 2-thienyl or 4-isoxazolyl each being optionally substituted with one or two groups selected from fluoro, chloro, methyl or methoxy;

or a pharmaceutically acceptable salt thereof.

According to a further embodiment of the invention, there is provided a thiazole derivative of formula (Id):—

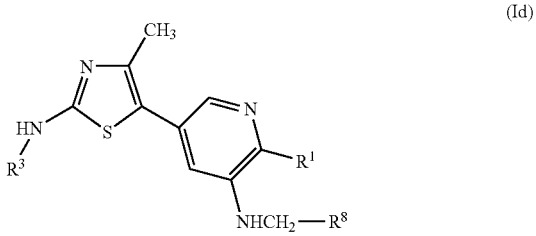

wherein R¹ is fluoro or chloro;

R⁸ is cyclopropyl, phenyl, 2-thienyl, 3-pyrrolyl, 4-imidazolyl, 3-pyridyl, 5-thiazolyl, 4-isoxazolyl, 4-pyrazolyl or 1,2,3-triazol-4-yl, each being optionally substituted with one or two groups independently selected from fluoro, cyano, methyl, methoxy, ethoxy, acetamido, phenyl or 3-pyridyl; and R³ is —(C=O)—NH₂ or (C=O)—R²³, and R²³ is methyl;

or a pharmaceutically acceptable salt thereof.

In an embodiment of the invention the compound of formula (I) is selected from:—

N-[5-(6-Chloropyridin-3-yl)-4-methyl-1,3-thiazol-2-yl]acetamide,
N-[5-(2-Chloropyridin-4-yl)-4-methyl-1,3-thiazol-2-yl]acetamide,
N-[5-(5-Methoxypyridin-3-yl)-4-methyl-1,3-thiazol-2-yl]acetamide,
N-[5-(6-Fluoropyridin-3-yl)-4-methyl-1,3-thiazol-2-yl]acetamide,
N-[5-(6-Methoxypyridin-3-yl)-4-methyl-1,3-thiazol-2-yl]acetamide,
N-[5-(2-Methoxypyrimidin-5-yl)-4-methyl-1,3-thiazol-2-yl]acetamide,
N-[5-(6-Chloro-5-methylsulfonylpyridin-3-yl)-4-methyl-1,3-thiazol-2-yl]acetamide,
N-{5-[5-(2-Hydroxyethylaminosulfonyl)pyridin-3-yl]-4-methyl-1,3-thiazol-2-yl}acetamide,
N-{4-Methyl-5-[5-(2-morpholinoethylaminosulfonyl)pyridin-3-yl]-1,3-thiazol-2-yl}acetamide,
N-[5-(5-Amino-6-chloropyridin-3-yl)-4-methyl-1,3-thiazol-2-yl]acetamide,
N-(5-{5-[(2,1,3-Benzothiadiazol-4-ylsulfonyl)amino]-6-chloropyridin-3-yl}-4-methyl-1,3-thiazol-2-yl)acetamide
N-(5-{6-Chloro-5-[(1-methyl-1H-imidazol-4-yl)sulfonylamino]pyridin-3-yl}-4-methyl-1,3-thiazol-2-yl]acetamide,
N-{5-[6-Chloro-5-(phenylsulfonylamino)pyridin-3-yl]-4-methyl-1,3-thiazol-2-yl}acetamide,
N-{5-[6-Chloro-5-(4-fluorophenylsulfonylamino)pyridin-3-yl]-4-methyl-1,3-thiazol-2-yl}acetamide,
N-{5-[6-Chloro-5-(5-pyridin-2-ylthien-2-ylsulfonylamino)pyridin-3-yl]-4-methyl-1,3-thiazol-2-yl}acetamide,
N-{5-[6-Chloro-5-(6-phenoxypyridin-3-ylsulfonylamino)pyridin-3-yl]-4-methyl-1,3-thiazol-2-yl}acetamide,
N-{5-[6-Chloro-5-(4-nitrophenylsulfonylamino)pyridin-3-yl]-4-methyl-1,3-thiazol-2-yl}acetamide,
N-{5-[6-Chloro-5-(3-methoxyphenylsulfonylamino)pyridin-3-yl]-4-methyl-1,3-thiazol-2-yl}acetamide,
N-{5-[6-Chloro-5-(2-cyanophenylsulfonylamino)pyridin-3-yl]-4-methyl-1,3-thiazol-2-yl}acetamide,
N-(5-{6-Chloro-5-[4-(2-cyanoethoxy)phenylsulfonylamino]pyridin-3-yl}-4-methyl-1,3-thiazol-2-yl)acetamide,
N-[5-(5-Benzylsulfonylamino-6-chloropyridin-3-yl)-4-methyl-1,3-thiazol-2-yl]acetamide,
N-{5-[6-Chloro-5-(4-chlorobenzylsulfonylamino)pyridin-3-yl]-4-methyl-1,3-thiazol-2-yl}acetamide,
N-{5-[6-Chloro-5-(6-morpholinopyridin-3-ylsulfonylamino}pyridin-3-yl]-4-methyl-1,3-thiazol-2-yl)acetamide,
N-(5-{6-Chloro-5-[4-(4-methoxyphenoxy)phenylsulfonylamino]pyridin-3-yl}-4-methyl-1,3-thiazol-2-yl)acetamide,
N-{5-[6-Chloro-5-(4-pyridin-2-yloxyphenylsulfonylamino)pyridin-3-yl]-4-methyl-1,3-thiazol-2-yl}acetamide,
N-{5-[6-Chloro-5-(3-chloropropylsulfonylamino)pyridin-3-yl]-4-methyl-1,3-thiazol-2-yl}acetamide,
N-[5-(6-Chloro-5-methylsulfonylaminopyridin-3-yl)-4-methyl-1,3-thiazol-2-yl]acetamide,
N-{5-[6-Chloro-5-(3-dimethylaminopropylsulfonylamino)pyridin-3-yl]-4-methyl-1,3-thiazol-2-yl}acetamide,
N-{5-[6-Chloro-5-(3-morpholinopropylsulfonylamino)pyridin-3-yl]-4-methyl-1,3-thiazol-2-yl}acetamide,
N-(5-{6-Chloro-5-[3-(4-methylpiperazin-1-yl)propylsulfonylamino]pyridin-3-yl}-4-methyl-1,3-thiazol-2-yl)acetamide,
N-{5-[5-(3-Benzylaminopropylsulfonylamino)-6-chloropyridin-3-yl]-4-methyl-1,3-thiazol-2-yl}acetamide,
N-{5-[6-Chloro-5-(3-cyclopentylaminopropylsulfonylamino)pyridin-3-yl]-4-methyl-1,3-thiazol-2-yl}acetamide,
N-{5-[6-Chloro-5-(3-neopentylaminopropylsulfonylamino)pyridin-3-yl]-4-methyl-1,3-thiazol-2-yl}acetamide,
N-(5-{6-Chloro-5-[5-(3-methylbutylamino)propylsulfonylamino]pyridin-3-yl}-4-methyl-1,3-thiazol-2-yl)acetamide,
N-(5-{6-Chloro-5-[3-(1H-tetrazol-5-ylamino)propylsulfonylamino]pyridin-3-yl}-4-methyl-1,3-thiazol-2-yl)acetamide,
N-(5-{6-Chloro-5-[3-(cyclohexylmethylamino)propylsulfonylamino]pyridin-3-yl}-4-methyl-1,3-thiazol-2-yl)acetamide,
N-(5-{6-Chloro-5-[3-(2,4-dimethoxybenzylamino)propylsulfonylamino]pyridin-3-yl}-4-methyl-1,3-thiazol-2-yl)acetamide,
N-[5-(2-Acetylamino-4-methyl-1,3-thiazol-5-yl)-2-chloropyridin-3-yl]propanamide,
N-[5-(2-Acetylamino-4-methyl-1,3-thiazol-5-yl)-2-chloropyridin-3-yl]-4-methylbenzamide,
N-[5-(2-Acetylamino-4-methyl-1,3-thiazol-5-yl)-2-chloropyridin-3-yl]-2-phenylacetamide,
N-[5-(2-Acetylamino-4-methyl-1,3-thiazol-5-yl)-2-chloropyridin-3-yl]-2-(4-methoxyphenyl)acetamide,
N-[5-(2-Acetylamino-4-methyl-1,3-thiazol-5-yl)-2-chloropyridin-3-yl]-2-(3-methoxyphenyl)acetamide,
N-[5-(2-Acetylamino-4-methyl-1,3-thiazol-5-yl)-2-chloropyridin-3-yl]-4-dimethylaminobutanamide,
N-[5-(2-Acetylamino-4-methyl-1,3-thiazol-5-yl)-2-chloropyridin-3-yl]-4-morpholinobutanamide, N-{5-[5-(Benzylamino)-6-chloropyridin-3-yl]-4-methyl-1,
3-thiazol-2-yl}acetamide,
N-(5-{5-[(Anilinocarbonyl)amino]-6-chloropyridin-3-yl}-
4-methyl-1,3-thiazol-2-yl)acetamide,
N-{5-[2-(Acetylamino)-4-methyl-1,3-thiazol-5-yl]-2-chloropyridin-3-yl}-N-(phenylsulfonyl)acetamide,
N-{2-Chloro-5-[2-(3-furan-2-ylmethylureido)-4-methyl-1,
3-thiazol-5-yl]pyridin-3-yl}methanesulfonamide,
N-[2-Chloro-5-(4-methyl-2-ureido-1,3-thiazol-5-yl)pyridin-
3-yl]benzenesulfonamide,
N-[5-(5-Benzenesulfonylamino-6-chloropyridin-3-yl)-4-
methyl-1,3-thiazol-2-yl]-5-methyl-2-phenyl-2H-[1,2,3]-
triazole-4-carboxamide,
N-[5-(5-Benzenesulfonylamino-6-chloropyridin-3-yl)-4-
methyl-1,3-thiazol-2-yl]-2-benzyloxyacetamide,
N-[5-(5-Benzenesulfonylamino-6-chloropyridin-3-yl)-4-
methyl-1,3-thiazol-2-yl]-2-(4-methoxyphenyl)acetamide,
N-[5-(5-Benzenesulfonylamino-6-chloropyridin-3-yl)-4-
methyl-1,3-thiazol-2-yl]-6-chloronicotinamide,
N-[5-(5-benzenesulfonylamino-6-chloropyridin-3-yl)-4-
methyl-1,3-thiazol-2-yl]furan-2-carboxamide and
N-[5-(5-Benzenesulfonylamino-6-chloropyridin-3-yl)-4-
methyl-1,3-thiazol-2-yl]-2-methoxyacetamide;

and pharmaceutically acceptable salts thereof.

In a further embodiment of the invention the thiazole derivative of formula (I) is selected from:—

N-{5-[6-Chloro-5-(phenylsulfonylamino)pyridin-3-yl]-4-
methyl-1,3-thiazol-2-yl}acetamide,
N-{5-[6-Chloro-5-(2,4-dimethoxyphenylsulfonylamino)pyridin-3-yl]-4-methyl-1,3-thiazol-2-yl}acetamide,
N-{5-[6-Chloro-5-(3,4-dimethoxyphenylsulfonylamino)pyridin-3-yl]-4-methyl-1,3-thiazol-2-yl}acetamide,
N-{5-[6-Chloro-5-(2,5-dimethoxyphenylsulfonylamino)pyridin-3-yl]-4-methyl-1,3-thiazol-2-yl}acetamide,
N-{5-[6-Chloro-5-(2-methoxy-5-methylphenylsulfonylamino)pyridin-3-yl]-4-methyl-1,3-thiazol-2-
yl}acetamide,
N-{5-[6-Chloro-5-(2-methoxy-4-methylphenylsulfonylamino)pyridin-3-yl]-4-methyl-1,3-thiazol-2-
yl}acetamide,
N-(5-{6-Chloro-5-[(1-methyl-1H-imidazol-4-yl)sulfonylamino]pyridin-3-yl}-4-methyl-1,3-thiazol-2-yl]acetamide,
N-{5-[6-Chloro-5-(1,2-dimethylimidazol-4-ylsulfonylamino)pyridin-3-yl]-4-methyl-1,3-thiazol-2-
yl}acetamide,
N-{5-[6-Chloro-5-(1,2-dimethylimidazol-5-ylsulfonylamino)pyridin-3-yl]-4-methyl-1,3-thiazol-2-
yl}acetamide,
N-{5-[6-Chloro-5-(5-chloro-1,2-dimethyl-1H-pyrazol-4-ylsulfonylamino)pyridin-3-yl]-4-methyl-1,3-thiazol-2-
yl}acetamide,
N-{5-[6-Chloro-5-(2,4-dimethyl-1,3-thiazol-5-ylsulfonylamino)pyridin-3-yl]-4-methyl-1,3-thiazol-2-
yl}acetamide,
N-{5-[5-(2,4-Dimethyl-1,3-thiazol-5-ylsulfonylamino)-6-
fluoropyridin-3-yl]-4-methyl-1,3-thiazol-2-yl}acetamide,
N-{5-[5-(2,4-Dimethyl-1,3-thiazol-5-ylsulfonylamino)-6-
methoxypyridin-3-yl]-4-methyl-1,3-thiazol-2-
yl}acetamide,
N-{5-[5-(2-Acetamido-4-methyl-1,3-thiazol-5-ylsulfonylamino)-6-chloropyridin-3-yl]-4-methyl-1,3-thiazol-2-
yl}acetamide and N-{5-[6-Chloro-5-(3,5-dimethylisoxazol-4-ylsulfonylamino)pyridin-3-yl]-4-methyl-1,3-thiazol-2-
yl}acetamide;

and pharmaceutically acceptable salts thereof.

In a further embodiment of the invention the thiazole derivative of formula (I) is selected from:—

N-{5-[6-Chloro-5-(N-methylsulfamoyl)pyridin-3-yl]-4-methyl-1,3-thiazol-2-yl]acetamide,
N-{5-[6-Chloro-5-(N-cyclopropylsulfamoyl)pyridin-3-yl]-
4-methyl-1,3-thiazol-2-yl]acetamide,
N-{5-[6-Chloro-5-(N-cyclopropylmethylsulfamoyl)pyridin-
3-yl]-4-methyl-1,3-thiazol-2-yl]acetamide,
N-{5-[6-Chloro-5-(N-phenylsulfamoyl)pyridin-3-yl]-4-methyl-1,3-thiazol-2-yl]acetamide,
N-(5-{6-Chloro-5-[N-(4-fluorophenyl)sulfamoyl]pyridin-3-
yl}-4-methyl-1,3-thiazol-2-yl)acetamide and
N-(5-{6-Chloro-5-[N-(4-tolyl)sulfamoyl]pyridin-3-yl}-4-
methyl-1,3-thiazol-2-yl)acetamide;

and pharmaceutically acceptable salts thereof.

In a further embodiment of the invention the thiazole derivative of formula (I) is selected from:—

N-[4-Methyl-5-(6-phenylsulfonylaminopyrazin-2-yl)-1,3-
thiazol-2-yl]acetamide and
N-[4-Methyl-5-(6-phenylsulfonylaminopyridazin-4-yl)-1,3-
thiazol-2-yl]acetamide;

and pharmaceutically acceptable salts thereof.

In a further embodiment of the invention the thiazole derivative of formula (I) is selected from:—

N-[5-(5-Benzylamino-6-chloropyridin-3-yl)-4-methyl-1,3-
thiazol-2-yl]acetamide,
N-{5-[6-Chloro-5-(4-fluorobenzylamino)pyridin-3-yl]-4-
methyl-1,3-thiazol-2-yl}acetamide,
N-{5-[6-Chloro-5-(2,4-dimethyl-1,3-thiazol-5-ylmethylamino)pyridin-3-yl]-4-methyl-1,3-thiazol-2-
yl}acetamide and
N-{5-[6-Chloro-5-(3,5-dimethylisoxazol-4-ylmethylamino)
pyridin-3-yl]-4-methyl-1,3-thiazol-2-yl}acetamide;

and pharmaceutically acceptable salts thereof.

A thiazole derivative of formula (I), or a pharmaceutically acceptable salt thereof, may be prepared by any process known to be applicable to the preparation of chemically-related compounds. Such processes, when used to prepare a thiazole derivative of formula (I) are provided as a further feature of the invention and are illustrated by the following representative process variants in which, unless otherwise stated, Ring A, $R^1$, $R^2$ and $R^3$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

Accordingly, the present invention further provides a process for the preparation of a compound of formula (I) as defined hereinbefore which comprises:—

(A) The reaction, conveniently in the presence of a transition metal catalyst, of a compound of formula (II)

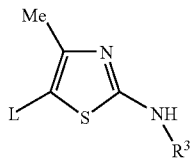

(II)

wherein $R^3$ is as defined hereinbefore and L represents a suitable leaving group, with an organoboron compound of formula (III)

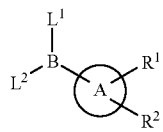

(III)

wherein each of $L^1$ and $L^2$, which may be the same or different, is a suitable ligand and Ring A, $R^1$ and $R^2$ are as defined hereinbefore.

(B) For the production of those compounds of formula (I) wherein $R^2$ is $R^6$-$R^7$, and $R^6$ is —$SO_2N(R^{11})$—, the reaction, conveniently in the presence of a suitable base, of a compound of formula (IV)

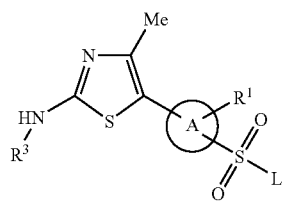

(IV)

wherein Ring A, $R^1$ and $R^3$ are as defined hereinbefore and L is a leaving group as defined hereinafter, with a compound of formula $R^7$—NH—$R^{10}$, wherein $R^7$ and $R^{10}$ are as defined hereinbefore.

(C) For the production of those compounds of formula (I) wherein $R^2$ is $R^6$-$R^7$, and $R^6$ is —$N(R^9)SO_2$—, the reaction, conveniently in the presence of a suitable base as defined hereinafter, of a compound of formula (V)

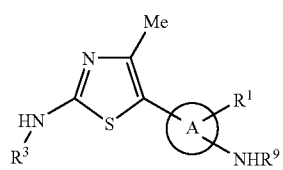

(V)

wherein Ring A, $R^1$, $R^3$ and $R^9$ are as defined hereinbefore, with a reactive derivative of a sulfonic acid of formula $R^7SO_2L$, wherein $R^7$ is as defined hereinbefore and L is a leaving group as defined hereinafter (such as chloro).

(D) For the production of those compounds of formula (I) wherein $R^2$ is $R^6$-$R^7$, and $R^7$ is $C_1$-$C_6$ alkyl substituted by $NR^{15}R^{16}$, the reaction, conveniently in the presence of a suitable base as defined hereinafter, of a compound of formula (VI)

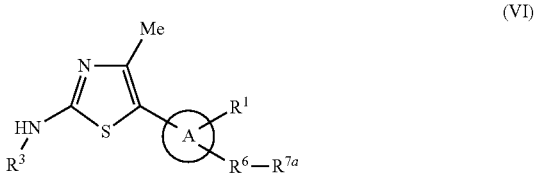

(VI)

wherein Ring A, $R^1$, $R^3$ and $R^6$ are as defined hereinbefore and $R^{7a}$ is $C_1$-$C_6$ substituted by a leaving group as defined hereinafter (such as halogen), with an amine of formula $HNR^{15}R^{16}$, wherein $R^{15}$ and $R^{36}$ are as defined hereinbefore.

(E) For the production of those compounds of formula (I) wherein $R^2$ is $R^6$-$R^7$, and $R^6$ is —$N(R^{11})$—$C(=O)$—, the reaction, conveniently in the presence of a suitable base as defined hereinafter, of a compound of formula (VII)

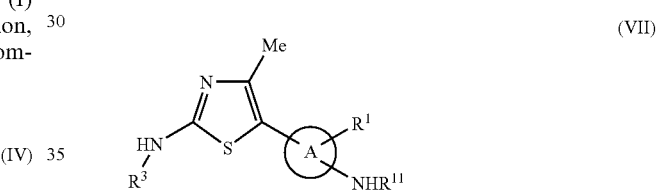

(VII)

wherein Ring A, $R^1$, $R^3$ and $R^{11}$ are as defined hereinbefore, with a reactive derivative of a carboxylic acid of formula $R^7CO_2H$, wherein $R^7$ is as defined hereinbefore.

(F) The reaction of a compound of formula (VIII)

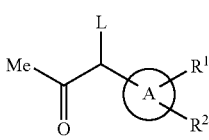

(VIII)

wherein Ring A, $R^1$, and $R^2$ are as defined hereinbefore, and L is a leaving group as defined hereinafter (such as halogen), with a thiourea compound of formula (IX)

(IX)

wherein $R^3$ is as defined hereinbefore.

(G) For the production of those compounds of formula (I) wherein $R^3$ is —(C=O)—(NH)—$R^{23}$, the coupling, conveniently in the presence of a suitable base as defined hereinafter, of phosgene, or a chemical equivalent thereof, with a 2-aminothiazole of formula (X)

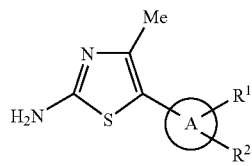

(X)

wherein Ring A, $R^1$, and $R^2$ are as defined hereinbefore, and with an amine of formula $HNR^{23}$, wherein $R^{23}$ is as defined hereinbefore.

(H) For the production of those compounds of formula (I) wherein $R^3$ is —(C=O)—$R^{23}$, the acylation, conveniently in the presence of a suitable base as defined hereinafter, of a 2-aminothiazole of formula (X)

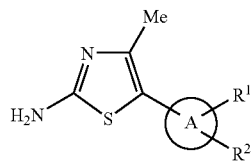

(X)

wherein Ring A, $R^1$, and $R^2$ are as defined hereinbefore, with a reactive derivative of a carboxylic acid of formula $R^{23}CO_2H$ (as defined hereinafter for the carboxylic acid of formula $R^7CO_2H$, e.g. an acid chloride of formula $R^{23}COCl$, or the product of the reaction of an acid of formula $R^{23}CO_2H$ and a coupling agent such as DCCI or HATU), wherein $R^{23}$ is as defined hereinbefore.

(I) For the production of those compounds of formula (I) wherein $R^2$ is $NR^4R^5$ and $R^4$ is —$CH_2$—$R^8$, the reaction, conveniently in the presence of a reducing agent (e.g. sodium cyanoborohydride), of a compound of formula (XI)

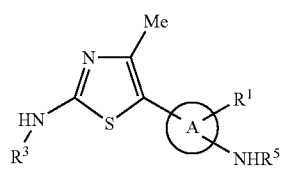

(XI)

wherein Ring A, $R^1$, $R^3$ and $R^5$ are as defined hereinbefore, with an aldehyde of formula $R^8CHO$, wherein $R^8$ is as defined hereinbefore.

(J) For the production of those compounds of formula (I) wherein $R^2$ is $R^6$-$R^7$, and $R^6$ is —N($R^{12}$)—C(=O)—NH—, the reaction, conveniently in the presence of a suitable base as defined hereinafter, of a compound of formula (XII),

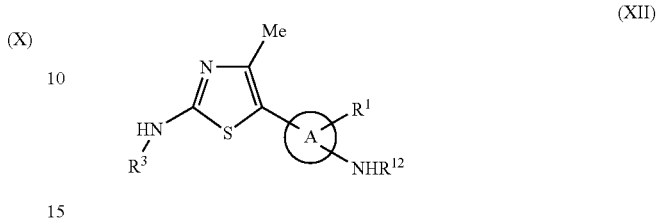

(XII)

wherein Ring A, $R^1$, $R^3$ and $R^{12}$ are as defined hereinbefore, with an isocyanate of formula $R^7NCO$, wherein $R^7$ is as defined hereinbefore.

(K) The reaction, conveniently in the presence of a transition metal catalyst as defined hereinafter and conveniently in the presence of a suitable base as defined hereinafter, of a compound of formula (XIII)

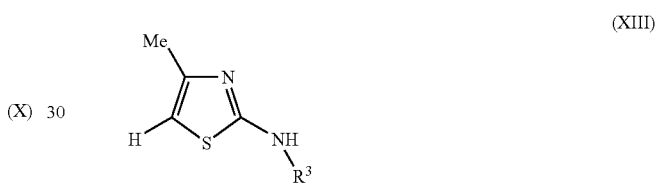

(XIII)

wherein $R^3$ is as defined hereinbefore, with a heteroaryl compound of formula (XIV)

(XIV)

wherein L is a suitable leaving group as defined hereinafter and Ring A, $R^1$ and $R^2$ are as defined hereinbefore.

(L) For the production of those compounds of formula (I) wherein $R^3$ is —(C=O)—$NH_2$ or —(C=O)—(NH)—$R^{23}$, the reaction, conveniently in the presence of a suitable base as defined hereinafter, of a 2-aminothiazole of formula (X)

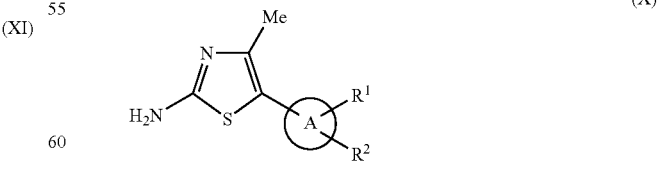

(X)

wherein Ring A, $R^1$, and $R^2$ are as defined hereinbefore, with an isocyanate of formula PG-NCO, wherein PG is a protecting group as defined hereinafter, or with an isocyanate of formula $R^{23}NCO$, wherein $R^{23}$ is as defined hereinbefore.

(M) For the production of those compounds of formula (I) wherein $R^2$ is $R^6$-$R^7$, and $R^6$ is —$SO_2$—, the reaction, conveniently in the presence of a suitable base as defined hereinafter, of a compound of formula (XV),

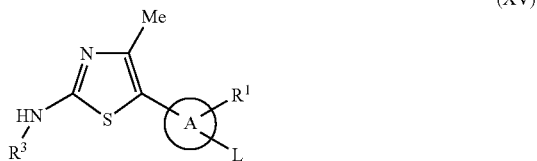

wherein Ring A, $R^1$ and $R^3$ are as defined hereinbefore and L is a suitable leaving group as defined hereinafter (e.g. bromo), with a sulfinic acid of formula $R^7$—$SO_2H$, wherein $R^7$ is as defined hereinbefore.

(N) For the production of those compounds of formula (I) wherein $R^2$ is $R^6$-$R^7$, and $R^6$ is —N($R^9$)—$SO_2$—, the reaction, conveniently in the presence of a suitable base as defined hereinafter, of a compound of formula (XV)

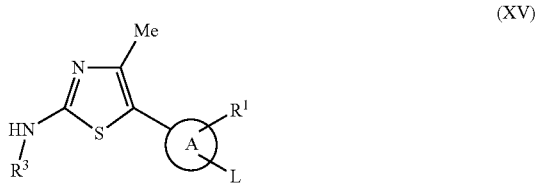

wherein Ring A, $R^1$ and $R^3$ are as defined hereinbefore and L is a suitable leaving group as defined hereinafter (e.g. chloro or bromo), with a sulfonamide of formula $R^7$—$SO_2NH(R^9)$, wherein $R^7$ and $R^9$ are as defined hereinbefore.

The following additional steps may optionally be carried out after any one of process steps (A) to (N):—

(i) the conversion of the compound so obtained to a further compound of the invention of formula (I); and (ii) forming a pharmaceutically acceptable salt of a compound of formula (I).

Process (A) may be carried out using known Suzuki reaction procedures or analogously, e.g. as hereinafter described in the Examples.

A suitable leaving group L is, for example, a halogeno, alkoxy, aryloxy or sulfonyloxy group, for example a chloro, bromo, iodo, methoxy, phenoxy, pentafluorophenoxy, methanesulfonyloxy, trifluoromethylsulfonyloxy or toluene-4-sulfonyloxy group. Preferably, the leaving group is iodo.

A suitable value for the ligands $L^1$ and $L^2$ which are present on the boron atom of the organoboron reagent include, for example, a hydroxy, $C_{1-4}$ alkoxy or $C_{1-6}$ alkyl ligand, for example a hydroxy, methoxy, ethoxy, prop oxy, isopropoxy, butoxy, methyl, ethyl, propyl, isopropyl or butyl ligand. Alternatively the ligands $L^1$ and $L^2$ may be linked such that, together with the boron atom to which they are attached, they form a ring. For example, $L^1$ and $L^2$ together may define an oxy-(2-6C)alkylene-oxy group, for example an oxyethyleneoxy, oxytrimethyleneoxy or —O—$C(CH_3)_2C(CH_3)_2$—O— group such that, together with the boron atom to which they are attached, they form a cyclic boronic acid ester group. Particularly suitable organoboron reagents include, for example, compounds wherein each of $L^1$ and $L^2$ is a hydroxy, a isopropoxy or an ethyl group or $L^1$ and $L^2$ together define a group of formula —O—$C(CH_3)_2C(CH_3)_2$—O—.

The transition metal catalyst may conveniently be a palladium catalyst, for example [1,1'-bis(diphenylphosphino)ferrocene]dichloropalladium.

A suitable transition metal catalyst for the reaction includes, for example, a catalyst such as a palladium(0), palladium(II), nickel(0) or nickel(II) catalyst, for example tetrakis(triphenylphosphine)palladium(0), palladium(II) chloride, palladium(II) bromide, bis(triphenylphosphine)palladium(II) chloride, tris(dibenzylideneacetone)dipalladium(0) tetrakis(triphenylphosphine)nickel(0), nickel(II) chloride, nickel(II) bromide or bis(triphenylphosphine)nickel(II) chloride. Conveniently, the catalyst is [1,1'-bis(diphenylphosphino)ferrocene]dichloropalladium(II). In addition, a free radical initiator may conveniently be added, for example an azo compound such as azo(bisisobutyronitrile). Conveniently, the reaction may be carried out in the presence of a suitable base such as an alkali or alkaline earth metal carbonate or hydroxide, for example sodium bicarbonate, sodium carbonate, potassium bicarbonate, potassium carbonate, calcium carbonate, caesium carbonate, sodium hydroxide or potassium hydroxide, or, for example, an alkali metal alkoxide, for example sodium tert-butoxide, or, for example, an alkali metal amide, for example sodium hexamethyldisilazane, or, for example, an alkali metal hydride, for example sodium hydride.

Conveniently, the process may be carried out in an organic solvent such as 1,4-dioxane in the presence of aqueous alkali metal carbonate. The reaction temperature may be from room temperature to 100° C., conveniently at about 80° C.

Compounds of formula (II) may be prepared by the method described in J. Org. Chem., 1965, 30(4), 1101, or analogously, e.g. as hereinafter described in the Examples.

Compounds of formula (III) are either commercially available or may be prepared by known methods. For example, organoboron reagents of formula (III) may be obtained by the reaction of, for example, an aryl-metal reagent where the metal is, for example, lithium or the magnesium halide portion of a Grignard reagent, with an organoboron compound of the formula L-B($L^1$)($L^2$) wherein L is a leaving group as defined hereinbefore. Preferably the compound of the formula L-B($L^1$)($L^2$) is, for example, a boric acid derivative such as bis(pinacolato)diboron or a tri($C_{1-4}$ alkyl) borate such as tri-isopropyl borate.

Process (B) may be carried out using known procedures for preparation of sulfonamides from sulfonyl derivatives such as sulfonyl chlorides, or analogously, e.g. as hereinafter described in the Examples. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

Conveniently, the process may be carried out in an organic solvent, e.g. 1,4-dioxane or THF. The reaction temperature may be from 0° C. to 100° C., conveniently at about room temperature.

Process (C) may be carried out using known procedures for reaction of amines with sulfonyl derivatives, or analogously, e.g. as hereinafter described in the Examples. A suitable reactive derivative of a sulfonic acid of formula $R^7SO_2L$ is, for example, a sulfonyl halide, for example a sulfonyl chloride formed by the reaction of the sulfonic acid with an inorganic acid chloride, for example thionyl chloride or the product of the reaction of the sulfonic acid with a carbodiimide such as dicyclohexylcarbodiimide (DCCI).

Conveniently, the process may be carried out in an organic basic solvent, e.g. pyridine. The reaction temperature may be from 0° C. to 100° C., conveniently about 45° C.

Process (D) may be carried out using known procedures for reaction of amines with alkyl chlorides, or analogously, e.g. as hereinafter described in the Examples. The process may be carried out in an organic solvent, e.g. tetrahydrofuran (THF). The reaction temperature may be from 0° C. to 65° C., conveniently about room temperature to 50° C.

Process (E) may be carried out using known procedures for reaction of amines with acyl chlorides, or analogously, e.g. as hereinafter described in the Examples. Conveniently, the process may be carried out in an organic basic solvent, e.g. pyridine using a reaction temperature of from 0° C. to 100° C., conveniently about 45° C.

A suitable reactive derivative of a carboxylic acid of formula $R^7CO_2H$ is, for example, an acyl halide, for example an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of the acid with a phenol such as pentafluorophenol, with an ester such as pentafluorophenyl trifluoroacetate or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide (DCCI) or with a uronium compound such as O-(7-azabenzotriazol-1-yl)-N,N,N',N'-tetramethyluronium hexafluorophosphate (HATU).

When process (E) is carried out using known procedures for reaction of amines with carboxylic acids in the presence of a coupling reagent, e.g. DCCI or HATU, the process may be carried out in an organic solvent, e.g. dimethylformamide (DMF) using a reaction temperature of from 0° C. to 100° C., conveniently at about room temperature.

Process (F) may be carried out using known procedures for the synthesis of aminothiazoles, or analogously, e.g. as hereinafter described in the Examples. The leaving group L is conveniently halogen, preferably bromine. Conveniently, the process may be carried out in an organic solvent, e.g. ethanol. The reaction temperature may be from 40° C. to reflux temperature of the solvent, but conveniently about 50° C. to 60° C.

Thiourea compounds of formula (IX) are either commercially available or may be prepared by known methods.

Compounds of formula (VIII) wherein the leaving group L is a halogen may be prepared by reacting a compound of formula (XVI)

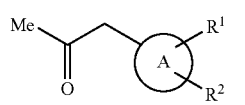

(XVI)

wherein Ring A, $R^1$ and $R^2$ are as hereinbefore defined, with a halogenating agent, e.g. bromine, or analogously, e.g. as hereinafter described in the Examples.

Compounds of formula (XVI) may be prepared by reacting a compound of formula (XVII)

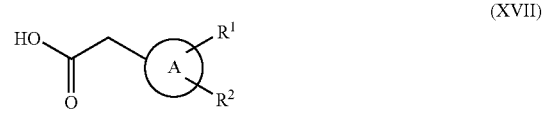

(XVII)

wherein Ring A, $R^1$ and $R^2$ are as hereinbefore defined, with acetic anhydride by the method described in *Chem. Pharm. Bull.*, 1992, 40(12), 3206, or analogously, e.g. as hereinafter described in the Examples. Compounds of formula (XVII) are either commercially available or may be prepared by known methods.

Alternatively, compounds of formula (XVI) may be prepared by reacting a compound of formula (XVIII)

(XVIII)

wherein Ring A, $R^1$ and $R^2$ are as hereinbefore defined with a strong base, e.g. butyllithium, and reacting the organometallic compound so formed with an acetamide, e.g. DMA, or analogously, e.g. as hereinafter described in the Examples. Compounds of formula (XVIII) are either commercially available or may be prepared by known methods.

Process (G) may be carried out by reacting the 2-aminothiazole of formula (X) with, for example, phenyl chloroformate using known procedures for the preparation of carbamates, or analogously, e.g. as hereinafter described in the Examples. The procedure may be carried out in organic solvents, e.g. THF and/or DMF, in the presence of an organic base, e.g. pyridine. The reaction temperature may be from 0° C. to 50° C., conveniently about room temperature. The resulting carbamate can be reacted with an amine of formula $HNR^{23}$ using known procedures for the preparation of ureido derivatives, or analogously, e.g. as hereinafter described in the Examples. The procedure may be carried out in an organic solvent, e.g. dimethylsulfoxide (DMSO). The reaction temperature may be from 0° C. to 50° C., conveniently about room temperature.

A suitable chemical equivalent of phosgene is, for example, a compound of formula

L'-CO-L"

wherein L' and L" are suitable leaving groups as defined hereinbefore. For example, a suitable leaving group L' or L" is, for example, a halogeno, alkoxy, aryloxy or sulphonyloxy group, for example a chloro, methoxy, phenoxy, methanesulfonyloxy or toluene-4-sulfonyloxy group. For example, a suitable chemical equivalent of phosgene is a formic acid derivative such as phenyl chloroformate. Alternatively, a suitable chemical equivalent of phosgene is a carbonate derivative such as disuccinimido carbonate.

The compound of formula (X) may be prepared by hydrolysing the corresponding 2-alkanoamidothiazoles (e.g. compound XIX, where $R^{25}$ is $C_1$-$C_6$ alkyl, preferably methyl), or analogously, e.g. as hereinafter described in the Examples.

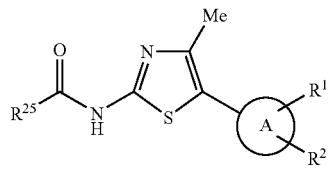

The process may be carried out in a mixture of aqueous hydrochloric acid and an organic solvent, e.g. ethanol. The reaction temperature may be elevated, conveniently to the reflux temperature of the mixture.

Process (H) may be carried out by reacting the 2-aminothiazole of formula (X) using known procedures for the reaction of amines with acyl chlorides, or analogously, e.g. as hereinafter described in the Examples. The process may be carried-out in an organic basic solvent, e.g. pyridine. The reaction temperature may be from 0° C. to 100° C., conveniently about 45° C. Alternatively, the amine of formula (X) may be reacted using known procedures for reaction of amines with a reactive derivative of a carboxylic acid, or analogously, e.g. as hereinafter described in the Examples. The process may be carried out in an organic solvent, e.g. DMF, in the presence of a coupling agent, for example DCCI or HATU. The reaction temperature may be from 0° C. to 100° C., conveniently about 45° C. The 2-aminothiazole of formula (X) may be prepared as described above.

Process (I) may be carried out using known procedures for the reductive amination of aldehydes, for example in the presence of a reducing agent, e.g. sodium cyanoborohydride, and a carboxylic acid, e.g. acetic acid, or analogously, e.g. as hereinafter described in the Examples. The process may be carried out in an organic solvent, e.g. N-methylpyrrolidin-2-one (NMP). The reaction temperature may be from 0° C. to 100° C., conveniently about room temperature.

Other suitable reducing agents for the reductive amination reaction include, for example, a hydride reducing agent, for example an alkali metal aluminium hydride such as lithium aluminium hydride or, preferably, an alkali metal borohydride such as sodium borohydride, sodium triethylborohydride, sodium trimethoxyborohydride and sodium triacetoxyborohydride. The reaction is conveniently performed in a suitable inert solvent, or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride.

Process (J) may be carried out using known procedures for reaction of amines with isocyanates, or analogously, e.g. as hereinafter described in the Examples. The process may be carried out in an organic solvent, e.g. THF. The reaction temperature may be from 0° C. to 65° C., conveniently about room temperature.

Process (K) may be carried out using known reaction procedures or analogously, e.g. as hereinafter described in the Examples.

A suitable transition metal catalyst for the reaction is, for example, a catalyst such as a palladium(0), palladium(II), nickel(0) or nickel(II) catalyst, for example tetrakis(triphenylphosphine)palladium(0), palladium(II) chloride, palladium(II) bromide, bis(triphenylphosphine)palladium(II) chloride, tris(dibenzylideneacetone)dipalladium(0) tetrakis(triphenylphosphine)nickel(0), nickel(II) chloride, nickel(II) bromide or bis(triphenylphosphine)nickel(II) chloride. Conveniently, the transition metal catalyst is a palladium catalyst, for example palladium(II) acetate.

Conveniently, a phosphine ligand for the transition metal is present, for example triphenylphosphine, tributylphosphine or 4,5-bis(diphenylphosphino)-9,9-dimethylxanthene. More conveniently, the phosphine ligand is tri-tert-butylphosphine.

A suitable base for the reaction is an alkali or alkaline earth metal carbonate or hydroxide, for example sodium bicarbonate, sodium carbonate, potassium bicarbonate, potassium carbonate, calcium carbonate, caesium carbonate, sodium hydroxide or potassium hydroxide. Conveniently, the reaction is carried out in the presence of caesium fluoride.

Conveniently, the process may be carried out in an organic solvent such as DMSO and the reaction temperature may be from about 60° C. to 200° C., conveniently at about 130° C. to 150° C.

Process (L) may be carried out using known procedures for reaction of amines with isocyanates, or analogously, e.g. as hereinafter described in the Examples. The process may be carried out in an organic solvent, e.g. THF, DME or DMF. The reaction temperature may be from 0° C. to 65° C., conveniently about room temperature. For less reactive isocyanates, the reaction temperature may be from 50° C. to 150° C., conveniently about 120° C.

In an isocyanate of formula PG-NCO, wherein PG is a protecting group, a suitable protecting group is, for example, a trialkylsilyl (e.g. trimethylsilyl or tert-butyldimethylsilyl) group or an alkanoyl (e.g. 2,2,2-trichloroacetyl or acetyl) group which may be removed when required using conventional reaction conditions.

Process (M) may be carried out using known procedures for reaction of a sulfinic acid with a heteroaryl halide, or analogously, e.g. as hereinafter described in the Examples. Conveniently, the reaction is catalysed using a metal salt such as a copper (I) halide (e.g. cuprous iodide). Further, conveniently, the reaction may be carried out in the presence of a suitable phosphine ligand (e.g. 4,5-bis(diphenylphosphino)-9,9-dimethylxanthene) and a suitable transition metal catalyst (e.g. tris(dibenzylideneacetone)dipalladium(0)). The process may be carried out in an organic solvent, e.g. DMSO or DMF. The reaction temperature may be from about 50° C. to 150° C., conveniently about 120° C.

Process (N) may be carried out using known procedures for reaction of a sulfonamide with a heteroaryl halide, or analogously, e.g. as hereinafter described in the Examples. Conveniently, the reaction is catalysed using a metal salt such as a copper (I) halide (e.g. cuprous iodide). The process may be carried out in an organic solvent, e.g. DMA, DME or DMF. The reaction temperature may be from 100° C. to 250° C., conveniently about 150° C. to 200° C.

The compounds of formula (I) in free or salt form can be isolated from reaction mixtures and purified in conventional manner.

It will be appreciated by those skilled in the art that in the processes of the present invention certain functional groups such as hydroxy, carboxyl or amino groups in the starting reagents or intermediate compounds may need to be protected by protecting groups. Thus, the preparation of the compounds of formula (I) may involve at a certain stage the removal of one or more protecting groups. For example, where necessary, functional groups on compounds of formulae (II) to (XII) may be protected by one or more protecting groups.

The protection and deprotection of functional groups is described in 'Protective Groups in Organic Synthesis', 2nd edition, T. W. Greene and P. G. M. Wuts, Wiley-Interscience (1991) and 'Protecting Groups', P. J. Kocienski, Georg Thieme Verlag (1994).

For example, protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain $C_{1-12}$ alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and $C_{2-6}$ alkenyl groups (for example alkyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example alkyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The compounds of formula (I) above may be converted to a pharmaceutically acceptable salt thereof as defined hereinbefore.

Many of the intermediates defined herein are novel and these are provided as a further feature of the invention. For example, many compounds of formulae V, VI, VII, X, XI and XII are novel compounds.

Biological Assays

The following assays can be used to measure the effects of the compounds of the present invention as PI3 kinase inhibitors, as mTOR PI kinase-related kinase inhibitors, as inhibitors in vitro of the activation of PI3 kinase signalling pathways, as inhibitors in vitro of the proliferation of MDA-MB-468 human breast adenocarcinoma cells, and as inhibitors in vivo of the growth in nude mice of xenografts of MDA-MB-468 carcinoma tissue.

(a) In Vitro PI3K Enzyme Assay

The assay used AlphaScreen technology (Gray et al., *Analytical Biochemistry*, 2003, 313: 234-245) to determine the ability of test compounds to inhibit phosphorylation by recombinant Type I PI3K enzymes of the lipid PI(4,5)P2.

DNA fragments encoding human PI3K catalytic and regulatory subunits were isolated from cDNA libraries using standard molecular biology and PCR cloning techniques. The selected DNA fragments were used to generate baculovirus expression vectors. In particular, full length DNA of each of the p110α, p110β and p110δ Type Ia human PI3K p110 isoforms (EMBL Accession Nos. HSU79143, S67334, Y10055 for p110α, p110β and p110δ respectively) were sub-cloned into a pDEST10 vector (Invitrogen Limited, Fountain Drive, Paisley, UK). The vector is a Gateway-adapted version of Fastbac1 containing a 6-His epitope tag. A truncated form of Type Ib human PI3K p110γ isoform corresponding to amino acid residues 144-1102 (EMBL Accession No. X8336A) and the full length human p85α regulatory subunit (EMBL Accession No. HSP13KIN) were also sub-cloned into pFastBac1 vector containing a 6-His epitope tag. The Type Ia p110 constructs were co-expressed with the p85α regulatory subunit. Following expression in the baculovirus system using standard baculovirus expression techniques, expressed proteins were purified using the His epitope tag using standard purification techniques.

DNA corresponding to amino acids 263 to 380 of human general receptor for phosphoinositides (Grp1) PH domain was isolated from a cDNA library using standard molecular biology and PCR cloning techniques. The resultant DNA fragment was sub-cloned into a pGEX 4T1 *E. coli* expression vector containing a GST epitope tag (Amersham Pharmacia Biotech, Rainham, Essex, UK) as described by Gray et al., *Analytical Biochemistry*, 2003, 313: 234-245). The GST-tagged Grp1 PH domain was expressed and purified using standard techniques.

Test compounds were prepared as 10 nM stock solutions in DMSO and diluted into water as required to give a range of final assay concentrations. Aliquots (2 µl) of each compound dilution were placed into a well of a Greiner 384-well low volume (LV) white polystyrene plate (Greiner Bio-one, Brunel Way, Stonehouse, Gloucestershire, UK Catalogue No. 784075). A mixture of each selected recombinant purified PI3K enzyme (15 ng), DiC8-PI(4,5)P2 substrate (40 µM; Cell Signals Inc., Kinnear Road, Columbus, USA, Catalogue No. 901), adenosine triphosphate (ATP; 4 µM) and a buffer solution [comprising Tris-HCl pH7.6 buffer (40 mM, 10 µl), 3-[(3-cholamidopropyl)dimethylammonio]-1-propane-sulphonate (CHAPS; 0.04%), dithiothreitol (DTT; 2 mM) and magnesium chloride (10 mM)] was agitated at room temperature for 20 minutes.

Control wells that produced a minimum signal corresponding to maximum enzyme activity were created by using 5% DMSO instead of test compound. Control wells that produced a maximum signal corresponding to fully inhibited enzyme were created by adding wortmannin (6 µM; Calbiochem/Merck Bioscience, Padge Road, Beeston, Nottingham, UK, Catalogue No. 681675) instead of test compound. These assay solutions were also agitated for 20 minutes at room temperature.

Each reaction was stopped by the addition of 10 µl of a mixture of EDTA (100 mM), bovine serum albumin (BSA; 0.045%) and Tris-HCl pH7.6 buffer (40 mM).

Biotinylated-DiC8-PI(3,4,5)P3 (50 nM; Cell Signals Inc., Catalogue No. 107), recombinant purified GST-Grp1 PH protein (2.5 nM) and AlphaScreen Anti-GST donor and acceptor beads (100 ng; Packard Bioscience Limited, Station Road, Pangbourne, Berkshire, UK, Catalogue No. 6760603M) were added and the assay plates were left for about 5 to 20 hours at room temperature in the dark. The resultant signals arising from laser light excitation at 680 nm were read using a Packard AlphaQuest instrument.

PI(3,4,5)P3 is formed in situ as a result of PI3K mediated phosphorylation of PI(4,5)P2. The GST-Grp1 PH domain protein that is associated with AlphaScreen Anti-GST donor beads forms a complex with the biotinylated PI(3,4,5)P3 that is associated with Alphascreen Streptavidn acceptor beads. The enzymatically-produced PI(3,4,5)P3 competes with biotinylated PI(3,4,5)P3 for binding to the PH domain protein. Upon laser light excitation at 680 nm, the donor bead:acceptor bead complex produces a signal that can be measured. Accordingly, PI3K enzyme activity to form PI(3,4,5)P3 and subsequent competition with biotinylated PI(3,4,5)P3 results in a reduced signal. In the presence of a PI3K enzyme inhibitor, signal strength is recovered.

PI3K enzyme inhibition for a given test compound was expressed as an $IC_{50}$ value.

Thereby, the inhibitory properties of compounds of formula (I) against PI3K enzymes, such as the Class Ia PI3K enzymes (e.g. PI3Kalpha, PI3Kbeta and PI3Kdelta) and the Class Ib PI3K enzyme (PI3Kgamma) may be demonstrated.

In addition, the inhibitory properties of compounds of formula (I) against PI3K enzymes, such as the Class Ia PI3K enzymes (e.g. PI3Kalpha, PI3Kbeta and PI3Kdelta) and the Class Ib PI3K enzyme (PI3Kgamma) may be demonstrated using the modified test procedures set out in the experimental section hereinafter.

(b) In Vitro mTOR PI Kinase-Related Kinase Assay

The assay used AlphaScreen technology (Gray et al., *Analytical Biochemistry*, 2003, 313: 234-245) to determine the ability of test compounds to inhibit phosphorylation by recombinant mTOR.

A C-terminal truncation of mTOR encompassing amino acid residues 1362 to 2549 of mTOR (EMBL Accession No. L34075) was stably expressed as a FLAG-tagged fusion in HEK293 cells as described by Vilella-Bach et al., *Journal of Biochemistry*, 1999, 274, 4266-4272. The HEK293 FLAG-tagged mTOR (1362-2549) stable cell line was routinely maintained at 37° C. with 5% $CO_2$ up to a confluency of 70-90% in Dulbecco's modified Eagle's growth medium (DMEM; Invitrogen Limited, Paisley, UK Catalogue No. 41966-029) containing 10% heat-inactivated foetal calf serum (FCS; Sigma, Poole, Dorset, UK, Catalogue No. F0392), 1% L-glutamine (Gibco, Catalogue No. 25030-024) and 2 mg/ml Geneticin (G418 sulphate; Invitrogen Limited, UK Catalogue No. 10131-027). Following expression in the mammalian HEK293 cell line, expressed protein was purified using the FLAG epitope tag using standard purification techniques.

Test compounds were prepared as 10 mM stock solutions in DMSO and diluted into water as required to give a range of final assay concentrations. Aliquots (2 µl) of each compound dilution were placed into a well of a Greiner 384-well low volume (LV) white polystyrene plate (Greiner Bio-one). A 30 µl mixture of recombinant purified mTOR enzyme, 1 µM biotinylated peptide substrate (Biotin-Ahx-Lys-Lys-Ala-Asn-Gln-Val-Phe-Leu-Gly-Phe-Thr-Tyr-Val-Ala-Pro-Ser-Val-Leu-Glu-Ser-Val-Lys-Glu-$NH_2$; Bachem UK Ltd), ATP (20 µM) and a buffer solution [comprising Tris-HCl pH7.4 buffer (50 mM), EGTA (0.1 mM), bovine serum albumin (0.5 mg/mil), DTT (1.25 mM) and manganese chloride (10 mM)] was agitated at room temperature for 90 minutes.

Control wells that produced a maximum signal corresponding to maximum enzyme activity were created by using 5% DMSO instead of test compound. Control wells that produced a minimum signal corresponding to fully inhibited enzyme were created by adding EDTA (83 mM) instead of test compound. These assay solutions were incubated for 2 hours at room temperature.

Each reaction was stopped by the addition of 10 µl of a mixture of EDTA (50 mM), bovine serum albumin (BSA; 0.5 mg/ml) and Tris-HCl pH7.4 buffer (50 mM) containing p70 S6 Kinase (T389) 1A5 Monoclonal Antibody (Cell Signalling Technology, Catalogue No. 9206B) and AlphaScreen Streptavidin donor and Protein A acceptor beads (200 ng; Perkin Elmer, Catalogue No. 6760002B and 6760137R respectively) were added and the assay plates were left for about 20 hours at room temperature in the dark. The resultant signals arising from laser light excitation at 680 nm were read using a Packard Envision instrument.

Phosphorylated biotinylated peptide is formed in situ as a result of mTOR mediated phosphorylation. The phosphorylated biotinylated peptide that is associated with AlphaScreen Streptavidin donor beads forms a complex with the p70 S6 Kinase (T389) 1A5 Monoclonal Antibody that is associated with Alphascreen Protein A acceptor beads. Upon laser light excitation at 680 nm, the donor bead: acceptor bead complex produces a signal that can be measured. Accordingly, the presence of mTOR kinase activity results in an assay signal. In the presence of an mTOR kinase inhibitor, signal strength is reduced.

mTOR enzyme inhibition for a given test compound was expressed as an $IC_{50}$ value.

(c) In Vitro phospho-Ser473 Akt Assay

This assay determines the ability of test compounds to inhibit phosphorylation of Serine 473 in Akt as assessed using Acumen Explorer technology (Acumen Bioscience Limited), a plate reader that can be used to rapidly quantitate features of images generated by laser-scanning.

A MDA-MB-468 human breast adenocarcinoma cell line (LGC Promochem, Teddington, Middlesex, UK, Catalogue No. HTB-132) was routinely maintained at 37° C. with 5% $CO_2$ up to a confluency of 70-90% in DMEM containing 10% heat-inactivated FCS and 1% L-glutamine.

For the assay, the cells were detached from the culture flask using 'Accutase' (Innovative Cell Technologies Inc., San Diego, Calif., USA; Catalogue No. AT104) using standard tissue culture methods and resuspended in media to give $1.7 \times 10^5$ cells per ml. Aliquots (90 μl) were seeded into each of the inner 60 wells of a black Packard 96 well plate (PerkinElmer, Boston, Mass., USA; Catalogue No. 6005182) to give a density of ~15000 cells per well. Aliquots (90 μl) of culture media were placed in the outer wells to prevent edge effects. The cells were incubated overnight at 37° C. with 5% $CO_2$ to allow them to adhere.

On day 2, the cells were treated with test compounds and incubated for 2 hours at 37° C. with 5% $CO_2$. Test compounds were prepared as 10 mM stock solutions in DMSO and serially diluted as required with growth media to give a range of concentrations that were 10-fold the required final test concentrations. Aliquots (10 μl) of each compound dilution were placed in a well (in triplicate) to give the final required concentrations. As a minimum response control, each plate contained wells having a final concentration of 100 μM LY294002 (Calbiochem, Beeston, UK, Catalogue No. 440202). As a maximum response control, wells contained 1% DMSO instead of test compound. Following incubation, the contents of the plates were mixed by treatment with a 1.6% aqueous formaldehyde solution (Sigma, Poole, Dorset, UK, Catalogue No. F1635) at room temperature for 1 hour.

All subsequent aspiration and wash steps were carried out using a Tecan 96 well late washer (aspiration speed 10 mm/sec). The fixing solution was removed and the contents of the plates were washed with phosphate-buffered saline (PBS; 50 μl; Gibco, Catalogue No. 10010015). The contents of the plates were treated for 10 minutes at room temperature with an aliquot (50 μl) of a cell permeabilisation buffer consisting of a mixture of PBS and 0.5% Tween-20. The 'permeabilisation' buffer was removed and non-specific binding sites were blocked by treatment for 1 hour at room temperature of an aliquot (50 μl) of a blocking buffer consisting of 5% dried skimmed milk ['Marvel' (registered trade mark); Premier Beverages, Stafford, GB] in a mixture of PBS and 0.05% Tween-20. The 'blocking' buffer was removed and the cells were incubated for 1 hour at room temperature with rabbit anti phospho-Akt (Ser473) antibody solution (50 μl per well; Cell Signalling, Hitchin, Herts, U.K., Catalogue No 9277) that had been diluted 1:500 in 'blocking' buffer. Cells were washed three times in a mixture of PBS and 0.05% Tween-20. Subsequently, cells were incubated for 1 hour at room temperature with Alexafluor488 labelled goat anti-rabbit IgG (50l per well; Molecular Probes, Invitrogen Limited, Paisley, UK, Catalogue No. A11008) that had been diluted 1:500 in 'blocking' buffer. Cells were washed 3 times with a mixture of PBS and 0.05% Tween-20. An aliquot of PBS (50 μl) was added to each well and the plates were sealed with black plate sealers and the fluorescence signal was detected and analysed.

Fluorescence dose response data obtained with each compound were analysed and the degree of inhibition of Serine 473 in Akt was expressed as an $IC_{50}$ value.

(d) In Vitro MDA-MB-468 Human Breast Adenocarcinoma Proliferation Assay

This assay determines the ability of test compounds to inhibit cell proliferation as assessed using Cellomics Arrayscan technology. A MDA-MB-468 human breast adenocarcinoma cell line (LGC Promochem, Catalogue No. HTB-132) was routinely maintained as described in Biological Assay (b) hereinbefore.

For the proliferation assay, the cells were detached from the culture flask using Accutase and seeded into the inner 60 wells of a black Packard 96 well plate at a density of 8000 cells per well in 100 μl of complete growth media. The outer wells contained 100 μl of sterile PBS. The cells were incubated overnight at 37° C. with 5% $CO_2$ to allow them to adhere.

On day 2, the cells were treated with test compounds and incubated for 48 hours at 37° C. with 5% $CO_2$. Test compounds were prepared as 10 mM stock solutions in DMSO and serially diluted as required with growth media to give a range of test concentrations. Aliquots (50 μl) of each compound dilution were placed in a well and the cells were incubated for 2 days at 37° C. with 5% $CO_2$. Each plate contained control wells without test compound.

On day 4, BrdU labelling reagent (Sigma, Catalogue No. B9285) at a final dilution of 1:1000 was added and the cells were incubated for 2 hours at 37° C. The medium was removed and the cells in each well were fixed by treatment with 100 μl of a mixture of ethanol and glacial acetic acid (90% ethanol, 5% glacial acetic acid and 5% water) for 30 minutes at room temperature. The cells in each well were washed twice with PBS (100 μl). Aqueous hydrochloric acid (2M, 100 μl) was added to each well. After 20 minutes at room temperature, the cells were washed twice with PBS. Hydrogen peroxide (3%, 50 μl; Sigma, Catalogue No. H1009) was added to each well. After 10 minutes at room temperature, the wells were washed again with PBS.

BrdU incorporation was detected by incubation for 1 hour at room temperature with mouse anti-BrdU antibody (50 μl; Caltag, Burlingame, Calif., US; Catalogue No. MD5200) that was diluted 1:40 in PBS containing 1% BSA and 0.05% Tween-20. Unbound antibody was removed with two washes of PBS. For visualisation of incorporated BrdU, the cells were treated for 1 hour at room temperature with PBS (50 μl) and 0.05% Tween-20 buffer containing a 1:1000 dilution of Alexa fluor 488-labelled goat anti-mouse IgG. For visualisation of the cell nucleus, a 1:1000 dilution of Hoechst stain (Molecular Probes, Catalogue No. H3570) was added. Each plate was washed in turn with PBS. Subsequently, PBS (100 μl) was added to each well and the plates were analysed using a Cellomics array scan to assess total cell number and number of BrdU positive cells.

Fluorescence dose response data obtained with each compound were analysed and the degree of inhibition of MDA-MB-468 cell growth was expressed as an $IC_{50}$ value.

(e) In Vivo MDA-MB-468 Xenograft Growth Assay

This test measures the ability of compounds to inhibit the growth of MDA-MB-468 human breast adenocarcinoma cells grown as a tumour in athymic nude mice (Alderley Park nu/nu strain). A total of about $5 \times 10^6$ MDA-MB-468 cells in matrigel (Beckton Dickinson Catalogue No. 40234) are injected subcutaneously into the left flank of each test mouse and the resultant tumours are allowed to grow for about 14 days. Tumour size is measured twice weekly using callipers and a theoretical volume is calculated. Animals are selected to provide control and treatment groups of approximately equal average tumour volume. Test compounds are prepared as a ball-milled suspension in 1% polysorbate vehicle and dosed orally once daily for a period of about 28 days. The effect on tumour growth is assessed.

Although the pharmacological properties of the compounds of formula (I) vary with structural change as expected, in general, activity possessed by compounds of formula (I) may be demonstrated at the following concentrations or doses in one or more of the above tests (a) to (e):—

Test (a):—$IC_{50}$ versus p110γ Type Ib human PI3K in the range, for example, 0.001-5 μM ($IC_{50}$ 0.001-0.5 μM for many compounds) and $IC_{50}$ versus p110α Type Ia human PI3K in the range, for example, 0.001-5 µM ($IC_{50}$ 0.001-0.5 µM for many compounds);

Test (b):—$IC_{50}$ versus mTOR PI kinase-related kinase in the range, for example, 0.001-5 µM ($IC_{50}$ 0.001-0.5 µM for many compounds);

Test (c):—$IC_{50}$ versus Serine-473 in Akt in the range, for example, 0.001-10 µM ($IC_{50}$ 0.001-1 µM for many compounds);

Test (d):—$IC_{50}$ in the range, for example, 0.01-20 µM;

Test (e):—activity in the range, for example, 1-200 mg/kg/day.

For example:—

(i) the thiazole compound disclosed within Example 13 possesses activity in Test (a) with an $IC_{50}$ versus p110α PI3K of approximately 0.01 µM, in Test (b) with an $IC_{50}$ versus mTOR PI kinase-related kinase of approximately 0.0 µM, and in Test (c) with an $IC_{50}$ versus Serine 473 in Akt of approximately 0.02 µM;

(ii) the thiazole compound disclosed within Example 28 possesses activity in Test (a) with an $IC_{50}$ versus p110α PI3K of approximately 0.01 µM, in Test (b) with an $IC_{50}$ versus mTOR PI kinase-related kinase of approximately 0.02 µM, and in Test (c) with an $IC_{50}$ versus Serine 473 in Akt of approximately 0.3 µM;

(iii) the thiazole compound disclosed as Compound No. 4 within Example 73 possesses activity in Test (a) with an $IC_{50}$ versus p110α PI3K of approximately 0.03 µM, in Test (b) with an $IC_{50}$ versus mTOR PI kinase-related kinase of approximately 0.7 µM, and in Test (c) with an $IC_{50}$ versus Serine 473 in Akt of approximately 0.2 µM; and (iv) the thiazole compound disclosed as Compound No. 3 within Example 79 possesses activity in Test (a) with an $IC_{50}$ versus p110α PI3K of approximately 0.2 µM, in Test (b) with an $IC_{50}$ versus mTOR PI kinase-related kinase of approximately 2 µM, and in Test (c) with an $IC_{50}$ versus Serine 473 in Akt of approximately 0.2 µM.

No untoward toxicological effects are expected when a compound of formula (I), or a pharmaceutically acceptable salt thereof, as defined hereinbefore is administered at the dosage ranges defined hereinafter.

The compound of formula (I), or a pharmaceutically acceptable salt thereof, may be used on its own but will generally be administered in the form of a pharmaceutical composition in which the compound of formula (I), or a pharmaceutically acceptable salt thereof, is in association with a pharmaceutically acceptable adjuvant, diluent or carrier.

The amount of active ingredient that is combined with one or more excipients to produce a single dosage form will necessarily vary depending upon the host treated and the particular route of administration. Depending on the mode of administration, the pharmaceutical composition will preferably comprise from 0.05 to 99% percent by weight, more preferably from 0.05 to 80% percent by weight, still more preferably from 0.1 to 70% percent by weight, and even more preferably from 0.1 to 50% percent by weight, of active ingredient, all percentages by weight being based on total composition. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients.

The compositions of the invention may be obtained by conventional procedures using conventional pharmaceutical excipients that are well known in the art. Thus, compositions intended for oral use may contain, for example, one or more colouring, sweetening, flavouring and/or preservative agents.

The invention further provides a process for the preparation of a pharmaceutical composition of the invention which comprises mixing a compound of formula (I), or a pharmaceutically acceptable salt thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, polyfluoroalkane aerosols and dry powder formulations, or systemically, e.g. by oral administration in the form of tablets, capsules, syrups, powders or granules, or by parenteral administration in the form of solutions or suspensions (for example as a sterile aqueous or oily solution for intravenous, subcutaneous, intraperitoneal or intramuscular dosing) or by rectal administration in the form of suppositories. Preferably the compound of the invention is administered orally.

The compounds of the present invention are advantageous in that they possess pharmacological activity. In particular, the compounds of the present invention modulate (in particular, inhibit) phosphatidylinositol-3-kinase (PI3K) enzymes, such as the Class Ia PI3K enzymes (e.g. PI3Kalpha, PI3Kbeta and PI3Kdelta) and the Class Ib PI3K enzyme (PI3Kgamma). In addition, the compounds of the present invention modulate (in particular, inhibit) mTOR phosphatidylinositol (PI) kinase-related kinases. The inhibitory properties of compounds of formula (I) may be demonstrated using the test procedures set out hereinbefore and in the experimental section. Accordingly, the compounds of formula (I) may be used in the treatment (therapeutic or prophylactic) of conditions/diseases in human and non-human animals which are exacerbated or caused by excessive or dysregulated production of PI3 kinase enzymes and/or mTOR PI kinase-related kinases.

In a further aspect, the present invention provides a thiazole of formula (I), or a pharmaceutically acceptable salt thereof, as hereinbefore defined for use in therapy. It will be appreciated that, in the context of the present specification, the term "therapy" also includes "prophylaxis" unless there are specific indications to the contrary. The terms "therapeutic" and "therapeutically" should be construed accordingly.

A compound of the invention, or a pharmaceutically acceptable salt thereof, can be used in the treatment of:—

(i) respiratory tract diseases: for example obstructive diseases of the airways including: asthma and bronchial, allergic, non-allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; eosinophilia, hypersensitivity pneumonitis; lung fibrosis, including cryptogenic fibrosing alveolitis, idiopathic interstitial pneumonias, fibrosis complicating antineoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

(ii) bone and joint diseases: for example arthritides associated with or including osteoarthritis/osteoarthrosis, both primary and secondary to e.g. congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behçet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

(iii) skin diseases: for example psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus and atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; and drug-induced disorders including fixed drug eruptions;

(iv) diseases of the eyes: for example blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; and infections including viral, fungal, and bacterial;

(v) diseases of the gastrointestinal tract: for example glossitis, gingivitis, periodontitis; oesophagitis, including reflux; eosinophilic gastro-enteritis, inflammatory bowel disease, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

(vi) abdominal diseases: for example hepatitis, including autoimmune, alcoholic and viral; fibrosis and cirrhosis of the liver; cholecystitis; pancreatitis, both acute and chronic;

(vii) genitourinary diseases: for example nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; and erectile dysfunction (both male and female);

(viii) allograft rejection: for example acute and chronic rejection following, for example, transplantation of the kidney, heart, liver, lung, bone marrow, skin or cornea or following blood transfusion; or chronic graft versus host disease;

(ix) diseases of the CNS: for example Alzheimer's disease and other demention disorders including CJD and mCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumour invasion, neuropathic pain syndromes including diabetic, post-herpetic, and HIV-associated neuropathies; neurosarcoidosis; and central and peripheral nervous system complications of malignant, infectious or autoimmune processes;

(x) other auto-immune and allergic disorders: for example Hashimoto's thyroiditis, Graves' disease, Addison's disease, diabetes mellitus, idiopathic thrombocytopaenic purpura, eosinophilic fasciitis, hyper-IgE syndrome and antiphospholipid syndrome;

(xi) other disorders with an inflammatory or immunological component: for example acquired immune deficiency syndrome (AIDS), leprosy, Sezary syndrome and paraneoplastic syndromes;

(xii) cardiovascular diseases: for example atherosclerosis affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (e.g. syphilitic); vasculitides; and disorders of the proximal and peripheral veins including phlebitis and thrombosis, including deep vein thrombosis and complications of varicose veins, heart failure, myocardial contractility disorder, cardiac hypertrophy, cardiac myocyte dysfunction, stroke, thromboembolism and ischemic reperfusion injury; and (xiii) diseases of metabolism: for example diabetes and obesity.

In another aspect, the invention provides a method of treating a disease or condition mediated by a PI3K enzyme (such as a Class Ia PI3K enzyme or a Class Ib PI3K enzyme) and/or a mTOR kinase (such as a mTOR PI kinase-related kinase) which comprises administering to a patient in need of such treatment an effective amount of a compound of formula (I), or a pharmaceutically acceptable salt thereof.

In another aspect, the invention provides the use of a compound of formula (I), or a pharmaceutically acceptable salt thereof, in the manufacture of a medicament for use in providing a PI3K enzyme inhibitory effect (such as a Class Ia PI3K enzyme or a Class Ib PI3K enzyme inhibitory effect) and/or a mTOR kinase inhibitory effect (such as a mTOR PI kinase-related kinase inhibitory effect).

In a further aspect, the invention provides the use of a compound as defined by formula (I), or a pharmaceutically acceptable salt thereof, in the manufacture of a medicament for treatment of respiratory diseases, allergies, osteoarthritis, rheumatic disorders, Crohn's disease, psoriasis, ulcerative colitis, cancer, heart failure, septic shock, atherosclerosis, diabetes, obesity, restenosis, and allograft rejection resulting from transplants.

The invention also provides a method of treating an obstructive airways disease (e.g. asthma or COPD) which comprises administering to a patient a therapeutically effective amount of a compound of formula (I), or a pharmaceutically acceptable salt thereof, as hereinbefore defined.

The compounds of the present invention may be used as pharmaceuticals for use in the treatment of inflammatory disorders such as rheumatoid arthritis, osteoarthritis, asthma and chronic obstructive pulmonary disease (COPD). Accordingly, the present invention provides the use of a compound of formula (I), or a pharmaceutically acceptable salt thereof, in the manufacture of a medicament for use in the treatment of an inflammatory disorder.

The present invention further provides a method of treating an inflammatory disorder (e.g. rheumatoid arthritis, osteoarthritis, asthma or chronic obstructive pulmonary disease) which comprises administering to a patient a therapeutically effective amount of a compound of formula (I), or a pharmaceutically acceptable salt thereof, as hereinbefore defined.

As stated above, it is known that PI3K enzymes and mTOR kinases contribute to tumourigenesis by one or more of the effects of mediating proliferation of cancer and other cells, mediating angiogenic events and mediating the motility, migration and invasiveness of cancer cells.

Accordingly, the compounds of the present invention are of value as anti-tumour agents, in particular as inhibitors of the proliferation, survival, motility, dissemination and invasiveness of mammalian cancer cells leading to inhibition of tumour growth and survival and to inhibition of metastatic tumour growth. Particularly, the compounds of the present invention are of value as anti-proliferative and anti-invasive agents in the containment and/or treatment of solid tumour disease.

Particularly, the compounds of the present invention are expected to be useful in the prevention or treatment of those tumours which are sensitive to inhibition of one or more of the multiple PI3K enzymes (such as the Class Ia PI3K enzymes and the Class Ib PI3K enzyme) that are involved in the signal transduction steps which lead to the proliferation and survival of tumour cells and the migratory ability and invasiveness of metastasising tumour cells. Further, the compounds of the present invention are expected to be useful in the prevention or treatment of those tumours which are mediated alone or in part by inhibition of a PI3K enzyme (such as the Class Ia PI3K enzymes and the Class Ib PI3K enzyme), i.e. the compounds may be used to produce a PI3K enzyme inhibitory effect in a patient in need of such treatment.

Further, the compounds of the present invention are expected to be useful in the prevention or treatment of those tumours which are sensitive to inhibition of a mTOR kinase (such as a mTOR PI kinase-related kinase) that are involved in the signal transduction steps which lead to the proliferation and survival of tumour cells and the migratory ability and invasiveness of metastasising tumour cells. Further, the compounds of the present invention are expected to be useful in the prevention or treatment of those tumours which are mediated alone or in part by inhibition of a mTOR kinase (such as a mTOR PI kinase-related kinase), i.e. the compounds may be used to produce a mTOR kinase inhibitory effect in a patient in need of such treatment.

As stated hereinbefore, inhibitors of a PI3K enzyme and/or inhibitors of mTOR kinase should be of therapeutic value for treatment of cell proliferative disorders, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including acute lymphoctic leukaemia (ALL) and chronic myelogenous leukaemia (CML)], multiple myeloma and lymphomas.

Accordingly, the present invention provides a compound of formula (I), or a pharmaceutically acceptable salt thereof, for use in the treatment of cell proliferative disorders in a patient in need of such treatment.

The present invention also provides the use of a compound of formula (I), or a pharmaceutically acceptable salt thereof, in the manufacture of a medicament for use in the treatment of cell proliferative disorders in a patient in need of such treatment.

The present invention also provides a method for the treatment of cell proliferative disorders in a patient in need of such treatment which comprises administering to said patient an effective amount of a compound of formula (I), or a pharmaceutically acceptable salt thereof.

The present invention also provides a compound of formula (I), or a pharmaceutically acceptable salt thereof, for use in the production of an anti-proliferative effect in a patient in need of such treatment.

The present invention also provides the use of a compound of formula (I), or a pharmaceutically acceptable salt thereof, to provide an anti-proliferative effect in a patient in need of such treatment.

The present invention also provides the use of a compound of formula (I), or a pharmaceutically acceptable salt thereof, in the manufacture of a medicament for use in the production of an anti-proliferative effect in a patient in need of such treatment.

The present invention also provides a method for producing an anti-proliferative effect in a patient in need of such treatment which comprises administering to said patient an effective amount of a compound of formula (I), or a pharmaceutically acceptable salt thereof.

The present invention also provides a compound of formula (I), or a pharmaceutically acceptable salt thereof, for use as an anti-invasive agent in the containment and/or treatment of solid tumour disease in a patient in need of such treatment.

The present invention also provides the use of a compound of formula (I), or a pharmaceutically acceptable salt thereof, in the manufacture of a medicament for use as an anti-invasive agent in the containment and/or treatment of solid tumour disease in a patient in need of such treatment.

The present invention also provides a method for producing an anti-invasive effect by the containment and/or treatment of solid tumour disease in a patient in need of such treatment which comprises administering to said patient an effective amount of a compound of formula (I), or a pharmaceutically acceptable salt thereof.

The present invention also provides the use of a compound of formula (I), or a pharmaceutically acceptable salt thereof, in the manufacture of a medicament for use in the prevention or treatment of solid tumour disease.

The present invention also provides a method for the prevention or treatment of solid tumour disease in a patient in need of such treatment which comprises administering to said patient an effective amount of a compound of formula (I), or a pharmaceutically acceptable salt thereof.

The present invention also provides a compound of formula (I), or a pharmaceutically acceptable salt thereof, for use in the prevention or treatment of those tumours which are sensitive to inhibition of a PI3K enzyme (such as the Class Ia enzymes and/or the Class Ib PI3K enzyme) and/or a mTOR kinase (such as a mTOR PI kinase-related kinase) that are involved in the signal transduction steps which lead to the proliferation, survival, invasiveness and migratory ability of tumour cells.

The present invention also provides the use of a compound of formula (I), or a pharmaceutically acceptable salt thereof, in the manufacture of a medicament for use in the prevention or treatment of those tumours which are sensitive to inhibition of a PI3K enzyme (such as the Class Ia enzymes and/or the Class Ib PI3K enzyme) and/or a mTOR kinase (such as a mTOR PI kinase-related kinase) that are involved in the signal transduction steps which lead to the proliferation, survival, invasiveness and migratory ability of tumour cells.

The present invention also provides a method for the prevention or treatment of those tumours which are sensitive to inhibition of a PI3K enzyme (such as the Class Ia enzymes and/or the Class Ib PI3K enzyme) and/or a mTOR kinase (such as a mTOR PI kinase-related kinase) that are involved in the signal transduction steps which lead to the proliferation, survival, invasiveness and migratory ability of tumour cells which comprises administering to a patient an effective amount of a compound of formula (I), or a pharmaceutically acceptable salt thereof.

This aspect of the present invention also provides a compound of formula (I), or a pharmaceutically acceptable salt thereof, for use in providing a PI3K enzyme (such as the Class Ia enzymes and/or the Class Ib PI3K enzyme) inhibitory effect and/or a mTOR kinase (such as a mTOR PI kinase-related kinase) inhibitory effect.

The present invention also provides the use of a compound of formula (I), or a pharmaceutically acceptable salt thereof, in the manufacture of a medicament for use in providing a PI3K enzyme (such as the Class Ia enzymes and/or the Class Ib PI3K enzyme) inhibitory effect and/or a mTOR kinase (such as a mTOR PI kinase-related kinase) inhibitory effect.

The present invention also provides a method for providing a PI3K enzyme (such as the Class Ia enzymes and/or the Class Ib PI3K enzyme) inhibitory effect and/or a mTOR kinase (such as a mTOR PI kinase-related kinase) inhibitory effect which comprises administering an effective amount of a compound of formula (I), or a pharmaceutically acceptable salt thereof.

The present invention also provides a compound of formula (I), or a pharmaceutically acceptable salt thereof, for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

The present invention also provides the use of a compound of the formula (I), or a pharmaceutically-acceptable salt thereof, in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

The present invention also provides a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas in patient that is in need of such treatment which comprises administering an effective amount of a compound of formula (I), or a pharmaceutically acceptable salt thereof.

The present invention also provides a compound of formula (I), or a pharmaceutically acceptable salt thereof, for use in the treatment of cancer of the breast, colorectum, lung (including small cell lung cancer, non-small cell lung cancer and bronchioalveolar cancer) and prostate.

The present invention also provides the use of a compound of formula (I), or a pharmaceutically acceptable salt thereof, in the manufacture of a medicament for use in the treatment of cancer of the breast, colorectum, lung (including small cell lung cancer, non-small cell lung cancer and bronchioalveolar cancer) and prostate.

The present invention also provides a method for treating cancer of the breast, colorectum, lung (including small cell lung cancer, non-small cell lung cancer and bronchioalveolar cancer) and prostate in a patient that is in need of such treatment which comprises administering an effective amount of a compound of the formula (I), or a pharmaceutically acceptable salt thereof.

It should be noted that the methods of treatment referred to herein can be administered to humans, and, where appropriate, to other warm blooded animals.

As stated hereinbefore, the in vivo effects of a compound of formula (I) may be exerted in part by one or more metabolites that are formed within the human or animal body after administration of a compound of formula (I).

For all the above-mentioned therapeutic uses, the dosage administered will, of course, vary with the compound employed, the mode of administration, the treatment desired and the disorder indicated. Generally, the daily dosage of the compound of formula (I), or a salt thereof, ("active ingredient") may be in the range from 0.001 mg/kg to 30 mg/kg. For example, in using a compound of formula (I) for therapeutic or prophylactic purposes, it will generally be administered so that a daily dose in the range, for example, 0.1 mg/kg to 30 mg/kg body weight is received, given if required in divided doses. In general, lower doses will be administered when a parenteral route is employed. Thus, for example, for intravenous administration, a dose in the range, for example, 0.01 mg/kg to 10 mg/kg body weight will generally be used. Similarly, for administration by inhalation, a dose in the range, for example, 0.01 mg/kg to 10 mg/kg body weight will be used. Oral administration is however preferred, particularly in tablet form. Typically, unit dosage forms will contain about 10 mg to 0.5 g of a compound of the invention.

Combination Therapies

The invention further relates to combination therapies wherein a compound of formula (I), or a pharmaceutically acceptable salt thereof, or a pharmaceutical composition or formulation comprising a compound of formula (I) is administered concurrently or sequentially or as a combined preparation with another therapeutic agent or agents, for the treatment of one or more of the conditions described hereinbefore.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents such as non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone and salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate, leflunomide; hydroxychloroquine, d-penicillamine, auranofin or other parenteral or oral gold preparations; analgesics; diacerein; intra-articular therapies such as hyaluronic acid derivatives; and nutritional supplements such as glucosamine.

The present invention still further relates to the combination of a compound of the invention together with a cytokine or an agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab and CDP-870) and TNF receptor antagonists including immunoglobulin molecules (such as etanercept) and low-molecular-weight agents such as pentoxyfylline.

The present invention still further relates to the combination of a compound of the invention together with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and $CX_3CR1$ (for the C-$X_3$-C family).

The present invention still further relates to the combination of a compound of the invention together with an inhibitor of matrix metalloproteases (MMPs), i.e. the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAYx1005.

The present invention still further relates to the combination of a compound of the invention together with a receptor antagonist for leukotrienes LTB4, LTC4, LTD4 or LTE4, for example phenothiazines such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAYx7195.

The present invention still further relates to the combination of a compound of the invention together with a phosphodiesterase (PDE) inhibitor such as the methylxanthines including theophylline and aminophylline; and selective PDE isoenzyme inhibitors including PDE4 inhibitors and inhibitors of the isoform PDE4D, and inhibitors of PDE5.

The present invention still further relates to the combination of a compound of the invention together with histamine type 1 receptor antagonists such as cetirizine, loratadine, desloratadine, fexofenadine, acrivastine, terfenadine, astemizole, azelastine, levocabastine, chlorpheniramine, promethazine, cyclizine and mizolastine applied orally, topically or parenterally.

The present invention still further relates to the combination of a compound of the invention together with a proton pump inhibitor (such as omeprazole) or gastroprotective histamine type 2 receptor antagonist.

The present invention still further relates to the combination of a compound of the invention with antagonists of the histamine type 4 receptor.

The present invention still further relates to the combination of a compound of the invention together with an alpha-1/alpha-2 adrenoceptor agonist vasoconstrictor sympathomimetic agent such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride and ethylnorepinephrine hydrochloride.

The present invention still further relates to the combination of a compound of the invention together with anticholinergic agents including muscarinic receptor (M1, M2, and M3) antagonists such as atropine, hyoscine, glycopyrrrolate, ipratropium bromide, tiotropium bromide, oxitropium bromide, pirenzepine and telenzepine.

The present invention still further relates to the combination of a compound of the invention together with a beta-adrenoceptor agonist (including beta receptor subtypes 1-4) such as isoprenaline, salbutamol, formoterol, salmeterol, terbutaline, orciprenaline, bitolterol mesylate and pirbuterol, including chiral enantiomers thereof.

The present invention still further relates to the combination of a compound of the invention together with a chromone, including sodium cromoglycate and nedocromil sodium.

The present invention still further relates to the combination of a compound of the invention together with a glucocorticoid such as flunisolide, triamcinolone acetonide, beclomethasone dipropionate, budesonide, fluticasone propionate, ciclesonide and mometasone furoate.

The present invention still further relates to the combination of a compound of the invention together with an agent that modulates nuclear hormone receptors such as PPARs.

The present invention still further relates to the combination of a compound of the invention together with an immunoglobulin (Ig) or Ig preparation or an antagonist or antibody modulating Ig function such as anti-IgE (e.g. omalizumab).

The present invention still further relates to the combination of a compound of the invention together with other systemic or topically-applied anti-inflammatory agents including thalidomide and derivatives, retinoids, dithranol and calcipotriol.

The present invention still further relates to the combination of a compound of the invention together with combinations of aminosalicylates and sulfapyridine such as sulfasalazine, mesalazine, balsalazide, and olsalazine; and immunomodulatory agents such as the thiopurines, and corticosteroids such as budesonide.

The present invention still further relates to the combination of a compound of the invention together with an antibacterial agent including penicillin derivatives, tetracyclines, macrolides, beta-lactams, fluoroquinolones, metronidazole and inhaled aminoglycosides; and antiviral agents including acyclovir, famciclovir, valaciclovir, ganciclovir and cidofovir; amantadine and rimantadine; ribavirin; zanamavir and oseltamavir; protease inhibitors such as indinavir, nelfinavir, ritonavir and saquinavir; nucleoside reverse transcriptase inhibitors such as didanosine, lamivudine, stavudine, zalcitabine and zidovudine; and non-nucleoside reverse transcriptase inhibitors such as nevirapine and efavirenz.

The present invention still further relates to the combination of a compound of the invention together with cardiovascular agents such as calcium channel blockers, beta-adrenoceptor blockers, angiotensin-converting enzyme (ACE) inhibitors, angiotensin-2 receptor antagonists; lipid lowering agents such as statins, and fibrates; modulators of blood cell morphology such as pentoxyfylline; thrombolytics; and anticoagulants including platelet aggregation inhibitors.

The present invention still further relates to the combination of a compound of the invention together with CNS agents such as antidepressants (such as sertraline), anti-Parkinsonian drugs (such as deprenyl, L-dopa, ropinirole, pramipexole, MAOB inhibitors such as selegine and rasagiline, comP inhibitors such as tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, rivastigmine, tacrine, COX-2 inhibitors, propentofylline or metrifonate.

The present invention still further relates to the combination of a compound of the invention together with agents for the treatment of acute and chronic pain, including centrally and peripherally-acting analgesics such as opioid analogues and derivatives, carbamazepine, phenytoin, sodium valproate, amitryptiline and other antidepressant agents, paracetamol and non-steroidal anti-inflammatory agents.

The present invention still further relates to the combination of a compound of the invention together with parenterally or topically-applied (including inhaled) local anaesthetic agents such as lignocaine and analogues.

The compounds of the present invention may also be used in combination with anti-osteoporosis agents including hormonal agents such as raloxifene, and bisphosphonates such as alendronate.

The present invention still further relates to the combination of a compound of the invention together with tryptase inhibitors; platelet activating factor (PAF) antagonists; interleukin converting enzyme (ICE) inhibitors; IMPDH inhibitors; adhesion molecule inhibitors including VLA-4 antagonists; cathepsins; Kinase inhibitors including but not limited to inhibitors of tyrosine kinases (such as Btk, Itk, Jak3 and MAP), Serine/threonine kinases (including but not limited to inhibitors of MAP kinases such as p38, JNK, protein kinases A, B and C and IKK), and kinases involved in cell cycle regulation (such as but not limited to the cyclin dependent kinases); glucose-6 phosphate dehydrogenase inhibitors; kinin-B-receptor antagonists; anti-gout agents, e.g. colchicine; xanthine oxidase inhibitors, e.g. allopurinol; uricosuric agents, e.g. probenecid, sulfinpyrazone, and benzbromarone; growth hormone secretagogues; transforming growth factor (TGFβ); platelet-derived growth factor (PDGF); fibroblast growth factor, e.g. basic fibroblast growth factor (bFGF); granulocyte macrophage colony stimulating factor (GM-CSF); capsaicin; tachykinin NK receptor antagonists such as the group consisting of NKP-608C, SB-233412 (talnetant) and D-4418; elastase inhibitors such as UT-77 and ZD0892; TNF-alpha converting enzyme (TACE) inhibitors; induced nitric oxide synthase (iNOS) inhibitors; chemoattractant receptor-homologous molecule expressed on TH2 cells (such as CRTH2 antagonists); agents modulating the function of Toll-like receptors (TLR); agents modulating the activity of purinergic receptors such as P2X7; and inhibitors of transcription factors activation such as NFkB, API, and STATS.

Combination Therapies for Oncology Disease

The invention further relates to combination therapies wherein a compound of formula (I), or a pharmaceutically acceptable salt thereof, or a pharmaceutical composition or formulation comprising a compound of formula (I) is administered concurrently or sequentially or as a combined preparation with another treatment of use in the control of oncology disease.

In particular, the anti-cancer treatment defined hereinbefore may be applied as a sole therapy or may involve, in addition to the thiazole derivative of the invention, conventional surgery or radiotherapy or chemotherapy. Accordingly, the compounds of the invention can also be used in combination with existing therapeutic agents for the treatment of cancer.

Suitable agents to be used in combination include:—

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, [for example the anti-vascular endothelial cell growth factor antibody bevacizurnab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), and compounds that work by other mechanisms (for example linomide, inhibitors of integrin αvβ3 function and angiostatin)];

(vi) vascular damaging agents such as combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense agent;

(viii) gene therapy approaches, including approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be further explained by reference to the following illustrative examples.

Unless stated otherwise, starting materials were commercially available. All solvents and commercial reagents were of laboratory grade and were used as received.

In the examples $^1$H NMR and $^{13}$C NMR spectra were recorded on a Varian Inova 400 MHz or a Varian Mercury-VX 300 MHz instrument. The central peaks of chloroform-d ($\delta_H$ 7.27 ppm), dimethylsulfoxide-d$_6$ ($\delta_H$ 2.50 ppm) or acetone-d$_6$ ($\delta_H$ 2.05 ppm) were used as internal references. The following abbreviations have been used: s, singlet; d, doublet; t, triplet; q, quartet; m, multiplet; br, broad.

Column chromatography was carried out using silica gel (0.04-0.063 mm, Merck). In general, a Kromasil KR-100-5-C18 reversed-phase column (250×20 mm, Akzo Nobel) was used for preparative HPLC with mixtures of acetonitrile and water [containing 0.1% trifluoroacetic acid (TFA)] used as the eluent at a flow rate of 10 mL/min.

The following method was used for liquid chromatography (LC)/mass spectral (MS) analysis:—Instrument: Agilent 1100; Column: Waters 'Symmetry' 2.1×30 mm; Mass Spectral analysis using chemical ionisation (APCI); Flow rate: 0.7 mL/min; Absorption Wavelength: 254 nm; Solvent A: water+ 0.1% TFA; Solvent B: acetonitrile+0.1% TFA; Solvent Gradient: 15-95% Solvent B for 2.7 minutes followed by 95% Solvent B for 0.3 minutes.

The following methods were used for LC analysis:—

Method A:—Instrument: Agilent 1100; Column: Kromasil C18 reversed-phase silica, 100×3 mm, 5 µm particle size; Solvent A: 0.1% TFA/water, Solvent B: 0.08% TFA/acetonitrile; Flow Rate: 1 mL/min; Solvent Gradient: 10-100% Solvent B for 20 minutes followed by 100% Solvent B for 1 minute; Absorption Wavelengths: 220, 254 and 280 nm. In general, the retention time of the product was noted.

Method B:—Instrument: Agilent 1100; Column: Waters 'Xterra' C8 reversed-phase silica, 100×3 mm, 5 µm particle size; Solvent A: 0.015M ammonia in water, Solvent B: acetonitrile; Flow Rate: 1 mL/min, Solvent Gradient: 10-100% Solvent B for 20 minutes followed by 100% Solvent B for 1 minute; Absorption Wavelength: 220, 254 and 280 mm. In general, the retention time of the product was noted.

The following abbreviations are used hereinbefore or within the following illustrative examples:—

HBTU O-(benzotriazol-1-yl)-N,N,N',N'-tetramethyluronium hexafluorophosphate;

HATU O-(7-azabenzotriazol-1-yl)-N,N,N',N'-tetramethyluronium hexafluorophosphate;

HOBT 1-hydroxybenzotriazole;

HOAT 1-hydroxy-7-azabenzotriazole;

DIEA N,N-diisopropylethylamine;

NMP N-methylpyrrolidin-2-one;

DMSO dimethylsulfoxide;

DMF N,N-dimethylformamide;

DMA N,N-dimethylacetamide;

THF tetrahydrofuran;

DME 1,2-dimethoxyethane;

DCCI dicyclohexylcarbodiimide.

EXAMPLE 1

N-[5-(6-Chloropyridin-3-yl)-4-methyl-1,3-thiazol-2-yl]acetamide trifluoroacetate A solution of N-(5-iodo-4-methyl-1,3-thiazol-2-yl)acetamide (prepared according to J. Org. Chem., Vol. 30, No. 4, 1965, 1101-1104; 50 mg, 0.213 mmol), (6-chloropyridin-3-yl)boronic acid (50 mg, 0.319-mmol), potassium carbonate (88 mg, 0.638 mmol) and [1,1'-bis(diphenylphosphino)ferrocene]dichloropalladium(II) 1:1 complex with dichloromethane (17 mg, 0.021 mmol) in 1,4-dioxane (3 mL) and water (1 mL) was heated at 80° C. for 12 hours. The reaction mixture was filtered through a plug of Celite. The resulting product was purified by preparative HPLC (Method A) to give the title compound (17 mg, 21%; retention time 7.1 minutes); $^1$H NMR Spectrum: (DMSOd$_6$) 12.23 (1H, s); 8.51 (1H, d); 7.94 (1H, dd); 7.59 (1H, d); 2.35 (3H, s); 2.15 (3H, s); Mass Spectrum: M+H$^+$ 268 and 270.

The title compounds of Examples 2-6 were prepared by a method analogous to that described in Example 1.

EXAMPLE 2

N-[5-(2-Chloropyridin-4-yl)-4-methyl-1,3-thiazol-2-yl]acetamide

The title compound was obtained from N-(5-iodo-4-methyl-1,3-thiazol-2-yl)acetamide and (2-chloropyridin-4-yl)boronic acid in 200% yield (Method A HPLC: retention time 5.1 minutes); $^1$H NMR Spectrum: (DMSOd$_6$) 12.33 (1H, s); 8.41 (1H, d); 7.55 (1H, d); 7.49 (1H, dd); 2.45 (3H, s); 2.17 (3H, s); Mass Spectrum: M+H$^+$ 268 and 270.

EXAMPLE 3

N-[5-(5-Methoxypyridin-3-yl)-4-methyl-1,3-thiazol-2-yl]acetamide trifluoroacetate The title compound was obtained from N-(5-iodo-4-methyl-1,3-thiazol-2-yl)acetamide and (5-methoxypyridin-3-yl)boronic acid in 14% yield (Method A HPLC: retention time 3.2 minutes); $^1$H NMR Spectrum: (DMSOd$_6$) 12.22 (1H, s); 8.31 (2H, m); 7.51 (1H, dd); 3.90 (3H, s); 2.37 (3H, s); 2.16 (3H, s); Mass Spectrum: M+H$^+$ 264.2

EXAMPLE 4

N-[5-(6-Fluoropyridin-3-yl)-4-methyl-1,3-thiazol-2-yl]acetamide trifluoroacetate The reaction of N-(5-iodo-4-methyl-1,3-thiazol-2-yl)acetamide and (6-chloropyridin-3-yl)boronic acid gave the title compound (Method A HPLC: retention time 6.2 minutes); $^1$H NMR Spectrum: (DMSOd$_6$) 12.20 (1H, s); 8.33 (1H, d); 8.07 (1H, td); 7.28 (1H, dd); 2.33 (3H, s); 2.15 (3H, s); Mass Spectrum: M+H$^+$ 252.

EXAMPLE 5

N-[5-(6-Methoxypyridin-3-yl)-4-methyl-1,3-thiazol-2-yl]acetamide trifluoroacetate The reaction of N-(5-iodo-4-methyl-1,3-thiazol-2-yl)acetamide and (6-methoxypyridin-3-yl)boronic acid gave the title compound (Method A HPLC: retention time 6.0 minutes); $^1$H NMR Spectrum: (DMSOd$_6$) 12.11 (1H, s); 8.25 (1H, d); 7.78 (1H, dd); 6.90 (1H, d); 3.89 (3H, s); 2.30 (3H, s); 2.14 (3H, s); Mass Spectrum: M+H$^+$ 264.1.

EXAMPLE 6

N-[5-(2-Methoxypyridin-5-yl)-4-methyl-1,3-thiazol-2-yl]acetamide

The reaction of N-(5-iodo-4-methyl-1,3-thiazol-2-yl)acetamide and (2-methoxypyrimidin-5-yl)boronic acid gave the title compound (Method A HPLC: retention time 4.7 minutes); $^1$H NMR Spectrum: (DMSOd$_6$) 12.19 (1H, s); 8.70 (2H, s); 3.96 (3H, s); 2.31 (3H, s); 2.15 (3H, s); Mass Spectrum: M+H$^+$ 265.2.

EXAMPLE 7

N-[5-(6-Chloro-5-methylsulfonyl-pyridin-3-yl)-4-methyl-1,3-thiazol-2-yl]acetamide A solution of 5-bromo-2-chloro-3-methylsulfonylpyridine (0.135 g, 0.5 mmol), [1,1'-bis(diphenylphosphino)ferrocene]dichloropalladium(II) 1:1 complex with dichloromethane (24 mg, 0.03 mmol), bis(pinacolato)diboron (0.135 g, 0.53 mmol) and potassium acetate (0.147 g, 1.5 mmol) in 1,4-dioxane (4 mL) was heated at 80° C. for 18 hours. The reaction mixture was cooled and N-(5-iodo-4-methyl-1,3-thiazol-2-yl)acetamide (100 mg, 0.35 mmol), 2M aqueous sodium carbonate (1.25 mL, 2.5 mmol), ethanol (0.6 mL) and [1,1'-bis(diphenylphosphino)ferrocene]dichloropalladium (II) 1:1 complex with dichloromethane (12 mg, 0.015 mmol) were added. The resultant mixture was heated again at 80° C. for 8 hours. The resultant mixture was filtered through a plug of celite and purified with preparative HPLC (Method A) to give the title compound (30 mg, 17%; retention time 6.3 minutes); $^1$H NMR Spectrum: (CDCl$_3$) 8.79 (1H, br s); 8.69 (1H, d); 7.50 (1H, d); 3.37 (3H, s); 2.44 (3H, s); 2.31 (3H; s); Mass Spectrum: M+H$^+$ 346.

The 5-bromo-2-chloro-3-methylsulfonylpyridine used as a starting material was prepared as follows 5-Bromo-2-chloro-3-nitropyridine was prepared according the method described by K. Jouve and J. Bergman, *J. Heterocyclic Chem.*, 40, 261 (2003) from 2-amino-5-bromo-3-nitropyridine except that one equivalent of lithium chloride was added and the yield was improved to 84%. The required product gave the characterising data:—$^1$H NMR Spectrum: (CDCl$_3$) 8.70 (1H, d); 8.37 (1H, d).

Using an analogous method to that described by K. Jouve and J. Bergman, *J. Heterocyclic Chem.*, 40, 261 (2003), 5-bromo-2-chloro-3-nitropyridine was converted into 5-bromo-2-chloro-3-aminopyridine; $^1$H NMR Spectrum: (CDCl$_3$) 7.85 (1H, d); 7.18 (1H, d); 4.17 (2H, br s).

Using an analogous method to that described by Ponticello et al, *J. Org. Chem.*, Vol. 44, No. 17, 1979, for the preparation of 2-chloro-3-methylthiopyridine, while maintaining the temperature below 5° C., a solution of sodium nitrite (1.4 g, 20 mmol) in water (5 mL) was added dropwise to a solution of 5-bromo-2-chloro-3-aminopyridine (4.2 g, 20 mmol) in 50% tetrafluoroboric acid (8 mL) and ethanol (20 mL) that was cooled in an ice bath. After completion of the addition, diethyl ether (25 mL) was added and the fluoroborate salt obtained was isolated by filtration and washed with diethyl ether. The damp solid so obtained was dissolved in acetonitrile (50 mL) was stirred in an ice bath and sodium methylmercaptide (1.4 g, 20 mmol) was added portionwise. After complete addition, the temperature was allowed to reach room temperature and the mixture was stirred for two hours. The solvents were removed under reduced pressure and the crude product was dissolved in a minimum amount of ethyl acetate and purified on silica by using heptane/ethyl acetate (9:1-4:1) as eluents. There was thus obtained 5-bromo-2-chloro-3-methylthiopyridine as a red brownish oil that crystallised on standing (2.6 g, 54% yield); $^1$H NMR Spectrum: (CDCl$_3$) 8.17 (1H, d); 7.51 (1H, d); 2.49 (3H, s); Mass Spectrum: M+H$^+$ 238 and 240.

Using an analogous method to that described by Ponticello et al, *J. Org. Chem.*, Vol. 44, No. 17, 1979, for the preparation of 2-chloro-3-methylsulfonylpyridine, a solution of 3-chloroperbenzoic acid (75% pure; 5 g, 22 mmol) in chloroform (50 mL) was added to a stirred solution of 5-bromo-2-chloro-3-methylthiopyridine (2.6 g, 10.9 mmol) in chloroform (50 mL) and the mixture was stirred at room temperature for 20 hours. The resultant solution was poured into a saturated aqueous sodium hydrogen carbonate solution. The organic phase was separated, washed twice with saturated aqueous sodium hydrogen carbonate solution and dried over sodium sulfate. The organic solvent was removed under reduced pressure and the residue was crystallised from a methanolic solution (20 mL). The resultant solid was filtered off and dried to afford 5-bromo-2-chloro-3-methylsulfonylpyridine (2.15 g, 73% yield); $^1$H NMR Spectrum: (CDCl$_3$) 8.70 (1H, d); 8.59 (1H, d); 3.34 (3H, s); Mass Spectrum: M+H$^+$ 270 and 272.

EXAMPLE 8

N-{5-[5-(2-Hydroxyethylaminosulfonyl)pyridin-3-yl]-4-methyl-1,3-thiazol-2-yl}acetamide Using an analogous method to that described in Example 7, N-(5-iodo-4-methyl-1,3-thiazol-2-yl)acetamide was reacted with 5-bromo-N-(2-hydroxyethyl)pyridine-3-sulfonamide to give the title compound (Method A HPLC: retention time 4.0 minutes; 10 mg, 23%); $^1$H NMR Spectrum: (DMSOd$_6$) 12.22 (1H, br s); 8.92 (1H, d); 8.86 (1H, d); 8.16 (1H, t); 7.96 (1H, br s); 4.73 (1H, t); 3.39 (2H, br q); 2.89 (2H, br t); 2.40 (3H, s); 2.17 (3H, s); Mass Spectrum: M+H$^+$ 357.

The 5-bromo-N-(2-hydroxyethyl)pyridine-3-sulfonamide used as a starting material was prepared as follows:—

A solution of 2-aminoethanol (0.78 g, 6 mmol) and 5-bromopyridine-3-sulfonyl chloride (crude product, obtained by brominating pyridine-3-sulfonyl chloride (0.43 g, 2 mmol)) in 1,4-dioxane (3 mL) was stirred at room temperature for one hour. The resultant mixture was partitioned between saturated aqueous sodium chloride and ethyl acetate. The organic solution was dried and evaporated. The crude product so obtained was purified on silica using ethyl acetate/heptane 2:1 with 1% ammonia as eluent. There was thus obtained 5-bromo-N-(2-hydroxyethyl)pyridine-3-sulfonamide (155 mg, 28% yield from the pyridine-3-sulfonyl chloride); $^1$H NMR Spectrum: (CDCl$_3$) 9.00 (1H, d); 8.88 (1H, d); 8.30 (1H, t); 5.04 (1H, br t); 3.77 (2H, q); 3.22 (2H, q); Mass Spectrum: M+H$^+$ 281 and 283.

EXAMPLE 9

N-{4-Methyl-5-[5-(2-morpholinoethylaminosulfonyl)pyridin-3-yl]-1,3-thiazol-2-yl}acetamide Using an analogous method to that described in Example 7, N-(5-iodo-4-methyl-1,3-thiazol-2-yl)acetamide was reacted with 5-bromo-N-(2-morpholinoethyl)pyridine-3-sulfonamide to give the title compound (Method A HPLC: retention time 3.7 minutes; 8 mg, 7%); $^1$H NMR Spectrum: (DMSOd$_6$) 12.27 (1H, br s); 8.91 (1H, d); 8.87 (1H, d); 8.17 (1H, br t); 7.96 (1H, br s); 3.42 (4H, br t); 3.00 (2H, t); 2.40 (3H, s); 2.29 (2H, t); 2.22 (4H, br t); 2.16 (3H, s); Mass Spectrum: M+H$^+$ 426.

The 5-bromo-N-(2-morpholinoethyl)pyridine-3-sulfonamide used as a starting material was prepared as follows:—

Using an analogous method to that described in the portion of Example 8 that is concerned with the preparation of starting materials, 5-bromopyridine-3-sulfonyl chloride was reacted with morpholine to give the required starting material (90 mg, 13% yield from the pyridine-3-sulfonyl chloride); Mass Spectrum: M+H$^+$ 350 and 352.

EXAMPLE 10

N-[5-(5-amino-6-chloropyridin-3-yl)-4-methyl-1,3-thiazol-2-yl]acetamide

Using an analogous method to that described in Example 7, N-(5-iodo-4-methyl-1,3-thiazol-2-yl)acetamide was reacted with 5-bromo-2-chloropyridin-3-amine to give the title compound (Method A HPLC: retention time 5.5 minutes) in 25% yield; $^1$H NMR Spectrum: (acetone-d$_6$) 12.17 (1H, br s); 7.68 (1H, d); 7.20 (1H, d); 5.70 (2H, br s); 2.34 (3H, s); 2.14 (3H, s); Mass Spectrum: M+H$^+$ 283 and 285.

EXAMPLE 11

N-(5-{5-[(2,1,3-Benzothiadiazol-4-ylsulfonyl)amino]-6-chloropyridin-3-yl}-4-methyl-1,3-thiazol-2-yl)acetamide bis(trifluoroacetate)

N-[5-(5-Amino-6-chloropyridin-3-yl)-4-methyl-1,3-thiazol-2-yl]acetamide (100 mg, 0.35 mmol) and 2,1,3-benzothiadiazole-4-sulfonyl chloride (230 mg, 0.98 mmol) were dissolved in pyridine (1 mL) and stirred and heated to 45° C. for 24 hours. The crude reaction mixture was purified by preparative HPLC (Method A) to give the title compound in 35% yield (HPLC retention time 8.0 minutes); $^1$H NMR Spectrum: (acetone-d$_6$) 11.00 (1H, br s); 8.93 (1H, br s); 8.39-8.35 (2H, m); 8.21 (1H, d); 8.11 (1H, d); 7.89 (1H, dd); 2.34 (3H, s); 2.27 (3H, s); Mass Spectrum: M+H$^+$ 481 and 483.

The title compounds of Examples 12-24 were prepared by a method analogous to that described in Example 11.

EXAMPLE 12

N-(5-{6-Chloro-5-[(1-methyl-1H-imidazol-4-yl)sulfonylamino]pyridin-3-yl}-4-methyl-1,3-thiazol-2-yl]acetamide trifluoroacetate Using an analogous method to that described in Example 11, N-[5-(5-amino-6-chloropyridin-3-yl)-4-methyl-1,3-thiazol-2-yl]acetamide was reacted with 1-methyl-1H-imidazole-4-sulfonyl chloride to give the title compound (Method A HPLC: retention time 5.2 minutes) in 17% yield; $^1$H NMR Spectrum: (DMSOd$_6$) 12.26 (1H, s); 10.18 (1H, br s); 8.29 (1H, d); 7.95 (1H, d); 7.85 (1H, s); 7.84 (1H, s); 3.71 (3H, s); 2.52 (3H, s); 2.16 (3H, s); Mass Spectrum: M+H$^+$ 427.

EXAMPLE 13

N-{5-[6-Chloro-5-(phenylsulfonylamino)pyridin-3-yl]-4-methyl-1,3-thiazol-2-yl}acetamide trifluoroacetate Using an analogous method to that described in Example 11, N-[5-(5-amino-6-chloropyridin-3-yl)-4-methyl-1,3-thiazol-2-yl]acetamide was reacted with benzenesulfonyl chloride to give the title compound (Method A HPLC: retention time 8.1 minutes) in 20% yield; $^1$H NMR Spectrum: (DMSOd$_6$) 12.24 (1H, s); 10.45 (1H, br s); 8.31 (1H, d); 7.80-7.76

(2H, m); 7.71-7.57 (4H, m); 2.27 (3H, s); 2.15 (3H, s); Mass Spectrum: M+H$^+$ 423 and 425.

EXAMPLE 14

N-{5-[6-Chloro-5-(4-fluorophenylsulfonylamino)pyridin-3-yl]-4-methyl-1,3-thiazol-2-yl}acetamide trifluoroacetate Using an analogous method to that described in Example 11, N-[5-(5-amino-6-chloropyridin-3-yl)-4-methyl-1,3-thiazol-2-yl]acetamide was reacted with 4-fluorobenzenesulfonyl chloride to give the title compound (Method A HPLC: retention time 8.5 minutes) in 5% yield; $^1$H NMR Spectrum: (DMSOd$_6$) 12.25 (1H, s); 10.50 (1H, br s); 8.35 (1H, br d); 7.80 (2H, m); 7.68 (2H, br d); 7.44 (2H, m); 2.29 (3H, s); 2.16 (3H, s); Mass Spectrum: M+H$^+$ 441 and 443.

EXAMPLE 15

N-{5-[6-Chloro-5-(5-pyridin-2-ylthien-2-ylsulfonylamino)pyridin-3-yl]-4-methyl-1,3-thiazol-2-yl}acetamide bis(trifluoroacetate)

Using an analogous method to that described in Example 11, N-[5-(5-amino-1-chloropyridin-3-yl)-4-methyl-1,3-thiazol-2-yl]acetamide was reacted with 5-pyridin-1-ylthiophene-2-sulfonyl chloride to give the title compound (Method A HPLC: retention time 8.5 minutes) in 7% yield; $^1$H NMR Spectrum: (acetone-d$_6$) 11.03 (1H, br s); 9.21 (1H, br s); 8.54 (1H, m); 8.33 (1H, d); 8.08 (1H, d); 7.97 (1H, d); 7.88 (1H, m); 7.76 (1H, d); 7.62 (1H, d); 7.37 (1H, m); 2.39 (3H, s); 2.27 (3H, s); Mass Spectrum: M+H$^+$ 506 and 508.

EXAMPLE 16

N-(5-{6-Chloro-5-[5-(4-chlorobenzamidomethyl)-2-thienylsulfonylamino]pyridin-3-yl}-4-methyl-1,3-thiazol-2-yl)acetamide trifluoroacetate Using an analogous method to that described in Example 11, N-[5-(5-amino-6-chloropyridin-3-yl)-4-methyl-1,3-thiazol-2-yl]acetamide was reacted with 5-(4-chlorobenzamidomethyl)thiophene-2-sulfonyl chloride to give the title compound (Method A HPLC: retention time 9.4 minutes) in 12% yield; $^1$H NMR Spectrum: (acetone-d$_6$) 11.07 (1H, br s); 9.05 (1H, br s); 8.62 (1H, br s); 8.29 (1H, d); 7.95 (1H, d); 7.90 (1H, m); 7.47 (1H, m); 7.11 (1H, d); 4.79 (1H, s); 4.78 (1H, s); 2.36 (3H, s); 2.29 (3H, s); Mass Spectrum: M+H$^+$ 596.

EXAMPLE 17

N-{5-[6-Chloro-5-(6-phenoxypyridin-3-ylsulfonylamino)pyridin-3-yl]-4-methyl-1,3-thiazol-2-yl}acetamide bis(trifluoroacetate)

Using an analogous method to that described in Example 11, N-[5-(5-amino-6-chloropyridin-3-yl)-4-methyl-1,3-thiazol-2-yl]acetamide was reacted with 6-phenoxypyridine-3-sulfonyl chloride to give the title compound (Method A HPLC: retention time 10.0 minutes) in 17% yield; $^1$H NMR Spectrum: (acetone-d$_6$) 11.07 (1H, br s); 9.17 (1H, br s); 8.51 (1H, m); 8.31 (1H, d); 8.21 (1H, m); 8.01 (1H, d); 7.45 (2H, m); 7.27 (1H, m); 7.20-7.15 (3H, m); 2.37 (3H, s); 2.27 (3H, s); Mass Spectrum: M+H$^+$ 516 and 518.

EXAMPLE 18

N-{5-[6-Chloro-5-(4-nitrophenylsulfonylamino)pyridin-3-yl]-4-methyl-1,3-thiazol-2-yl}acetamide trifluoroacetate Using an analogous method to that described in Example 11, N-[5-(5-amino-6-chloropyridin-3-yl)-4-methyl-1,3-thiazol-2-yl]acetamide was reacted with nitrobenzenesulfonyl chloride to give the title compound (Method A HPLC: retention time 10.0 minutes) in 50% yield; $^1$H NMR Spectrum: (acetone-d$_6$) 11.08 (1H, br s); 9.40 (1H, br); 8.45 (2H, m); 8.34 (1H, d); 8.15 (2H, m); 8.02 (1H, d); 2.37 (3H, s); 2.27 (3H, s); Mass Spectrum: M+H$^+$ 468 and 470.

EXAMPLE 19

N-{5-[6-Chloro-5-(3-methoxyphenylsulfonylamino)pyridin-3-yl]-4-methyl-1,3-thiazol-2-yl}acetamide trifluoroacetate Using an analogous method to that described in Example 11, N-[5-(5-amino-6-chloropyridin-3-yl)-4-methyl-1,3-thiazol-2-yl]acetamide was reacted with 3-methoxybenzenesulfonyl chloride to give the title compound (Method A HPLC: retention time 8.53 minutes) in 36% yield; $^1$H NMR Spectrum: (DMSOd$_6$) 12.25 (1H, s); 10.48 (1H, s); 8.32 (1H, d); 7.63 (1H, d); 7.52 (1H, t); 7.34 (1H, d); 7.29-7.23 (2H, m); 3.82 (3H, s); 2.27 (3H, s); 2.16 (3H, s); Mass Spectrum: M+H$^+$ 453 and 455.

EXAMPLE 20

N-{5-[6-Chloro-5-(2-cyanophenylsulfonylamino)pyridin-3-yl]-4-methyl-1,3-thiazol-2-yl}acetamide trifluoroacetate Using an analogous method to that described in Example 11, N-[5-(5-amino-6-chloropyridin-3-yl)-4-methyl-1,3-thiazol-2-yl]acetamide was reacted with 2-cyanobenzenesulfonyl chloride to give the title compound (Method A HPLC: retention time 8.02 minutes); $^1$H NMR Spectrum: (DMSOd$_6$) 12.26 (11H, s); 8.40 (11H, d); 8.09 (11H, d); 8.02 (1H, d); 7.96-7.85 (2H, m); 7.83 (1H, d); 2.33 (3H, s); 2.16 (3H, s); Mass Spectrum: M+H$^+$ 448 and 450.

EXAMPLE 21

N-(5-{6-Chloro-5-[4-(2-cyanoethoxy-phenylsulfonylamino]pyridin-3-yl}-4-methyl-1,3-thiazol-2-yl)acetamide trifluoroacetate Using an analogous method to that described in Example 11, N-[5-(5-amino-6-chloropyridin-3-yl)-4-methyl-1,3-thiazol-2-yl]acetamide was reacted with 4-(2-cyanoethoxy)benzenesulfonyl chloride to give the title compound (Method A HPLC: retention time 7.95 minutes); $^1$H NMR Spectrum: (DMSOd$_6$) 12.25 (1H, s); 10.32 (1H, s); 8.31 (1H, d); 7.72

(2H, d); 7.63 (1H, d); 7.15 (2H, d); 4.28 (2H, t); 3.04 (2H, t); 2.29 (3H, s); 2.16 (3H, s); Mass Spectrum: M+H$^+$ 492 and 494.

EXAMPLE 22

N-[5-(5-Benzylsulfonylamino-6-chloropyridin-3-yl)-4-methyl-1,3-thiazol-2-yl]acetamide trifluoroacetate Using an analogous method to that described in Example 11, N-[5-(5-amino-6-chloropyridin-3-yl)-4-methyl-1,3-thiazol-2-yl]acetamide was reacted with phenylmethanesulfonyl chloride to give the title compound (Method A HPLC: retention time 7.91 minutes); $^1$H NMR Spectrum: (DMSOd$_6$) 12.23 (1H, s); 9.82 (1H, s); 8.22 (1H, d); 7.45 (1H, d); 7.42-7.38 (2H, m); 7.34-7.26 (3H, m); 4.66 (2H, s); 2.30 (3H, s); 2.17 (3H, s); Mass Spectrum: M+H$^+$ 437 and 439.

EXAMPLE 23

N-{5-[6-Chloro-5-(4-chlorobenzylsulfonylamino) pyridin-3-yl]-4-methyl-1,3-thiazol-2-yl}acetamide trifluoroacetate Using an analogous method to that described in Example 11, N-[5-(5-amino-6-chloropyridin-3-yl)-4-methyl-1,3-thiazol-2-yl]acetamide was reacted with 4-chlorophenylmethanesulfonyl chloride to give the title compound (Method A HPLC: retention time 9.0 minutes); $^1$H NMR Spectrum: (DMSOd$_6$) 12.23 (1H, s); 9.86 (1H, s); 8.25 (1H, d); 7.52 (1H, d); 7.40 (4H, q); 4.69 (2H, s); 2.31 (3H, s); 2.16 (3H, s); Mass Spectrum: M+H$^+$ 471 and 473.

EXAMPLE 24

N-{5-[6-Chloro-5-(6-morpholinopyridin-3-ylsulfonylamino}pyridin-3-yl]-4-methyl-1,3-thiazol-2-yl}acetamide bis(trifluoroacetate)

Using an analogous method to that described in Example 11, N-[5-(5-amino-6-chloropyridin-3-yl)-4-methyl-1,3-thiazol-2-yl]acetamide was reacted with 6-morpholinopyridine-3-sulfonyl chloride to give the title compound (Method A HPLC: retention time 7.22 minutes); $^1$H NMR Spectrum: (acetone-d$_6$) 11.07 (1H, s); 8.81 (1H, s); 8.49 (1H, d); 8.27 (1H, d); 8.00 (1H, d); 7.86 (1H, dd); 6.87 (1H, d); 3.74-3.63 (8H, m); 2.37 (3H, s); 2.27 (3H, s); Mass Spectrum: M+H$^+$ 509 and 511.

EXAMPLE 25

N-(5-{6-Chloro-5-[4-(4-methoxyphenoxy)phenylsulfonylamino]pyridin-3-yl}-4-methyl-1,3-thiazol-2-yl) acetamide trifluoroacetate N-[5-(5-Amino-6-chloropyridin-3-yl)-4-methyl-1,3-thiazol-2-yl]acetamide (30 mg, 0.11 mmol) and 4-(4-methoxyphenoxy)benzenesulfonyl chloride (53 mg, 0.22 mmol) in pyridine (0.5 mL) was stirred in a 'CEM-Discover' monomode microwave apparatus at 110° C. for 15 min. Pure title compound (7 mg, 13%) was obtained by preparative HPLC (Method A, retention time 5.49 minutes); $^1$H NMR Spectrum: (DMSOd$_6$) 12.26 (1H, s); 10.36 (1H, s); 8.32 (1H, d); 7.74 (2H, d); 7.63 (1H, d); 7.09-6.98 (6H, m); 3.77 (3H, s); 2.29 (3H, s); 2.16 (3H, s); Mass Spectrum: M+H$^+$ 545 and 547.

EXAMPLE 26

N-{5-[6-Chloro-5-(4-pyridin-2-yloxyphenylsulfonylamino)pyridin-3-yl]-4-methyl-1,3-thiazol-2-yl}acetamide bis(trifluoroacetate)

Using an analogous method to that described in Example 25, N-[5-(5-amino-6-chloropyridin-3-yl)-4-methyl-1,3-thiazol-2-yl]acetamide was reacted with 4-pyridin-2-yloxybenzenesulfonyl chloride to give the title compound (Method A HPLC: retention time 8.9 minutes); $^1$H NMR Spectrum: (DMSOd$_6$) 12.26 (1H, s); 10.48 (1H, s); 8.33 (1H, d); 8.19 (1H, m); 7.95-7.89 (1H, m); 7.82 (2H, d); 7.71 (1H, d); 7.32 (2H, d); 7.22 (1H, q); 7.14 (1H, d); 2.31 (3H, s); 2.16 (3H, s); Mass Spectrum: M+H$^+$ 516 and 518.

EXAMPLE 27

N-{5-[6-Chloro-5-(3-chloropropylsulfonylamino) pyridin-3-yl]-4-methyl-1,3-thiazol-2-yl}acetamide trifluoroacetate 3-Chloropropane-1-sulfonyl chloride (0.2 mL, 1.7 mmol) was added to a solution of N-[5-(5-amino-6-chloropyridin-3-yl)-4-methyl-1,3-thiazol-2-yl]acetamide (148 mg, 0.52 mmol) in THF that had been cooled to 0° C. The reaction-mixture was stirred at room temperature for 15 hours, evaporated and the residue was dissolved in THF (2 mL). A 10% aqueous sodium hydroxide solution (2 mL) was added and the resultant-mixture was stirred at room temperature for 15 hours. The reaction-mixture was extracted five times with ethyl acetate and the combined organic phases were dried over magnesium sulfate and evaporated. The product was purified by preparative HPLC to give the title compound (Method A HPLC: retention time 7.7 minutes) in 23% yield; $^1$H NMR Spectrum: (DMSOd$_6$) 12.25 (1H, s); 10.1 (1H, s); 8.39 (1H, d); 7.96 (1H, d); 3.76 (2H, t); 3.38 (2H, s); 2.37 (3H, s); 2.22 (2H, m); 2.16 (3H, s); Mass Spectrum: M+H$^+$ 423.

EXAMPLE 28

N-[5-(6-Chloro-5-methylsulfonylaminopyridin-3-yl)-4-methyl-1,3-thiazol-2-yl]acetamide trifluoroacetate Using an analogous method to that described in Example 27, N-[5-(5-amino-6-chloropyridin-3-yl)-4-methyl-1,3-thiazol-2-yl]acetamide was reacted with methanesulfonyl chloride to give the title compound (Method A HPLC: retention time 5.5 minutes) in 12% yield; $^1$H NMR Spectrum: (DMSOd$_6$) 12.25 (1H, s); 9.19 (1H, s); 8.39 (1H, d); 7.96 (1H, d); 3.18 (3H, s); 2.37 (3H, s); 2.16 (3H, s); Mass Spectrum: M+H$^+$ 361 and 363.

EXAMPLE 29

N-{5-[6-Chloro-5-(3-dimethylaminopropylsulfonylamino)pyridin-3-yl]-4-methyl-1,3-thiazol-2-yl}acetamide bis(trifluoroacetate)

N-{5-[6-Chloro-5-(3-chloropropylsulfonylamino)pyridin-3-yl]-4-methyl-1,3-thiazol-2-yl}acetamide (30 mg, 0.071 mmol) was dissolved in THF (0.5 mL). Dimethylamine (1 mL, 25 mmol) was added in portions and the reaction-mixture was stirred at room temperature for 15 hours. Following evaporation of the solvent, the reaction product was purified by preparative HPLC (Method A) to give the title product in 43% yield (retention time 4.1 minutes); $^1$H NMR Spectrum: (DMSOd$_6$) 12.24 (1H, s); 10.10 (1H, br s); 9.36 (1H, br s); 8.40 (1H, d); 7.90 (1H, d); 7.44 (2H, m); 3.22-3.14 (4H, m); 2.79 (3H, s); 2.78 (3H, s); 2.57 (3H, s); 2.18-2.08 (2H, m); 2.16 (3H, s); Mass Spectrum: M+H$^+$ 432 and 434.

EXAMPLE 30

N-{5-[6-Chloro-5-(3-morpholinopropylsulfonylamino)pyridin-3-yl]-4-methyl-1,3-thiazol-2-yl}acetamide bis(trifluoroacetate)

The title compound was obtained from N-{5-[6-chloro-5-(3-chloropropylsulfonylamino)pyridin-3-yl]-4-methyl-1,3-thiazol-2-yl}acetamide and morpholine by a method analogous to that described in Example 29, except that morpholine was used both as a reagent and as a solvent. The reaction product was purified by preparative HPLC (Method A) to give the title product in 12% yield (retention time 4.5 minutes); $^1$H NMR Spectrum: (DMSOd$_6$) 12.28 (1H, s); 9.87 (1H, br s); 8.38 (1H, d); 7.90 (1H, d); 7.90 (1H, d); 3.72-3.56 (4H, m); 2.94-2.64 (4H, m); 2.66 (2H, s); 2.37 (3H, s); 2.32 (2H, m); 2.16 (3H, s); 2.09-1.98 (2H, m); Mass Spectrum: M+H$^+$ 474 and 476.

EXAMPLE 31

N-(5-{6-Chloro-5-[3-(4-methylpiperazin-1-yl)propylsulfonylamino]pyridin-3-yl}-4-methyl-1,3-thiazol-2-yl)acetamide bis(trifluoroacetate)

The title compound was obtained from N-{5-[6-chloro-5-(3-chloropropylsulfonylamino)pyridin-3-yl]-4-methyl-1,3-thiazol-2-yl}acetamide and 1-methylpiperazine by a method analogous to that described in Example 29. The reaction product was purified by preparative HPLC (Method A) to give the title product (retention time 4.17 minutes); Mass Spectrum: M+H$^+$ 487 and 489.

EXAMPLE 32

N-{5-[5-(3-Benzylaminopropylsulfonylamino)-6-chloropyridin-3-yl]-4-methyl-1,3-thiazol-2-yl}acetamide The title compound was obtained from N-{5-[6-chloro-5-(3-chloropropylsulfonylamino)pyridin-3-yl]-4-methyl-1,3-thiazol-2-yl}acetamide and 1-phenylmethaneamine by a method analogous to that described in example 29, except that the product was purified by preparative HPLC (Method A, retention time 5.6 minutes) and by column chromatography on silica using dichloromethane and methanol (9:1) with 1% ammonia as eluent. The product was obtained in 12% yield; $^1$H NMR Spectrum: (acetone-d$_6$) 8.11 (1H, d); 8.04 (1H, d); 7.39-7.21 (5H, m) 3.91 (2H, s); 3.37 (2H, t); 2.93 (2H, m); 2.37 (3H, s); 2.26 (3H, s); 2.12 (2H, m); Mass Spectrum: M+H$^+$ 494 and 496.

EXAMPLE 33

N-{5-[6-Chloro-5-(3-cyclopentylaminopropylsulfonylamino)pyridin-3-yl]-4-methyl-1,3-thiazol-2-yl}acetamide bis(trifluoroacetate)

The title compound was obtained from N-{5-[6-chloro-5-(3-chloropropylsulfonylamino)pyridin-3-yl]-4-methyl-1,3-thiazol-2-yl}acetamide and cyclopentaneamine by a method analogous to that described in example 29. The reaction product was purified by preparative HPLC (Method A) to give the title product (retention time 5.3 minutes) in 40% yield; $^1$H NMR Spectrum: (acetone-d$_6$) 11.05 (11H, br s); 9.21 (1H, br s); 9.03 (1H, br s); 8.32 (1H, d); 8.05 (1H, d); 3.75 (1H, m); 3.55 (2H, t); 3.45 (2H, m); 2.46 (2H, m); 2.37 (3H, s); 2.26 (3H, s); 2.14-2.05 (2H, m); 1.88-1.76 (2H, m); 1.65-1.59 (2H, m); Mass Spectrum: M+H$^+$ 472 and 474.

EXAMPLE 34

N-{5-[6-Chloro-5-(3-neopentylaminopropylsulfonylamino)pyridin-3-yl]-4-methyl-1,3-thiazol-2-yl}acetamide trifluoroacetate The title compound was obtained from N-{5-[6-chloro-5-(3-chloropropylsulfonylamino)pyridin-3-yl]-4-methyl-1,3-thiazol-2-yl}acetamide and 2,2-dimethylpropylamine by a method analogous to that described in Example 29. The reaction product was purified by preparative HPLC (Method A) to give the title product (retention time 5.4 minutes); $^1$H NMR Spectrum: (acetone-d$_6$) 11.05 (1H, s); 9.00 (2H, br s); 8.32 (1H, d); 8.03 (1H, d); 3.52 (2H, t); 3.06 (2H, s); 2.51 (2H, q); 2.38 (3H, s); 2.27 (3H, s); 1.09 (9H, s); Mass Spectrum: M+H$^+$ 474 and 476.

EXAMPLE 35

N-(5-{6-Chloro-5-[3-(3-methylbutylamino)propylsulfonylamino]pyridin-3-yl}-4-methyl-1,3-thiazol-2-yl)acetamide trifluoroacetate The title compound was obtained from N-{5-[6-chloro-5-(3-chloropropylsulfonylamino}pyridin-3-yl]-4-methyl-1,3-thiazol-2-yl}acetamide and 3-methylbutylamine by a method analogous to that described in Example 29. The reaction product was purified by preparative HPLC (Method A) to give the title product (retention time 5.6 minutes); $^1$H NMR Spectrum: (acetone-d$_6$) 11.04 (11H, s); 9.28 (2H, br s); 8.31 (1H, d); 8.04 (1H, d); 3.54 (2H, t); 3.42 (2H, t); 3.2 (2H, t); 2.46 (2H, q); 2.38 (3H, s); 2.27 (3H, s); 1.64-1.70 (3H, m); 0.92 (6H, d); Mass Spectrum: M+H$^+$ 474 and 476.

EXAMPLE 36

N-(5-{6-Chloro-5-[3-(1H-tetrazol-5-ylamino)propylsulfonylamino]pyridin-3-yl}-4-methyl-1,3-thiazol-2-yl)acetamide The title compound was obtained from N-{5-[6-chloro-5-(3-chloropropylsulfonylamino}pyridin-3-yl]-4-methyl-1,3-thiazol-2-yl}acetamide and 1H-tetrazol-5-amine by a method analogous to that described in Example 29. The reaction product was purified by preparative HPLC (Method A) to give the title product (retention time 4.9 minutes); $^1$H NMR Spectrum: (acetone-d$_6$) 11.04 (1H, s); 8.73 (1H, br s); 8.31 (1H, d); 8.07 (1H, d); 6.06 (2H, br s); 4.37 (2H, t); 3.47 (2H, t); 2.44 (2H, q); 2.37 (3H, s); 2.27 (3H, s); Mass Spectrum: M+H$^+$ 472 and 474.

EXAMPLE 37

N-(5-{6-Chloro-5-[3-(cyclohexylmethylamino)propylsulfonylamino]pyridin-3-yl}-4-methyl-1,3-thiazol-2-yl)acetamide trifluoroacetate The title compound was obtained from N-{5-[6-chloro-5-(3-chloropropylsulfonylamino}pyridin-3-yl]-4-methyl-1,3-thiazol-2-yl}acetamide and (cyclohexylmethyl)amine by a method analogous to that described in Example 29. The reaction product was purified by preparative HPLC (Method A) to give the title product (retention time 6.7 minutes); $^1$H NMR Spectrum: (acetone-$d_6$) 11.05 (11H, s); 9.13 (2H, br s); 8.31 (1H, d); 8.04 (1H, d); 3.54 (2H, t); 3.39-3.44 (4H, m); 3.02-3.05 (2H, m); 2.47 (2H, q); 2.38 (3H, s); 2.07 (3H, s); 1.6-1.88 (6H, m); 0.95-1.3 (5H, m); Mass Spectrum: M+H$^+$ 500 and 502.

EXAMPLE 38

N-(5-{6-Chloro-5-[3-(2,4-dimethoxybenzylamino)propylsulfonylamino]pyridin-3-yl}-4-methyl-1,3-thiazol-2-yl)acetamide trifluoroacetate The title compound was obtained from N-{5-[6-chloro-5-(3-chloropropylsulfonylamino}pyridin-3-yl]-4-methyl-1,3-thiazol-2-yl}acetamide and 2,4-dimethoxybenzylamine by a method analogous to that described in Example 29. The reaction product was purified by preparative HPLC (Method A) to give the title product (retention time 6.6 minutes); $^1$H NMR Spectrum: (acetone-$d_6$) 11.03 (11H, s); 9.33 (2H, br s); 8.31 (1H, d); 8.03 (1H, d); 7.35 (1H, d); 6.61 (1H, d); 6.54 (1H, dd); 4.29 (2H, s); 3.87 (3H, s); 3.82 (3H, s); 3.53 (2H, t); 3.37 (2H, t); 2.47 (2H, q); 2.37 (3H, s); 2.27 (3H, s); Mass Spectrum: M+H$^+$ 554 and 556.

The title compounds of Examples 39-42 were prepared by a method analogous to that described in Example 11.

EXAMPLE 39

N-[5-(2-Acetylamino-4-methyl-1,3-thiazol-5-yl)-2-chloropyridin-3-yl]propanamide trifluoroacetate Using an analogous method to that described in Example 11, N-[5-(5-amino-6-chloropyridin-3-yl)-4-methyl-1,3-thiazol-2-yl]acetamide was reacted with propanoyl chloride. The reaction product was purified by preparative HPLC (Method A) to give the title product (retention time 6.26 minutes); $^1$H NMR Spectrum: (DMSO$d_6$) 12.23 (1H, s); 9.67 (11H, s); 8.30 (2H, d); 2.46 (2H, q); 2.38 (3H, s); 2.16 (3H, s); 1.10 (3H, t); Mass Spectrum: M+H$^+$ 339 and 341.

EXAMPLE 40

N-[5-(2-Acetylamino-4-methyl-1,3-thiazol-5-yl)-2-chloropyridin-3-yl]-4-methylbenzamide trifluoroacetate Using an analogous method to that described in Example 11, N-[5-(5-amino-6-chloropyridin-3-yl)-4-methyl-1,3-thiazol-2-yl]acetamide was reacted with 4-methylbenzoyl chloride. The reaction product was purified by preparative HPLC (Method A) to give the title product (retention time 9.98 minutes); $^1$H NMR Spectrum: (DMSO$d_6$) 12.25 (11H, s); 10.16 (1H, s); 8.40 (1H, d); 8.18 (1H, d); 7.92 (2H, d); 7.37 (2H, d); 2.40 (6H, s); 2.16 (3H, s); Mass Spectrum: M+H$^+$ 401 and 403.

EXAMPLE 41

N-[5-(2-Acetylamino-4-methyl-1,3-thiazol-5-yl)-2-chloropyridin-3-yl]-2-phenylacetamide trifluoroacetate Using an analogous method to that described in Example 11, N-[5-(5-amino-6-chloropyridin-3-yl)-4-methyl-1,3-thiazol-2-yl]acetamide was reacted with phenylacetyl chloride. The reaction product was purified by preparative HPLC (Method A) to give the title product (retention time 9.04 minutes); $^1$H NMR Spectrum: (DMSO$d_6$) 12.23 (1H, s); 9.92 (1H, s); 8.30 (2H, m); 7.35 (4H, q); 7.27 (1H, m); 3.82 (2H, s); 2.36 (3H, s); 2.15 (3H, s); Mass Spectrum: M+H$^+$ 401 and 403.

EXAMPLE 42

N-[5-(2-Acetylamino-4-methyl-1,3-thiazol-5-yl)-2-chloropyridin-3-yl]-2-(4-methoxyphenyl)acetamide trifluoroacetate Using an analogous method to that described in Example 11, N-[5-(5-amino-6-chloropyridin-3-yl)-4-methyl-1,3-thiazol-2-yl]acetamide was reacted with 2-(4-methoxyphenyl)acetyl chloride. The reaction product was purified by preparative HPLC (Method A) to give the title product (retention time 8.96 minutes); $^1$H NMR Spectrum: (DMSO$d_6$) 12.23 (1H, s); 9.84 (1H, s); 8.29 (2H, m); 7.28 (2H, d); 6.90 (2H, d); 3.73 (5H, s); 2.36 (3H, s); 2.15 (3H, s); Mass Spectrum: M+H$^+$ 431 and 433.

EXAMPLE 43

N-[5-(2-Acetylamino-4-methyl-1,3-thiazol-5-yl)-2-chloropyridin-3-yl]-2-(3-methoxyphenyl)acetamide trifluoroacetate 2-(3-Methoxyphenyl)acetic acid (12 mg, 0.072 mmol) was stirred in oxalyl chloride (1 mL) at 65° C. for 30 minutes. The oxalyl chloride was evaporated. N-[5-(5-Amino-6-chloropyridin-3-yl)-4-methyl-1,3-thiazol-2-yl]acetamide (10 mg, 0.036 mmol) and DIEA (0.04 mL) in dichloromethane were added and the mixture was stirred at 40° C. for 30 minutes. The reaction product was purified by preparative HPLC (Method A) to give the title product (retention time 8.72 minutes; 4.3 mg, 28%); $^1$H NMR Spectrum: (DMSO$d_6$) 12.23 (1H, s); 9.90 (1H, s); 8.31-8.28 (2H, m); 7.25 (1H, t); 6.96-6.91 (2H, m); 6.85-6.81 (1H, m); 3.78 (2H, s); 3.75 (3H, s); 2.36 (3H, s); 2.15 (3H, s); Mass Spectrum: M+H$^+$ 431 and 433.

EXAMPLE 44

N-[5-(2-Acetylamino-4-methyl-1,3-thiazol-5-yl)-2-chloro-pyridin-3-yl]-4-dimethylaminobutanamide bis(trifluoroacetate)

A mixture of N-[5-(2-acetylamino-4-methyl-1,3-thiazol-5-yl)-2-chloropyridin-3-yl]-4-chlorobutanamide (10 mg, 0.026 mmol) and dimethylamine (500 μl) in THF (0.5 mL) was stirred at 60° C. overnight. The reaction product was purified by preparative HPLC (Method A) to give the title product (retention time 3.93 minutes; 4 mg, 39%); $^1$H NMR Spectrum: (DMSO$d_6$) 12.25 (1H, s); 9.85 (1H, s); 9.30 (1H, s); 8.32 (2H, s); 3.15-3.06 (2H, m); 2.80 (6H, d); 2.56 (2H, t); 2.38 (3H, s); 2.16 (3H, s); 1.98-1.89 (2H, m); Mass Spectrum: M+H$^+$ 396 and 398.

The N-[5-(2-acetylamino-4-methyl-1,3-thiazol-5-yl)-2-chloropyridin-3-yl]-4-chlorobutanamide used as a starting material was prepared as follows:—

Using an analogous method to that described in Example 11, N-[5-(5-amino-6-chloropyridin-3-yl)-4-methyl-1,3-thiazol-2-yl]acetamide was reacted with 4-chlorobutanoyl chloride to give the required starting material; Mass Spectrum: M+H$^+$ 387 and 389.

EXAMPLE 45

N-[5-(2-Acetylamino-4-methyl-1,3-thiazol-5-yl)-2-chloropyridin-3-yl]-4-morpholinobutanamide bis (trifluoroacetate)

Using an analogous method to that described in Example 44, N-[5-(2-acetylamino-4-methyl-1,3-thiazol-5-yl)-2-chloropyridin-3-yl]-4-chlorobutanamide was reacted with morpholine. The reaction product was purified by preparative HPLC (Method A) to give the title product (retention time 3.99 minutes); $^1$H NMR Spectrum: (DMSOd$_6$) 12.25 (1H, s); 9.86 (1H, s); 9.53 (1H, s); 8.32 (2H, s); 3.99 (2H, d); 3.76 (1H, t); 3.63 (2H, t); 3.47 (2H, d); 3.21-3.01 (4H, m); 2.61-2.55 (2H, m); 2.38 (3H, s); 2.16 (3H, s); 2.02-1.92 (2H, m); Mass Spectrum: M+H$^+$ 438 and 440.

EXAMPLE 46

N-{5-[5-(Benzylamino)-6-chloropyridin-3-yl]-4-methyl-1,3-thiazol-2-yl}acetamide

N-[5-(5-amino-6-chloropyridin-3-yl)-4-methyl-1,3-thiazol-2-yl]acetamide (30 mg, 0.11 mmol), benzaldehyde (0.016 mL, 0.16 mmol) and sodium cyanoborohydride (13 mg, 0.21 mmol) were mixed in NMP (0.9 mL) and acetic acid (0.1 mL). Chlorotrimethylsilane (0.04 mL, 0.32 mmol) was added and the mixture was stirred overnight. The reaction product was purified by preparative HPLC (Method A) to give the title product (retention time 9.73 minutes; 19 mg); $^1$H NMR Spectrum: (DMSOd$_6$) 12.13 (1H, s); 7.60 (1H, d); 7.38-7.30 (4H, m); 7.22 (1H, t); 6.80 (1H, d); 6.67 (1H, s); 4.47 (2H, s); 2.12 (3H, s); 2.03 (3H, s); Mass Spectrum: M+H$^+$ 373 and 375.

EXAMPLE 47

N-(5-{5-[(Anilinocarbonyl)amino]-6-chloropyridin-3-yl}-4-methyl-1,3-thiazol-2-yl)acetamide N-[5-(5-Amino-6-chloropyridin-3-yl)-4-methyl-1,3-thiazol-2-yl]acetamide (20 mg, 0.07 mmol) and phenyl isocyanate (0.023 mL, 0.21 mmol) were stirred in THF (0.6 mL) at 40° C. for 2 hours. The reaction product was purified by preparative HPLC (Method A) to give the title product (retention time 8.93 minutes; 10 mg, 36%); $^1$H NMR Spectrum: (DMSOd$_6$) 12.23 (1H, s); 9.56 (1H, s); 8.69 (1H, d); 8.54 (1H, s); 8.15 (1H, d); 7.48 (2H, d); 7.32 (2H, t); 7.02 (1H, t); 2.40 (3H, s); 2.16 (3H, s); Mass Spectrum: M+H$^+$ 402 and 404.

EXAMPLE 48

N-{5-[2-(Acetylamino)-4-methyl-1,3-thiazol-5-yl]-2-chloro pyridin-3-yl}-N-(phenylsulfonyl)acetamide N-{5-[6-Chloro-5-(phenylsulfonylamino)pyridin-3-yl]-4-methyl-1,3-thiazol-2-yl)acetamide was dissolved in THF. Triethylamine (0.113 mL, 0.811 mmol) was added. The solution was placed in an ice-bath and acetyl chloride (0.058 mL, 0.81 mmol) was added dropwise. The mixture was stirred at room temperature for 2 hours and then evaporated. Water and ethyl acetate were added. The organic phase was dried with magnesium sulfate, filtered and evaporated. The reaction product was purified by preparative HPLC (Method A) to give the title product (retention time 9.2 minutes) in 91% yield; $^1$H NMR Spectrum: (DMSOd$_6$) 12.33 (1H, s); 8.69 (1H, d); 8.24 (1H, d); 8.06-8.00 (2H, m); 7.82 (1H, t); 7.72-7.67 (2H); 2.42 (3H, s); 2.17 (3H, s); 1.96 (3H, s); Mass Spectrum: M+H$^+$ 465 and 467.

EXAMPLE 49

N-{2-Chloro-5-[2-(3-furan-2-ylmethylureido)-4-methyl-1,3-thiazol-5-yl]pyridin-3-yl}methanesulfonamide N-[5-(2-Amino-4-methyl-1,3-thiazol-5-yl)-2-chloropyridin-3-yl]methanesulfonamide (63 mg, purity 88%, 0.17 mmol) was dissolved in a mixture of THF (1 mL) and DMF (1 mL) and cooled to 0° C. Pyridine (0.103 mL, 1.27 mmol) was added followed by phenyl chloroformate (0.027 mL, 0.2 mmol). The stirring was continued for 25 minutes at 0° C. and at room temperature for 1 hour. Additional phenyl chloroformate (0.013 mL, 0.1 mmol) was added and the stirring was continued for 45 minutes. The reaction mixture was partitioned between ethyl acetate and saturated aqueous sodium hydrogen carbonate. The organic phase was washed with saturated aqueous sodium hydrogen carbonate, twice with water and finally with brine. Evaporation of the organic solvent at reduced pressure gave N-[5-(6-chloro-5-methanesulfonylaminopyridin-3-yl)-4-methyl-1,3-thiazol-2-yl]carbamic acid phenyl ester which was used without purification; Mass Spectrum: M+H$^+$ 439 and 441.

The material so obtained (purity approximately 25%; 0.04 mmol) was dissolved in dry DMSO (0.5 mL) and furfurylamine (0.03 mL) was added. The reaction mixture was stirred at room temperature for 4 hours. After dilution with a mixture of acetonitrile-water (1:2; 4.5 mL) containing 0.1% trifluoroacetic acid, the reaction product was purified by preparative HPLC (Method A) to give the title product (retention time 7.4 minutes). Fractions containing the title compound were collected and the acetonitrile was evaporated at reduced pressure. The residual solution was stored overnight at 4° C. The resultant precipitate was filtered off to give the title compound (9 mg); $^1$H NMR Spectrum: (DMSOd$_6$) 10.59 (1H, br s, NH); 9.83 (1H, s, NH); 8.32 (1H, d); 7.86 (1H, d); 7.60 (1H, m); 7.00 (1H, br t, NH); 6.41 (1H, dd); 6.28 (1H, d); 4.34 (2H, d); 3.16 (3H, s); 2.32 (3H, s); Mass Spectrum: M+H$^+$ 442 and 444.

The N-[5-(2-amino-4-methyl-1,3-thiazol-5-yl)-2-chloropyridin-3-yl]methanesulfonamide used as a starting material was prepared as follows:—

N-[5-(6-Chloro-5-methanesulfonylaminopyridin-3-yl)-4-methyl-1,3-thiazol-2-yl]acetamide (73 mg, approximately 0.2 mmol) was heated to reflux in a mixture of ethanol (14 mL) and aqueous hydrochloric acid (5M, 7 mL) for 130 minutes. The ethanol was evaporated under reduced pressure and the reaction mixture was made alkaline with aqueous sodium hydroxide (5M). Preparative HPLC under neutral conditions gave the required starting material (63 mg, purity 88%), sufficiently pure to be used in the next step; $^1$H NMR Spectrum: (DMSOd$_6$) 9.87 (1H, br s, NH); 7.62 (1H, d); 7.55

(1H, d); 7.02 (2H, s, NH); 2.75 (3H, s); 2.17 (3H, s); Mass Spectrum: M+H⁺ 319 and 321.

EXAMPLE 50

N-[2-Chloro-5-(4-methyl-2-ureido-1,3-thiazol-5-yl) pyridin-3-yl]benzenesulfonamide N-[5-(2-Amino-4-methyl-1,3-thiazol-5-yl)-2-chloropyridin-3-yl]benzenesulfonamide (19 mg, 0.05 mmol) was dissolved in dry DMF (1 mL). Trichloroacetyl isocyanate (10 µL, 0.08 mmol) was added and the mixture was stirred for 90 min at room temperature. Additional trichloroacetyl isocyanate (0.01 mL, 0.08 mmol) was added and the stirring was continued for 1 hour. Methanolic ammonia (1 mL, 7M) was added and the mixture was stirred for 35 minutes at room temperature. The mixture was partitioned between saturated aqueous sodium hydrogen carbonate and n-butanol. The aqueous phase was extracted with saturated aqueous butanol and the combined organic phases were washed with water and evaporated. Preparative HPLC (Reprosil 100 C-18, 20×250 mm; 10→70% solvent B over 40 minutes) and freeze drying gave the title compound as its trifluoroacetic acid salt (15.5 mg, 57%); ¹H NMR Spectrum: (DMSOd₆+D₂O) 8.28 (1H, d); 7.80-7.75 (2H, m); 7.68 (1H, br t); 7.63-7.57 (3H); 2.21 (3H, s); Mass Spectrum: M+H⁺ 424.

The N-[5-(2-amino-4-methyl-1,3-thiazol-5-yl)-2-chloropyridin-3-yl]benzenesulfonamide used as a starting material was prepared as follows:—

Using an analogous method to that described in the portion of Example 49 that is concerned with the preparation of starting materials, N-[5-(6-chloro-5-benzenesulfonylaminopyridin-3-yl)-4-methyl-1,3-thiazol-2-yl]acetamide was hydrolysed with aqueous hydrochloric acid. Preparative HPLC under neutral conditions gave the required starting material which was sufficiently pure to be used in the next step.

EXAMPLE 51

N-[5-(5-Benzenesulfonylamino-6-chloropyridin-3-yl)-4-methyl-1,3-thiazol-2-yl]-5-methyl-2-phenyl-2H-[1,2,3]-triazole-4-carboxamide N-[5-(2-Amino-4-methyl-1,3-thiazol-5-yl)-2-chloropyridin-3-yl]benzenesulfonamide (19 mg, 0.05 mmol) was dissolved in dry DMF (1 mL). 5-Methyl-2-phenyl-2H-[1,2,3]-triazole-4-carbonyl chloride (12.5 mg, 0.056 mmol) was added and the mixture was stirred at room temperature for 35 minutes. The progress of the reaction was analyzed by HPLC (system A). Additional 5-methyl-2-phenyl-2H-[1,2,3]-triazole-4-carbonyl chloride (2 mg, 0.01 mmol) was added and stirring was continued for 40 minutes. The mixture was partitioned between aqueous saturated sodium hydrogen carbonate and ethyl acetate. The organic phase was washed with water and brine and evaporated. The residue was subjected to preparative HPLC (Reprosil 100 C-18, 20×250 mm; 10→60% solvent B over 40 minutes). Appropriate fractions were pooled, concentrated and freeze dried to give the title compound as its trifluoroacetic acid salt (12 mg, 30%); ¹H NMR Spectrum: (DMSOd₆+D₂O) 8.67 (1H, d); 8.35 (1H, d); 8.19 (2H, d); 7.91 (1H, t); 7.79 (2H, t); 7.53 (4H, d); 7.51-7.44 (1H, m); 2.50 (3H, s); 2.24 (3H, s); Mass Spectrum: M+H⁺ 566.

The title compounds of Examples 52-56 were prepared by a method analogous to that described in Example 51.

EXAMPLE 52

N-[5-(5-Benzenesulfonylamino-6-chloropyridin-3-yl)-4-methyl-1,3-thiazol-2-yl]-2-benzyloxyacetamide Using an analogous method to that described in Example 51, N-[5-(2-amino-4-methyl-1,3-thiazol-5-yl)-2-chloropyridin-3-yl]benzenesulfonamide was reacted with 2-benzyloxyacetyl chloride. The reaction product was purified by preparative HPLC (Method A) to give the title product (retention time 9.6 minutes); ¹H NMR Spectrum: (DMSOd₆+D₂O) 8.56 (1H, d); 8.09 (1H, d); 8.03 (2H, br d); 7.83 (1H, t); 7.70 (2H, t); 7.31-7.26 (3H); 7.26-7.24 (2H); 4.41 (2H, AB system); 4.12 (1H, d); 3.86 (1H, d); 2.24 (3H, s); Mass Spectrum: M+H⁺ 529.

EXAMPLE 53

N-[5-(5-Benzenesulfonylamino-6-chloropyridin-3-yl)-4-methyl-1,3-thiazol-2-yl]-2-(4-methoxyphenyl) acetamide Using an analogous method to that described in Example 51, N-[5-(2-amino-4-methyl-1,3-thiazol-5-yl)-2-chloropyridin-3-yl]benzenesulfonamide was reacted with 2-(4-methoxybenzyl)acetyl chloride. The reaction product was purified by preparative HPLC (Method A) to give the title product (retention time 9.1 minutes); ¹H NMR Spectrum: (DMSOd₆+D₂O) 8.60 (1H, d); 8.01 (2H, d); 7.93 (1H, d); 7:81 (2H, t); 7.68 (2H, t); 6.85 (1H, d); 6.78 (2H, d); 3.68 (3H, s); 3.52 (1H, d); 3.34 (1H, d); 2.26 (3H, s); Mass Spectrum: M+H⁺ 529.

EXAMPLE 54

N-[5-(5-Benzenesulfonylamino-6-chloropyridin-3-yl)-4-methyl-1,3-thiazol-2-yl]-6-chloronicotinamide Using an analogous method to that described in Example 51, N-[5-(2-amino-4-methyl-1,3-thiazol-5-yl)-2-chloropyridin-3-yl]benzenesulfonamide was reacted with 6-chloronicotinoyl chloride. The reaction product was purified by preparative HPLC (Method A) to give the title product (retention time 8.5 minutes); ¹H NMR Spectrum: (DMSO-d₆+D₂O) 8.58 (2H, dd); 8.44 (1H, d); 8.02 (3H, d); 7.86 (1H, t); 7.71 (2H, t); 7.51 (2H, d); 2.28 (3H, s); Mass Spectrum: M+H⁺ 520.

EXAMPLE 55

N-[5-(5-benzenesulfonylamino-6-chloropyridin-3-yl)-4-methyl-1,3-thiazol-2-yl]furan-2-carboxamide Using an analogous method to that described in Example 51, N-[5-(2-amino-4-methyl-1,3-thiazol-5-yl)-2-chloropyridin-3-yl]benzenesulfonamide was reacted with 2-furoyl chloride. The reaction product was purified by preparative HPLC (Method A) to give the title product (retention time 8.0 minutes); ¹H NMR Spectrum: (DMSOd₆+D₂O) 8.57 (1H, d); 8.27 (1H, d); 8.05 (2H, d); 7.83 (1H, t); 7.76 (1H, d); 7.69 (2H, t); 6.75 (1H, d); 6.55 (1H, dd); 2.25 (3H, s); Mass Spectrum: M+H⁺ 475.

EXAMPLE 56

N-[5-(5-Benzenesulfonylamino-6-chloropyridin-3-yl)-4-methyl-1,3-thiazol-2-yl]-2-methoxyacetamide Using an analogous method to that described in Example 51, N-[5-(2-amino-4-methyl-1,3-thiazol-5-yl)-2-chloropyridin-3-yl]benzenesulfonamide was reacted with 2-methoxyacetyl chloride. The reaction product was purified by preparative HPLC (Method A) to give the title product (retention time 7.0 minutes); $^1$H NMR Spectrum: (DMSOd$_6$+D$_2$O) 8.59 (1H, d); 8.14 (1H, d); 8.03 (2H, d); 7.83 (1H, t); 7.70 (2H, t); 4.01 (1H, d); 3.72 (1H, d); 3.18 (3H, s); 2.27 (3H, s); Mass Spectrum: M+H$^+$ 453.

EXAMPLE 57

N-{5-[6-Chloro-5-(2,4-dimethoxyphenylsulfonylamino)pyridin-3-yl]-4-methyl-1,3-thiazol-2-yl}acetamide 2,4-Dimethoxyphenylsulfonyl chloride (*J. Med. Chem.*, 1977, 20, 1235; 376 mg) was added to a stirred solution of N-[5-(5-amino-6-chloropyridin-3-yl)-4-methyl-1,3-thiazol-2-yl]acetamide (150 mg) in pyridine (1.5 mL) and the resultant solution was heated at 50° C. for 16 hours. The mixture was cooled to room temperature and concentrated by evaporation. The residue was purified by preparative HPLC on Kromasil C18 reversed-phase silica using a solvent gradient of 10% to 100% acetonitrile in water (containing 1% acetic acid) as eluent at a flow rate of about 10 mL/minute. The material so obtained was triturated under diethyl ether to give the title compound as a white solid (70 mg); $^1$H NMR Spectrum: (DMSOd$_6$) 2.16 (s, 3H), 2.29 (s, 3H), 3.76 (s, 3H), 3.83 (s, 3H), 6.60 (m, 1H), 6.69 (d, 1H), 9.64 (d, 1H), 6.75 (d, 1H), 8.25 (br s, 1H), 9.80 (s, 1H); Mass Spectrum: M+H$^+$ 483.

The N-[5-(5-amino-6-chloropyridin-3-yl)-4-methyl-1,3-thiazol-2-yl]acetamide used as a starting material was prepared as follows:—

A mixture of 2-acetamido-4-methylthiazole (20 g), 3-amino-5-bromo-2-chloropyridine (*J. Het. Chem.*, 2003, 40, 261; 16.5 g), caesium fluoride (43.68 g), palladium(II) acetate (1.73 g) and dry DMSO (480 mL) was stirred and purged with nitrogen for 40 minutes. Tri-tert-butylphosphine (0.34M solution in hexane; 44 mL) was added and the reaction mixture was stirred at room temperature for 30 minutes. The resultant mixture was stirred and heated to 135° C. under nitrogen for 4 hours. The mixture was subsequently stirred at room temperature for 18 hours. The resultant mixture was poured into stirred, cooled water and the precipitate was isolated, washed with water and dried. The solid was dissolved in a heated 1:1 mixture of dichloromethane and methanol and decolourising charcoal was added. The hot mixture was filtered and the filtrate was evaporated. Toluene was added to the residue and the mixture was evaporated. The resultant residue was triturated under diethyl ether. The solid so obtained was isolated, washed with diethyl ether and dried to give the required starting material (21 g); $^1$H NMR Spectrum: (DMSO-d$_6$) 2.15 (s, 3H), 2.36 (s, 3H), 5.73 (s, 2H), 7.2 (s, 2H), 7.67 (s, 1H), 12.2 (s, 1H); Mass Spectrum: M–H$^-$ 281.

EXAMPLE 58

Using an analogous method to that described in Example 57, the appropriate N-[5-(5-aminopyridin-3-yl)-4-methyl-1,3-thiazol-2-yl]acetamide was reacted with the appropriate sulfonyl chloride to give the compounds described in Table I. Unless otherwise stated, each reaction product was purified by preparative HPLC on Kromasil C18 reversed-phase silica using a solvent gradient of 10% to 100% acetonitrile in water (containing 1% acetic acid) as eluent at a flow rate of about 10 mL/minute.

Unless otherwise stated, each sulfonyl chloride was a commercially available material.

TABLE I

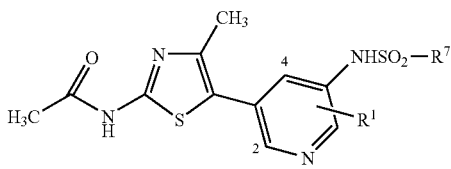

| No. & Note | R$^1$ | R$^7$ |
|---|---|---|
| [1] | 6-chloro | 3-fluorophenyl |
| [2] | 6-chloro | 2-fluorophenyl |
| [3] | 6-chloro | 2,6-difluorophenyl |
| [4] | 6-chloro | 2,5-difluorophenyl |
| [5] | 6-chloro | 2,4-difluorophenyl |
| [6] | 6-chloro | 3,4-difluorophenyl |
| [7] | 6-chloro | 3,5-difluorophenyl |
| [8] | 6-chloro | 4-methoxyphenyl |
| [9] | 6-chloro | 3,4-dimethoxyphenyl |
| [10] | 6-chloro | 2,5-dimethoxyphenyl |
| [11] | 6-chloro | 2-methoxy-5-methylphenyl |
| [12] | 6-chloro | 2-methoxy-4-methylphenyl |
| [13] | 6-chloro | 3-methylphenyl |
| [14] | 6-chloro | 4-methylphenyl |
| [15] | 6-chloro | 4-methyl-3-nitrophenyl |
| [16] | 6-chloro | 4-trifluoromethoxyphenyl |
| [17] | 6-chloro | 3-nitrophenyl |
| [18] | 6-chloro | 2-nitrophenyl |
| [19] | 6-chloro | 4-cyanophenyl |
| [20] | 6-chloro | 4-acetamidophenyl |
| [21] | 6-chloro | 3-acetamidophenyl |
| [22] | 6-chloro | 3-acetamido-4-ethoxyphenyl |
| [23] | 6-chloro | 4-methylsulfonylphenyl |
| [24] | 6-chloro | 4-acetylphenyl |
| [25] | 6-chloro | 3-(4-methoxyphenoxy)phenyl |
| [26] | 6-chloro | 3-(4-chlorophenoxy)phenyl |
| [27] | 6-chloro | 3-(4-tolyloxy)phenyl |
| [28] | 6-chloro | 4-(3-chloro-2-cyanophenoxy)phenyl |
| [29] | 6-chloro | benzo-2,1,3-oxadiazol-4-yl |
| [30] | 6-chloro | N-trifluoroacetyl-1,2,3,4-tetrahydroisoquinolin-7-yl |
| [31] | 6-chloro | N-methyl-2-oxo-1,2,3,4-tetrahydroquinolin-6-yl |
| [32] | 6-chloro | 2-thienyl |
| [33] | 6-chloro | 3-thienyl |
| [34] | 6-chloro | 5-(2-methylthiopyrimidin-4-yl)thien-2-yl |
| [35] | 6-chloro | 1,2-dimethylimidazol-4-yl |
| [36] | 6-chloro | 1,2-dimethylimidazol-5-yl |
| [37] | 6-chloro | 5-chloro-1,3-dimethyl-1H-pyrazol-4-yl |
| [38] | 6-chloro | 2,4-dimethyl-1,3-thiazol-5-yl |
| [39] | 6-chloro | 2-acetamido-4-methyl-1,3-thiazol-5-yl |
| [40] | 6-chloro | 3,5-dimethylisoxazol-4-yl |
| [41] | 6-fluoro | 2,4-dimethyl-1,3-thiazol-5-yl |
| [42] | 6-methoxy | 2,4-dimethyl-1,3-thiazol-5-yl |
| [43] | 6-chloro | 3-pyridyl |
| [44] | 6-fluoro | 3-pyridyl |
| [45] | 6-methoxy | 3-pyridyl |
| [46] | 6-chloro | n-propyl |
| [47] | 6-fluoro | methyl |
| [48] | 6-methoxy | methyl |
| [49] | 6-chloro | ethyl |
| [50] | 6-chloro | 2,2,2-trifluoroethyl |
| [51] | 6-methyl | phenyl |
| [52] | 6-fluoro | phenyl |
| [53] | 6-methoxy | phenyl |
| [54] | H | phenyl |

TABLE I-continued

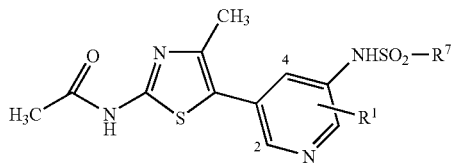

| No. & Note | $R^1$ | $R^7$ |
|---|---|---|
| [55] | H | 4-fluorophenyl |
| [56] | 6-chloro | 2-nitrobenzyl |
| [57] | 6-chloro | 3-(4-methoxyphenoxy)propyl |

Notes

The products gave the characterising data shown below.

[1] $^1$H NMR Spectrum: (DMSOd$_6$) 2.16 (s, 3 H), 2.29 (s, 3 H), 7.54-7.63 (m, 3 H), 7.64-7.70 (m, 2 H), 8.33 (br s, 1 H), 10.66 (br s, 1 H), 12.26 (s, 1 H); Mass Spectrum: M + H$^+$ 441.
[2] $^1$H NMR Spectrum: (DMSOd$_6$) 2.16 (s, 3 H), 2.30 (s, 3 H), 7.36 (m, 1 H), 7.46 (m, 1 H), 7.71-7.79 (m, 3 H), 8.34 (br s, 1 H), 10.83 (br s, 1 H), 12.26 (s, 1 H); Mass Spectrum: M + H$^+$ 441.
[3] $^1$H NMR Spectrum: (DMSOd$_6$) 2.17 (s, 3 H), 2.32 (s, 3 H), 7.30 (m, 2 H), 7.71-7.80 (m, 1 H), 7.83 (d, 1 H): 8.38 (s, 1 H), 11.19 (br s, 1 H), 12.27 (s, 1 H); Mass Spectrum: M + H$^+$ 459.
[4] $^1$H NMR Spectrum: (DMSOd$_6$) 2.17 (s, 3 H), 2.31 (s, 3 H), 7.51-7.60 (m, 2 H), 7.60-7.68 (m, 1 H), 7.78 (d, 1 H), 8.36 (s, 1 H), 11.03 (br s, 1 H), 12.27 (s, 1 H); Mass Spectrum: M + H$^+$ 459.
[5] $^1$H NMR Spectrum: (DMSOd$_6$) 2.16 (s, 3 H), 2.32 (s, 3 H), 7.26 (m, 1 H), 7.58 (m, 1 H), 7.78-7.84 (m, 1 H), 7.79 (s, 1 H), 8.35 (s, 1 H), 10.91 (br s, 1 H), 12.27 (s, 1 H); Mass Spectrum: M + H$^+$ 459.
[6] $^1$H NMR Spectrum: (DMSOd$_6$) 2.16 (s, 3 H), 2.31 (s, 3 H), 2.61-2.76 (m, 3 H), 7.87 (m, 1 H), 8.35 (s, 1 H), 10.69 (br s, 1 H), 12.27 (s, 1 H); Mass Spectrum: M + H$^+$ 459.
[7] $^1$H NMR Spectrum: (DMSOd$_6$) 2.16 (s, 3 H), 2.31 (s, 3 H), 7.45-7.55 (m, 2 H), 7.65-7.76 (m, 2 H), 8.37 (d, 1 H), 10.82 (br s, 1 H), 12.27 (br s, 1 H); Mass Spectrum: M + H$^+$ 459.
[8] $^1$H NMR Spectrum: (DMSOd$_6$) 2.17 (s, 3 H), 2.29 (s, 3 H), 3.83 (s, 3 H), 7.12 (d, 2 H), 7.66 (s, 1 H), 7.71 (d, 1 H), 8.29 (s, 1 H), 10.30 (br s, 1 H), 12.26 (s, 1 H); Mass Spectrum: M + H$^+$ 453.
[9] $^1$H NMR Spectrum: (DMSOd$_6$) 2.16 (s, 3 H), 2.27 (s, 3 H), 3.76 (s, 3 H), 3.82 (s, 3 H), 7.11 (d, 1 H), 7.31 (d, 1 H), 7.34 (m, 1 H), 7.64 (d, 1 H), 8.28 (s, 1 H), 10.28 (s, 1 H); Mass Spectrum: M + H$^+$ 483.
[10] $^1$H NMR Spectrum: (DMSOd$_6$) 2.16 (s, 3 H), 2.28 (s, 3 H), 3.68 (s, 3 H), 3.73 (s, 3 H), 7.15 (d, 1 H), 7.21 (d, 1 H), 7.24 (d, 1 H), 7.73 (s, 1 H), 8.27 (br s, 1 H), 10.05 (s, 1 H); Mass Spectrum: M + H$^+$ 483.
[11] $^1$H NMR Spectrum: (DMSOd$_6$) 2.17 (s, 3 H), 2.27 (s, 3 H), 2.28 (s, 3 H), 3.73 (s, 3 H), 7.11 (d, 1 H), 7.44 (m, 1 H), 7.56 (s, 1 H), 7.72 (d, 1 H), 8.27 (s, 1 H), 9.94 (s, 1 H), 12.26 (s, 1 H); Mass Spectrum: M + H$^+$ 467. 2-Methoxy-5-methylphenylsulfonyl chloride is described in Tetrahedron, 1997, 53, 4145.
[12] $^1$H NMR Spectrum: (DMSOd$_6$) 2.16 (s, 3 H), 2.29 (s, 3 H), 2.36 (s, 3 H), 3.75 (s, 3 H), 6.87 (d, 1 H), 7.05 (s, 1 H), 7.60 (d, 1 H), 7.74 (d, 1 H), 8.27 (s, 1 H), 9.90 (s, 1 H), 12.26 (s, 1 H); Mass Spectrum: M + H$^+$ 467.
[13] $^1$H NMR Spectrum: (DMSOd$_6$) 2.16 (s, 3 H), 2.29 (s, 3 H), 3.83 (s, 3 H), 7.12 (d, 2 H), 7.66 (s, 1 H), 7.71 (d, 2 H), 8.29 (s, 1 H), 10.30 (s, 1 H), 12.26 (s, 1 H); Mass Spectrum: M + H$^+$ 437.
[14] The reaction conditions were varied as follows:- 4-Toluenesulfonyl chloride (141 mg) was added to stirred mixture of N-[5-(5-amino-6-chloropyridin-3-yl)-4-methyl-1,3-thiazol-2-yl]acetamide (70 mg) and dry pyridine (2.3 mL) and the mixture was stirred at room temperature for 5 hours. Water was added and the mixture was evaporated. The residue was dissolved in 7 N methanolic ammonia and the mixture was stirred at room temperature for 18 hours. The mixture was evaporated and water was added. The resultant precipitate was isolated, washed with distilled water and dried. The material so obtained was purified by column chromatography using a 49:1 mixture of dichloromethane and methanol as eluent. There was thus obtained the required product (32 mg); $^1$HNMR Spectrum: (DMSOd$_6$) 2.17 (s, 3 H), 2.28 (s, 3 H), 2.4 (s, 3 H), 7.4 (d, 2 H), 7.6 (s, 1 H), 7.66 (d, 2 H), 8.3 (s, 1 H), 10.4 (s, 1 H), 12.25 (s, 1 H); Mass Spectrum: M + H$^+$ 437.
[15] $^1$H NMR Spectrum: (DMSOd$_6$) 2.17 (s, 3 H), 2.29 (s, 3 H), 2.61 (s, 3 H), 7.66 (d, 1 H), 7.74 (d, 1 H), 7.96 (m, 1 H), 8.31 (br s, 1 H), 8.33 (d, 1 H), 10.80 (br d, 1 H), 12.26 (s, 1 H); Mass Spectrum: M + H$^+$ 482.
[16] $^1$H NMR Spectrum: (DMSOd$_6$) 2.16 (s, 3 H), 2.26 (s, 3 H), 7.59 (d, 2 H), 7.66 (s, 1 H), 7.89 (d, 2 H), 8.31 (br s, 1 H), 10.60 (br s, 1 H), 12.25 (s, 1 H); Mass Spectrum: M+ H$^+$ 507.
[17] $^1$H NMR Spectrum: (acetone-d$_6$) 11.08 (1 H, br s), 9.42 (1 H, br s), 8.68 (1 H, s), 8.56 (1 H, d), 8.33 (1 H, d), 8.26 (1 H, d), 8.02 (1 H, d), 7.95 (1 H, t), 2.31 (3 H, s), 2.27 (3 H, s); Mass Spectrum: M + H$^+$ 468 and 470.
[18] $^1$H NMR Spectrum: (DMSOd$_6$) 2.17 (s, 3 H), 2.28 (s, 3 H), 7.70 (d, 1 H), 7.87 (m, 1 H), 7.91 (m, 1 H), 7.95-8.02 (m, 2 H), 8.39 (s, 1 H), 10.93 (br s, 1 H), 12.27 (s, 1 H); Mass Spectrum: M + H$^+$ 468.
[19] $^1$H NMR Spectrum: (DMSOd$_6$) 2.17 (s, 3 H), 2.31 (s, 3 H), 7.73 (d, 1 H), 7.93 (d, 2 H), 8.09 (d, 2 H), 8.36 (d, 1 H), 10.86 (br s, 1 H), 12.27 (s, 1 H); Mass Spectrum: M + H$^+$ 448.
[20] $^1$H NMR Spectrum: (DMSOd$_6$) 12.22 (1 H, s), 10.35 (1 H, s), 8.30 (1 H, s), 8.19 (1 H, d), 7.75 (2 H, d), 7.68 (2 H, d), 7.67 (1 H, d), 2.30 (3 H, s), 2.18 (3 H, s), 2.07 (3 H, s); Mass Spectrum: M + H$^+$ 480 and 482.
[21] $^1$H NMR Spectrum: (DMSOd$_6$) 2.04 (s, 3 H), 2.16 (s, 3 H), 2.26 (s, 3 H), 7.40 (d, 1 H), 7.49 (m, 1 H), 7.62 (br s, 1 H), 7.75 (d, 1 H), 8.13 (s, 1 H): 8.28 (br s, 1 H), 10.24 (s, 1 H), 10.50 (s, 1 H); Mass Spectrum: M + H$^+$ 480.
[22] $^1$H NMR Spectrum: (DMSOd$_6$) 1.39 (t, 3 H), 2.11 (s, 3 H), 2.17 (s, 3 H), 2.28 (s, 3 H), 4.19 (q, 2 H), 7.19 (d, 1 H), 7.43 (m, 1 H), 7.62 (s, 1 H), 8.29 (s, 1 H), 8.55 (s, 1 H), 9.18 (s, 1 H), 10.30 (s, 1 H), 12.25 (s, 1 H); Mass Spectrum: M + H$^+$ 524.
[23] $^1$H NMR Spectrum: (DMSOd$_6$) 2.17 (s, 3 H), 2.29 (s, 3 H), 3.30 (s, 3 H), 7.71 (d, 1 H), 8.03 (d, 1 H), 8.16 (d, 2 H), 8.35 (s, 1 H): 10.87 (br s, 1 H), 12.27 (s, 1 H); Mass Spectrum: M + H$^+$ 501.
[24] $^1$H NMR Spectrum: (DMSOd$_6$) 2.16 (s, 3 H), 2.29 (s, 3 H), 2.63 (s, 3 H), 7.67 (s, 1 H), 7.90 (d, 2 H), 8.13 (d, 2 H), 8.30 (br s, 1 H), 10.73 (br s, 1 H), 12.26 (s, 1 H); Mass Spectrum: M + H$^+$ 465.
[25] $^1$H NMR Spectrum: (acetone-d$_6$) 11.05 (1 H, br s); 8.88 (1 H, br s); 8.33 (1 H, d); 7.94 (1 H, d); 7.57 (2 H, m); 7.29 (1 H, m); 7.08 (1 H, br s); 6.94 (3 H, s); 3.75 (2 H, d); 2.30 (3 H, s); 2.28 (3 H, s); Mass Spectrum: M + H$^+$ 545 and 547.

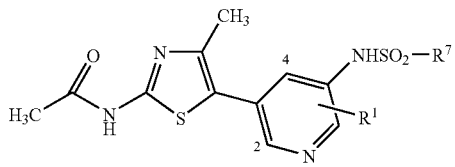

| No. & Note | $R^1$ | $R^7$ |
|---|---|---|

[26] $^1$H NMR Spectrum: (DMSOd$_6$) 12.22 (1 H, s); 10.45 (1 H, s); 8.37 (1 H, d); 7.68 (1 H, d); 7.63 (1 H, t); 7.52 (1 H, dd); 7.44-7.38 (3 H); 7.10 (1 H, t); 7.02 (2 H, m); 2.27 (3 H, s); 2.16 (3 H, s); Mass Spectrum: M + H$^+$ 549 and 551.
[27] $^1$H NMR Spectrum: (acetone-d$_6$) 11.05 (1 H, br s); 8.88 (1 H, br s); 8.34 (1 H, d); 7.95 (1 H, d); 7.58 (2 H, m); 7.31 (1 H, m); 7.16 (1 H, d); 7.09 (1 H, br s); 6.85 (2 H, d); 2.29 (3 H, s); 2.28 (3 H, s); 2.26 (3 H, s); Mass Spectrum: M + H$^+$ 529 and 531.
[28] $^1$H NMR Spectrum: (DMSOd$_6$) 12.26 (1 H, br s); 10.53 (1 H, br s); 8.34 (1 H, d); 7.84 (2 H, d); 7.73 (1 H, t); 7.69 (1 H, d); 7.58 (1 H, d); 7.37 (2 H, d); 7.12 (1 H, d); 2.30 (3 H, s); 2.15 (3 H, s); Mass Spectrum: M + H$^+$ 574 and 575.
[29] $^1$H NMR Spectrum: (DMSOd$_6$) 2.17 (s, 3 H), 2.35 (s, 3 H), 7.74 (m, 1 H), 7.90 (d, 1 H), 8.07 (d, 1 H), 8.37 (s, 1 H), 8.41 (d, 1 H), 11.13 (br s, 1 H), 12.28 (s, 1 H); Mass Spectrum: M + H$^+$ 465.
[30] $^1$H NMR Spectrum: (acetone-d$_6$) 8.27 (1 H, d); 7.89 (1 H, d); 7.60 (1 H, m); 7.74 (1 H, m); 7.47 (1 H, m); 4.93 (1 H, s); 4.87 (1 H, s); 3.93 (2 H, m); 3.10 (2 H, m); 2.35 (3 H, s); 2.27 (3 H, s); Mass Spectrum: M + H$^+$ 574 and 576.
[31] $^1$H NMR Spectrum: (DMSOd$_6$) 2.15 (s, 3 H), 2.28 (s, 3 H), 2.53-2.61 (m, 2 H), 2.92-2.97 (m, 2 H), 3.26 (s, 3 H), 7.26 (d, 1 H), 7.59 (d, 1 H), 7.65-7.70 (m, 2 H), 8.30 (s, 1 H), 10.37 (s, 1 H); Mass Spectrum: M + H$^+$ 506.
[32] $^1$H NMR Spectrum: (DMSOd$_6$) 2.16 (s, 3 H), 2.33 (s, 3 H), 7.18 (m, 1 H), 7.56 (d, 1 H), 7.74 (d, 1 H), 7.99 (d, 1 H), 8.37 (s, 1 H), 10.66 (br s, 1 H), 12.28 (s, 1 H); Mass Spectrum: M + H$^+$ 429.
[33] $^1$H NMR Spectrum: (DMSOd$_6$) 2.16 (s, 3 H), 2.29 (s, 3 H), 7.33 (m, 1 H), 7.66 (d, 1 H), 7.78 (m, 1 H), 8.19 (m, 1 H), 8.31 (d, 1 H), 10.43 (br s, 1 H); Mass Spectrum: M + H$^+$ 429.
[34] $^1$H NMR Spectrum: (DMSOd$_6$) 12.22 (1 H, s); 10.85 (1 H, br s); 8.70 (1 H, d); 8.31 (1 H, br s); 8.06 (1 H, d); 7.78 (1 H, d); 7.76 (1 H, br s); 7.59 (1 H, d); 2.32 (3 H, s); 2.15 (3 H, s); Mass Spectrum: M + H$^+$ 553 and 555.
[35] $^1$H NMR Spectrum: (DMSOd$_6$) 2.17 (s, 3 H), 2.34 (s, 3 H), 2.36 (s, 3 H), 3.61 (s, 3 H), 7.73 (br s, 1 H), 7.91 (s, 1 H), 8.28 (br s, 1 H), 10.08 (br s, 1 H). 2.16 (s, 3 H), 2.32 (s, 3 H), 7.26 (m, 1 H), 7.58 (m, 1 H), 7.78-7.84 (m, 1 H), 7.79 (s, 1 H), 8.35 (s, 1 H), 10.91 (br s, 1 H), 12.27 (s, 1 H); Mass Spectrum: M + H$^+$ 441.
[36] $^1$H NMR Spectrum: (DMSOd$_6$) 2.15 (s, 3 H), 2.30 (s, 3 H), 2.40 (s, 3 H), 3.79 (s, 3 H), 7.37 (br s, 1 H), 7.71 (s, 1 H), 8.11 (br s, 1 H); Mass Spectrum: M + H$^+$ 441.
[37] $^1$H NMR Spectrum: (DMSOd$_6$) 2.17 (s, 3 H), 2.20 (s, 3 H), 2.34 (s, 3 H), 3.75 (s, 3 H), 7.75 (s, 1 H), 8.38 (s, 1 H), 10.49 (br s, 1 H), 12.27 (br s, 1 H); Mass Spectrum: M + H$^+$ 476. 5-Chloro-1,3-dimethyl-1H-pyrazol-4-ylsulfonyl chloride is commercially available and is described in J. Chem. Research Synopses, 1986, 388.
[38] $^1$H NMR Spectrum: (DMSOd$_6$) 2.15 (s, 3 H), 2.30 (s, 3 H), 2.40 (s, 3 H), 3.79 (s, 3 H), 7.37 (br s, 1 H), 7.71 (s, 1 H), 8.11 (br s, 1 H); Mass Spectrum: M + H$^+$ 458. 2,4-Dimethyl-1,3-thiazol-5-ylsulfonyl chloride is commercially available and is described in J. Het. Chem., 1981, 18, 997.
[39] $^1$H NMR Spectrum: (DMSOd$_6$) 2.10 (s, 3 H), 2.14 (s, 3 H), 2.17 (s, 3 H), 2.37 (s, 3 H), 7.43 (d, 1 H), 7.55 (d, 1 H) 2.16 (s, 3 H), 2.34 (s, 3 H), 2.35 (s, 3 H), 2.63 (s, 3 H), 7.77 (d, 1 H), 8.39 (s, 1 H), 10.87 (br s, 1 H); Mass Spectrum: M + H$^+$ 501.
[40] $^1$H NMR Spectrum: (DMSOd$_6$) 2.16 (s, 3 H), 2.23 (s, 3 H), 2.35 (s, 3 H), 2.36 (s, 3 H), 7.88 (d, 1 H), 8.43 (d, 1 H), 10.86 (br s, 1 H); Mass Spectrum: M + H$^+$ 442. 3,5-Dimethyl-isoxazol-4-ylsulfonyl chloride is commercially available and is described in J. Het. Chem., 1981, 18, 997.
[41] $^1$H NMR Spectrum: (DMSOd$_6$) 2.16 (s, 3 H), 2.29 (s, 3 H), 2.37 (s, 3 H), 2.62 (s, 3 H), 7.79 (d, 1 H), 8.15 (s, 1 H), 11.00 (s, 1 H), 12.24 (s, 1 H); Mass Spectrum: M + H$^+$ 442. The N-[5-(5-amino-6-fluoropyridin-3-yl)-4-methyl-1,3-thiazol-2-yl]acetamide used as a starting material was prepared as follows:- Solid N-iodosuccinimide (22.7 g) was added portionwise over a period of 1 hour to a stirred solution of 2-acetamido-4-methylthiazole (15 g) in acetonitrile (150 mL) that had been cooled in an ice-bath. The resultant suspension was allowed to stir at room temperature for 16 hours. Water (100 mL) was added and the resultant precipitate was collected by filtration, washed with water and dried to a constant weight in a vacuum oven at 40° C. There was thus obtained 2-acetamido-5-iodo-4-methylthiazole (24 g); $^1$H NMR Spectrum: (CDCl$_3$) 2.23 (s, 3 H), 2.36 (s, 3 H), 10.3 (br s, 1 H). Potassium acetate (4.72 g) was added to a stirred mixture of 2-acetamido-5-iodo-4-methylthiazole (7 g), [1,1'-bis(diphenylphosphino)ferrocene]dichloropalladium(II) 1:1 complex with dichloromethane (1.84 g), bis(pinacolato)diboron (9.8 g) and 1,4-dioxane (100 mL). The resulting suspension was purged with nitrogen, stirred and heated to 105° C. for 2 hours. The reaction mixture was cooled to room temperature and 2-acetamido-5-iodo-4-methylthiazole (7.7 g) was added followed by a 2 N aqueous solution of sodium carbonate (80 mL). The resultant mixture was heated to 105° C. for 1 hour. The mixture was cooled to room temperature and concentrated by evaporation. The residue was triturated under water. The resultant dark precipitate was collected by filtration, suspended in ethanol (100 mL), stirred, filtered, washed with ethanol and diethyl ether and dried to a constant weight in a vacuum oven. There was thus obtained N-[5-(6-amino-5-nitropyridin-3-yl)-4-methyl-1,3-thiazol-2-yl]acetamide as a brown solid (8 g) which was used without further purification; $^1$H NMR Spectrum: (DMSOd$_6$) 2.10 (s, 3 H), 2.24 (s, 3 H), 8.01 (br s, 2 H), 8.28 (s, 1 H), 8.49 (s, 1 H). Sodium nitrite (395 mg) was added to a stirred suspension of N-[5-(6-amino-5-nitropyridin-3-yl)-4-methyl-1,3-thiazol-2-yl]acetamide (420 mg) in aqueous hydrofluoroboric acid (48%, 2.5 mL) that had been cooled to −10° C. THF (5 mL) was subsequently added to aid agitation. The reaction mixture was allowed to warm to room temperature and extracted with dichloromethane (50 mL). The organic phase was dried over magnesium sulfate and evaporated. The residue was purified by column chromatography on silica using a solvent gradient from pure dichloromethane to 50% ethyl acetate in dichloromethane as eluent. There was thus obtained N-[5-(6-fluoro-5-nitropyridin-3-yl)-4-methyl-1,3-thiazol-2-yl]acetamide as a yellow solid (195 mg); Mass Spectrum: M + H$^+$ 293. A mixture of N-[5-(6-fluoro-5-nitropyridin-3-yl)-4-methyl-1,3-thiazol-2-yl]acetamide (443 mg), 10% palladium on carbon catalyst (220 mg), ethanol (20 mL) and dichloromethane (5 mL) was stirred under 1.5 atmospheres pressure of hydrogen at room temperature for 25 hours. The catalyst was removed by filtration and the filtrate was evaporated. The residue was titurated under petroleum ether to give N-[5-(5-amino-6-fluoropyridin-3-yl)-4-methyl-1,3-thiazol-2-yl]acetamide as a white solid (330 mg); Mass Spectrum: M + H$^+$ 267.

TABLE I-continued

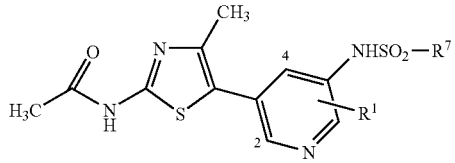

No. & Note    R¹    R⁷

[42] The reaction mixture was heated to 50° C. for 30 minutes. The reaction product was purified by column chromatography on silica using increasingly polar mixtures of dichloromethane and methanol as eluent. The product gave the following characterising data: $^1$H NMR Spectrum: (DMSOd$_6$) 2.15 (s, 3 H), 2.29 (s, 3 H), 2.35 (s, 3 H), 2.61 (s, 3 H), 3.72 (s, 3 H), 7.61 (d, 1 H), 8.10 (s, 1 H), 10.37 (s, 1 H), 12.16 (s, 1 H); Mass Spectrum: M + H⁺ 454. The N-[5-(5-amino-6-methoxypyridin-3-yl)-4-methyl-1,3-thiazol-2-yl]acetamide used as a starting material was prepared as follows:- tert-Butyl nitrite (4.25 mL) was added dropwise over a period of 30 minutes to a stirred suspension of N-[5-(6-amino-5-nitropyridin-3-yl)-4-methyl-1,3-thiazol-2-yl]acetamide (7 g) and cuprous chloride (3.2 g) in acetonitrile (140 mL) under an atmosphere of nitrogen at room temperature. The resultant suspension was heated to reflux for 1 hour. Two additional portions of tert-butyl nitrite (each 2.13 mL) were added and heating was continued for 1 hour. The resultant solution was cooled to 0° C. and 1 N aqueous hydrochloric acid (100 mL) was added carefully. The resultant suspension was filtered and the isolated solid was washed with ethyl acetate. The filtrate was extracted with ethyl acetate. The organic phases were combined and washed with water and brine and dried over magnesium sulfate. The solution was evaporated and the residue was purified by column chromatography on silica using a 1:1 mixture of dichloromethane and ethyl acetate as eluent. There was thus obtained N-[5-(5-chloro-5-nitropyridin-3-yl)-4-methyl-1,3-thiazol-2-yl]acetamide as a solid (0.95 g); $^1$H NMR Spectrum: (DMSOd$_6$) 2.17 (s, 3 H), 2.41 (s, 3 H), 8.61 (s, 1 H), 8.82 (s, 1 H). Anhydrous sodium methoxide (69 mg) was added in one portion to a stirred solution of N-[5-(6-chloro-5-nitropyridin-3-yl)-4-methyl-1,3-thiazol-2-yl]acetamide (200 mg) in methanol (4 mL) at room temperature. The resultant solution was stirred at room temperature overnight. The mixture was evaporated and the residue was partitioned between a saturated aqueous solution of ammonium chloride and dichloromethane (50 mL). The organic phase was washed with water and brine and dried over magnesium sulfate. The solvent was evaporated and the residue was purified by column chromatography on silica using increasingly polar mixtures of dichloromethane and ethyl acetate as eluent. There was thus obtained N-[5-(5-nitro-6-methoxypyridin-3-yl)-4-methyl-1,3-thiazol-2-yl]acetamide as a white solid (132 mg); $^1$H NMR Spectrum: (DMSOd$_6$) 2.16 (s, 3 H), 2.34 (s, 3 H), 4.07 (s, 3 H), 8.54 (s, 1 H), 8.61 (s, 1 H). A mixture of N-[5-(5-nitro-6-methoxypyridin-3-yl)-4-methyl-1,3-thiazol- 2-yl]acetamide (300 mg), Raney nickel (50 mg) and ethanol (20 mL) was warmed to 50° C. and hydrazine monohydrate (0.28 mL) was added dropwise. The resultant mixture was filtered and the filtrate was evaporated. The residue was purified by column chromatography on silica using a solvent gradient from dichloromethane to 6% methanol in dichloromethane as eluent. There was thus obtained N-[5-(5-amino-6-methoxypyridin-3-yl)-4-methyl-1,3-thiazol-2-yl]acetamide as a white solid (235 mg); $^1$H NMR Spectrum: (DMSOd$_6$) 2.17 (s, 3 H), 2.35 (s, 3 H), 4.04 (s, 3 H), 7.7 (s, 1 H), 8.15 (s, 1 H); Mass Spectrum: M + H⁺ 279.

[43] $^1$H NMR Spectrum: (DMSOd$_6$) 12.27 (1 H, s); 10.78 (1 H, br s); 8.90 (1 H, d); 8.86 (1 H, dd); 8.37 (1 H, d); 8.13 (1 H, m); 7.75 (1 H, d); 7.65 (1 H, dd); 2.32 (3 H, s); 2.16 (3 H, s); Mass Spectrum: M + H⁺ 424 and 426.

[44] Analogous reaction conditions and purification procedures to those of Note [42] were used. The product gave the following characterising data: $^1$H NMR Spectrum: (DMSOd$_6$) 2.10 (s, 3 H), 2.12 (s, 3 H), 7.28 (m, 1 H), 7.38-7.45 (m, 2 H), 8.03 (m, 1 H), 8.56 (m, 1 H), 8.84 (d, 1 H); Mass Spectrum: M + H⁺ 408.

[45] Analogous reaction conditions and purification procedures to those of Note [42] were used. The product gave the following characterising data: $^1$H NMR Spectrum: (DMSOd$_6$) 2.14 (s, 3 H), 2.26 (s, 3 H), 3.63 (s, 3 H), 7.59 (s, 1 H), 7.62 (m, 1 H), 8.02 (s, 1 H), 8.11 (d, 1 H), 8.80 (d, 1 H), 8.88 (d, 1 H), 10.34 (br s, 1 H), 12.15 (s, 1 H); Mass Spectrum: M + H⁺ 420.

[46] The reaction conditions were varied as follows:- n-Propylsulfonyl chloride (0.238 mL) was added to a stirred mixture of N-[5-(5-amino-6-chloropyridin-3-yl)-4-methyl-1,3-thiazol-2-yl]acetamide (200 mg), triethylamine (0.295 mL) and THF (2 mL) that had been cooled to 0° C. under an argon atmosphere. The resultant solution was stirred at room temperature for 30 minutes. A solution of 7 M methanolic ammonia (2 mL) was added and the mixture was stirred at room temperature for 16 hours. The mixture was evaporated and the residue was purified by preparative HPLC on reverse phase silica using a solvent gradient of 10% to 100% acetonitrile in water (containing 1% acetic acid) as eluent at a flow rate of about 10 mL/minute. The material so obtained was triturated under diethyl in ether to give the required product as a white solid (138 mg); $^1$H NMR Spectrum: (DMSOd$_6$) 0.98 (t, 3 H), 1.72-1.83 (m, 2 H), 2.16 (s, 3 H), 2.37 (s, 3 H), 3.17-3.24 (m, 2 H), 7.89 (d, 1 H), 8.32 (d, 1 H), 9.89 (s, 1 H); Mass Spectrum: M + H⁺ 389.

[47] Analogous reaction conditions to those of Note [46] were used. The product gave the following characterising data:- $^1$H NMR Spectrum: (DMSOd$_6$) 2.15 (s, 3 H), 2.34 (s, 3 H), 3.10 (s, 3 H), 7.89 (d, 1 H), 8.01 (d, 1 H), 10.04 (br s, 1 H), 12.21 (br s, 1 H); Mass Spectrum: M + H⁺ 345.

[48] Analogous reaction conditions to those of Note [46] were used. The product gave the following characterising data:- $^1$H NMR Spectrum: (DMSOd$_6$) 2.15 (s, 3 H), 2.32 (s, 3 H), 3.07 (s, 3 H), 3.95 (s, 3 H), 7.67 (d, 1 H), 8.06 (d, 1 H), 9.38 (br s, 1 H), 12.14 (s, 1 H); Mass Spectrum: M + H⁺ 357.

[49] Analogous reaction conditions to those of Note [46] were used. The product gave the following characterising data:- $^1$H NMR Spectrum: (DMSOd$_6$) 1.29 (t, 3 H), 2.16 (s, 3 H), 2.37 (s, 3 H), 3.23 (q, 2 H), 7.89 (d, 1 H), 8.31 (d, 1 H), 9.88 (br s, 1 H); Mass Spectrum: M + H⁺ 375.

[50] Analogous reaction conditions to those of Note [46] were used. The product gave the following characterising data:- $^1$H NMR Spectrum: (DMSOd$_6$) 2.16 (s, 3 H), 2.37 (s, 3 H), 4.74 (q, 2 H), 7.97 (d, 1 H), 8.41 (d, 1 H), 10.61 (br s, 1 H); Mass Spectrum: M + H⁺ 429.

TABLE I-continued

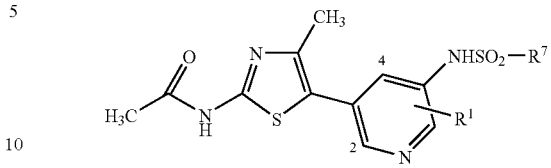

No. & Note    R¹    R⁷

[51] Analogous reaction conditions to those of Note [46] were used. The product gave the following characterising data:- $^1$H NMR Spectrum: (DMSOd$_6$) 2.15 (s, 3 H), 2.20 (s, 3 H), 2.21 (s, 3 H), 7.34 (d, 1 H), 7.59 (m, 2 H), 6.67 (m, 1 H), 7.71 (d, 2 H), 8.34 (d, 1 H), 10.03 (br s, 1 H), 12.18 (s, 1 H); Mass Spectrum: M + H⁺ 403. The N-[5-(5-amino-6-methylpyridin-3-yl)-4-methyl-1,3-thiazol-2-yl]acetamide used as a starting material was prepared as follows:- A mixture of N-[5-(5-amino-6-chloropyridin-3-yl)-4-methyl-1,3-thiazol-2-yl]acetamide (178 mg), [1,1'-bis(diphenylphosphino)ferrocene]dichloropalladium(II) 1:1 complex with dichloromethane (20 mg), trimethoxyboroxine (0.09 mL), caesium carbonate (492 mg) and DME (2 mL) was heated in a microwave apparatus to 180° C. for 45 minutes. The resultant mixture was cooled to room temperature and filtered. The filtrate was evaporated and the residue was purified by column chromatography on silica using a solvent gradient of 0% to 6% 7 M methanolic ammonia in dichloromethane as eluent. There was thus obtained the required starting material as a solid (63 mg); $^1$H NMR Spectrum: (DMSOd$_6$) 2.13 (s, 3 H), 2.28 (s, 3 H), 2.33 (s, 3 H), 5.20 (s, 2 H), 6.99 (d, 1 H), 7.74 (d, 1 H), 12.10 (s, 1 H).

[52] Analogous reaction conditions to those of Note [14] were used. The product gave the following characterising data:- $^1$H NMR Spectrum: (DMSOd$_6$) 2.15 (s, 3 H), 2.23 (s, 3 H), 7.60 (m, 2 H), 7.68 (d, 1 H), 7.72 (m, 1 H), 7.80 (d, 2 H), 8.05 (s, 1 H), 10.70 (br s, 1 H), 12.23 (s, 1 H); Mass Spectrum: M + H⁺ 407.

[53] Analogous reaction conditions to those of Note [14] were used. The product gave the following characterising data:- $^1$H NMR Spectrum: (DMSOd$_6$) 2.16 (s, 3 H), 2.25 (s, 3 H), 3.70 (s, 3 H), 7.55-7.61 (m, 3 H), 7.65 (m, 1 H), 7.80 (d, 2 H), 8.01 (s, 1 H); Mass Spectrum: M + H⁺ 419.

[54] Analogous reaction conditions and purification procedures to those of Note [42] were used. The product gave the following characterising data:- $^1$H NMR Spectrum: (DMSOd$_6$ + CD$_3$CO$_2$D) 2.16 (s, 3 H), 2.29 (s, 3 H), 7.61 (m, 2 H), 7.68 (d, 1 H), 7.70 (m, 1 H), 7.86 (d, 2 H), 8.33 (d, 1 H), 8.48 (d, 1 H); Mass Spectrum: M + H⁺ 389. The N-[5-(5-aminopyridin-3-yl)-4-methyl-1,3-thiazol-2-yl]acetamide used as a starting material was prepared as follows:- A mixture of N-[5-(5-amino-6-chloropyridin-3-yl)-4-methyl-1,3-thiazol-2-yl]acetamide (170 mg), hydrazine monohydrate (0.73 mL), Raney nickel (300 mg) and ethanol (15 mL) was stirred and heated to 60° C. for 6 hours. The suspension was filtered and the filtrate was concentrated. The residue was purified by column chromatography on silica using a solvent gradient from dichloromethane to 6% 7 M methanolic ammonia in dichloromethane as eluent. There was thus obtained the required starting material as a white solid (75 mg); $^1$H NMR Spectrum: (DMSOd$_6$) 2.14 (s, 3 H), 2.34 (s, 3 H), 5.46 (s, 2 H), 6.98 (t, 1 H), 7.18 (d, 1 H), 7.87 (d, 1 H), 12.13 (s, 1 H).

[55] Analogous reaction conditions and purification procedures to those of Note [42] were used. The product gave the following characterising data:- $^1$H NMR Spectrum: (DMSOd$_6$) 2.15 (s, 3 H), 2.26 (s, 3 H), 7.43 (m, 2 H), 7.49 (s, 1 H), 7.86 (m, 2 H), 8.23 (s, 1 H), 8.35 (s, 1 H), 10.76 (br s, 1 H), 12.23 (s, 1 H); Mass Spectrum: M + H⁺ 407.

[56] $^1$H NMR Spectrum: (acetone-d$_6$) 7.82-7.79 (2 H); 7.58-7.51 (3 H); 7.42 (1 H, m); 4.64 (2 H, s); 2.34 (3 H, s); 2.24 (3 H, s); Mass Spectrum: M + H⁺ 482 and 484.

[57] $^1$H NMR Spectrum: (acetone-d$_6$) 8.62 (1 H, s); 8.30 (1 H, d); 8.10 (1 H, d); 6.80 (4 H, s); 4.08 (2 H, m); 3.73 (3 H, s); 3.51 (2 H, t); 2.37 (3 H, s); 2.32 (2 H, m); 2.26 (3 H, s); Mass Spectrum: M + H⁺ 511 and 513.

EXAMPLE 59

N-{5-[6-Chloro-5-(N,N-dimethylsulphamoylamino) pyridin-3-yl]-4-methyl-1,3-thiazol-2-yl}acetamide Dimethylsulfamoyl chloride (0.108 mL) was added to a stirred mixture of N-[5-(5-amino-6-chloropyridin-3-yl)-4-methyl-1,3-thiazol-2-yl]acetamide (142 mg), diisopropylethylamine (0.175 mL) and 1,4-dioxane (5 mL) and the reaction mixture was heated to reflux for 18 hours. Further portions of diisopropylethylamine (0.175 mL) and dimethylsulfamoyl chloride (0.081 mL) were added and the mixture was heated to reflux for 6 hours more. The reaction mixture was evaporated and the residue was dissolved in ethyl acetate. The organic solution was washed with water, dried over magnesium sulfate and evaporated. The residue was purified by preparative HPLC. There was thus obtained the title compound (37 mg); $^1$H NMR Spectrum: (DMSOd$_6$) 2.16 (s, 3H), 2.38 (s, 3H), 2.77 (s, 6H), 7.92 (d, 1H), 8.31 (d, 1H), 9.85 (br s, 1H), 12.23 (s, 1H); Mass Spectrum: M+H⁺ 390.

EXAMPLE 60

N-[5-(5-Chloro-6-phenylsulphonylaminopyridin-3-yl)-4-methyl-1,3-thiazol-2-yl]acetamide Phenylsulfonyl chloride (0.108 mL) was added to a stirred solution of N-[5-(6-amino-5-chloropyridin-3-yl)-4-methyl-1,3-thiazol-2-yl]acetamide (80 mg) in pyridine (1 mL) and the resultant solution was heated to 50° C. for 4 hours. The mixture was cooled to room temperature and concentrated by evaporation. The residue was purified by column chromatography on silica using increasingly polar mixtures of dichloromethane and methanol as eluent. The material so obtained was triturated under diethyl ether. There was thus obtained the title compound as a white solid (38 mg); $^1$H NMR Spectrum: (DMSOd$_6$) 2.13 (s, 3H), 2.29 (s, 3H), 7.60 (m, 2H), 7.75 (m, 1H), 7.98 (s, 1H), 8.02 (d, 2H), 8.18 (br s, 1H), 10.95 (br s, 1H); Mass Spectrum: M+H$^+$ 423.

The N-[5-(6-amino-5-chloropyridin-3-yl)-4-methyl-1,3-thiazol-2-yl]acetamide used as a starting material was prepared as follows A mixture of 2-acetamido-4-methylthiazole (300 mg), caesium fluoride (876 mg), 2-amino-5-bromo-3-chloropyridine (435 mg), palladium(II) acetate (22 mg), tri-tert-butylphosphine (0.046 mL) and DMSO (3 mL) was stirred and purged with nitrogen for 15 minutes. The resultant mixture was heated to 130° C. for 2 hours. The mixture was cooled to room temperature and water (10 mL) was added. The resultant solid was collected by filtration, washed with acetonitrile and dried. The solid so obtained was purified by column chromatography on silica using a solvent gradient of 0% to 8% methanol in dichloromethane as eluent. There was thus obtained the required starting material as a solid (252 mg); $^1$H NMR Spectrum: (DMSOd$_6$) 2.19 (s, 3H), 2.27 (s, 3H), 6.50 (s, 2H), 7.65 (s, 1H), 7.97 (s, 1H).

The 2-amino-5-bromo-3-chloropyridine used as a starting material was prepared as follows:—

N-Chlorosuccinimide (508 mg) was added to a solution of 2-amino-5-bromopyridine (600 mg) in DMF (1.5 mL) that had been cooled to 0° C. The resultant mixture was stirred at 0° C. for 1 hour. The mixture was diluted with water, neutralised to pH7 by the addition of dilute aqueous sodium hydroxide solution and extracted with diethyl ether. The organic layer was dried over magnesium sulfate and evaporated. The residue was purified by column chromatography on silica using a solvent gradient from 0% to 15% ethyl acetate in petroleum ether as eluent. There was thus obtained 2-amino-5-bromo-3-chloropyridine as a solid (535 mg); $^1$H NMR Spectrum: (DMSOd$_6$) 6.53 (s, 2H), 7.84 (s, 1H), 7.98 (s, 1H).

EXAMPLE 61

N-[5-(2-Amino-4-methyl-1,3-thiazol-5-yl)-2-chloropyridin-3-yl]-5-chloro-1,3-dimethyl-1H-pyrazole-4-sulfonamide A mixture of N-{5-[6-chloro-5-(5-chloro-1,3-dimethyl-1H-pyrazol-4-ylsulfonamido)pyridin-3-yl]-4-methyl-1,3-thiazol-2-yl}acetamide (300 mg), a 6N aqueous hydrochloric acid solution (5 mL) and ethanol (5 mL) was stirred and heated to 80° C. for 5 hours. The mixture was cooled to room temperature and concentrated by evaporation. The residue was purified by preparative HPLC. There was thus obtained the title compound as a white solid (100 mg); $^1$H NMR Spectrum: (DMSOd$_6$) 2.19 (s, 6H), 3.73 (s, 3H), 7.39 (br s, 2H), 7.66 (s, 1H), 8.25 (s, 1H); Mass Spectrum: M+H$^+$ 433.

EXAMPLE 62

N-[5-(2-Amino-4-methyl-1,3-thiazol-5-yl)-2-chloropyridin-3-yl]methanesulfonamide Using an analogous procedure to that described in Example 61, N-[5-(6-chloro-5-methylsulfonylaminopyridin-3-yl)-4-methyl-1,3-thiazol-2-yl]acetamide was hydrolysed with aqueous hydrochloric acid solution to give the title compound; $^1$H NMR Spectrum: (DMSOd$_6$) 2.22 (s, 3H); 3.13 (s, 3H); 7.23 (s, 2H); 7.76 (d, 1H); 8.21 (d, 1H); 8.79 (br s, 1H); Mass Spectrum: M+H$^+$ 319.

EXAMPLE 63

N-[5-(2-Amino-4-methyl-1,3-thiazol-5-yl)-2-chloropyridin-3-yl]benzenesulfonamide Using an analogous procedure to that described in Example 61, N-[5-(6-chloro-5-phenylsulfonylaminopyridin-3-yl)-4-methyl-1,3-thiazol-2-yl]acetamide was hydrolysed with aqueous hydrochloric acid solution to give the title compound; $^1$H NMR Spectrum: (DMSOd$_6$) 2.11 (s, 3H), 7.24 (s, 2H), 7.50 (d, 1H), 7.60 (m, 2H), 7.68 (m, 1H), 7.77 (d, 2H), 8.14 (s, 1H), 10.42 (br s, 1H); Mass Spectrum: M+H$^+$ 381.

EXAMPLE 64

N-[5-(2-Amino-4-methyl-1,3-thiazol-5-yl)-2-chloropyridin-3-yl]-2,4-dimethyl-1,3-thiazole-5-sulfonamide Using an analogous procedure to that described in Example 61, N-{5-[6-chloro-5-(2,4-dimethyl-1,3-thiazol-5-ylsulfonamido)pyridin-3-yl]-4-methyl-1,3-thiazol-2-yl}acetamide was hydrolysed with aqueous hydrochloric acid solution to give the title compound; $^1$H NMR Spectrum: (DMSOd$_6$) 2.18 (s, 3H), 2.35 (s, 3H), 2.61 (s, 3H), 7.30 (s, 2H), 7.64 (d, 11H), 8.22 (s, 1H), 10.80 (br s, 1H); Mass Spectrum: M+H$^+$ 416.

EXAMPLE 65

N-[2-Chloro-5-(2-methylamino-4-methyl-1,3-thiazol-5-yl)pyridin-3-yl]methanesulfonamide A mixture of N-[2-chloro-5-(2-chloro-4-methyl-1,3-thiazol-5-yl)pyridin-3-yl]-N-(methylsulfonyl)methanesulfonamide (94 mg) and a 13% solution of methylamine in ethanol (5.0 mL) was stirred and heated to 120° C. in a sealed glass tube in a microwave reactor for 2.5 hours. The resultant mixture was evaporated. Ethanol was added and the mixture was re-evaporated. The material so obtained was purified by reversed phase preparative HPLC. There was thus obtained the title compound (25 mg); $^1$H NMR Spectrum: (DMSOd$_6$) 2.23 (s, 3H), 2.83 (d, 3H), 3.13 (s, 3H), 7.76 (s, 1H), 7.82 (s, 1H), 8.23 (s, 1H), 9.77 (s, 1H); Mass Spectrum: M+H$^+$ 333.

The N-[2-chloro-5-(2-chloro-4-methyl-1,3-thiazol-5-yl)pyridin-3-yl]-N-(methylsulfonyl)methanesulfonamide used as a starting material was prepared as follows:—

Methanesulfonyl chloride (2.74 mL) was added to a stirred mixture of N-[5-(5-amino-6-chloropyridin-3-yl)-4-methyl-1,3-thiazol-2-yl]acetamide (2 g), triethylamine (9.8 mL) and dry THF (100 mL) and the reaction mixture was stirred at room temperature for 18 hours. The mixture was partitioned between ethyl acetate and water. The organic solution was washed with water and with saturated sodium chloride solution, dried with anhydrous sodium sulfate and evaporated. There was thus obtained N-{5-[5-bis(methylsulfonyl)amino-6-chloropyridin-3-yl]-4-methyl-1,3-thiazol-2-yl}acetamide (2.48 g); $^1$H NMR Spectrum: (DMSOd$_6$) 2.23 (s, 3H), 2.45 (s, 3H), 3.72 (s, 6H), 8.4 (s, 1H), 8.7 (s, 3H), 12.35 (s, 1H); Mass Spectrum: M+H$^+$ 439.

A mixture of the material so obtained, concentrated hydrochloric acid (31 mL), water (31 mL) and ethanol (125 mL) was stirred and heated to 90° C. for 6 hours. The ethanol was evaporated off at 40° C. and the residue was diluted with water. The solution was cooled in ice and the acidity of the solution was reduced to pH6 by the addition of 40% aqueous sodium hydroxide solution. The resultant precipitate was isolated, washed with water and dried. There was thus obtained N-[5-(2-amino-4-methyl-1,3-thiazol-5-yl)-2-chloropyridin-3-yl]-(methylsulfonyl)methanesulfonamide (1.43 g); $^1$H NMR Spectrum: (DMSOd$_6$) 2.3 (s, 3H), 3.65 (s, 6H), 8.3 (s, 11H), 8.63 (s, 11H), 9.13 (s, 2H); Mass Spectrum: M+H$^+$ 397.

Isoamyl nitrite (0.05 mL) was added to a stirred suspension of anhydrous cuprous chloride (40 mg) in acetonitrile (2 mL). N-[5-(2-Amino-4-methyl-1,3-thiazol-5-yl)-2-chloropyridin-3-yl]-N-(methylsulfonyl)methanesulfonamide (100 mg) was added and the mixture was stirred and heated to reflux for 1 hour. The reaction mixture was partitioned between ethyl acetate and a 10% aqueous hydrochloric acid solution. The organic solution was washed with water and a saturated sodium chloride, dried with anhydrous sodium sulfate and evaporated. There was thus obtained the required starting material (100 mg); $^1$H NMR Spectrum: (DMSOd$_6$) 2.4 (s, 3H), 3.17 (s, 6H), 8.4 (s, 1H), 8.68 (s, 1H); Mass Spectrum: M+H$^+$ 416.

EXAMPLE 66

N-[2-Chloro-5-(4-methyl-2-pyrimidin-2-ylamino-1, 3-thiazol-5-yl)pyridin-3-yl]methanesulfonamide Methanesulfonyl chloride (0.063 mL) was added to a stirred mixture of 2-{N-[5-(5-amino-6-chloropyridin-3-yl)-4-methyl-1,3-thiazol-2-yl]amino}pyrimidine (85 mg), triethylamine (0.226 mL) and THF (5 mL) and the reaction was stirred at room temperature for 18 hours. Additional portions of methanesulfonyl chloride (0.063 mL) and triethylamine (0.226 mL) were added and the reaction mixture was stirred at room temperature for a further 2 hours. The resultant mixture was heated to reflux for 4 hours. The mixture was evaporated and the residue was triturated under water. The resultant precipitate was isolated, washed with water and dried. The solid was suspended in a 12% solution of methylamine in ethanol (4 mL) and the mixture was stirred at room temperature for 18 hours. The resultant mixture was evaporated. Ethanol was added and the mixture was re-evaporated. The material so obtained was purified by reversed phase preparative HPLC to give a product which was triturated under methanol. The solid so obtained was isolated, washed with methanol and dried. There was thus obtained the title compound (32 mg); $^1$H NMR Spectrum: 2.4 (s, 3H), 3.2 (s, 3H), 7.05 (t, 1H), 7.9 (s, 1H), 8.36 (s, 1H), 8.65 (d, 2H), 9.8 (s, 1H), 11.85 (s, 1H); Mass Spectrum: M+H$^+$ 397.

The 2-{N-[5-(5-amino-6-chloropyridin-3-yl)-4-methyl-1,3-thiazol-2-yl]amino}pyrimidine used as a starting material was prepared as follows:—

A stirred mixture of 2-amino-4-methylthiazole (285 mg), 2-chloropyrimidine (301 mg), powdered anhydrous potassium phosphate (742 mg) and 1,4-dioxane was purged with nitrogen for 15 minutes. Tris(dibenzylideneacetone)dipalladium(0) (87 mg) and 4,5-bis(diphenylphosphino)-9,9-dimethylxanthene (46 mg) were added and the resultant mixture was stirred and heated to 100° C. under nitrogen for 18 hours. The reaction mixture was cooled to room temperature and partitioned between ethyl acetate and water. The organic solution was washed with water and with a saturated sodium chloride solution, dried over anhydrous sodium sulfate and evaporated. The material so obtained was triturated under methanol. The resultant solid was isolated and washed in turn with methanol, diethyl ether and dichloromethane. There was thus obtained 2-[N-(4-methyl-1,3-thiazol-2-yl)amino]pyrimidine (311 mg); $^1$H NMR Spectrum: (DMSOd$_6$) 2.26 (s, 3H), 6.65 (d, 1H), 7.00 (t, 1H), 8.61 (d, 2H), 11.54 (s, 1H); Mass Spectrum: M+H$^+$ 193.

Using an analogous procedure to that described in the portion of Example 57 that is concerned with the preparation of starting materials, 2-[N-(4-methyl-1,3-thiazol-2-yl)amino]pyrimidine (113 mg) was reacted with 3-amino-5-bromo-2-chloropyridine (122 mg). The cooled reaction mixture was poured into stirred, cooled water and the resultant precipitate was isolated, washed with water and dried. The material so obtained was triturated under a 4:1 mixture of dichloromethane and methanol. The solid so obtained was isolated, washed with the same solvent mixture and dried. There was thus obtained 2-{N-[5-(5-amino-6-chloropyridin-3-yl)-4-methyl-1,3-thiazol-2-yl]amino}pyrimidine (105 mg); $^1$H NMR Spectrum: (DMSOd$_6$) 2.4 (s, 3H), 5.68 (s, 2H), 7.05 (t, 1H), 7.26 (s, 1H), 7.72 (s, 1H), 8.66 (d, 1H), 11.75 (s, 1H); Mass Spectrum: M+H$^+$ 319.

EXAMPLE 67

N-(5-{6-Chloro-5-[N-(4-fluorophenylsulfonyl)-N-methylamino]pyridin-3-yl}-4-methyl-1,3-thiazol-2-yl)acetamide trifluoroacetate Using an analogous method to that described in Example 7, N-(5-iodo-4-methyl-1,3-thiazol-2-yl)acetamide was reacted with N-(5-bromo-2-chloropyridin-3-yl)-N-methyl-4-fluorobenzenesulfonamide to give the title compound (Method A HPLC: retention time 10.1 minutes) in 26% yield; $^1$H NMR Spectrum: 12.26 (1H, s); 8.52 (1H, d); 7.85 (2H, m); 7.65 (1H, d); 7.49 (2H, m); 3.22 (3H, s); 2.29 (3H, s); 2.16 (3H, s); Mass Spectrum: M+H$^+$ 455.

The N-(5-bromo-2-chloropyridin-3-yl)-N-methyl-4-fluorobenzenesulfonamide used as a starting material was prepared as follows:—

Using an analogous method to that described in Example 11, 3-amino-5-bromo-2-chloropyridine was reacted with and 4-fluorobenzenesulfonyl chloride to give N-(5-bromo-2-chloropyridin-3-yl)-4-fluorobenzenesulfonamide in 82% yield; $^1$H NMR Spectrum: (CDCl$_3$) 8.21 (1H, d); 8.15 (1H, d); 7.84 (2H, m); 7.20 (2H, m); 6.97 (1H, br s); Mass Spectrum: M+H$^+$ 365.

A mixture of N-(5-bromo-2-chloropyridin-3-yl)-4-fluorobenzenesulfonamide (0.366 g, 1 mmol), caesium carbonate (0.366 g, 1.1 mmol) and 1,4-dioxane (5 n-L) was stirred and heated to 50° C. for 1 hour. Methyl iodide (0.375 mL, 6 mmol) was added heating was continued for two hours. The resultant mixture was evaporated and the residue was purified by preparative HPLC. There was thus obtained the required starting material in 79% yield; $^1$H NMR Spectrum: (DMSOd$_6$) 8.61

(1H, d); 7.97 (1H, d); 7.82 (2H, m); 7.50 (2H, m); 3.16 (3H, s); Mass Spectrum: M+H+ 379.

EXAMPLE 68

N-{2-Chloro-5-[2-(3-ethylureido)-4-methyl-1,3-thiazol-5-yl]pyridin-3-yl}methanesulfonamide Ethyl isocyanate (0.036 mL) was added to a stirred solution of N-[5-(2-amino-4-methyl-1,3-thiazol-5-yl)-2-chloropyridin-3-yl]methanesulfonamide (48 mg) in THF (0.5 mL) and the mixture was placed in a sealed glass reaction vessel and heated to 125° C. in a microwave reactor for 1 hour. The resultant mixture was evaporated and the residue was purified by column chromatography on silica using a solvent gradient of 0% to 6% methanol in dichloromethane as eluent. The material so obtained was purified further by preparative HPLC on reversed-phase silica using a solvent gradient of 10% to 100% acetonitrile in water (containing 1% acetic acid) as eluent. The material so obtained was triturated under diethyl ether. There was thus obtained the title compound as a solid (16 mg); $^1$H NMR Spectrum: (DMSOd$_6$) 1.07 (t, 3H), 2.31 (s, 3H), 3.1, (s, 3H), 3.10-3.20 (m, 2H), 6.54 (br s, 11H), 7.82 (d, 1H), 8.24 (s, 1H), 9.84 (s, 1H), 10.53 (s, 1H); Mass Spectrum: M+H+ 390.

EXAMPLE 69

N-[2-Chloro-5-(2-ureido-4-methyl-1,3-thiazol-5-yl)pyridin-3-yl]-2,4-dimethyl-1,3-thiazole-5-sulfonamide A mixture of trimethylsilyl isocyanate (0.032 mL), N-[5-(2-amino-4-methyl-1,3-thiazol-5-yl)-2-chloropyridin-3-yl]-2,4-dimethylthiazole-5-sulfonamide (46 mg) and DME (1 mL) was placed in a sealed glass reaction vessel and heated to 115° C. in a microwave reactor for 18 hours. The resultant mixture was evaporated and the residue was purified by preparative HPLC on reversed-phase silica using a solvent gradient of 10% to 100% acetonitrile in water (containing 1% acetic acid) as eluent. The material so obtained was triturated under diethyl ether. There was thus obtained the title compound as a solid (16 mg); $^1$H NMR Spectrum: (DMSOd$_6$) 2.28 (s, 3H), 2.34 (s, 3H), 2.62 (s, 3H), 6.47 (br s, 2H), 7.71 (s, 1H), 8.34 (br s, 1H), 10.55 (s, 1H), 10:85 (br s, 1H); Mass Spectrum: M+H+ 459.

EXAMPLE 70

Using analogous procedures to those described in Example 49, the appropriate 2-amino-1,3-thiazole was reacted with phenyl chloroformate and the phenyl N-(1,3-thiazol-2-yl)carbamate so obtained was reacted with the appropriate alkylamine to give the compounds described in Table II.

Alternatively, using an analogous procedure to that described in Example 68, the appropriate 2-amino-1,3-thiazole was reacted with the appropriate alkyl isocyanate to give the compounds described in Table II.

Unless otherwise stated, each reaction product was purified by preparative HPLC on Kromasil C18 reversed-phase silica using a solvent gradient of 10% to 100% acetonitrile in water (containing 1% acetic acid) as eluent at a flow rate of about 10 mL/minute.

Unless otherwise stated, each required alkylamine and alkyl isocyanate was a commercially available material.

TABLE II

| No. & Note | R$^{23}$ | R$^7$ |
|---|---|---|
| [1] | isopropyl | phenyl |
| [2] | ethyl | 2,4-dimethyl-1,3-thiazol-5-yl |
| [3] | cyclopropyl | methyl |
| [4] | 2-hydroxyethyl | methyl |
| [5] | (1R)-1-(hydroxymethyl)propyl | methyl |
| [6] | 4-chlorophenyl | methyl |
| [7] | 3,4-dimethoxybenzyl | methyl |
| [8] | 5-methylfuran-2-ylmethyl | methyl |
| [9] | 2-thienylmethyl | methyl |
| [10] | 2-(3,5-dimethylisoxazol-4-yl)ethyl | methyl |

Notes
The products gave the characterising data shown below.
[1] The procedure of Example 68 was used. The product gave the following characterising data:- $^1$H NMR Spectrum: (DMSOd$_6$) 1.12 (d, 6 H), 2.21 (s, 3 H), 3.74-3.85 (m, 1 H), 6.43 (d, 1 H), 7.59 (m, 2 H), 7.62 (d, 1 H), 7.67 (m, 1 H), 7.77 (d, 2 H), 8.24 (br s, 1 H), 10.30 (s, 1 H), 10.47 (br s, 1 H); Mass Spectrum: M + H+ 466.
[2] The procedure of Example 68 was used. The product gave the following characterising data:- $^1$H NMR Spectrum: (DMSOd$_6$) 1.07 (t, 3 H), 2.28 (s, 3 H), 2.35 (s, 3 H), 2.62 (s, 3 H), 3.12-3.20 (m, 2 H), 6.55 (br s, 1 H), 7.73 (d, 1 H), 8.35 (br s, 1 H), 10.56 (s, 1 H), 10.85 (br s, 1 H); Mass Spectrum: M + H+ 487.
[3] The procedures of Example 49 were used. The product gave the following characterising data:- $^1$H NMR Spectrum: (DMSOd$_6$ + D$_2$O) 8.31 (1 H, d); 7.85 (1 H, d); 3.15 (3 H, s); 2.61-2.53 (1 H, m); 2.31 (3 H, s); 0.75-0.57 (2 H, m); 0.54-0.36 (2 H, m); Mass Spectrum: M + H+ 402 and 404.
[4] The procedures of Example 49 were used. The product gave the following characterising data:- $^1$H NMR Spectrum: (DMSOd$_6$ + D$_2$O) 8.31 (1 H, d); 7.85 (1 H, d); 3.20 (2 H, t); 3.15 (3 H, s); 2.31 (3 H, s); Mass Spectrum: M + H+ 406 and 408.
[5] The procedures of Example 49 were used. The reaction product was diluted with water (3 mL; containing 0.1% trifluoroacetic acid) and acetonitrile (1 mL) and the solution was purified by preparative HPLC. Fractions containing the product were collected and lyophilized to give the required product as it trifluoroacetic acid salt which gave the following characterising data:- $^1$H NMR Spectrum: (DMSOd$_6$ + D$_2$O) 8.31 (1 H, d); 7.82 (1 H, d); 3.42 (1 H, dd); 3.37 (1 H, dd); 3.15 (3 H, s); 2.30 (3 H, s); 1.64-1.48 (1 H, m); 1.47-1.30 (1 H, m); 0.85 (3 H, t); Mass Spectrum: M + H+ 434 and 436.
[6] The procedure of Example 68 was used. The product gave the following characterising data:- $^1$H NMR Spectrum: (DMSOd$_6$) 2.36 (s, 3 H), 3.17 (s, 3 H), 7.33 (d, 2 H), 7.48 (d, 2 H), 7.90 (d, 1 H), 8.35 (d, 1 H), 8.82 (s, 1 H), 9.14 (s, 1 H), 9.83 (s, 1 H), 10.70 (s, 1 H); Mass Spectrum: M + H+ 472.
[7] The procedures of Example 49 were used. The product gave the following characterising data:- $^1$H NMR Spectrum: (DMSOd$_6$ + D$_2$O) 8.31 (1 H, d); 7.84 (1 H, d); 6.90 (1 H, dd); 6.81 (1 H, d); 4.25 (2 H, s); 3.73 (3 H, s); 3.71 (3 H, s); 3.14 (3 H, s); 2.30 (3 H, s); Mass Spectrum: M + H+ 512 and 514.
[8] The procedures of Example 49 were used. The product gave the following characterising data:- $^1$H NMR Spectrum: (DMSOd$_6$ + D$_2$O) 8.31 (1 H, d); 7.85 (1 H, d); 6.14 (1 H, d); 5.99 (1 H, m); 4.27 (2 H, br s); 3.15 (3 H, s); 2.31 (3 H, s); 2.23 (3 H, s); Mass Spectrum: M + H+ 456 and 458.
[9] The procedures of Example 49 were used. The product gave the following characterising data:- $^1$H NMR Spectrum: (DMSOd$_6$ + D$_2$O) 8.32 (1 H, d); 7.86 (1 H, d); 7.40 (1 H, dd); 7.01 (1 H, br d); 6.97 (1 H, m); 4.50 (2 H, s); 3.16 (3 H, s); 2.31 (3 H, s); Mass Spectrum: M + H+ 458 and 460.
[10] The procedures of Example 49 were used. The product gave the following characterising data:- $^1$H NMR Spectrum: (DMSOd$_6$ + D$_2$O) 8.31 (1 H, d); 7.85 (1 H, d); 3.21 (2 H, s); 3.15 (3 H, s); 2.31 (3 H, s); 2.27 (3 H, s); 2.16 (3 H, s); Mass Spectrum: M + H+ 485 and 487.

EXAMPLE 71

N-[5-(6-Chloro-5-methylsulfonylaminopyridin-3-yl)-4-methyl-1,3-thiazol-2-yl]benzamide A mixture of benzoic acid (27 mg), diisopropylethylamine (0.053 mL), 2-(7-azabenzotriazol-1-yl)-1,1,3,3-tetramethyluronium hexafluorophosphate(V) (84 mg) and DMA (0.5 mL) was stirred at room temperature under an atmosphere of nitrogen for 5 minutes. N-[5-(2-Amino-4-methyl-1,3-thiazol-5-yl)-2-chloropyridin-3-yl]methanesulfonamide (32 mg) was added and the mixture was stirred and heated to 80° C. for 30 minutes. The solvent was evaporated and the residue was triturated under water. The resultant gum was purified by HPLC using a Phenomenex 'Luna' preparative reversed-phase column (10 microns silica, 21 mm diameter, 150 mm length) using decreasingly polar mixtures of water (containing 0.2% trifluoroactic acid) and acetonitrile as eluent. There was thus obtained the title compound as a solid (17 mg); NMR Spectrum: (DMSOd$_6$) 2.44 (s, 3H), 3.19 (s, 3H), 7.57 (t, 2H), 7.64-7.69 (m, 1H), 7.95 (s, 1H), 8.12 (d, 2H), 8.42 (s, 1H), 9.91 (s, 1H), 12.87 (s, 1H): Mass Spectrum: M−H$^-$ 421.

EXAMPLE 72

N-(5-{6-Chloro-5-[N-(4-chlorobenzyl)sulfamoyl]pyridin-3-yl}-4-methyl-1,3-thiazol-2-yl)acetamide 4-Chlorobenzylamine (0.17 mL) and triethylamine (0.12 mL) were added in turn to a stirred slurry of 5-(2-acetamido-4-methyl-1,3-thiazol-5-yl)-2-chloropyridine-3-sulfonyl chloride (250 mg) in THF (20 mL) that had been cooled to 0° C. The resultant mixture was stirred at 0° C. for 30 minutes and at room temperature for 1 hour. The mixture was evaporated and the residue was partitioned between dichloromethane and water. The organic solution was washed with a saturated aqueous sodium chloride solution, filtered, dried over magnesium sulfate and evaporated. The material so obtained was purified by 'basic reversed-phase chromatography' (Waters 'Xterra' C18 reversed-phase silica, 150×21 mm, solvent gradient of 5-50% acetonitrile in water (containing 1% aqueous ammonium hydroxide (d=0.88) solution). The material so obtained was triturated under diethyl ether, isolated and dried at 55° C. under vacuum. There was thus obtained the title compound as a white solid (155 mg); $^1$H NMR Spectrum: (DMSOd$_6$) 2.22 (s, 3H), 2.40 (s, 3H), 4.24 (s, 2H), 7.25 (s, 4H), 8.06 (m, 1H), 8.63 (m, 1H), 9.06 (br s, 1H), 12.54 (br s, 1H); Mass Spectrum: M+H$^+$ 471 and 473.

The 5-(2-acetamido-4-methyl-1,3-thiazol-5-yl)-2-chloropyridine-3-sulfonyl chloride used as a starting material was prepared as follows:—

Whilst using an ice-bath to maintain the temperature of the reaction mixture below 10° C., concentrated hydrochloric acid (32% w/w; 1.08 mL) was added to N-[5-(5-amino-6-chloropyridin-3-yl)-4-methyl-1,3-thiazol-2-yl]acetamide (283 mg). The resultant slurry was heated to 45° C. for 10 minutes. The slurry was cooled to −5° C. and, whilst maintaining the temperature of the reaction mixture between −5 and 0° C. using an ice/acetone bath, a solution of sodium nitrite (83 mg) in water (0.5 mL) was added dropwise. The resultant orange solution was stirred at −3° C. for 10 minutes.

In a separate reaction vessel, whilst maintaining the temperature of the mixture between 0 and 7° C., thionyl chloride (0.33 mL) was added dropwise to water (2.8 mL). The resultant solution was allowed to warm to 18° C. during 5 hours. Cuprous chloride (1.19 mg) was added and the resultant solution was cooled to −3° C. using an ice-acetone bath. The orange solution from step 1 above was cooled to −5° C. and added dropwise whilst maintaining the reaction temperature between −5 and 0° C. When the addition was complete, the reaction mixture was stirred at −3° C. for 45 minutes. The resultant precipitate was isolated and dried under vacuum at room temperature. There was thus obtained 5-(2-acetamido-4-methyl-1,3-thiazol-5-yl)-2-chloropyridine-3-sulfonyl chloride as a pale yellow solid (271 mg) that was used without any further purification; $^1$H NMR Spectrum: (DMSOd$_6$) 2.12 (s, 3H), 2.31 (s, 3H), 7.20 (br s, 1H), 8.12 (m, 1H), 8.38 (m, 1H), 12.45 (s, 1H); Mass Spectrum: M+H$^+$ 366 and 368.

EXAMPLE 73

Using an analogous procedure to that described in Example 72 except that triethylamine was omitted, the appropriate pyridine-3-sulfonyl chloride was reacted with the appropriate amine (5 equivalents) to give the compounds described in Table III.

Unless otherwise stated, each reaction product was purified by preparative HPLC on Kromasil C18 reversed-phase silica using a solvent gradient of 10% to 100% acetonitrile in water (containing 1% acetic acid) as eluent at a flow rate of about 10 mL/minute.

Unless otherwise stated, each required amine was a commercially available material.

TABLE III

| No. & Note | R$^1$ | R$^7$ |
|---|---|---|
| [1] | 6-chloro | methyl |
| [2] | 6-chloro | cyclopropyl |
| [3] | 6-fluoro | cyclopropylmethyl |
| [4] | 6-chloro | phenyl |
| [5] | 6-chloro | 4-tolyl |
| [6] | 6-chloro | 4-fluorophenyl |
| [7] | 6-chloro | 2-morpholinoethyl |

Notes

The products gave the characterising data shown below.

[1] $^1$H NMR Spectrum: (DMSOd$_6$) 2.18 (s, 3 H), 2.40 (s, 3 H), 2.58 (s, 3 H), 8.12 (br s, 1 H), 8.26 (m, 1 H), 8.74 (m, 1 H), 12.64 (br s, 1 H); Mass Spectrum: M − H$^-$ 359.
[2] $^1$H NMR Spectrum: (DMSOd$_6$) 0.49 (m, 2 H), 0.61 (m, 2 H), 2.30 (s, 3 H), 2.52 (s, 3 H), 8.39 (m, 1 H), 8.72 (d, 1 H), 8.85 (m, 1 H), 12.50 (s, 1 H); Mass Spectrum: M + H$^+$ 387.
[3] $^1$H NMR Spectrum: (DMSOd$_6$) 0.00 (m, 2 H), 0.23 (m, 2 H), 0.73 (m, 1 H), 2.13 (s, 3 H), 2.34 (s, 3 H), 2.79 (d, 2 H), 8.21 (m, 1 H), 8.40 (br s, 1 H), 8.66 (m, 1 H), 12.41 (s, 1 H); Mass Spectrum: M + H$^+$ 401.
[4] $^1$H NMR Spectrum: (DMSOd$_6$) 2.19 (s, 3 H), 2.30 (s, 3 H), 7.05 (m, 1 H), 7.15 (m, 2 H), 7.26 (m, 2 H), 8.27 (m, 1 H), 8.68 (m, 1 H), 10.97 (s, 1 H), 12.32 (s, 1 H); Mass Spectrum: M + H$^+$ 423.
[5] $^1$H NMR Spectrum: (DMSOd$_6$) 2.16 (s, 6 H), 2.27 (s, 3 H), 7.13 (s, 4 H), 8.17 (m, 1 H), 8.61 (m, 1 H), 10.88 (s, 1 H), 12.39 (s, 1 H); Mass Spectrum: M + H$^+$ 437.
[6] $^1$H NMR Spectrum: (DMSOd$_6$) 2.13 (s, 3 H), 2.24 (s, 3 H), 7.05 (m, 4 H), 8.18 (m, 1 H), 8.63 (m, 1 H), 10.99 (s, 1 H), 12.36 (s, 1 H); Mass Spectrum: M + H$^+$ 441.
[7] $^1$H NMR Spectrum: (DMSOd$_6$) 2.22 (s, 5 H), 2.28 (t, 2 H), 2.43 (s, 3 H), 3.12 (m, 2 H), 3.38 (s, 4 H), 8.19 (m, 1 H), 8.31 (m, 1 H), 8.74 (m, 1 H), 12.41 (s, 1 H); Mass Spectrum: M + H$^+$ 460.

EXAMPLE 74

N-[5-(2-Acetylamino-1,3-thiazol-5-yl)-2-chloropyridin-3-yl]-2,4-dimethyl-1,3-thiazole-5-carboxamide Phosphorus oxychloride (296 mg) was added to a stirred mixture of N-[5-(5-amino-6-chloropyridin-3-yl)-4-methyl-1,3-thiazol-2-yl]acetamide (180 mg), 2,4-dimethylthiazole-5-carboxylic acid (*J. Med. Chem.*, 1999, 42, 5064; 109 mg) and acetonitrile (10 mL) that had been heated to reflux. The resultant mixture was stirred and heated to reflux for 1 hour. The mixture was cooled to room temperature and the precipitate was collected by filtration, washed with acetonitrile and dried under vacuum. There was thus obtained the title compound (172 mg); $^1$H NMR Spectrum: (DMSOd$_6$) 2.16 (s, 3H), 2.39 (s, 3H), 2.62 (s, 3H), 2.68 (s, 3H), 8.21 (s, 1H), 8.40 (s, 1H); Mass Spectrum: M+H$^+$ 422.

EXAMPLE 75

N-(5-{6-Chloro-5-[3-(2,4-difluorophenyl)ureido]pyridin-3-yl}-4-methyl-1,3-thiazol-2-yl)acetamide 2,4-Difluorophenyl isocyanate (0.022 mL) was added to a stirred solution of N-[5-(5-amino-6-chloropyridin-3-yl)-4- methyl-1,3-thiazol-2-yl]acetamide (50 mg) in THF (1 mL) and the resultant solution was stirred and heated to 50° C. for 1 hour. The mixture was cooled to room temperature and concentrated by evaporation. The residue was purified by preparative HPLC. There was thus obtained the title compound as a white solid (20 mg); $^1$H NMR Spectrum: (DMSOd$_6$) 2.16 (s, 3H), 2.39 (s, 3H), 7.05-7.08 (m, 1H), 7.33-7.37 (m, 1H), 8.09-8.14 (m, 1H), 8.17 (s, 1H), 8.67 (m, 1H), 8.67 (s, 1H), 9.48 (s, 1H); Mass Spectrum: M+H$^+$ 438.

EXAMPLE 76

N-(5-{6-Chloro-5-[3-(2,4-dimethyl-1,3-thiazol-5-yl) ureido]pyridin-3-yl}-4-methyl-1,3-thiazol-2-yl)acetamide Diphenylphosphoryl azide (0.228 mL) was added to a stirred mixture of 2,4-dimethylthiazole-5-carboxylic acid (137 mg), triethylamine (0.148 mL) and toluene (3 mL) and the resultant mixture was heated to 100° C. for 1 hour. N-[5-(5-Amino-6-chloropyridin-3-yl)-4-methyl-1,3-thiazol-2-yl] acetamide (100 mg) was added followed by 1,4-dioxane (3 mL) and the resultant solution was stirred and heated to 100° C. for 2 hours. The mixture was cooled to room temperature and concentrated by evaporation. The residue was purified by preparative HPLC. There was thus obtained the title compound as a white solid (69 mg, 45%); $^1$H NMR Spectrum: (DMSOd$_6$) 2.16 (s, 3H), 2.27 (s, 3H), 2.39 (s, 3H), 2.54 (s, 3H), 8.17 (s, 1H), 8.65 (s, 1H), 8.82 (s, 1H), 9.75 (s, 1H); Mass Spectrum: M+H$^+$ 437.

EXAMPLE 77

N-[4-Methyl-5-(5-methylsulfonylpyridin-3-yl)-1,3-thiazol-2-yl]acetamide

A solution of N-[5-(5-bromopyridin-3-yl)-4-methyl-1,3-thiazol-2-yl]acetamide (312.2 mg), sodium methanesulfinate (123 mg), cuprous iodide (19 mg), sodium hydroxide (8 mg), L-proline (23 mg) and DMSO (2.5 mL) was purged with nitrogen for 10 minutes. The reaction mixture was placed in a glass tube that was sealed and heated to 115° C. for 24 hours. Additional sodium methanesulfinate (20.5 mg) and cuprous iodide (19 mg) were added and the reaction mixture was heated to 115° C. for 3 days. The resultant mixture was cooled to room temperature. The solvent was evaporated and the residue was dissolved in dichloromethane and washed with water and with brine. The organic layer was dried over magnesium sulfate and evaporated. The material so obtained was purified by column chromatography on silica increasingly polar mixtures of dichloromethane, ethyl acetate and methanol (45:45:1 to 47:47:6) as eluent. The material so obtained was purified further by 'basic reversed-phase chromatography' as described hereinbefore. The material so obtained was dried under vacuum at 50° C. for 16 hours. There was thus obtained the title compound as a white solid (160 mg); $^1$H NMR Spectrum: (DMSOd$_6$) 2.21 (s, 3H), 2.44 (s, 3H), 3.44 (s, 3H), 8.30 (m, 1H), 9.01 (m, 2H), 12.36 (s, 1H). Mass Spectrum: M+H$^+$ 312.

The N-[5-(5-bromopyridin-3-yl)-4-methyl-1,3-thiazol-2-yl]acetamide used as a starting material was prepared as follows:— n-Butyllithium (2.5M solution in hexane; 22 mL) was added dropwise to a mixture of 3,5-dibromopyridine (10 g), triisopropylborate (16 mL) and anhydrous diethyl ether (150 mL) that had been cooled to −75° C. under an atmosphere of nitrogen. The reaction mixture was stirred at this temperature for 30 minutes and at room temperature for 1 hour. The mixture was re-cooled to −78° C. and a further portion of triisopropylborate (16 mL) was added, followed by the dropwise addition of n-butyllithium (2.5M solution in hexane; 22 mL). The resultant mixture was stirred at this temperature for 30 minutes and at room temperature for 1 hour. A solution of anhydrous pinacol (7.5 g) in anhydrous diethyl ether (50 mL) was added followed, after 10 minutes, by a solution of glacial acetic acid (2.6 mL) in anhydrous diethyl ether (20 mL). The mixture was stirred at room temperature for 2 hours. A 5% aqueous sodium hydroxide solution was added followed by the dropwise addition of 2N aqueous hydrochloric acid, whilst keeping the internal temperature below 5° C., to bring the aqueous phase to pH6.5. The organic phase was separated and the aqueous phase was extracted with diethyl ether. The organic solutions were combined and washed with brine, dried over magnesium sulfate and evaporated. The residue was triturated under acetonitrile and the resultant solid was dried under vacuum at 60° C. for 16 hours. There was thus obtained 3-bromo-5-(4,4,5,5-tetramethyl-1,3,2-dioxaborolan-2-yl)pyridine as a white solid (8.2 g); $^1$H NMR Spectrum: (DMSOd$_6$) 1.21 (s, 6H), 1.36 (s, 6H), 8.51 (m, 1H), 8.73 (m, 1H), 8.86 (m, 1H); Mass Spectrum: M+H$^+$ 283.

A solution of N-(5-iodo-4-methyl-1,3-thiazol-2-yl)acetamide (7.9 g) in 1,4-dioxane (150 mL) was purged with nitrogen and tetrakis(triphenylphosphine)palladium(0) (684 mg) was added. The resultant was stirred at room temperature for 35 minutes under a nitrogen atmosphere. 3-Bromo-5-(4,4,5,5-tetramethyl-1,3,2-dioxaborolan-2-yl)pyridine (7.9 g) was added followed by a solution of sodium bicarbonate (5.9 g) in water (33 mL). The reaction mixture was purged with nitrogen and heated to 80° C. for 16 hours. The mixture was evaporated and the residue was partitioned between dichloromethane and water. The organic solution was washed with brine, dried over magnesium sulfate and evaporated. The residue was purified by column chromatography on silica using increasingly polar mixtures of dichloromethane and ethyl acetate (9:1 to 10:0) and dichloromethane, ethyl acetate and methanol (20:20:1) as eluent. The solid so obtained was purified further by column chromatography on an 'isolute SCX' ion exchange column (50 g). The column was washed initially with methanol to remove triphenylphosphine oxide and then eluted with 7M methanolic ammonia solution. The solid so obtained was dried under vacuum at 40° C. for 16 hours. There was thus obtained the required starting material as a beige solid (3.64 g); $^1$H NMR Spectrum: (DMSOd$_6$) 2.21 (s, 3H), 2.41 (s, 3H), 8.14 (m, 1H), 8.66 (m, 2H), 12.22 (s, 1H); Mass Spectrum: M+H$^+$ 312.

EXAMPLE 78

N-[4-Methyl-5-(5-phenylsulfonylpyridin-3-yl)-1,3-thiazol-2-yl]acetamide

A mixture of N-[5-(5-bromopyridin-3-yl)-4-methyl-1,3-thiazol-2-yl]acetamide (26 mg), sodium benzenesulfinate (17 mg), 4,5-bis(diphenylphosphino)-9,9-dimethylxanthene (2.9 mg), caesium carbonate (41 mg) and toluene (3 mL) was purged with nitrogen. Tris(dibenzylideneacetone)dipalladium(0) (1.9 mg) was added and the reaction mixture was heated to 110° C. for 16 hours under a nitrogen atmosphere. A further portion of sodium benzenesulfinate (14 mg) and DMF (1 mL) were added and the reaction mixture was transferred to a microwave vial and heated in a microwave apparatus to 145° C. for 4 hours. The resultant mixture was evaporated and the residue was partitioned between dichloromethane and water. The organic phase was washed with brine, dried over magnesium sulfate and evaporated. The residue was purified by 'basic reversed-phase chromatography' as described hereinbefore. There was thus obtained the title compound as a solid (7 mg); $^1$H NMR Spectrum: (DMSOd$_6$) 2.24 (s, 3H), 2.42 (s, 3H), 7.72 (m, 2H), 7.81 (m, 1H), 8.17 (m, 2H), 8.37 (m, 1H), 9.01 (m, 1H), 9.12 (m, 1H), 12.32 (s, 1H); Mass Spectrum: M+H$^+$ 374.

EXAMPLE 79

Using an analogous procedure to that described in Example 46, the appropriate 3-aminopyridine was reacted with the appropriate aldehyde to give the compounds described in Table IV.

Unless otherwise stated, each reaction product was purified by preparative HPLC on Kromasil C18 reversed-phase silica using a solvent gradient of 10% to 100% acetonitrile in water (containing 1% acetic acid) as eluent at a flow rate of about 10 mL/minute.

Unless otherwise stated, each required aldehyde was a commercially available material.

TABLE IV

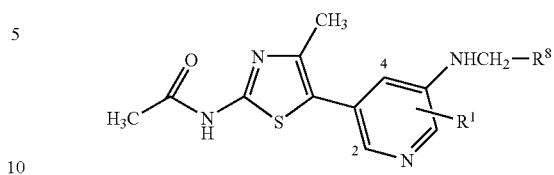

| No. & Note | R$^1$ | R$^8$ |
|---|---|---|
| [1] | 6-chloro | n-propyl |
| [2] | 6-chloro | cyclopropyl |
| [3] | 6-chloro | 4-fluorophenyl |
| [4] | 6-chloro | 2-fluorophenyl |
| [5] | 6-chloro | 2,4-difluorophenyl |
| [6] | 6-chloro | 4-tolyl |
| [7] | 6-chloro | 4-methoxyphenyl |
| [8] | 6-chloro | 2-methoxyphenyl |
| [9] | 6-chloro | 4-ethoxyphenyl |
| [10] | 6-chloro | 4-(2-hydroxyethoxy)phenyl |
| [11] | 6-chloro | 4-(2-diethylaminoethoxy)phenyl |
| [12] | 6-chloro | 4-cyanophenyl |
| [13] | 6-chloro | 4-acetamidophenyl |
| [14] | 6-chloro | 4-methylsulphonylphenyl |
| [15] | 6-chloro | 5-methoxycarbonyl-1-methyl-1H-pyrrol-3-yl |
| [16] | 6-chloro | 5-pyridin-2-ylthien-2-yl |
| [17] | 6-chloro | 1H-imidazol-4-yl |
| [18] | 6-chloro | 3,5-dimethylisoxazol-4-yl |
| [19] | 6-chloro | 2,4-dimethylthiazol-5-yl |
| [20] | 6-chloro | 1-phenyl-1H-1,2,3-triazol-4-yl |
| [21] | 6-chloro | 3-pyridyl |
| [22] | 6-chloro | benzyloxymethyl |

Notes
The products gave the characterising data shown below.
[1] HPLC: (Method A) retention time 10.37 minutes; Mass Spectrum: M + H$^+$ 339 and 341.
[2] $^1$H NMR Spectrum: (DMSOd$_6$) 0.03 (m, 2 H), 0.23 (m, 2 H), 0.85 (m, 1 H), 1.9 (s, 3 H), 2.1 (s, 3 H), 2.83 (t, 2 H), 5.53 (t, 1 H), 6.8 (s, 1 H), 7.4 (s, 1 H), 12.0 (s, 1 H); Mass Spectrum: M + H$^+$ 337.
[3] $^1$H NMR Spectrum: (DMSOd$_6$) 2.05 (s, 3 H), 2.13 (s, 3 H), 4.46 (d, 2 H), 6.73 (t, 1 H), 6.82 (s, 1 H), 7.16 (t, 1 H), 7.4 (m, 1 H), 7.62 (s, 1 H), 12.1 (s, 1 H); Mass Spectrum: M + H$^+$ 391.
[4] $^1$H NMR Spectrum: (DMSOd$_6$) 2.02 (s, 3 H), 2.04 (s, 3 H), 4.53 (d, 1 H), 6.6 (t, 1 H), 6.83 (s, 1 H), 7.2 (m, 2 H), 7.33 (m, 2 H), 7.67 (s, 1 H), 12.1 (s, 1 H); Mass Spectrum: M + H$^+$ 391.
[5] $^1$H NMR Spectrum: (DMSOd$_6$) 2.15 (s, 6 H), 4.5 (d, 2 H), 6.6 (t, 1 H), 6.85 (s, 1 H), 7.06 (t, 1 H), 7.23 (t, 1 H), 7.4 (m, 1 H), 7.66 (s, 1 H), 12.13 (s, 1 H); Mass Spectrum: M + H$^+$ 409.
[6] $^1$H NMR Spectrum: (DMSOd$_6$) 2.08 (s, 3 H), 2.14 (s, 3 H), 2.26 (s, 3 H), 4.42 (d, 2 H), 6.63 (t, 1 H), 6.8 (s, 1 H), 7.13 (d, 2 H), 7.24 (d, 2 H), 7.6 (s, 1 H), 12.13 (s, 1 H); Mass Spectrum: M + H$^+$ 387.
[7] $^1$H NMR Spectrum: (DMSOd$_6$) 2.1 (s, 3 H), 2.14 (s, 3 H), 3.73 (s, 3 H), 4.4 (d, 2 H), 6.63 (t, 1 H), 6.83 (s, 1 H), 6.9 (d, 2 H), 7.3 (d, 2 H), 7.6 (s, 1 H), 12.1 (s, 1 H); Mass Spectrum: M + H$^+$ 403.
[8] HPLC: (Method A) retention time 10.46 minutes; Mass Spectrum: M + H$^+$ 403 and 405.
[9] HPLC: (Method A) retention time 9.75 minutes; Mass Spectrum: M + H$^+$ 417 and 419.
[10] HPLC: (Method A) retention time 7.77 minutes; Mass Spectrum: M + H$^+$ 433 and 435.

TABLE IV-continued

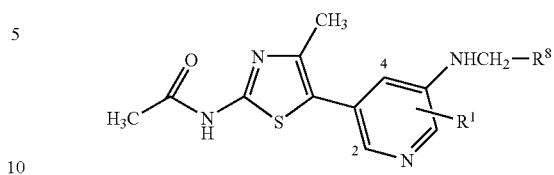

| No. & Note | R$^1$ | R$^8$ |
|---|---|---|

[11] HPLC: (Method A) retention time 7.02 minutes; Mass Spectrum: M + H$^+$ 488 and 490.
[12] HPLC: (Method A) retention time 9.03 minutes; Mass Spectrum: M + H$^+$ 398 and 400.
[13] HPLC: (Method A) retention time 7.37 minutes; Mass Spectrum: M + H$^+$ 430 and 432.
[14] Mass Spectrum: M + H$^+$ 451 and 453.
[15] HPLC: (Method A) retention time 9.29 minutes; Mass Spectrum: M + H$^+$ 434 and 436.
[16] HPLC: (Method A) retention time 7.09 minutes; Mass Spectrum: M + H$^+$ 456 and 458.
[17] HPLC: (Method A) retention time 4.47 minutes; Mass Spectrum: M + H$^+$ 363 and 365.
[18] $^1$H NMR Spectrum: (DMSOd$_6$) 2.23 (s, 3 H), 2.26 (s, 3 H), 2.33 (s, 3 H), 2.45 (s, 3 H), 4.3 (d, 2 H), 6.27 (t, 1 H), 6.95 (s, 1 H), 7.76 (s, 1 H), 12.25 (s, 1 H); Mass Spectrum: M − H$^−$ 390.
[19] $^1$H NMR Spectrum: (DMSOd$_6$) 2.15 (s, 3 H), 2.2 (s, 3 H), 2.35 (s, 3 H), 3.23 (s, 3 H), 4.55 (d, 2 H), 6.53 (t, 1 H), 6.88 (s, 1 H), 7.65 (s, 1 H), 12.13 (s, 1 H); Mass Spectrum: M + H$^+$ 408.
[20] HPLC: (Method A) retention time 9.39 minutes; Mass Spectrum: M + H$^+$ 440 and 442.
[21] HPLC: (Method A) retention time 7.38 minutes; Mass Spectrum: M + H$^+$ 374 and 376.
[22] HPLC: (Method A) retention time 10.69 minutes; Mass Spectrum: M + H$^+$ 417 and 419.

EXAMPLE 80

N-[4-Methyl-5-(6-phenylsulfonylamino-pyridin-2-yl)-1,3-thiazol-2-yl]acetamide

Benzenesulfonyl chloride (0.77 mL) was added to a stirred mixture of N-[5-(6-aminopyridin-2-yl)-4-methyl-1,3-thiazol-2-yl]acetamide (249 mg) and pyridine (10 mL) and the reaction mixture was stirred at room temperature for 30 minutes. The resultant mixture was poured into isohexane (400 mL). The supernatant liquid was decanted from a residual gum. A 7M methanolic ammonia solution (20 mL) was added to the residual gum and the mixture was stirred at room temperature for 1 hour. The resultant mixture was evaporated and the residue was purified by preparative HPLC. There was thus obtained the title compound (296 mg); $^1$H NMR Spectrum: (DMSO-d$_6$) 2.18 (s, 3H), 2.44 (s, 3H), 6.83 (d, 1H), 7.20 (d, 1H), 7.62 (m, 3H), 7.70 (t, 1H), 8.03 (d, 2H), 11.17 (br s, 1H), 12.12 (s, 1H); Mass Spectrum: M+H$^+$ 389.

The N-[5-(6-aminopyridin-2-yl)-4-methyl-1,3-thiazol-2-yl]acetamide used as a starting material was prepared as follows:—

A mixture of 2-acetamido-4-methylthiazole (3.43 g), caesium fluoride (7.55 g) and DMSO (40 mL) in a first reaction flask was heated under a flow of nitrogen to 145° C. In a second reaction flask, a mixture of 2-amino-6-bromopyridine (3.46 g), palladium(II) acetate (360 mg), DMSO (30 mL) and di-(2-methoxyethyl)ether (20 mL) was stirred at room temperature for 10 minutes. Whilst the mixture was purged with a flow of nitrogen, a 10% solution of tri-tert-butylphosphine in hexane (9.4 mL) was added. Using a syringe pump, this solution was added over 2 hours to the hot reaction mixture in the first flask. The temperature was maintained at 145° C. during the addition and for a further 130 minutes after the addition was complete. The resultant mixture was cooled and evaporated and the residue was stirred in water (100 mL) for 1 hour. The water was decanted and the residue was dissolved in acetic acid (100 mL) and filtered through a silica pad, washing the pad with 1:1 mixture of acetic acid and methanol. The filtrate was evaporated. Ethyl acetate was added to the residue and the mixture was filtered. The filtrate was evaporated and the resultant residue was purified by column chromatography on silica using increasingly polar mixtures of diethyl ether and THF as eluent. There was thus obtained the required starting material (667 mg); $^1$H NMR Spectrum: (DMSO-d$_6$) 2.13 (s, 3H), 2.48 (s, 3H), 6.02 (br s, 1H), 6.32 (d, 1H), 6.75 (d, 1H), 7.41 (t, 1H), 12.00 (br s, 11H); Mass Spectrum: M+H$^+$ 249.

EXAMPLE 81

N-[4-Methyl-5-(6-methylsulfonylaminopyridin-2-yl)-1,3-thiazol-2-yl]acetamide

A mixture of N-[5-(6-aminopyridin-2-yl)-4-methyl-1,3-thiazol-2-yl]acetamide (249 mg), methanesulfonic anhydride (1.74 g) and pyridine (10 mL) was heated to 80° C. for 2 minutes. The mixture was cooled and poured into isohexane (400 n-L). The supernatant liquid was decanted from the oily residue. A 7M methanolic ammonia solution (20 mL) was added to the residue and the mixture was stirred at room temperature for 1 hour. The resultant mixture was evaporated and the residue was purified by column chromatography on silica using increasingly polar mixtures of dichloromethane and methanol as eluent. There was thus obtained the title compound (133 mg); $^1$H NMR Spectrum: (DMSO-d$_6$) 2.15 (s, 3H), 2.55 (s, 3H), 3.42 (s, 3H), 6.78 (d, 1H), 7.27 (d, 1H), 7.76 (t, 1H), 10.67 (br s, 1H), 12.14 (s, 1H); Mass Spectrum: M+H$^+$ 327.

EXAMPLE 82

N-[4-Methyl-5-(4-phenylsulfonylaminopyridin-2-yl)-1,3-thiazol-2-yl]acetamide

A mixture of N-(2-bromopyridin-4-yl)benzenesulfonamide (700 mg), 2-acetamido-4-methylthiazole (384 mg), palladium(II) acetate (41 mg), caesium fluoride (1.01 g), tri-tert-butylphosphine (0.34M solution in hexane, 1.06 mL) and DMSO (20 mL) was purged with nitrogen. The resultant mixture was heated to 150° C. for 5 hours under an atmosphere of nitrogen. The bulk of the DMSO was evaporated and the residue was treated with water (40 mL). Water was decanted from the resultant gum which was purified by column chromatography on silica using a solvent gradient of 2% to 5% methanol in dichloromethane as eluent. There was thus obtained the title compound as a solid (116 mg); $^1$H NMR Spectrum: (DMSOd$_6$) 2.14 (s, 3H), 2.44 (s, 3H), 6.93 (d, 1H), 7.32 (s, 1H), 7.60-7.70 (m, 3H), 7.91 (m, 2H), 8.29 (d, 1H), 11.25 (s, 1H), 12.13 (s, 1H); Mass Spectrum: M+H$^+$ 389.

The N-(2-bromopyridin-4-yl)benzenesulfonamide used as a starting material was prepared as follows:—

Benzenesulfonyl chloride (0.443 mL) was added to a stirred mixture of 2-bromo-4-aminopyridine (498 mg) and pyridine (10 mL) and the resultant mixture was stirred at room temperature for 1 hour. The pyridine was evaporated and the residue was partitioned between dichloromethane and an aqueous citric acid solution. The organic phase was washed with water, dried over magnesium sulfate and evaporated. The residual solid was purified by column chromatography on silica using a solvent gradient of 2% to 4% methanol in dichloromethane as eluent. There was thus obtained the required starting material as a solid (705 mg); $^1$H NMR Spectrum: (DMSOd$_6$) 7.12 (m, 1H), 7.19 (m, 1H), 7.62-7.73 (m, 3H), 7.90 (m, 2H), 8.14 (d, 1H), 11.45 (s, 1H); Mass Spectrum: M+H$^+$ 313.

EXAMPLE 83

N-[4-Methyl-5-(5-phenylsulfonylaminopyridin-2-yl)-1,3-thiazol-2-yl]acetamide

Benzenesulfonyl chloride (0.062 mL) was added to a stirred mixture of N-[5-(5-aminopyridin-2-yl)-4-methyl-1,3-thiazol-2-yl]acetamide (100 mg) and pyridine (1 mL) and the reaction mixture was stirred at room temperature for 16 hours. The reaction mixture was evaporated and the residue was triturated under methanol. The resultant precipitate was filtered off, washed in turn with methanol and diethyl ether and dried. There was thus obtained the title compound (85 mg); $^1$H NMR Spectrum: (DMSOd$_6$) 2.13 (s, 3H), 2.47 (s, 3H), 7.55-7.65 (m, 5H), 7.80 (m, 2H), 8.26 (m, 1H), 10.58 (s, 1H), 12.05 (s, 1H); Mass Spectrum: M+H$^+$ 389.

The N-[5-(5-aminopyridin-2-yl)-4-methyl-1,3-thiazol-2-yl]acetamide used as a starting material was prepared as follows:—

Methyl 5-tert-butoxycarbonylaminopyridine-2-carboxylate (J. Med. Chem., 1991, 34, 1594; 5 g) was dissolved in THF (75 mL) and the mixture was cooled to 0° C. Lithium aluminium hydride (1M in THF, 19.8 mL) was added dropwise and the mixture was stirred at room temperature for 1 hour. The mixture was re-cooled to 0° C. and water (0.75 mL) was carefully added followed in turn by 2N aqueous sodium hydroxide solution (0.75 mL) and water (2.25 mL). The resultant mixture was stirred for 30 minutes and filtered. The filtrate was dried over magnesium sulfate and evaporated. There was thus obtained 5-tert-butoxycarbonylamino-2-hydroxymethylpyridine as a solid (2.8 g); $^1$H NMR Spectrum: (DMSOd$_6$) 1.47 (s, 9H), 4.46 (d, 2H), 5.24 (t, 1H), 7.33 (d, 1H), 7.84 (m, 1H), 8.49 (d, 1H), 9.44 (s, 1H); Mass Spectrum: M+H$^+$ 225.

A mixture of carbon tetrabromide (3.19 g) and dichloromethane (15 mL) was added slowly to a stirred mixture of 5-tert-butoxycarbonylamino-2-hydroxymethylpyridine (1.8 g), triphenylphosphine (2.53 g) and dichloromethane (80 mL) that had been cooled to 0° C. The resultant mixture was stirred at 0° C. for 30 minutes. The mixture was evaporated and the residue was purified by column chromatography on silica using a 200:1 mixture of dichloromethane and methanol as eluent. There was thus obtained 2-bromomethyl-5-tert-butoxycarbonylaminopyridine.

A mixture of the material so obtained, thiourea (0.61 g) and ethanol (100 mL) was stirred at room temperature for 5 minutes. The mixture was evaporated. There was thus obtained S-(5-tert-butoxycarbonylaminopyridin-2-ylmethyl)isothiouronium bromide as an oil (2.88 g containing about 20% triphenylphosphine oxide); $^1$H NMR Spectrum: (DMSOd$_6$) 1.47 (s, 9H), 4.49 (s, 2H), 7.4 (d, 1H), 7.90 (m, 1H), 8.59 (d, 1H), 8.93 (br s, 2H), 9.51 (br s, 2H), 9.68 (s, 1H); Mass Spectrum: M+H$^+$ 283.

A mixture of the material so obtained, sodium acetate (0.5 g) and acetic anhydride (22 mL) was stirred at room temperature for 30 minutes. Water (22 mL) was added and the mixture was stirred at room temperature for 1 hour. The resultant mixture was extracted with ethyl acetate. The organic extract was washed with a saturated aqueous sodium bicarbonate solution, dried over magnesium sulfate and evaporated. The residue was purified by column chromatography using increasingly polar mixtures of isohexane and ethyl acetate as eluent. There was thus obtained N,N'-diacetyl-S-(5-tert-butoxycarbonylaminopyridin-2-ylmethyl)isothiourea (1.7 g containing about 10% triphenylphosphine oxide); $^1$H NMR Spectrum: (DMSOd$_6$) 1.47 (s, 9H), 2.03 (br s, 6H), 4.15 (s, 2H), 7.31 (d, 1H), 7.8 (m, 1H), 9.53 (d, 1H), 9.53 (s, 1H), 11.02 (br s, 1H); Mass Spectrum: M+H$^+$ 366.

A mixture of the material so obtained, sodium acetate (31 mg) and ethanol (15 mL) was heated to reflux for 2 hours. The mixture was cooled to room temperature and the precipitate was filtered off, washed with diethyl ether and dried. There was thus obtained N-[5-(5-tert-butoxycarbonylaminopyridin-2-yl)-4-methyl-1,3-thiazol-2-yl]acetamide as a solid (0.7 g); $^1$H NMR Spectrum: (DMSOd$_6$) 1.5 (s, 9H), 2.14 (s, 3H), 2.5 (s, 3H), 7.56 (d, 1H), 7.95 (m, 1H), 8.59 (d, 1H), 9.61 (s, 1H), 12.02 (s, 1H); Mass Spectrum: M+H$^+$ 349.

A mixture of the material so obtained and a 4M hydrogen chloride solution in 1,4-dioxane (15 mL) was stirred at room temperature for 2 hours. The mixture was evaporated and the residue was basified by the addition of a 5M methanolic ammonia solution. The resultant mixture was evaporated, dissolved in aqueous methanol and loaded onto a Waters 'Isolute SCX' ion exchange column. The column was eluted initially with methanol. The product was eluted using a 5M methanolic ammonia solution. There was thus obtained N-[5-(5-aminopyridin-2-yl)-4-methyl-1,3-thiazol-2-yl]acetamide as a solid (0.5 g); $^1$H NMR Spectrum: (DMSOd$_6$) 2.10 (s, 3H), 2.42 (s, 3H), 5.41 (s, 2H), 6.96 (m, 1H), 7.29 (d, 1H), 7.92 (d, 1H), 11.87 (s, 1H); Mass Spectrum: M+H$^+$ 249.

EXAMPLE 84

N-{5-[5-(4-Cyanophenylsulfonylamino)pyridin-2-yl]-4-methyl-1,3-thiazol-2-yl}acetamide Using an analogous procedure to that described in Example 83, N-[5-(5-aminopyridin-2-yl)-4-methyl-1,3-thiazol-2-yl]acetamide was reacted with 4-cyanophenylsulfonyl chloride to give the title compound; $^1$H NMR Spectrum: (DMSOd$_6$) 2.14 (s, 3H), 2.48 (s, 3H), 7.57 (m, 2H), 7.94 (d, 2H), 8.07 (d, 2H), 8.26 (m, 1H), 10.86 (br s, 1H), 12.06 (s, 1H); Mass Spectrum: M+H$^+$ 414.

EXAMPLE 85

N-{5-[5-(4-Methoxyphenylsulfonylamino)pyridin-2-yl]-4-methyl-1,3-thiazol-2-yl}acetamide Using an analogous procedure to that described in Example 83, N-[5-(5-aminopyridin-2-yl)-4-methyl-1,3-thiazol-2-yl]acetamide was reacted with 4-methoxyphenylsulfonyl chloride to give the title compound; $^1$H NMR Spectrum: (DMSOd$_6$) 2.13 (s, 3H), 2.47 (s, 3H), 3.81 (s, 3H), 7.09 (d, 2H), 7.55 (m, 2H), 7.73 (d, 2H), 8.26 (m, 1H), 10.42 (s, 1H), 12.05 (s, 1H); Mass Spectrum: M+H$^+$ 419.

EXAMPLE 86

N-[4-Methyl-5-(2-phenylsulfonylaminopyrimidin-5-yl)-1,3-thiazol-2-yl]acetamide

Benzenesulfonyl chloride (0.192 mL) was added to a stirred mixture of N-[5-(2-aminopyrimidin-5-yl)-4-methyl-1,3-thiazol-2-yl]acetamide (195 mg) and pyridine (10 mL) and the reaction mixture was heated to reflux for 18 hours. Additional benzenesulfonyl chloride (0.384 mL) was added and the mixture was heated to reflux for 2 hours. The reaction mixture was evaporated. A 7M methanolic ammonia solution (10 mL) was added to the residue and the mixture was stirred at room temperature for 1 hour. The resultant mixture was evaporated and the residue was purified by preparative HPLC. There was thus obtained the title compound (55 mg); $^1$H NMR Spectrum: (DMSOd$_6$) 2.13 (s, 3H), 2.27 (s, 3H), 7.61 (m, 3H), 8.02 (m, 2H), 8.60 (s, 2H), 12.00 (br s, 1H), 12.20 (s, 1H); Mass Spectrum: M+H$^+$ 390.

The N-[5-(2-aminopyrimidin-5-yl)-4-methyl-1,3-thiazol-2-yl]acetamide used as a starting material was prepared as follows:—

A mixture of 2-amino-5-bromopyrimidine (1.74 g), 2-acetamido-4-methylthiazole (1.72 g), caesium fluoride (3.77 g), palladium(II) acetate (180 mg) and DMSO (50 mL) was purged with nitrogen. Under a flow of nitrogen, a 10% solution of tri-tert-butylphosphine in hexane (4.71 mL) was added and the resultant mixture was heated to 145° C. for 3 hours. The mixture was evaporated and the residue was stirred in water for 15 minutes. The resultant solid was filtered off, washed with water, dried and purified by column chromatography on silica using increasingly polar mixtures of dichloromethane and acetic acid as eluent. There was thus obtained the required starting material (1.25 g); $^1$H NMR Spectrum: (DMSOd$_6$) 2.13 (s, 3H), 2.27 (s, 3H), 6.87 (s, 1H), 8.31 (s, 2H), 12.1 (br s, 1H); Mass Spectrum: M+H$^+$ 250.

EXAMPLE 87

N-[4-Methyl-5-(2-methylsulfonylaminopyrimidin-5-yl)-1,3-thiazol-2-yl]acetamide

A mixture of N-[5-(2-aminopyrimidin-5-yl)-4-methyl-1,3-thiazol-2-yl]acetamide (195 mg), methanesulfonic anhydride (0.65 g) and pyridine (20 mL) was heated to 100° C. for 10 minutes. Additional methanesulfonic anhydride (0.65 g) was added and heating to 100° C. was continued for a further 10 minutes. The mixture was cooled and poured into isohexane (400 mL). The supernatant liquid was decanted from the oily residue which was purified by preparative HPLC. There was thus obtained the title compound (37 mg); $^1$H NMR Spectrum: (DMSOd$_6$) 2.15 (s, 3H), 2.33 (s, 3H), 3.34 (s, 3H), 8.68 (s, 2H), 11.53 (br s, 11H), 12.20 (br s, 1H); Mass Spectrum: M+H$^+$ 328.

EXAMPLE 88

N-[4-Methyl-5-(2-phenylsulfonylaminopyrazin-2-yl)-1,3-thiazol-2-yl]acetamide

Benzenesulfonyl chloride (0.115 mL) was added to a stirred mixture of N-[5-(5-aminopyrazin-2-yl)-4-methyl-1,3-thiazol-2-yl]acetamide (75 mg) and pyridine (5 mL) and the reaction mixture was heated to 85° C. for 2 hours. Additional benzenesulfonyl chloride (0.115 mL) was added and the mixture was heated to reflux for 10 minutes. The reaction mixture was evaporated. A 7M methanolic ammonia solution (10 mL) was added to the residue and the mixture was stirred at room temperature for 1 hour. The resultant mixture was evaporated and the residue was purified by preparative HPLC. There was thus obtained the title compound (22 mg); $^1$H NMR Spectrum: (DMSOd$_6$) 2.12 (s, 3H), 2.46 (s, 3H), 7.58 (m, 3H), 7.92 (m, 2H), 8.31 (s, 1H), 8.41 (s, 1H), 11.56, (br s, 1H), 12.11 (s, 1H); Mass Spectrum: M+H$^+$ 390.

The N-[5-(5-aminopyrazin-2-yl)-4-methyl-1,3-thiazol-2-yl]acetamide used as a starting material was prepared as follows:—

Using an analogous procedure to that described in the portion of Example 86 that is concerned with the preparation of starting materials, 2-acetamido-4-methylthiazole was reacted with 5-amino-2-bromopyrazine. There was thus obtained the required starting material; $^1$H NMR Spectrum: (DMSOd$_6$) 2.13 (s, 3H), 2.43 (s, 3H), 6.58 (s, 2H), 7.90 (d, 1H), 8.16 (d, 1H), 12.05 (br s, 1H); Mass Spectrum: M+H$^+$ 250.

EXAMPLE 89

N-[4-Methyl-5-(6-phenylsulfonylaminopyrazin-2-yl)-1,3-thiazol-2-yl]acetamide

A mixture of 2-acetamido-4-methylthiazole (891 mg), N-(6-chloropyrazin-2-yl)benzenesulfonamide (1.4 g), palladium acetate (94 mg), caesium fluoride (2.35 g), tri-tert-butylphosphine (0.34M in hexane, 2.4 mL) and DMSO (45 mL) was purged with nitrogen. The resultant mixture was stirred and heated to 160° C. for 3.5 hours. The bulk of the DMSO was evaporated and water (50 mL) was added. The resultant solid was filtered off, washed with water and dried under vacuum. A 19:1 mixture of dichloromethane and methanol was added and the mixture was filtered. The filtrate was evaporated and the residue was purified by column chromatography on silica using a solvent gradient of 3% to 5% methanol in dichloromethane as eluent. There was thus obtained the title compound as a solid (95 mg); $^1$H NMR Spectrum: (DMSOd$_6$) 2.20 (s, 3H), 2.49 (s, 3H), 7.60-7.70 (m, 3H), 8.06 (m, 2H), 8.11 (s, 1H), 8.47 (s, 1H), 11.68 (s, 1H), 12.27 (s, 1H); Mass Spectrum: M+H$^+$ 390.

The N-(6-chloropyrazin-2-yl)benzenesulfonamide used as a starting material was prepared as follows A mixture of 2,6-dichloropyrazine (2 g), benzenesulfonamide (2.11 g), caesium carbonate (4.6 g) and DMA (30 mL) was stirred and heated to 100° C. for 4 hours. The reaction mixture was cooled to room temperature, poured into water (125 mL) and acidified with aqueous citric acid solution. The resultant solid was filtered off, washed with water and dried. There was thus obtained the required starting material (2.84 g); $^1$H NMR Spectrum: (DMSOd$_6$) 7.61-7.71 (m, 3H), 7.98 (m, 2H), 8.31 (s, 1H), 8.35 (s, 1H), 11.99 (br s, 1H); Mass Spectrum: M−H$^-$ 268.

EXAMPLE 90

N-[4-Methyl-5-(6-phenylsulfonylaminopyridazin-3-yl)-1,3-thiazol-2-yl]acetamide

A mixture of 2-acetamido-4-methylthiazole (78 mg), N-(6-chloropyridazin-3-yl)benzenesulfonamide (80 mg), potassium carbonate (374 mg), palladium (I) tri-tert-butylphosphine bromide dimer (commercially available from Alfa Aesar (Johnson-Matthey company); 241 mg) and DMSO (5 mL) was purged with nitrogen. The resultant mixture was heated to 150° C. for 30 minutes. The mixture was cooled to room temperature, filtered and purified directly by preparative HPLC. There was thus obtained the title compound as a solid (23 mg); $^1$H NMR Spectrum: (DMSOd$_6$) 2.15 (s, 3H), 2.46 (s, 3H), 7.53-7.60 (m, 3H), 7.78 (m, 1H), 7.86-7.88 (m, 2H), 7.95-7.97 (br d, 1H); Mass Spectrum: M+H$^+$ 390.

The N-(6-chloropyridazin-3-yl)benzenesulfonamide used as a starting material was prepared as follows:—

Benzenesulfonyl chloride (1.67 g) was added to a stirred solution of 6-amino-3-chloropyridazine (400 mg) in pyridine (5 mL). The resultant solution was stirred and heated to 50° C. for 16 hours. The mixture was cooled to room temperature and evaporated. The residue was purified by column chromatography on silica using dichloromethane as eluent. There was thus obtained the required starting material as a white solid (250 mg); $^1$H NMR Spectrum: (DMSOd$_6$) 7.57-7.66 (m, 4H), 7.77-7.79 (d, 1H), 7.90-7.92 (d, 2H); Mass Spectrum: M+H$^+$ 270.

EXAMPLE 91

N-[4-Methyl-5-(6-chloro-5-phenylsulfonylaminopyridazin-3-yl)-1,3-thiazol-2-yl]acetamide Lithium hexamethyldisilazane (1M solution in THF; 0.81 mL) was added to a mixture of N-[5-(5-amino-6-chloropyridazin-3-yl)-4-methyl-1,3-thiazol-2-yl]acetamide (77 mg) and THF (1.3 mL) that had been cooled to 0° C. The reaction mixture was allowed to warm and was stirred at room temperature for 30 minutes. Benzenesulfonyl chloride (0.069 mL) was added and the reaction mixture was stirred at room temperature for 2 hours. Water (2 drops) was added to the reaction mixture. The mixture was evaporated and the residual solid was purified by preparative HPLC. The material so obtained was purified further by column chromatography on silica using a solvent gradient of 0% to 20% methanol in dichloromethane as eluent. There was thus obtained the title compound as a solid (2.5 mg); $^1$H NMR Spectrum: (DMSOd$_6$) 2.15 (s, 3H), 2.40 (s, 3H), 7.05 (s, 1H), 7.45 (m, 3H), 7.80 (m, 2H); Mass Spectrum: M+H$^+$ 424.

The N-[5-(5-amino-6-chloropyridazin-3-yl)-4-methyl-1,3-thiazol-2-yl]acetamide used as a starting material was prepared as follows:— tert-Butanol (6 mL), diphenylphosphoryl azide (2.4 mL) and triethylamine (1.6 mL) were added in turn to a stirred mixture of 3,6-dichloropyridazine-4-carboxylic acid (2 g) and 1,4-dioxane (30 mL). The resultant mixture was heated to 110° C. for 4 hours. The mixture was cooled and the solvent was evaporated. The residue was partitioned between ethyl acetate and a dilute aqueous citric acid solution. The organic layer was dried over magnesium sulfate and evaporated. The residue was purified by column chromatography on silica using a solvent gradient of 0% to 30% ethyl acetate in petroleum ether as eluent. There was thus obtained tert-butyl N-(3,6-dichloropyridazin-4-yl)carbamate as a white solid (4.55 g); $^1$H NMR Spectrum: (DMSOd$_6$) 1.50 (s, 9H), 8.20 (s, 1H), 9.65 (br s, 1H).

A 4M solution of hydrogen chloride in 1,4-dioxane (60 mL) was added to a solution of tert-butyl N-(3,6-dichloropyridazin-4-yl)carbamate (4.55 g) in dichloromethane (30 mL) and the reaction mixture was stirred at room temperature overnight. The resultant precipitate was isolated and suspended in dichloromethane (20 mL). The mixture was basified by the addition of a 7M methanolic ammonia solution. The resultant mixture was filtered and the filtrate was evaporated to give 3,6-dichloropyridazin-4-amine as a white solid (1.3 g); $^1$H NMR Spectrum: (DMSOd$_6$) 6.85 (s, 1H), 7.15 (br s, 2H).

3,6-Dichloropyridazin-4-amine (683 mg) was added portionwise to a suspension of sodium hydride (60% dispersion in mineral oil; 230 mg) in THF (15 mL) that had been cooled to 0° C. The reaction mixture was allowed to warm to room temperature over 45 minutes. The mixture was re-cooled to 0° C. and trityl chloride (1.25 equivalents) was added. The resultant mixture was heated to 60° C. for 1 hour. Water (5 mL) was added and mixture was extracted with ethyl acetate. The organic layer was evaporated and the residue was purified by column chromatography on silica using a solvent gradient of 0% to 15% diethyl ether in dichloromethane as eluent. There was thus obtained 3,6-dichloro-N-tritylpyridazin-4-amine as a solid (150 mg); Mass Spectrum: M+H$^+$ 404.

A mixture of 2-acetamido-4-methylthiazole (139 mg), 3,6-dichloro-N-tritylpyridazin-4-amine (300 mg), palladium (I) tri-tert-butylphosphine bromide dimer (172 mg), potassium carbonate (407 mg) and DMSO (3 mL) was purged with nitrogen. The resultant mixture was stirred and heated to 140° C. for 1 hour. The mixture was cooled to room temperature, water (3 mL) was added and the heterogeneous mixture was stirred for 30 minutes. The precipitate was isolated, washed with water and purified by column chromatography on silica using a solvent gradient of 0% to 100% ethyl acetate in isohexane as eluent. There was thus obtained N-[5-(6-chloro-5-tritylaminopyridazin-3-yl)-4-methyl-1,3-thiazol-2-yl]acetamide as a solid (295 mg); Mass Spectrum: M+H$^+$ 524.

Trifluoroacetic acid (1.5 mL) was added to a stirred mixture of N-[5-(6-chloro-5-tritylaminopyridazin-3-yl)-4-methyl-1,3-thiazol-2-yl]acetamide (300 mg), methanol (0.5 mL) and dichloromethane (4 mL) that had been cooled to 0° C. The resultant mixture was heated to 55° C. for 5 hours. The mixture was evaporated and the residue was basified to pH8 by the addition of a saturated aqueous sodium bicarbonate solution. The resultant solid was isolated and washed with diethyl ether. The solid was dissolved in dichloromethane and a 7M methanolic ammonia solution was added. The mixture was evaporated to give N-[5-(5-amino-6-chloropyridazin-3-yl)-4-methyl-1,3-thiazol-2-yl]acetamide as a solid; Mass Spectrum: M+H$^+$ 282.

EXAMPLE 92

N-[4-Methyl-5-(6-phenylsulfonylaminopyridazin-4-yl)-1,3-thiazol-2-yl]acetamide

A mixture of N-[5-(6-chloropyridazin-4-yl)-4-methyl-1,3-thiazol-2-yl]acetamide (55 mg), benzenesulphonamide (49 mg), caesium carbonate (101 mg), cuprous iodide (30 mg) and DMA (1.5 mL) was heated in a microwave reactor to 200° C. under an argon atmosphere for 3 hours. The resultant mixture was evaporated and the residue was purified by preparative HPLC on reversed phase silica using a solvent gradient of 10% to 100% acetonitrile in water (containing 1% acetic acid) as eluent. The material so obtained was triturated under diethyl ether. There was thus obtained the title compound as a solid (7.3 mg); $^1$H NMR Spectrum: (DMSOd$_6$+ CD$_3$CO$_2$D) 2.20 (s, 3H), 2.43 (s, 3H), 7.51-7.64 (m, 3H), 7.75 (s, 1H), 7.89 (d, 2H), 8.51 (s, 1H); Mass Spectrum: M+H$^+$ 390.

The N-[5-(6-chloropyridazin-4-yl)-4-methyl-1,3-thiazol-2-yl]acetamide used as a starting material was prepared as follows A mixture of 2-acetamido-4-methylthiazole (625 mg), 5-iodo-2,3-dihydropyridazin-3-one (1.6 g), palladium(II) acetate (117 mg), tri-tert-butylphosphine (0.155 mL), caesium fluoride (1.82 g) and DMSO (10 mL) was purged with nitrogen. The resultant mixture was heated to 120° C. for 23 hours. The mixture was cooled to room temperature and evaporated. The residue was triturated under water (10 mL). The resultant solid was collected by filtration, and dried under vacuum. There was thus obtained N-[4-methyl-5-(6-oxo-1,6-dihydropyridazin-4-yl)-1,3-thiazol-2-yl]acetamide which was used without further purification; Mass Spectrum: M+H$^+$ 251.

A mixture of the material so obtained (500 mg) and phosphoryl chloride (0.91 mL) was heated to 60° C. for 20 minutes. The mixture was cooled to room temperature and dichloromethane was added. A cooled saturated aqueous sodium bicarbonate solution was added to neutralise the mixture (pH 7.5). The resultant solid was isolated, washed with ethanol and dried under vacuum at 50° C. The solid was purified by column chromatography on silica using a solvent gradient of 0% to 5% methanol in dichloromethane as eluent. There was thus obtained the required starting material (127 mg); $^1$H NMR Spectrum: (DMSOd$_6$) 2.18 (s, 6H), 7.94 (s, 1H), 9.37 (s, 1H).

Additional Pharmacological Analysis

PI3K Assay Technology

In order to assess the ability of compounds to inhibit PI3K enzymes, especially PI3Kγ, a novel PI3K assay technology was established. The PI3K enzyme reaction product phosphatidylinositol 3,4,5-trisphosphate (PtdIns(3,4,5)P$_3$) is detected using the pleckstrin homology (PH) domain from general receptor for phosphoinositides (GRP1) as probe. Thus, complexes form between GRP1 PH and PtdIns(3,4,5) P$_3$, and if the lipid is biotinylated and the PH domain tagged with glutathion transferase (GST), the complexes can be detected using AlphaScreen® (PerkinElmer) technology. The signal generated by the complex between GRP1 PH-GST and PtdIns(3,4,5)P$_3$-biotin can be quenched by introduction of non-biotinylated PtdIns(3,4,5)P$_3$, forming the basis for an assay measuring the production of PtdIns(3,4,5)P$_3$ by PI3K enzyme activity.

Detection of Biotinylated Phosphoinositide/PH Domain Complexes

Biotinylated PtdIns(3,4,5)P$_3$ was detected using AlphaScreen® technology. Detection was in 384-well microplates in 50 mM Hepes, pH7.4, 50 mM NaCl and 0.1% BSA. The biotinylated, short chain (diC8) phosphoinositide and GRP1 PH-GST were added at 15 nM and 3.75 nM, respectively. Donor and acceptor AlphaScreen® beads (Perkin Elmer) were added at 5 μg/ml to a final volume of 50 μl. Plates were incubated in the dark for 5 hours to ensure binding was complete and then read in an AlphaQuest AD instrument (Perkin Elmer) using standard settings.

The GRP1 PH domain (amino acids 263 to 380) was PCR cloned from a mouse brain cDNA library (Stratagene), expressed in *E. coli* and purified using standard protocols. Lipids were from Echelon Research Laboratories, Salt Lake City, Utah, or Cell Signals Inc., Lexington, Ky., USA.

PI 3-Kinase Assay

The assay used AlphaScreen® based detection of PI(3,4, 5)P3 (Gray et al., *Anal. Biochem.*, 2003, 313, 234-245) to determine the ability of test compounds to inhibit phosphorylation of recombinant PI3Ks of PI(4,5)P$_2$.

DNA fragments encoding human PI3K catalytic and regulatory subunits were isolated from cDNA libraries using standard molecular biology and PCR cloning techniques. The selected DNA fragments were used to generate baculovirus expression vectors. In particular, full length DNA of each of the p110α, p110β and p110δ Type Ia human PI3K p110 isoforms (EMBL Accession Nos. HSU79143, S67334, Y10055 for p110α, p110β and p110δ, respectively) were sub-cloned into a pDEST10 vector (Invitrogen Limited, Fountain Drive, Paisley, UK). The vector is a Gateway-adapted version of Fastbac1 containing a 6-His epitope tag. The full length human p85 (regulatory subunit (EMBL Accession No. HSP13KIN) was also sub-cloned into pFast-Bac1 vector containing a 6-His epitope tag. The Type Ia p110 constructs were co-expressed with the p85α regulatory subunit. Residues 2-1102 of human PI3Kγ were inserted between the BamHI and Not1 cloning sites of the pFastBACiiii HTb vector for expression of His(6)-tagged (N-terminal), full length PI3Kγ in baculo virus infected Sf9 insect cells. Following expression in the baculovirus system using standard baculovirus expression techniques, expressed proteins were purified using standard His epitope tag purification techniques.

Standard enzyme reactions were performed in 50 mM Hepes, pH7.4, 50 mM NaCl, 5 nM $MgCl_2$, 5 mM DTT and 0.05% CHAPS containing 40 μM ATP, 40 μM diC8 PtdIns(4,5)P2 and 2-20 ng of Type 1 PI3K in a total volume of 20 μl. The reaction was stopped by the addition of 10 μl of EDTA/diC6 PtdIns(3,4,5)$P_3$-biotin followed by 20 μl of GRP1 PH-GST/AlphaScreen beads both in 50 mM Hepes, pH7.4, 50 mM NaCl and 0.1% BSA. Final concentrations were 50 mM EDTA, 15 nM biotinylated diC6PtdIns(3,4,5)$P_3$, 3.75 nM GRP1 PH-GST and 5 μg/ml of AlphaScreen beads. Inhibitors were added to dry wells in 0.5 μl of 100% DMSO giving a final DMSO concentration of 2.5% in the assay. Control wells contained 2.5% DMSO in the absence of test compound. Inhibition of PI3K by test compounds was expressed as an $IC_{50}$ value.

In general, compounds of the invention possessed activity as both Type Ia and Type Ib PI3K enzyme inhibitors. For example, compounds of the invention had an $IC_{50}$ versus p110γ in the range of <0.1 μM-40 μM. Furthermore, compounds of the invention had an $IC_{50}$ versus p110α Type Ia human PI3K in the range of <0.1 μM-4.5 μM. Inhibitory effects were also observed for p110β Type Ia human PI3K and for p110δ Type Ia human PI3K.

The following table shows the $IC_{50}$ figures for p10γ Type Ib human PI3K and for p110α, p110β and p110δ Type Ia human PI3Ks for a selection of compounds:—

| Example No. | $IC_{50}$ (μM) | | | |
| --- | --- | --- | --- | --- |
| | p110γ | p110α | p110β | p110δ |
| 7 | 0.22 | 0.42 | 0.74 | 0.15 |
| 8 | 0.40 | 0.57 | 1.89 | 0.20 |
| 31 | 0.16 | 0.05 | 0.25 | 0.01 |
| 46 | 0.12 | 0.28 | 0.63 | 0.20 |
| 56 | 0.26 | 0.23 | 0.12 | <0.10 |

The invention claimed is:
1. A thiazole derivative of formula (I), or a pharmaceutically acceptable salt thereof,

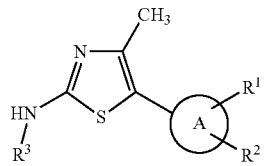

(I)

wherein,
Ring A is pyridine with the pyridyl nitrogen disposed in a meta position relative to the bond connecting Ring A to the thiazole ring shown in formula (I);
$R^1$ is hydrogen, halo, $C_1$-$C_6$ alkyl or $C_1$-$C_6$ alkoxy;
$R^2$ is —$R^6$—$R^7$;
$R^6$ is —N($R^9$)—$SO_2$—, —$SO_2$—N($R^{10}$)—, —N($R^{11}$)—C(=O)—, —N($R^{12}$)—C(=O)—N($R^{13}$)—, —N($R^9$)—$SO_2$—N($R^{10}$)— or —$SO_2$—;
$R^7$ is $R^{14}$ or $C_1$-$C_6$ alkyl or $C_2$-$C_8$ alkoxyalkyl;
or $R^7$ is $C_1$-$C_6$ alkyl substituted with one or more groups selected from halogen, or hydroxy,
or $R^7$ is $C_1$-$C_6$ alkyl substituted with $R^{14}$,
or $R^7$ is $C_1$-$C_6$ alkyl substituted with $NR^{15}R^{16}$,
or $R^7$ is —$R^{17}$—X—$R^{18}$;
$R^{14}$ is $C_3$-$C_7$ cycloalkyl, phenyl, benzyl, phenoxy, thienyl, furanyl, pyrrolyl, imidazolyl, pyridyl, pyrazinyl, pyrimidinyl, pyridazinyl, triazinyl, oxazolyl, thiazolyl, isoxazolyl, isothiazolyl, pyrazolyl, oxadiazolyl, thiadiazolyl, triazolyl, benzoxadiazolyl, benzothiadiazolyl, indolyl or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —C(=O)—$NH_2$, —$NO_2$, halogen, —$OCF_3$, —C(=O)—$CF_3$, $C_1$-$C_6$ alkylcarbonyl, $C_2$-$C_6$ alkanoylamino, —O—$CH_2$—$CH_2$—CN, $C_1$-$C_6$ alkylsulfonyl, or —$NR^{19}R^{20}$;
$R^{15}$ is independently H, $C_3$-$C_6$ cycloalkyl or $C_1$-$C_6$ alkyl optionally substituted with $C_3$-$C_6$ cycloalkyl;
or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;
$R^{16}$ is independently H, or $C_1$-$C_6$ alkyl; or
$R^{15}$ and $R^{16}$ together with the nitrogen to which they are attached form a 5 or 6-membered saturated ring optionally containing a further heteroatom selected from O or N, and optionally being substituted with $C_1$-$C_6$ alkyl or $C_1$-$C_6$ alkylcarbonyl;
$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, cyano, $C_1$-$C_6$ alkyl, $C_1$-$C_6$ alkoxy or $C_1$-$C_6$ alkylthio;
X is a bond, —$CH_2$—NH—C(=O)—, or O;
$R^{19}$ and $R^{20}$ are independently H or $C_1$-$C_6$ alkyl,
or $R^{19}$ and $R^{20}$ together with the nitrogen to which they are attached form a 5 or 6-membered saturated ring optionally containing a further heteroatom independently selected from O or N, and optionally being substituted with $C_1$-$C_6$ alkyl or $C_1$-$C_6$ alkylcarbonyl;
and $R^3$ is phenyl or benzyl, each being optionally substituted with one or more groups selected from halo, $C_1$-$C_6$ alkyl, or $C_1$-$C_6$ alkoxy;
or $R^3$ is a 5 or 6-membered heteroaromatic ring containing nitrogen and optionally one or more further heteroatoms independently selected from O, S or N, said ring being optionally substituted with one or more of the following groups: (i) halogen or $C_1$-$C_6$ alkyl optionally substituted by carboxy, $C_1$-$C_6$ alkoxycarbonyl, —$NR^{21}R^{22}$ or a 5 or 6-membered heterocyclic ring containing at least one heteroatom independently selected from O, S or N,
(ii) $C_1$-$C_6$ alkoxy, —$NR^{21}R^{22}$, $C_3$-$C_8$ cycloalkyl optionally substituted with carboxy, or
(iii) a 5 or 6-membered heterocyclic ring containing at least one heteroatom independently selected from O, S or N optionally substituted with $C_1$-$C_6$ alkyl;
or $R^3$ is —(C=O)—(NH)$_p$—$R^{23}$, —(C=O)—(NH)$_q$—$CH_2$—$R^{24}$, —(C=O)—(NH)$_q$—$CH_2$—$CH_2$—$R^{24}$ or —(C=O)—$NH_2$;
p and q are each independently 0 or 1;
or $R^3$ is hydrogen or $C_1$-$C_6$ alkyl;
$R^{21}$ is hydrogen or $C_1$-$C_6$ alkyl;
$R^{22}$ is $C_1$-$C_6$ alkyl optionally substituted with hydroxy, $C_1$-$C_6$ alkoxy, di($C_1$-$C_6$ alkyl)amino or a 5 or 6-membered heterocyclic ring containing at least one heteroatom selected from O, S or N and optionally substituted with $C_1$-$C_6$ alkyl;

$R^{23}$ is $C_1$-$C_6$ alkyl or $C_3$-$C_7$ cycloalkyl each being optionally substituted with one or more groups selected from halogen, hydroxy, amino, $C_1$-$C_6$ alkylamino, di($C_1$-$C_6$ alkyl)amino, $C_1$-$C_6$ alkoxycarbonyl, nitrile, carboxy, $C_1$-$C_6$ alkoxy optionally substituted with hydroxy, $C_3$-$C_8$ cycloalkyl optionally substituted with hydroxy, or phenyl optionally substituted with hydroxy or $C_1$-$C_6$ alkyl, or $R^{23}$ is phenyl, benzyl, or a 5 or 6-membered heteroaromatic ring containing at least one heteroatom independently selected from O, S or N, each being optionally substituted with one or more groups selected from halogen, hydroxy, $C_1$-$C_6$ alkyl, $C_1$-$C_6$ alkoxy, or by a 5 or 6-membered saturated heterocyclic ring containing at least one heteroatom independently selected from O, S or N, or $R^{23}$ is a 5 or 6-membered heteroaromatic ring containing at least one heteroatom independently selected from O, S or N, which ring is substituted with phenyl and is optionally substituted with one or more groups selected from halogen, hydroxy, $C_1$-$C_6$ alkyl or $C_1$-$C_6$ alkoxy;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$, $R^{10}$, $R^{11}$, $R^{12}$, and $R^{13}$ are H, $C_1$-$C_6$ alkyl, or $C_1$-$C_6$ alkylcarbonyl.

2. A thiazole derivative of formula (I), or a pharmaceutically acceptable salt thereof, according to claim 1 wherein:—
$R^2$ is —$R^6$-$R^7$ and $R^6$ is —NH—$SO_2$— and $R^7$ has any of the meanings defined in claim 1.

3. A thiazole derivative of formula (I), or a pharmaceutically acceptable salt thereof, according to claim 1 wherein:—
$R^1$ is halogen.

4. A thiazole derivative of formula (I), or a pharmaceutically acceptable salt thereof, according to claim 1 wherein:—
$R^3$ is —(C=O)—(NH)$_p$—$R^{23}$ or —(C=O)—(NH)$_q$—$CH_2$—$R^{24}$, or —(C=O)—$NH_2$ where p and q are independently 0 or 1 and each of $R^{23}$ and $R^{24}$ has any of the meanings defined in claim 1.

5. A thiazole derivative of formula (I), or a pharmaceutically acceptable salt thereof, according to claim 1 wherein:—
$R^3$ is —(C=O)—(NH)$_p$—$R^{23}$ where p is equal to zero and $R^{23}$ is $C_1$-$C_6$ alkyl.

6. A thiazole derivative of formula (I), or a pharmaceutically acceptable salt thereof,

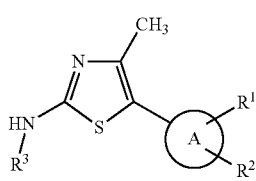

(I)

wherein:—
Ring A is pyridine with the pyridyl nitrogen disposed in a meta position relative to the bond connecting Ring A to the thiazole ring shown in formula (I);
$R^1$ is hydrogen, halo, $C_1$-$C_6$ alkyl or $C_1$-$C_6$ alkoxy;

$R^2$ is —$R^6$-$R^7$;
$R^6$ is —N($R^9$)—$SO_2$—;
$R^7$ is $R^{14}$ or $C_1$-$C_6$ alkyl or $C_2$-$C_8$ alkoxyalkyl;
or $R^7$ is $C_1$-$C_6$ alkyl substituted with one or more groups selected from halogen, or hydroxy,
or $R^7$ is $C_1$-$C_6$ alkyl substituted with $R^{14}$ or phenoxy,
or $R^7$ is $C_1$-$C_6$ alkyl substituted with $NR^{15}R^{16}$,
or $R^7$ is —$R^{17}$—X—$R^{18}$;
$R^{14}$ is phenyl, benzyl, thienyl, furanyl, pyrrolyl, imidazolyl, pyridyl, pyrazinyl, pyrimidinyl, pyridazinyl, triazinyl, oxazolyl, thiazolyl, isoxazolyl, isothiazolyl, pyrazolyl, oxadiazolyl, thiadiazolyl, triazolyl, benzoxadiazolyl, benzothiadiazolyl, indolyl, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —$NO_2$, halogen, —O—$CH_2$—$CH_2$—CN,
$C_1$-$C_6$ alkylsulfonyl, or —$NR^{19}R^{20}$;
$R^{15}$ is independently H, $C_3$-$C_6$ cycloalkyl or $C_1$-$C_6$ alkyl optionally substituted with $C_3$-$C_6$ cycloalkyl;
or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;
$R^{16}$ is independently H, or $C_1$-$C_6$ alkyl; or
$R^{15}$ and $R^{16}$ together with the nitrogen to which they are attached form a 6-membered saturated ring optionally containing a further heteroatom selected from O or N, and optionally being substituted with $C_1$-$C_6$ alkyl;
$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, $C_1$-$C_6$ alkyl, or $C_1$-$C_6$ alkoxy;
X is a bond, —$CH_2$—NH—C(=O)—, or O;
$R^{19}$ and $R^{20}$ are independently H or $C_1$-$C_6$ alkyl,
or $R^{19}$ and $R^{20}$ together with the nitrogen to which they are attached form a 6-membered saturated ring optionally containing a further heteroatom independently selected from O or N, and optionally being substituted with $C_1$-$C_6$ alkyl;
and $R^3$ is phenyl or benzyl, each being optionally substituted with one or more groups selected from halo, $C_1$-$C_6$ alkyl, or $C_1$-$C_6$ alkoxy;
or $R^3$ is a 5 or 6-membered heteroaromatic ring containing nitrogen and optionally one or more further heteroatoms independently selected from O, S or N, said ring being optionally substituted with one or more of the following groups: (i) halogen or $C_1$-$C_6$ alkyl optionally substituted by carboxy, $C_1$-$C_6$ alkoxycarbonyl, —$NR^{21}R^{22}$ or a 5 or 6-membered heterocyclic ring containing at least one heteroatom independently selected from O, S or N,
(ii) $C_1$-$C_6$ alkoxy, —$NR^{21}R^{22}$, $C_3$-$C_8$ cycloalkyl optionally substituted with carboxy, or
(iii) a 5 or 6-membered heterocyclic ring containing at least one heteroatom independently selected from O, S or N optionally substituted with $C_1$-$C_6$ alkyl;
or $R^3$ is —(C=O)—(NH)$_p$—$R^{23}$, —(C=O)—(NH)$_q$—$CH_2$—$R^{24}$ or —(C=O)—$NH_2$;
p and q are each independently 0 or 1;
$R^{21}$ is hydrogen or $C_1$-$C_6$ alkyl;
$R^{22}$ is $C_1$-$C_6$ alkyl optionally substituted with hydroxy, $C_1$-$C_6$ alkoxy, di($C_1$-$C_6$ alkyl)amino or a 5 or 6-membered heterocyclic ring containing at least one heteroatom selected from O, S or N and optionally substituted with $C_1$-$C_6$ alkyl;

$R^{23}$ is $C_1$-$C_6$ alkyl optionally substituted with one or more groups selected from halogen, hydroxy, amino, $C_1$-$C_6$ alkylamino, di($C_1$-$C_6$ alkyl)amino, $C_1$-$C_6$ alkoxycarbonyl, nitrile, carboxy, $C_1$-$C_6$ alkoxy optionally substituted with hydroxy, $C_3$-$C_s$ cycloalkyl optionally substituted with hydroxy, or phenyl optionally substituted with hydroxy or $C_1$-$C_6$ alkyl, or $R^{23}$ is phenyl, benzyl, or a 5 or 6-membered heteroaromatic ring containing at least one heteroatom independently selected from O, S or N, each being optionally substituted with one or more groups selected from halogen, hydroxy, $C_1$-$C_6$ alkyl, $C_1$-$C_6$ alkoxy, or by a 5 or 6-membered saturated heterocyclic ring containing at least one heteroatom independently selected from O, S or N, or $R^{23}$ is a 5 or 6-membered heteroaromatic ring containing at least one heteroatom independently selected from O, S or N, which ring is substituted with phenyl;

$R^{24}$ is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and $R^9$ is H, $C_1$-$C_6$ alkyl, or $C_1$-$C_6$ alkylcarbonyl.

7. A thiazole derivative, or a pharmaceutically acceptable salt thereof, according to claim 1 wherein formula (I) is replaced with formula (Ia)

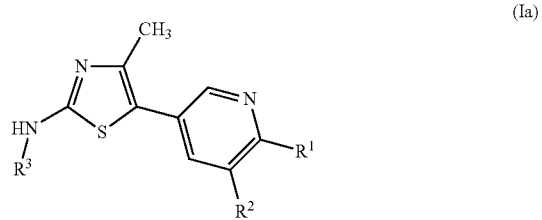

(Ia)

wherein,
$R^1$ is hydrogen, halo, $C_1$-$C_6$ alkyl or $C_1$-$C_6$ alkoxy;
$R^2$ is —$R^6$-$R^7$;
$R^6$ is —N($R^9$)—$SO_2$—, —$SO_2$—N($R^{10}$)—, —N($R^{11}$)—C(=O)—, —N($R^{12}$)—C(=O)—N($R^{13}$)—, or —$SO_2$—;
$R^7$ is $R^{14}$ or $C_1$-$C_6$ alkyl or $C_2$-$C_8$ alkoxyalkyl;
or $R^7$ is $C_1$-$C_6$ alkyl substituted with one or more groups selected from halogen, or hydroxy,
or $R^7$ is $C_1$-$C_6$ alkyl substituted with $R^{14}$ or phenoxy,
or $R^7$ is $C_1$-$C_6$ alkyl substituted with $NR^{15}R^{16}$,
or $R^7$ is —$R^{17}$—X—$R^{18}$;
$R^{14}$ is phenyl, benzyl, thienyl, furanyl, pyrrolyl, imidazolyl, pyridyl, pyrazinyl, pyrimidinyl, pyridazinyl, triazinyl, oxazolyl, thiazolyl, isoxazolyl, isothiazolyl, pyrazolyl, oxadiazolyl, thiadiazolyl, triazolyl, benzoxadiazolyl, benzothiadiazolyl, indolyl, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —$NO_2$, halogen, —O—$CH_2$—$CH_2$—CN, $C_1$-$C_6$ alkylsulfonyl, or —$NR^{19}R^{20}$;

$R^{15}$ is independently H, $C_3$-$C_6$ cycloalkyl or $C_1$-$C_6$ alkyl optionally substituted with $C_3$-$C_6$ cycloalkyl;

or $R^{15}$ is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;

$R^{16}$ is independently H, or $C_1$-$C_6$ alkyl; or $R^{15}$ and $R^{16}$ together with the nitrogen to which they are attached form a 6-membered saturated ring optionally containing a further heteroatom selected from O or N, and optionally being substituted with $C_1$-$C_6$ alkyl;

$R^{17}$ and $R^{18}$ are independently phenyl, or a 5 or 6-membered heteroaromatic ring containing 1 or 2 heteroatoms independently selected from O, S or N, wherein one or both of $R^{17}$ and $R^{18}$ may be optionally and independently substituted with one or more groups selected from halogen, $C_1$-$C_6$ alkyl, or $C_1$-$C_6$ alkoxy;

X is a bond, —$CH_2$—NH—C(=O)—, or O;

$R^{19}$ and $R^{20}$ are independently H or $C_1$-$C_6$ alkyl, or $R^{19}$ and $R^{20}$ together with the nitrogen to which they are attached form a 6-membered saturated ring optionally containing a further heteroatom independently selected from O or N, and optionally being substituted with $C_1$-$C_6$ alkyl;

and $R^3$ is phenyl or benzyl, each being optionally substituted with one or more groups selected from halo, $C_1$-$C_6$ alkyl, or $C_1$-$C_6$ alkoxy;

or $R^3$ is a 5 or 6-membered heteroaromatic ring containing nitrogen and optionally one or more further heteroatoms independently selected from O, S or N, said ring being optionally substituted with one or more of the following groups: (i) halogen or $C_1$-$C_6$ alkyl optionally substituted by carboxy, $C_1$-$C_6$ alkoxycarbonyl, —$NR^{21}R^{22}$ or a 5 or 6-membered heterocyclic ring containing at least one heteroatom independently selected from O, S or N, (ii) $C_1$-$C_6$ alkoxy, —$NR^{21}R^{22}$ or $C_3$-$C_8$ cycloalkyl optionally substituted with carboxy, (iii) a 5 or 6-membered heterocyclic ring containing at least one heteroatom independently selected from O, S or N optionally substituted with $C_1$-$C_6$ alkyl;

or $R^3$ is —(C=O)—(NH)$_p$—$R^{23}$, —(C=O)—(NH)$_q$—$CH_2$—$R^{24}$ or —(C=O)—$NH_2$;

p and q are each independently 0 or 1;

$R^{21}$ is hydrogen or $C_1$-$C_6$ alkyl;

$R^{22}$ is $C_1$-$C_6$ alkyl optionally substituted with hydroxy, $C_1$-$C_6$ alkoxy, di($C_1$-$C_6$ alkyl)amino or a 5 or 6-membered heterocyclic ring containing at least one heteroatom selected from O, S or N and optionally substituted with $C_1$-$C_6$ alkyl;

$R^{23}$ is $C_1$-$C_6$ alkyl optionally substituted with one or more groups selected from halogen, hydroxy, amino, $C_1$-$C_6$ alkylamino, di($C_1$-$C_6$ alkyl)amino, $C_1$-$C_6$ alkoxycarbonyl, nitrile, carboxy, $C_1$-$C_6$ alkoxy optionally substituted with hydroxy, $C_3$-$C_8$ cycloalkyl optionally substituted with hydroxy, or phenyl optionally substituted with hydroxy or $C_1$-$C_6$ alkyl, or $R^{23}$ is phenyl, benzyl, or a 5 or 6-membered heteroaromatic ring containing at least one heteroatom independently selected from O, S or N, each being optionally substituted with one or more groups selected from halogen, hydroxy, $C_1$-$C_6$ alkyl, $C_1$-$C_6$ alkoxy, or by a 5 or 6-membered saturated heterocyclic ring containing at least one heteroatom independently selected from O, S or N, or $R^{23}$ is a 5 or 6-membered heteroaromatic ring containing at least one heteroatom independently selected from O, S or N, which ring is substituted with phenyl;

R[24] is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and R[9], R[10], R[11], R[12], and R[13] are H, $C_1$-$C_6$ alkyl, or $C_1$-$C_6$ alkylcarbonyl.

8. A thiazole derivative of formula (I), or a pharmaceutically acceptable salt thereof, according to claim 1 wherein formula (I) is replaced with formula (Ia):—

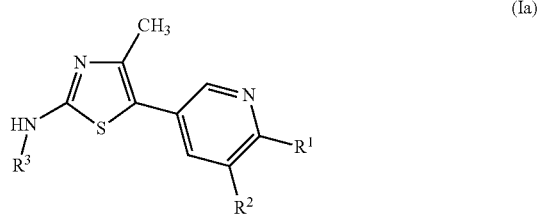

(Ia)

wherein R[1] is hydrogen or halo;
R[2] is —R[6]-R[7];
R[6] is —N(R[9])—$SO_2$—;
R[7] is R[14] or $C_1$-$C_6$ alkyl or $C_2$-$C_8$ alkoxyalkyl;
or R[7] is $C_1$-$C_6$ alkyl substituted with one or more groups selected from halogen, or hydroxy,
or R[7] is $C_1$-$C_4$ alkyl substituted with either R[14] or phenoxy,
or R[7] is $C_1$-$C_6$ alkyl substituted with NR[15]R[16];
or R[7] is —R[17]—X—R[18];
R[14] is phenyl, benzyl, thienyl, furanyl, pyrrolyl, imidazolyl, pyridyl, pyrazinyl, pyrimidinyl, pyridazinyl, triazinyl, oxazolyl, thiazolyl, isoxazolyl, isothiazolyl, pyrazolyl, oxadiazolyl, thiadiazolyl, triazolyl, benzoxadiazolyl, benzothiadiazolyl, indolyl, or a phenyl-fused 5 or 6-membered cycloheteroalkyl ring containing 1 or 2 heteroatoms independently selected from O, S or N, each being optionally substituted with one or more groups independently selected from $C_1$-$C_6$ alkyl, $C_1$-$C_6$ alkoxy, cyano, —$NO_2$, halogen, —O—$CH_2$—$CH_2$—CN, $C_1$-$C_6$ alkylsulfonyl, or —NR[19]R[20];
R[15] is independently H, $C_3$-$C_6$ cycloalkyl or $C_1$-$C_6$ alkyl optionally substituted with $C_3$-$C_6$ cycloalkyl;
or R[15] is phenyl, a 5 or 6-membered heteroaromatic ring containing 1 to 4 heteroatoms independently selected from O, S and N, or benzyl, each being optionally substituted with one or more groups selected from halo, $C_1$-$C_6$ alkyl, $C_1$-$C_6$ alkoxy or hydroxy;
R[16] is independently H, or $C_1$-$C_6$ alkyl; or
R[15] and R[16] together with the nitrogen to which they are attached form a 6-membered saturated ring optionally containing a further heteroatom selected from O or N, and optionally being substituted with $C_1$-$C_6$ alkyl;
R[17] and R[18] are independently phenyl, or a 5 or 6-membered heteroaromatic ring containing 1 or 2 heteroatoms independently selected from O, S or N, wherein one or both of R[17] and R[18] may be optionally and independently substituted with one or more groups selected from halogen, $C_1$-$C_6$ alkyl, or $C_1$-$C_6$ alkoxy;
X is a bond, —$CH_2$—NH—C(=O)—, or O;
R[19] and R[20] are independently H or $C_1$-$C_6$ alkyl,
or R[19] and R[20] together with the nitrogen to which they are attached form a 6-membered saturated ring optionally containing a further heteroatom selected from O or N, and optionally being substituted with $C_1$-$C_6$ alkyl;

R[3] is —(C=O)—$NH_2$, —(C=O)—R[23] or —(C=O)—(NH)$_q$—$CH_2$—R[24];
q is 0 or 1;
R[23] is $C_1$-$C_6$ alkyl or $C_2$-$C_6$ alkoxy-alkyl,
or R[23] is phenyl, benzyl, or a 5 or 6-membered heteroaromatic ring containing at least one heteroatom selected from the group consisting of O, S or N, each being optionally substituted with one or more groups selected from halogen, hydroxy, $C_1$-$C_6$ alkyl, $C_1$-$C_6$ alkoxy, or with a 5 or 6-membered saturated heterocyclic ring containing at least one heteroatom selected from the group consisting of O, S or N;
or R[23] is a 5 or 6-membered heteroaromatic ring containing at least one heteroatom selected from the group consisting of O, S or N, which ring is substituted with phenyl;
R[24] is benzyloxy or a 5 to 7-membered heteroaromatic ring containing 1 to 3 heteroatoms independently selected from O, S and N, either of which being optionally substituted with one or more groups selected from halogen, $C_1$-$C_6$ alkyl or $C_1$-$C_6$ alkoxy; and
R[9] is H, $C_1$-$C_6$ alkyl, or $C_1$-$C_6$ alkylcarbonyl.

9. A thiazole derivative of formula (I) according to claim 1 wherein formula (I) is replaced with formula (Ib):—

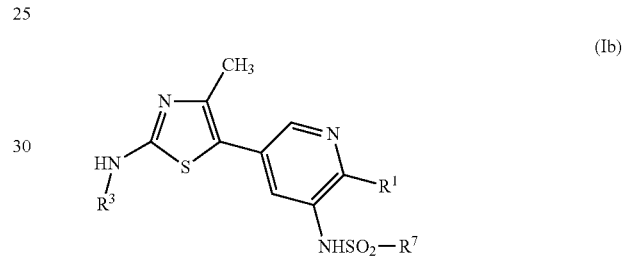

(Ib)

wherein R[1] is H, fluoro, chloro, methyl, ethyl or methoxy;
R[7] is R[14] or methyl, ethyl or propyl, or R[7] is methyl substituted with R[14], or R[7] is propyl substituted with NR[15]R[16], or R[7] is —R[17]—X—R[18];
R[14] is phenyl, benzyl, 2-thienyl, 3-thienyl, 4-imidazolyl, 3-pyridyl, 5-oxazolyl, 5-thiazolyl, 4-isoxazolyl, 4-isothiazolyl, 4-pyrazolyl, benzo-2,1,3-oxadiazol-4-yl or 2,1,3-benzothiadiazol-4-yl, each being optionally substituted with one, two or three groups independently selected from methyl, ethyl, methoxy, ethoxy, cyano, nitro, fluoro, chloro, trifluoromethoxy, acetyl, acetamido, 2-cyanoethoxy, methylsulfonyl, methylamino, dimethylamino, piperidino, morpholino, piperazin-1-yl or 4-methylpiperazin-1-yl;
R[15] is independently H, cyclopentyl, methyl, ethyl, neopentyl, 3-methylbutyl, cyclopentylmethyl or cyclohexylmethyl, or R[15] is phenyl or benzyl, each being optionally substituted with one or two groups selected from fluoro, chloro, methyl, methoxy or hydroxy, and R[16] is independently H or methyl, or R[15] and R[16] together with the nitrogen to which they are attached form piperidino, morpholino, piperazin-1-yl or 4-methylpiperazin-1-yl;
R[17] is phenyl, 2-thienyl or 3-pyridyl, X is a bond or O, and R[18] is phenyl, 2-pyridyl or 4-pyrimidinyl, each being optionally substituted with one or two groups selected from chloro, cyano, methyl, methoxy or methylthio; and
R[3] is —(C=O)—$NH_2$ or —(C=O)—(NH)$_p$—R[23], p is 0 or 1 and R[23] is methyl or ethyl;
or a pharmaceutically acceptable salt thereof.

10. A thiazole derivative of formula (I) according to claim 1 wherein formula (I) is replaced with formula (Ib):—

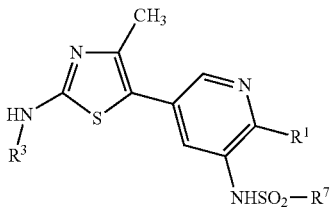

(Ib)

wherein $R^1$ is fluoro, chloro, methyl or methoxy;
$R^7$ is phenyl, 3-tolyl, 4-tolyl, 3-methoxyphenyl, 4-methoxyphenyl, 2,4-dimethoxyphenyl, 3,4-dimethoxyphenyl, 2,5-dimethoxyphenyl, 2-methoxy-4-methylphenyl, 2-methoxy-5-methylphenyl, 2-thienyl, 3-thienyl, 1-methyl-1H-imidazol-4-yl, 1,2-dimethylimidazol-4-yl, 1,2-dimethylimidazol-5-yl, 2,4-dimethyl-1,3-thiazol-5-yl, 2-acetamido-4-methyl-1,3-thiazol-5-yl, 3,5-dimethylisoxazol-4-yl, 5-chloro-1,3-dimethyl-1H-pyrazol-4-yl or 3-pyridyl; and
$R^3$ is acetyl;
or a pharmaceutically acceptable salt thereof.

11. A thiazole derivative of formula (I) according to claim 1 wherein formula (I) is replaced with formula (Ia):—

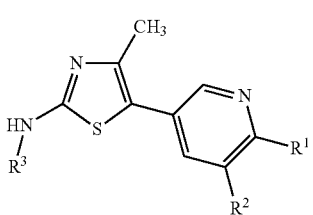

(Ia)

wherein $R^1$ is H, fluoro, chloro, bromo, methyl, ethyl, methoxy or ethoxy;
$R^2$ is —$R^6$-$R^7$;
$R^6$ is —$SO_2$—$N(R^{10})$— and $R^{10}$ is H, methyl, ethyl or acetyl;
$R^7$ is $R^{14}$ or methyl, ethyl or propyl,
or $R^7$ is 2,2-difluoroethyl, 2,2,2-trifluoroethyl, 2-chloroethyl, 3-chloropropyl, 2-hydroxyethyl or 3-hydroxypropyl,
or $R^7$ is methyl substituted with $R^{14}$,
or $R^7$ is methyl, ethyl or propyl substituted with $NR^{15}R^{16}$,
or $R^7$ is —$R^{17}$—X—$R^{18}$;
$R^{14}$ is phenyl, benzyl, phenoxy, cyclopropyl, thienyl, imidazolyl, pyridyl, pyrazinyl, pyrimidinyl, pyridazinyl, oxazolyl, thiazolyl, isoxazolyl, isothiazolyl, pyrazolyl, oxadiazolyl, thiadiazolyl or triazolyl, each being optionally substituted with one, two or three groups independently selected from methyl, ethyl, propyl, isopropyl, methoxy, ethoxy, cyano, nitro, fluoro, chloro, trifluoromethoxy, acetyl, propionyl, acetamido, propionamido, 2-cyanoethoxy, methylsulfonyl, methylamino, ethylamino, dimethylamino, diethylamino, pyrrolidin-1-yl, piperidino, morpholino, piperazin-1-yl, 4-methylpiperazin-1-yl or 4-acetylpiperazin-1-yl;
$R^{15}$ is independently H, cyclopropyl, cyclobutyl, cyclopentyl, cyclohexyl, methyl, ethyl, propyl, isopropyl, butyl, isobutyl, pentyl, neopentyl, 3-methylbutyl, cyclopropylmethyl, cyclobutylmethyl, cyclopentylmethyl or cyclohexylmethyl, or $R^{15}$ is phenyl or benzyl, each being optionally substituted with one or two groups selected from fluoro, chloro, methyl, methoxy or hydroxy, and $R^{16}$ is independently H or methyl, or $R^{15}$ and $R^{16}$ together with the nitrogen to which they are attached form pyrrolidin-1-yl, piperidino, morpholino, piperazin-1-yl, 4-methylpiperazin-1-yl or 4-acetylpiperazin-1-yl;
$R^{17}$ is phenyl, 2-thienyl, 2-pyridyl or 3-pyridyl, X is a bond or O, and $R^{18}$ is phenyl, 2-pyridyl, 3-pyridyl or 4-pyrimidinyl, each $R^{18}$ ring being optionally substituted with one or two groups selected from fluoro, chloro, cyano, methyl, methoxy or methylthio; and
$R^3$ is —(C=O)—$NH_2$, —(C=O)—$(NH)_p$—$R^{23}$, or —(C=O)—(NH)—$CH_2$—$R^{24}$, p is 0 or 1,
$R^{23}$ is methyl, ethyl, propyl, isopropyl, 1-methylpropyl, 2-hydroxyethyl or 1-hydroxymethylpropyl, or $R^{23}$ is phenyl, benzyl, 2-furanyl or 3-pyridyl, each being optionally substituted with one or two groups selected from fluoro, chloro, methyl or methoxy, and
$R^{24}$ is 2-furanyl, 2-thienyl or 4-isoxazolyl each being optionally substituted with one or two groups selected from fluoro, chloro, methyl or methoxy;
or a pharmaceutically acceptable salt thereof.

12. A thiazole derivative of formula (I) according to claim 1 which is selected from:—
N-{5-[6-Chloro-5-(phenylsulfonylamino)pyridin-3-yl]-4-methyl-1,3-thiazol-2-yl}acetamide,
N-{5-[6-Chloro-5-(2,4-dimethoxyphenylsulfonylamino)pyridin-3-yl]-4-methyl-1,3-thiazol-2-yl}acetamide,
N-{5-[6-Chloro-5-(3,4-dimethoxyphenylsulfonylamino)pyridin-3-yl]-4-methyl-1,3-thiazol-2-yl}acetamide,
N-{5-[6-Chloro-5-(2,5-dimethoxyphenylsulfonylamino)pyridin-3-yl]-4-methyl-1,3-thiazol-2-yl}acetamide,
N-{5-[6-Chloro-5-(2-methoxy-5-methylphenylsulfonylamino)pyridin-3-yl]-4-methyl-1,3-thiazol-2-yl acetamide,
N-{5-[6-Chloro-5-(2-methoxy-4-methylphenylsulfonylamino)pyridin-3-yl]-4-methyl-1,3-thiazol-2-yl acetamide,
N-(5-{6-Chloro-5-[(1-methyl-1H-imidazol-4-yl)sulfonylamino]pyridin-3-yl}-4-methyl-1,3-thiazol-2-yl-4) acetamide,
N-{5-[6-Chloro-5-(1,2-dimethylimidazol-4-ylsulfonylamino)pyridin-3-yl]-4-methyl-1,3-thiazol-2-yl}acetamide,
N-{5-[6-Chloro-5-(1,2-dimethylimidazol-5-ylsulfonylamino)pyridin-3-yl]-4-methyl-1,3-thiazol-2-yl}acetamide,
N-{5-[6-Chloro-5-(5-chloro-1,2-dimethyl-1H-pyrazol-4-ylsulfonylamino)pyridin-3-yl]-4-methyl-1,3-thiazol-2-yl}acetamide,
N-{5-[6-Chloro-5-(2,4-dimethyl-1,3-thiazol-5-ylsulfonylamino)pyridin-3-yl]-4-methyl-1,3-thiazol-2-yl}acetamide,
N-{5-[5-(2,4-Dimethyl-1,3-thiazol-5-ylsulfonylamino)-6-fluoropyridin-3-yl]-4-methyl-1,3-thiazol-2-yl}acetamide,
N-{5-[5-(2,4-Dimethyl-1,3-thiazol-5-ylsulfonylamino)-6-methoxypyridin-3-yl]-4-methyl-1,3-thiazol-2-yl}acetamide,
N-{5-[5-(2-Acetamido-4-methyl-1,3-thiazol-5-ylsulfonylamino)-6-chloropyridin-3-yl]-4-methyl-1,3-thiazol-2-yl}acetamide and
N-{5-[6-Chloro-5-(3,5-dimethylisoxazol-4-ylsulfonylamino)pyridin-3-yl]-4-methyl-1,3-thiazol-2-yl]acetamide;
and pharmaceutically acceptable salts thereof.

13. A thiazole derivative of formula (I) according to claim 1 which is selected from:—
N-{5-[6-Chloro-5-(N-methylsulfamoyl)pyridin-3-yl]-4-methyl-1,3-thiazol-2-yl]acetamide,
N-{5-[6-Chloro-5-(N-cyclopropylsulfamoyl)pyridin-3-yl]-4-methyl-1,3-thiazol-2-yl]acetamide,
N-{5-[6-Chloro-5-(N-cyclopropylmethylsulfamoyl)pyridin-3-yl]-4-methyl-1,3-thiazol-2-yl}acetamide,
N-{5-[6-Chloro-5-(N-phenylsulfamoyl)pyridin-3-yl]-4-methyl-1,3-thiazol-2-yl}acetamide,
N-(5-{6-Chloro-5-[N-(4-fluorophenyl)sulfamoyl]pyridin-3-yl}-4-methyl-1,3-thiazol-2-yl)acetamide and
N-(5-{6-Chloro-5-[N-(4-tolyl)sulfamoyl]pyridin-3-yl}-4-methyl-1,3-thiazol-2-yl)acetamide;
and pharmaceutically acceptable salts thereof.

14. A process for the preparation of a compound of formula (I) as defined hereinbefore which comprises:—

(A) the reaction of a compound of formula (II)

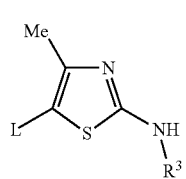

(II)

wherein $R^3$ is as defined in claim 1 and L represents a suitable leaving group, with an organoboron compound of formula (III)

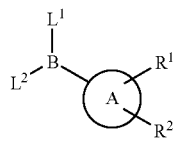

(III)

wherein each of $L^1$ and $L^2$, which may be the same or different, is a suitable ligand and Ring A, $R^1$ and $R^2$ are as defined in claim 1;

(B) for the production of those compounds of formula (I) wherein $R^2$ is $R^6$-$R^7$, and
$R^6$ is —SO$_2$N($R^{10}$)—, the reaction of a compound of formula (IV)

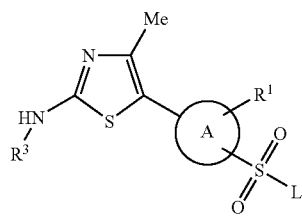

(IV)

wherein Ring A, $R^1$ and $R^3$ are as defined in claim 1 and L is a leaving group, with a compound of formula $R^7$—NH—$R^{10}$, wherein $R^7$ and $R^{10}$ are as defined in claim 1;

(C) for the production of those compounds of formula (I) wherein $R^2$ is $R^6$-$R^7$, and $R^6$ is —N($R^9$)SO$_2$—, the reaction of a compound of formula (V)

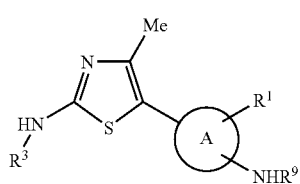

(V)

wherein Ring A, $R^1$, $R^3$ and $R^9$ are as defined in claim 1, with a reactive derivative of a sulfonic acid of formula $R^7$SO$_2$L, wherein $R^7$ is as defined in claim 1 and L is a leaving group;

(D) for the production of those compounds of formula (I) wherein $R^2$ is $R^6$-$R^7$, and
$R^7$ is $C_1$-$C_6$ alkyl substitued by $NR^{15}R^{16}$, the reaction of a compound of formula (VI)

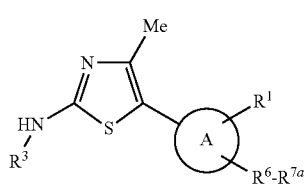

(VI)

wherein Ring A, $R^1$, $R^3$ and $R^6$ are as defined in claim 1 and $R^{7a}$ is $C_1$-$C_6$ substituted by a leaving group, with an amine of formula $HNR^{15}R^{16}$, wherein $R^{15}$ and $R^{16}$ are as defined in claim 1;

(E) for the production of those compounds of formula (I) wherein $R^2$ is $R^6$-$R^7$, and
$R^6$ is —N($R^{11}$)—C(=O)—, the reaction of a compound of formula (VII)

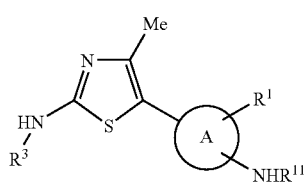

(VII)

wherein Ring A, $R^1$, $R^3$ and $R^{11}$ are as defined in claim 1, with a reactive derivative of a carboxylic acid of formula $R^7CO_2H$, wherein $R^7$ is as defined in claim 1;

(F) the reaction of a compound of formula (VIII)

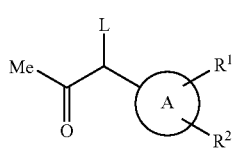

(VIII)

wherein Ring A, $R^1$, and $R^2$ are as defined in claim 1 and L is a leaving group, with a thiourea compound of formula (IX)

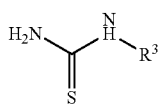

(IX)

wherein R³ is as defined in claim 1;

(G) for the production of those compounds of formula (I) wherein R³ is —(C=O)—(NH)—R²³, the coupling of phosgene, or a chemical equivalent thereof, with a 2-aminothiazole of formula (X)

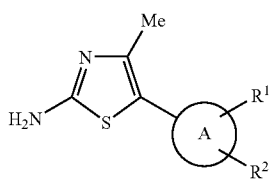

(X)

wherein Ring A, R¹, and R² are as defined in claim 1, and with an amine of formula HNR²³, wherein R²³ is as defined in claim 1;

(H) for the production of those compounds of formula (I) wherein R³ is —(C=O)—R²³, the acylation of a 2-aminothiazole of formula (X)

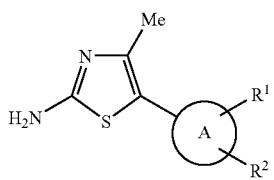

(X)

wherein Ring A, R¹, and R² are as defined in claim 1, with a reactive derivative of a carboxylic acid of formula R²³CO₂H, wherein R²³ is as defined in claim 1;

(I) for the production of those compounds of formula (I) wherein R² is R⁶-R⁷, and R⁶ is —N(R¹²)—C(=O)—NH—, the reaction of a compound of formula (XII),

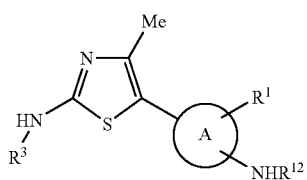

(XII)

wherein Ring A, R¹, R³ and R¹² are as defined in claim 1, with an isocyanate of formula R⁷NCO, wherein R⁷ is as defined in claim 1;

(J) the reaction of a compound of formula (XIII)

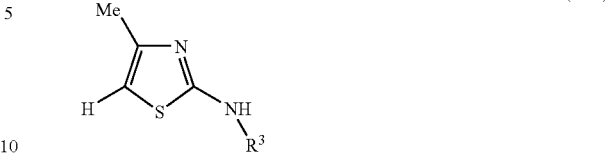

(XIII)

wherein R³ is as defined in claim 1, with a heteroaryl compound of formula (XIV)

(XIV)

wherein L is a suitable leaving group and Ring A, R¹ and R² are as defined in claim 1;

(K) for the production of those compounds of formula (I) wherein R³ is —(C=O)—NH₂ or —(C=O)—(NH)—R²³, the reaction of a 2-aminothiazole of formula (X)

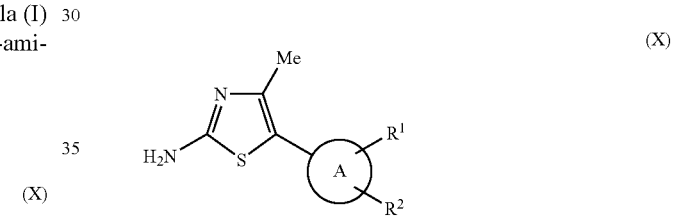

(X)

wherein Ring A, R¹, and R² are as defined in claim 1, with an isocyanate of formula PG—NCO, wherein PG is a protecting group, or with an isocyanate of formula R²³NCO, wherein R²³ is as defined in claim 1;

(L) for the production of those compounds of formula (I) wherein R² is R⁶-R⁷, and R⁶ is —SO₂—, the reaction of a compound of formula (XV),

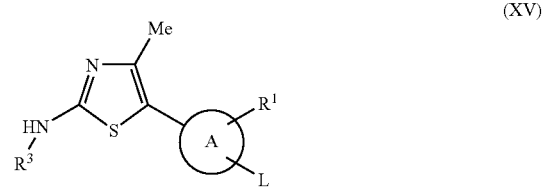

(XV)

wherein Ring A, R¹ and R³ are as defined in claim 1 and L is a suitable leaving group, with a sulfinic acid of formula R⁷—SO₂H, wherein R⁷ is as defined in claim 1; or (M) for the production of those compounds of formula (I) wherein R² is R⁶-R⁷, and R⁶ is —N(R⁹)—SO₂—, the reaction of a compound of formula (XV)

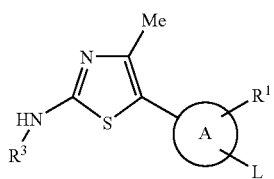

(XV)

wherein Ring A, R¹ and R³ are as defined in claim 1 and L is a suitable leaving group, with a sulfonamide of formula $R^7$—$SO_2NH(R^9)$, wherein $R^7$ and $R^9$ are as defined in claim 1;

and, after any one of process steps (A) to (M), optionally carrying out the following additional steps:—
(i) the conversion of the compound so obtained to a further compound of the invention of formula (I); and
(ii) forming a pharmaceutically acceptable salt of a compound of formula (I).

15. A pharmaceutical composition comprising a thiazole derivative of formula (I), or a pharmaceutically acceptable salt thereof, according to claim 1 in association with a pharmaceutically acceptable adjuvant, diluent or carrier.

16. A method of treating cancer which comprises administering to a patient in need of such treatment an effective amount of a compound of formula (I), or a pharmaceutically acceptable salt thereof, according to claim 1.

* * * * *